(12) United States Patent
Kane, Jr. et al.

(10) Patent No.: US 11,406,644 B2
(45) Date of Patent: *Aug. 9, 2022

(54) TROPOMYOSIN-RELATED KINASE (TRK) INHIBITORS

(71) Applicant: Genzyme Corporation, Cambridge, MA (US)

(72) Inventors: John L. Kane, Jr., Maynard, MA (US); Gloria Matthews, Boylston, MA (US); Markus Metz, Encinitas, CA (US); Michael Kothe, Medway, MA (US); Jinyu Liu, Acton, MA (US); Andrew Scholte, Somerville, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,692

(22) Filed: Sep. 25, 2020

(65) Prior Publication Data

US 2021/0169894 A1 Jun. 10, 2021

Related U.S. Application Data

(63) Continuation of application No. 16/194,696, filed on Nov. 19, 2018, now abandoned, which is a
(Continued)

(51) Int. Cl.

| *A61K 31/4184* | (2006.01) |
| *A61K 31/437* | (2006.01) |
| *A61K 31/551* | (2006.01) |
| *C07F 9/6506* | (2006.01) |
| *A61K 31/4439* | (2006.01) |
| *A61K 31/444* | (2006.01) |
| *A61K 31/4545* | (2006.01) |
| *A61K 31/4725* | (2006.01) |
| *A61K 31/496* | (2006.01) |
| *C07D 403/04* | (2006.01) |
| *C07D 401/04* | (2006.01) |
| *C07D 401/12* | (2006.01) |
| *C07D 401/14* | (2006.01) |
| *C07D 403/14* | (2006.01) |
| *C07D 405/14* | (2006.01) |
| *C07D 487/04* | (2006.01) |
| *C07D 487/10* | (2006.01) |
| *C07D 413/14* | (2006.01) |

(Continued)

(52) U.S. Cl.
CPC ........ *A61K 31/551* (2013.01); *A61K 31/4184* (2013.01); *A61K 31/437* (2013.01); *A61K 31/444* (2013.01); *A61K 31/4439* (2013.01); *A61K 31/4545* (2013.01); *A61K 31/4725* (2013.01); *A61K 31/496* (2013.01); *A61K 31/501* (2013.01); *A61K 31/506* (2013.01); *A61K 31/5377* (2013.01); *C07D 401/04* (2013.01); *C07D 401/12* (2013.01); *C07D 401/14* (2013.01); *C07D 403/04* (2013.01); *C07D 403/14* (2013.01); *C07D 405/14* (2013.01); *C07D 413/04* (2013.01); *C07D 413/14* (2013.01); *C07D 417/14* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *C07D 519/00* (2013.01); *C07F 9/5022* (2013.01); *C07F 9/6506* (2013.01); *C07F 9/6561* (2013.01); *C07F 9/65583* (2013.01)

(58) Field of Classification Search
CPC .............. A61K 31/551; A61K 31/4184; A61K 31/437; A61K 31/4439; A61K 31/444; A61K 31/4545; A61K 31/4725; A61K 31/496; C07F 9/6506
See application file for complete search history.

(56) References Cited

U.S. PATENT DOCUMENTS 4,612,323 A 9/1986 Kisida et al.
4,663,339 A 5/1987 Kisida et al.
(Continued)

FOREIGN PATENT DOCUMENTS

CA 2089689 A1 8/1993
DE 19718181 A1 11/1998
(Continued)

OTHER PUBLICATIONS

Arthritis Advisory Committee Meeting Announcement Mar. 12, 2012, Retrieved from the Internet: URL: http:/lwwwJdapov/ AdvisoryCommittees/Calendar/ucm286556_pdf.
(Continued)

*Primary Examiner* — Laura L Stockton
(74) *Attorney, Agent, or Firm* — Dechert LLP

(57) ABSTRACT

Tropomyosin-related kinase inhibitors (Trk inhibitors) are small molecule compounds useful in the treatment of disease. Trk inhibitors can be used as pharmaceutical agents and in pharmaceutical compositions. Trk inhibitors are useful in the treatment of inflammatory diseases, autoimmune disease, defects of bone metabolism and/or cancer, and are particularly useful in the treatment of osteoarthritis (OA), pain, and pain associated with OA. Trk inhibitors are also useful for inhibiting tropomyosin-related kinase A (TrkA), tropomyosin-related kinase B (TrkB), tropomyosin-related kinase C (TrkC), and/or c-FMS (the cellular receptor for colony stimulating factor-1 (CSF-1)).

21 Claims, No Drawings

Related U.S. Application Data continuation of application No. 15/436,195, filed on Feb. 17, 2017, now Pat. No. 10,166,239, which is a continuation of application No. 14/741,017, filed on Jun. 16, 2015, now Pat. No. 9,611,265, which is a continuation of application No. 14/628,876, filed on Feb. 23, 2015, now Pat. No. 9,174,986, which is a continuation of application No. 14/564,773, filed on Dec. 9, 2014, now Pat. No. 9,067,914.

(60) Provisional application No. 62/040,750, filed on Aug. 22, 2014, provisional application No. 61/914,128, filed on Dec. 10, 2013.

(51) Int. Cl.

| | | |
|---|---|---|
| C07D 417/14 | (2006.01) | |
| C07D 487/08 | (2006.01) | |
| C07F 9/6558 | (2006.01) | |
| C07F 9/6561 | (2006.01) | |
| C07D 413/04 | (2006.01) | |
| C07D 471/04 | (2006.01) | |
| C07D 471/08 | (2006.01) | |
| C07D 471/10 | (2006.01) | |
| C07D 519/00 | (2006.01) | |
| C07F 9/50 | (2006.01) | |
| A61K 31/501 | (2006.01) | |
| A61K 31/506 | (2006.01) | |
| A61K 31/5377 | (2006.01) | |

(56) References Cited

U.S. PATENT DOCUMENTS

| | | | |
|---|---|---|---|
| 5,441,969 | A | 8/1995 | Axelsson et al. |
| 5,702,637 | A | 12/1997 | Johnson et al. |
| 5,972,241 | A | 10/1999 | Johnson et al. |
| 7,067,665 | B2 | 6/2006 | Nazare et al. |
| 7,312,214 | B2 | 12/2007 | Qiao et al. |
| 7,462,427 | B2 | 12/2008 | Goodby et al. |
| 7,465,825 | B2 | 12/2008 | Van Zandt et al. |
| 7,491,748 | B2 | 2/2009 | Tani et al. |
| 7,582,652 | B2 | 9/2009 | Bonjouklian et al. |
| 7,799,820 | B2 | 9/2010 | Takahashi et al. |
| 9,067,914 | B1 | 6/2015 | Kane, Jr. et al. |
| 9,174,986 | B2 | 11/2015 | Kane, Jr. et al. |
| 9,611,265 | B2 | 4/2017 | Kane, Jr. et al. |
| 10,166,239 | B2 | 1/2019 | Kane, Jr. et al. |
| 10,219,998 | B2 | 3/2019 | Lieberman et al. |
| 11,110,055 | B2 | 9/2021 | Lieberman et al. |
| 2004/0002145 | A1 | 1/2004 | Shewchuk et al. |
| 2007/0185197 | A1 | 8/2007 | Fujikura et al. |
| 2008/0242695 | A1 | 10/2008 | Morgan et al. |
| 2009/0286984 | A1 | 11/2009 | Raeppel et al. |
| 2010/0204246 | A1 | 8/2010 | Davies et al. |
| 2012/0184535 | A1 | 7/2012 | Brzozka et al. |
| 2019/0183903 | A1 | 6/2019 | Kane, Jr. et al. |
| 2020/0048222 | A1 | 2/2020 | Lieberman et al. |
| 2021/0169894 | A1 | 6/2021 | Kane, Jr. et al. |

FOREIGN PATENT DOCUMENTS

| | | | |
|---|---|---|---|
| EP | 132606 | A1 | 2/1985 |
| EP | 0186190 | | 7/1986 |
| JP | S60158180 | A | 8/1985 |
| JP | 61-17569 | | 1/1986 |
| JP | 2006273879 | | 12/2006 |
| WO | WO 99/01454 | | 1/1999 |
| WO | WO-99000372 | A1 | 1/1999 |
| WO | WO-99001454 | A1 | 1/1999 |
| WO | WO 02/092575 | A1 | 11/2002 |
| WO | WO-2004089951 | A1 | 10/2004 |
| WO | WO-2005075478 | A1 | 8/2005 |
| WO | WO 2005/108384 | A1 | 11/2005 |
| WO | WO-2006087530 | A1 | 8/2006 |
| WO | WO-2007041863 | A1 | 4/2007 |
| WO | WO 2010/088518 | | 8/2010 |
| WO | WO 2011/051452 | | 5/2011 |
| WO | WO-2011058139 | A1 | 5/2011 |
| WO | WO-2012003576 | A1 | 1/2012 |
| WO | WO 2012/137089 | | 10/2012 |
| WO | WO 2013/088256 | A1 | 6/2013 |
| WO | WO 2013/176970 | | 11/2013 |
| WO | WO 2015/089139 | A1 | 6/2015 |
| WO | WO-2015086509 | A1 | 6/2015 |
| WO | WO 2016/100677 | A2 | 6/2016 |

OTHER PUBLICATIONS

Bertrand, et al., The Crystal Structures of TrkA and TrkB Suggest Key Regions for Achieving Selective Inhibition, Journal of Molecular Biology, 423(3): 439-453 (2012).

Chemical Abstract Registry No. 215242-13-0, indexed in the Registry filed on STN CAS On Line Dec. 8, 1998 (Year: 1998).

Chemical Abstract Registry No. 782462-52-6, indexed in the Registry filed on STN CAS Online Nov. 17, 2004 (Year: 2004).

Corrected Notice of Allowability for U.S. Appl. No. 14/741,017, "Tropomyosin-Related Kinase (TRK) Inhibitors", dated Dec. 6, 2016.

Final Office Action dated Dec. 19, 2019 for U.S. Appl. No. 16/194,696, "Tropomyosin-Related Kinase (TRK) Inhibitors".

Final Office Action for U.S. Appl. No. 14/741,017, "Tropomyosin-Related Kinase (TRK) Inhibitors", dated May 9, 2016.

Final Office Action U.S. Appl. No. 15/436,195, "Tropomyosin-Related Kinase (TRK) Inhibitors", dated Feb. 20, 2018.

Golub et al., "Molecular Classification of Cancer: Class Discovery and Class Prediction by Gene Expression Monintoring," Science, vol. 286, Oct. 15, 1999, pp. 531-537. (Year: 1999).

International Preliminary Report on Patentability for International Application No. PCT/US2014/069469, "Tropomyosin-Related Kinase (TRK) Inhibitors", dated Jun. 23, 2016.

International Preliminary Report on Patentability for International Application No. PCT/US2015/066396, "Pharmaceutical Formulations of Tropomyosin Related Kinase (TRK) Inhibitors", dated Jun. 29, 2017.

International Search Report for International Application No. PCT/US2014/069469, "Tropomyosin-Related Kinase (TRK) Inhibitors", dated Feb. 11, 2015.

International Search Report or International Application No. PCT/US2015/066396, "Pharmaceutical Formulations of Tropomyosin Related Kinase (TRK) Inhibitors", dated Jun. 21, 2016.

Karaman, et al., "A Quantitative Analysis of Kinase Inhibitor Selectivity", Nature Biotechnology, 26(1): 127-132 (2008).

Kishida, et al., Chemical Abstract 104: 186419, 1986.

Lane, et aL, "Tanezumab for the Treatment of Pain From Osteoarthritis of the Knee," The New England Journal of Medicine, 2010, vol. 363, pp. 1521-1531.

Mizuno, et al., "Design, Synthesis and Docking Studies of Novel Benzimidazoles for the Treatment of Metabolic syndrome", J. Med. Chem., (2010), vol. 53, p. 1076-1085.

Nicol, G.D., et al., "Unraveling the story of NGF-Mediated Sensitization of Nociceptive Sensory Neurons. On or Off the Trks?," Molecular Interventions, 2007, vol. 7 (1), pp. 26-41.

Notice of Allowance for U.S. Appl. No. 14/564,773, "Tropomyosin-Related Kinase (TRK) Inhibitors", dated Feb. 9, 2015.

Notice of Allowance for U.S. Appl. No. 14/628,876, "Tropomyosin-Related Kinase (TRK) Inhibitors", dated Jun. 29, 2015.

Notice of Allowance for U.S. Appl. No. 14/741,017, "Tropomyosin-Related Kinase (TRK) Inhibitors", dated Nov. 18, 2016.

Notice of Allowance for U.S. Appl. No. 15/436,195, Tropomyosin-Related Kinase (TRK) Inhibitors, dated Aug. 8, 2018.

Notice of Allowance for U.S. Appl. No. 15/536,544, "Pharmaceutical Formulations of Tropomyosin Related Kinase (TRK) Inhibitors", dated Oct. 4, 2018.

Office Action dated May 6, 2019 for U.S. Appl. No. 16/194,696, "Tropomyosin-Related Kinase (TRK) Inhibitors".

(56) References Cited

OTHER PUBLICATIONS

Office Action for U.S. Appl. No. 14/628,876, "Tropomyosin-Related Kinase (TRK) Inhibitors", dated Apr. 24, 2015.
Office Action for U.S. Appl. No. 14/741,017, "Tropomyosin-Related Kinase (TRK) Inhibitors", dated Mar. 25, 2016.
Office Action U.S. Appl. No. 15/436,195, "Tropomyosin-Related Kinase (TRK) Inhibitors", dated Jul. 27, 2017.
Office Action U.S. Appl. No. 16/194,696, "Tropomyosin-Related Kinase (TRK) Inhibitors", dated Mar. 27, 2020.
Office Action U.S. Appl. No. 16/239,904, "Pharmaceutical Formulations of Tropomyosin Related Kinase (TRK) Inhibitors", dated Jun. 8, 2020.
Supplemental Notice of Allowability for U.S. Appl. No. 14/564,773, "Tropomyosin-Related Kinase (TRK) Inhibitors", dated Mar. 10, 2015.
Written Opinion for International Application No. PCT/US2014/069469, "Tropomyosin-Related Kinase (TRK) Inhibitors", dated Feb. 11, 2015.
Written Opinion for International Application No. PCT/US2015/066396, "Pharmaceutical Formulations of Tropomyosin Related Kinase (TRK) Inhibitors", dated Jun. 21, 2016.
Yadav, A.V., et al., "Co-Crystals: A Novel Approach to Modify Phsicochemical Properties of Active Pharmaceutical Ingredients", Indian J. Pham. Sci. Jul.-Aug. 2009; 71(4): 359-370.
Hameed p. Shahul, et al. "Aminoazabenzimidazoles, a Novel Class of Orally Active Antimalarial Agents," *J. Med. Chem.*, 57(13), pp. 5702-5713 (2014).

TROPOMYOSIN-RELATED KINASE (TRK) INHIBITORS

RELATED APPLICATIONS

This application is a continuation of U.S. application Ser. No. 16/194,696, filed Nov. 19, 2018, which is a continuation of U.S. application Ser. No. 15/436,195, now U.S. Pat. No. 10,166,239, filed Feb. 17, 2017, which is a continuation of U.S. application Ser. No. 14/741,017, now U.S. Pat. No. 9,611,265, filed Jun. 16, 2015, which is a continuation of U.S. application Ser. No. 14/628,876, now U.S. Pat. No. 9,174,986, filed Feb. 23, 2015, which is a continuation of U.S. application Ser. No. 14/564,773, now U.S. Pat. No. 9,067,914, filed Dec. 9, 2014, which claims the benefit of U.S. Provisional Application Nos. 62/040,750, filed Aug. 22, 2014, and 61/914,128, filed Dec. 10, 2013. The above applications are incorporated by reference in entirety.

BACKGROUND OF THE INVENTION

Field of the Invention

This invention relates to tropomyosin-related kinase inhibitors ("Trk inhibitors"). This invention also relates to pharmaceutical compositions comprising Trk inhibitors and to the use of Trk inhibitors and pharmaceutical compositions comprising Trk inhibitors to treat disease. This invention further relates to the use of Trk inhibitors to treat inflammatory diseases, autoimmune disease, defects of bone metabolism and cancer. The Trk inhibitors of the present invention can be used to treat osteoarthritis (OA), to treat pain, to treat post-operative pain, to treat pain associated with OA, and to inhibit tropomyosin-related kinase A (TrkA), tropomyosin-related kinase B (TrkB), and/or tropomyosin-related kinase C (TrkC), and to inhibit c-FMS (the cellular receptor for colony stimulating factor-1 (CSF-1)).

Definitions

As used herein, the term "amino" means a functional group having a nitrogen atom and 1 to 2 hydrogen atoms. "Amino" generally may be used herein to describe a primary, secondary, or tertiary amine, and those of skill in the art will readily be able to ascertain the identification of which in view of the context in which this term is used in the present disclosure. The term "amine" or "amine group" or "ammonia group" means a functional group containing a nitrogen atom derived from ammonia ($NH_3$). The amine groups are preferably primary amines, meaning the nitrogen is bonded to two hydrogen atoms and one substituent group comprising a substituted or unsubstituted alkyl or aryl group or an aliphatic or aromatic group. The amine groups may be secondary amines meaning, the nitrogen is bonded to one hydrogen atom and two substituent groups comprising a substituted or unsubstituted alkyl or aryl groups or an aliphatic or aromatic group, as defined below. The amine groups may be tertiary amines meaning the nitrogen is bonded to three substituent groups comprising a substituted or unsubstituted alkyl or aryl groups or an aliphatic or aromatic group. The amine groups may also be quaternary amines meaning the designated amine group is bonded to a fourth group, resulting in a positively charged ammonium group.

It is understood that any or all of the amines in the present invention may be in the free amine form (that is, as $—NH_2$ for a primary amine) or in a protonated form with a pharmaceutically acceptable anion (that is, as $—NH_3^+Y^-$ for a primary amine, where $Y^-$ is the pharmaceutically acceptable anion).

As used herein, the term "amide group" means a functional group comprising a carbonyl group linked to a nitrogen. A "carbonyl group" means a functional group comprising a carbon atom double bonded to an oxygen atom, represented by (C=O).

The term "alkane" means a saturated hydrocarbon, bonded by single bonds. Alkanes can be linear or branched. "Cycloalkanes" are saturated hydrocarbons rings bonded by single bonds.

As used herein, the term "$(C_1-C_{10})$alkyl" means a saturated straight chained or branched or cyclic hydrocarbon consisting essentially of 1 to 10 carbon atoms and a corresponding number of hydrogen atoms. Typically straight chained or branched groups have from one to ten carbons, or more typically one to five carbons. Exemplary $(C_1-C_{10})$alkyl groups include methyl (represented by $—CH_3$), ethyl (represented by $—CH_2—CH_3$), n-propyl, isopropyl, n-butyl, isobutyl, etc. Other $(C_1-C_{10})$alkyl groups will be readily apparent to those of skill in the art given the benefit of the present disclosure.

As used herein, the term "$(C_2-C_9)$heteroalkyl" means a saturated straight chained or branched or cyclic hydrocarbon consisting essentially of 2 to 10 atoms, wherein 2 to 9 of the atoms are carbon and the remaining atom(s) is selected from the group consisting of nitrogen, sulfur, and oxygen. Exemplary $(C_2-C_9)$heteroalkyl groups will be readily apparent to those of skill in the art given the benefit of the present disclosure.

As used herein, the term "$(C_3-C_{10})$cycloalkyl" means a nonaromatic saturated hydrocarbon group, forming at least one ring consisting essential of 3 to 10 carbon atoms and a corresponding number of hydrogen atoms. $(C_3-C_{10})$cycloalkyl groups can be monocyclic or multicyclic. Individual rings of multicyclic cycloalkyl groups can have different connectivities, for example, fused, bridged, spiro, etc., in addition to covalent bond substitution. Exemplary $(C_3-C_{10})$ cycloalkyl groups include cyclopropyl, cyclobutyl, cyclopentyl, cyclohexyl, norbornanyl, bicyclo-octanyl, octahydro-pentalenyl, spiro-decanyl, cyclopropyl substituted with cyclobutyl, cyclobutyl substituted with cyclopentyl, cyclohexyl substituted with cyclopropyl, etc. Other $(C_3-C_{10})$ cycloalkyl groups will be readily apparent to those of skill in the art given the benefit of the present disclosure.

As used herein, the term "$(C_2-C_9)$heterocycloalkyl" means a nonaromatic group having 3 to 10 atoms that form at least one ring, wherein 2 to 9 of the ring atoms are carbon and the remaining ring atom(s) is selected from the group consisting of nitrogen, sulfur, and oxygen. $(C_2-C_9)$heterocycloalkyl groups can be monocyclic or multicyclic. Individual rings of such multicyclic heterocycloalkyl groups can have different connectivities, for example, fused, bridged, spiro, etc., in addition to covalent bond substitution. Exemplary $(C_2-C_9)$heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. The ($C_2$-$C_9$) heterocycloalkyl group is typically attached to the main structure via a carbon atom or a nitrogen atom. Other ($C_2$-$C_9$)heterocycloalkyl groups will be readily apparent to those of skill in the art given the benefit of the present disclosure.

The term "aliphatic group" or "aliphatic" means a non-aromatic group consisting of carbon and hydrogen, and may optionally include one or more double and/or triple bonds. In other words, an aliphatic group is any group consisting of carbon and hydrogen which contains no aromatic functionality. An aliphatic group may be straight chained, branched or cyclic and typically contains between about one and about 24 carbon atoms.

The term "aryl group" may be used interchangeably with "aryl," "aryl ring," "aromatic," "aromatic group," and "aromatic ring." Aryl groups include carbocyclic aromatic groups, typically with six to fourteen ring carbon atoms. Aryl groups also include heteroaryl groups, which typically have five to fourteen ring atoms with one or more heteroatoms selected from nitrogen, oxygen and sulfur.

As used herein, the term "($C_6$-$C_{14}$)aryl" means an aromatic functional group having 6 to 14 carbon atoms that form at least one ring.

As used herein, the term "($C_2$-$C_9$)heteroaryl" means an aromatic functional group having 5 to 10 atoms that form at least one ring, wherein 2 to 9 of the ring atoms are carbon and the remaining ring atom(s) is selected from the group consisting of nitrogen, sulfur, and oxygen. ($C_2$-$C_9$)heteroaryl groups can be monocyclic or multicyclic. Individual rings of such multicyclic heteroaryl groups can have different connectivities, for example, fused, etc., in addition to covalent bond substitution. Exemplary ($C_2$-$C_9$)heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. The ($C_2$-$C_9$)heteroaryl group is typically attached to the main structure via a carbon atom, however, those of skill in the art will realize when certain other atoms, for example, hetero ring atoms, can be attached to the main structure. Other ($C_2$-$C_9$)heteroaryl groups will be readily apparent to those of skill in the art given the benefit of the present disclosure.

As used herein, the term "alkyl amine" means an ($C_1$-$C_{10}$)alkyl containing a primary, secondary, or tertiary amine group in place of one hydrogen atom, represented by ($C_1$-$C_{10}$)alkyl amine and (($C_1$-$C_{10}$)alkyl)$_2$ amine.

The term "alkyl ester" means a ($C_1$-$C_{10}$)alkyl containing an ester group in place of one hydrogen atom, represented by —O(O)C—($C_1$-$C_{10}$)alkyl.

The term "alkyl acid" means an ($C_1$-$C_{10}$)alkyl containing a carboxylic acid group in place of one hydrogen atom, represented by ($C_1$-$C_{10}$)alkyl-COOH.

The term "aliphatic acid" means an acid of nonaromatic hydrocarbons, represented by ($C_1$-$C_{10}$)alkyl-COOH and ($C_3$-$C_{10}$)cycloalkyl-COOH.

The term "halo" means a fluorine (F), chlorine (Cl), bromine (Br), iodine (I), or astatine (At) ion.

The term "methoxy" means a ($C_1$)alkyl containing an oxygen in place of one hydrogen atom, represented by —(O)$CH_3$.

The term "polyol" means an alcohol containing multiple hydroxyl (—OH) groups.

"Substituted" means the substitution of a carbon in alkyl, heterocyclic or aryl groups with one or more non-carbon substituents. Non-carbon substituents are selected from nitrogen, oxygen and sulfur.

"Unsubstituted" means the group is comprised of only hydrogen and carbon.

A 3 to 10 member ring means a closed ring; the 3 to 10 member ring may be acyclic, aromatic or heterocyclic.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate.

The term "dicarbonyl" refers to an organic molecule containing two or more adjacent carbonyl groups. Carbonyl groups, represented by C═O, can be, for example, aldehydes, ketones, and other groups with an oxygen atom doubly bonded to a carbon atom. Examples include but are not limited to glyoxal, methylglyoxal, dimethyl glyoxal, and 3-deoxyglucosone.

Related Art

Not applicable

BRIEF SUMMARY OF THE INVENTION

The present invention relates to a compound with the structure of Formula (I):

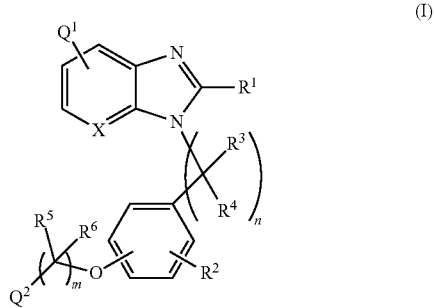

(I)

wherein:

n is 1, 2, 3, 4 or 5;

m is 0, 1, 2, 3 or 4;

$Q^1$ is H, halo or ($C_6$-$C_{14}$)aryl, ($C_2$-$C_9$)heteroaryl, ($C_3$-$C_{10}$) cycloalkyl, ($C_2$-$C_9$)heterocycloalkyl, wherein the ($C_6$-$C_{14}$)aryl, ($C_2$-$C_9$)heteroaryl, ($C_3$-$C_{10}$) cycloalkyl, or ($C_2$-$C_9$)heterocycloalkyl is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—,
  wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;

$Q^2$ is $(C_6-C_{14})$aryl, $(C_2-C_9)$heteroaryl, $(C_3-C_{10})$cycloalkyl, or $(C_2-C_9)$heterocycloalkyl,
  wherein the $(C_6-C_{14})$aryl, $(C_2-C_9)$heteroaryl, $(C_3-C_{10})$cycloalkyl, or $(C_2-C_9)$heterocycloalkyl is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—,
  wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;

X is CH, N, halo or $CR^9$,
  wherein $R^9$ is $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$;

$R^1$ is H, halo, $(C_1-C_{10})$alkyl, $(C_2-C_9)$heteroalkyl, $(C_1-C_{10})$alkylamine, or NH$_2$;

$R^2$ is H, halo, $(C_1-C_{10})$alkyl, $(C_2-C_9)$heteroalkyl, $(C_1-C_{10})$alkylamine, $(C_1-C_{10})$alkyl-O—, or NH$_2$, $R^3$ and $R^4$ are each independently H, $(C_1-C_{10})$alkyl, $(C_2-C_9)$heteroalkyl, $(C_1-C_{10})$alkylamine, O—$(C_1-C_{10})$alkyl, or NH$_2$ or $R^3$ and $R^4$ are taken together with the carbon to which they are attached to form a 3 to 10 member ring,
  wherein the 3 to 10 member ring is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$; and $R^5$ and $R^6$ are each independently H, $(C_1-C_{10})$alkyl, $(C_2-C_9)$heteroalkyl, $(C_1-C_{10})$alkylamine, O—$(C_1-C_{10})$alkyl, or NH$_2$ or $R^5$ and $R^6$ are taken together with the carbon to which they are attached to form a 3 to 10 member ring,
  wherein the 3 to 10 member ring is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$;

or a pharmaceutically acceptable salt thereof.

The present invention further relates to a compound of Formula (I), wherein n is 1, 2, or 3.

The present invention further relates to a compound of Formula (I), wherein m is 0, 1, or 2.

The present invention further relates to a compound of Formula (I), wherein n is 1 and m is 1.

The present invention further relates to a compound of Formula (I), wherein $Q^1$ is H or $(C_6-C_{14})$aryl or $(C_2-C_9)$heteroaryl wherein the $(C_6-C_{14})$aryl or $(C_2-C_9)$heteroaryl is optionally substituted by one to four selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

The present invention further relates to a compound of Formula (I), wherein $Q^2$ is $(C_6-C_{14})$aryl or $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

The present invention further relates to a compound of Formula (I), wherein X is CH or N.

The present invention further relates to a compound of Formula (I), wherein $R^1$ is H, halo, NH$_2$, or $(C_1-C_{10})$alkyl.

The present invention further relates to a compound of Formula (I), wherein $R^2$ is H, halo, $(C_1-C_{10})$alkyl, or $(C_1-C_{10})$alkyl-O—. The present invention further relates to a compound of Formula wherein $R^2$ is $CH_3$—O—, or $CH_3$—$CH_2$—O—.

The present invention further relates to a compound of Formula (I), wherein $R^3$ and $R^4$ are each H.

The present invention further relates to a compound of Formula (I), wherein $R^5$ and $R^6$ are each H.

The present invention further relates to a compound of Formula (I), with the structure of Formula (II):

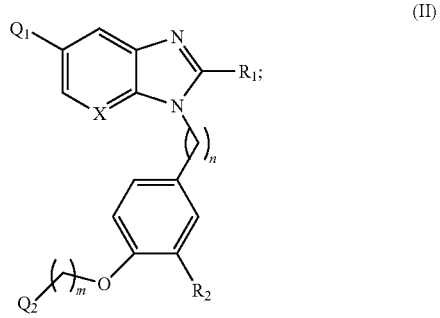

(II)

or a pharmaceutically acceptable salt thereof.

The present invention further relates to pharmaceutical compositions comprising a compound of Formula (I).

The present invention further relates to methods of treating inflammatory diseases, autoimmune disease, defects of bone metabolism or cancer in a patient in need thereof comprising administering to the patient a compound according to Formula (I).

The present invention further relates to methods of treating osteoarthritis in a patient in need thereof comprising administering to the patient a compound according to Formula (I).

The present invention further relates to methods of treating pain in a patient in need thereof comprising administering to the patient a compound according to Formula (I).

The present invention further relates to methods of treating pain associated with osteoarthritis in a patient in need thereof comprising administering to the patient a compound according to Formula (I).

The present invention further relates to methods of inhibiting tropomyosin-related kinase A in a patient comprising administering to the patient a compound according to Formula (I).

The present invention further relates to methods of inhibiting tropomyosin-related kinase B in a patient comprising administering to the patient a compound according to Formula (I).

The present invention further relates to methods of inhibiting tropomyosin-related kinase C in a patient comprising administering to the patient a compound according to Formula (I).

The present invention further relates to methods of inhibiting c-FMS in a patient comprising administering to the patient a compound according to Formula (I).

BRIEF DESCRIPTION OF THE SEVERAL VIEWS OF THE DRAWING(S)

Not applicable

DETAILED DESCRIPTION OF THE INVENTION

This invention relates to tropomyosin-related kinase inhibitors (Trk inhibitors). This invention also relates to pharmaceutical compositions comprising Trk inhibitors and to the use of Trk inhibitors and pharmaceutical compositions comprising Trk inhibitors to treat disease. This invention further relates to the use of Trk inhibitors to treat inflammatory diseases, autoimmune disease, defects of bone metabolism and cancer. The Trk inhibitors of the present invention can be used to treat osteoarthritis (OA), to treat pain associated with OA, and to inhibit tropomyosin-related kinase A (TrkA), tropomyosin-related kinase B (TrkB), tropomyosin-related kinase C (TrkC), and to inhibit c-FMS (the cellular receptor for colony stimulating factor-1 (CSF-1)).

Tropomyosin-related kinases (Trk) are high affinity receptors activated by soluble growth factors called neutrophins (NT). TrkA, also known as neurotrophic tyrosine kinase receptor type 1, is activated by nerve growth factor (NGF). TrkB is activated by brain derived growth factor and NT-4/5. TrkC is activated by NT3. The activation of Trk leads to the activation of downstream kinases that are implicated in cell signaling, including cell proliferation, survival, angiogenesis and metastasis. Trk have been implicated in a number of diseases, including OA.

The invention also relates to inhibitors of c-FMS (the cellular receptor for colony stimulating factor-1 (CSF-1). C-FMS plays a role in the regulation of macrophage function, and is believed to play a role in inflammatory diseases, autoimmune disease, defects of bone metabolism and cancer (Burns and Wilks, 2011, *Informa Healthcare*).

OA is a prevalent and debilitating joint disease characterized by chronic pain and destruction of articular cartilage. Recent clinical trials have confirmed a role for blocking NGF in OA knee pain, demonstrating significant pain relief and high responder rates in patients treated by intravenous infusion with anti-NGF blocking antibodies (Lane, 2010, *N Engl J Med*). However, this modality may lead to an increased risk for adverse events due to systemic inhibition of NGF signaling (FDA Arthritis Advisory Committee Meeting to Discuss Safety Issues Related to the Anti-Nerve Growth Factor Agents) Accordingly, a novel approach toward targeting NGF-mediated OA pain has been adopted through the development of Trk inhibitors, specifically TrkA inhibitors, the high-affinity receptor for NGF (Nicol, 2007, *Molecular Interv*). The Trk inhibitors of the present invention are delivered locally and thereby avoid the systemic distribution observed with intravenous anti-NGF administration. This treatment strategy provides enhanced dosing convenience, as well greater safety by allowing for the maintenance of physiologically necessary NGF signaling (i.e. sensory/sympathetic nerve maintenance, angiogenesis) at non-local sites.

The Trk inhibitors of the present invention are benzimidazole derivatives. The Trk inhibitors are small molecules for local administration.

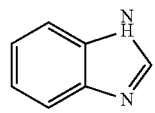

FIG. 1: Benzimidazole

This invention relates to pharmaceutical compositions comprising Trk inhibitors. This invention also relates to methods of inhibiting Trk with Trk inhibitors and methods of treating disease with Trk inhibitors. The invention also pertains to methods of treating OA, methods with treating pain, and methods of treating post-operative pain, and methods of treating pain associated with OA with Trk inhibitors. The Trk inhibitors and the pharmaceutical compositions comprising Trk inhibitors can be administered in multiple dosage forms, including an injection for local delivery. The Trk inhibitors are the active pharmaceutical ingredient in pharmaceutical compositions comprising Trk inhibitors; the Trk inhibitors can also be co-administered and/or co-formulated with other active ingredients for the treatment of disease, including OA and pain associated with OA.

The present invention relates to a compound with the structure of Formula (I):

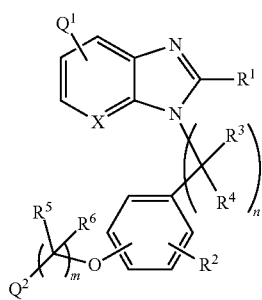

(I)

wherein:

n is 1, 2, 3, 4 or 5;

m is 0, 1, 2, 3 or 4;

$Q^1$ is H, halo or $(C_6-C_{14})$aryl, $(C_2-C_9)$heteroaryl, $(C_3-C_{10})$ cycloalkyl, $(C_2-C_9)$heterocycloalkyl, wherein the $(C_6-C_{14})$aryl, $(C_2-C_9)$heteroaryl, $(C_3-C_{10})$ cycloalkyl, or $(C_2-C_9)$heterocycloalkyl is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$ heteroaryl, $(C_1-C_{10})$alkylamine, $(C_1-C_{10})$alkyl-C(O) O—, COOH—$(C_1-C_{10})$alkyl, COOH—$(C_3-C_{10})$ cycloalkyl, $(C_1-C_{10})$alkyl-O—, —OH, —NH$_2$, $R^7R^8$N—, $R^7R^8$N(O)C—, $R^7$(O)CR$^8$N—, F$_3$C—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$ heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$ cycloalkyl(O)S—, $(C_6-C_{14})$aryl(O)S—, $(C_2-C_9)$ heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8$NO$_2$S—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;

$Q^2$ is $(C_6-C_{14})$aryl, $(C_2-C_9)$heteroaryl, $(C_3-C_{10})$cycloalkyl, or $(C_2-C_9)$heterocycloalkyl, wherein the $(C_6-C_{14})$aryl, $(C_2-C_9)$heteroaryl, $(C_3-C_{10})$ cycloalkyl, or $(C_2-C_9)$heterocycloalkyl is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$ heteroaryl, $(C_1-C_{10})$alkylamine, $(C_1-C_{10})$alkyl-C(O) O—, COOH—$(C_1-C_{10})$alkyl, COOH—$(C_3-C_{10})$ cycloalkyl, $(C_1-C_{10})$alkyl-O—, —OH, —NH$_2$, $R^7R^8$N—, $R^7R^8$N(O)C—, $R^7$(O)CR$^8$N—, F$_3$C—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$ heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$ cycloalkyl(O)S—, $(C_6-C_{14})$aryl(O)S—, $(C_2-C_9)$ heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8$NO$_2$S—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;

X is CH, N, halo or CR$^9$, wherein $R^9$ is $(C_1-C_{10})$alkyl, $(C_2-C_9)$heteroalkyl, $(C_3-C_{10})$cycloalkyl, $(C_2-C_9)$heterocycloalkyl, $(C_6-C_{14})$ aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$;

$R^1$ is H, halo, $(C_1-C_{10})$alkyl, $(C_2-C_9)$heteroalkyl, $(C_1-C_{10})$ alkylamine, or NH$_2$;

$R^2$ is H, halo, $(C_1-C_{10})$alkyl, $(C_2-C_9)$heteroalkyl, $(C_1-C_{10})$ alkylamine, $(C_1-C_1)$alkyl-O—, or NH$_2$;

$R^3$ and $R^4$ are each independently H, $(C_1-C_{10})$alkyl, $(C_2-C_9)$heteroalkyl, $(C_1-C_{10})$alkylamine, O—$(C_1-C_{10})$alkyl, or NH$_2$ or $R^3$ and $R^4$ are taken together with the carbon to which they are attached to form a 3 to 10 member ring, wherein the 3 to 10 member ring is optionally substituted by one to four groups selected from $(C_1-C_{10})$ alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$ heteroaryl, $(C_1-C_{10})$alkylamine, $(C_1-C_{10})$alkyl-C(O) O—, COOH—$(C_1-C_{10})$alkyl, COOH—$(C_3-C_{10})$ cycloalkyl, $(C_1-C_{10})$alkyl-O—, —OH, —NH$_2$; and $R^5$ and $R^6$ are each independently H, $(C_1-C_{10})$alkyl, $(C_2-C_9)$heteroalkyl, $(C_1-C_1)$alkylamine, O—$(C_1-C_{10})$alkyl, or NH$_2$ or $R^5$ and $R^6$ are taken together with the carbon to which they are attached to form a 3 to 10 member ring, wherein the 3 to 10 member ring is optionally substituted by one to four groups selected from $(C_1-C_{10})$ alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$ heteroaryl, $(C_1-C_{10})$alkylamine, $(C_1-C_{10})$alkyl-C(O) O—, COOH—$(C_1-C_{10})$alkyl, COOH—$(C_3-C_{10})$ cycloalkyl, $(C_1-C_{10})$alkyl-O—, —OH, —NH$_2$;

or a pharmaceutically acceptable salt thereof.

In a preferred embodiment, the present invention relates to a compound of Formula (I), wherein n is 1, 2, or 3. In another embodiment, the present invention relates to a compound of Formula (I), wherein n is 1. In another embodiment, the present invention relates to a compound of Formula (I), wherein n is 2. In yet another embodiment, the present invention relates to a compound of Formula (I), wherein n is 3.

In a preferred embodiment, the present invention relates to a compound of Formula (I), wherein m is 0, 1, or 2. In another embodiment, the present invention relates to a compound of Formula (I), wherein m is 0. In another embodiment, the present invention relates to a compound of Formula (I), wherein m is 1. In yet another embodiment, the present invention relates to a compound of Formula (I), wherein m is 2.

In a preferred embodiment, the present invention relates to a compound of Formula (I), wherein n is 1 and m is 1.

In a preferred embodiment, the present invention further relates to a compound of Formula (I), wherein $Q^1$ is H or $(C_6-C_{14})$aryl or $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In another embodiment, the present invention further relates to a compound of Formula (I), wherein $Q^1$ is H. In yet another embodiment, the present invention further relates to a compound of Formula (I), wherein $Q^1$ is $(C_6-C_{14})$aryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In yet another embodiment, the present invention further relates to a compound of Formula (I), wherein $Q^1$ is $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

In a preferred embodiment, the present invention further relates to a compound of Formula (I), wherein $Q^2$ is $(C_6-C_{14})$aryl or $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In another embodiment, the present invention further relates to a compound of Formula (I), wherein $Q^2$ is $(C_6-C_{14})$aryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In yet another embodiment, the present invention further relates to a compound of Formula (I), wherein $Q^2$ is $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

In a preferred embodiment, the present invention further relates to a compound of Formula (I), wherein X is CH or N. In another embodiment, the present invention further relates to a compound of Formula (I), wherein X is CH. In yet another embodiment the present invention further relates to a compound of Formula (I), wherein X is N.

In a preferred embodiment, the present invention further relates to a compound of Formula (I), wherein $R^1$ is H, halo, $NH_2$, or $(C_1-C_{10})$alkyl. In another embodiment, the present invention further relates to a compound of Formula (I), wherein $R^1$ is H. In another embodiment, the present invention further relates to a compound of Formula (I), wherein $R^1$ is halo. In another embodiment, the present invention further relates to a compound of Formula (I), wherein $R^1$ is $NH_2$. In yet another embodiment, the present invention further relates to a compound of Formula (I), wherein $R^1$ is $(C_1-C_{10})$alkyl.

In a preferred embodiment, the present invention relates to a compound of Formula (I), wherein $R^2$ is H, halo, $(C_1-C_{10})$alkyl, or $(C_1-C_{10})$alkyl-O—. In another embodiment, the present invention relates to a compound of Formula (I), wherein $R^2$ is H. In another embodiment, the present invention relates to a compound of Formula (I), wherein $R^2$ is halo. In another embodiment, the present invention relates to a compound of Formula (I), wherein $R^2$ is $(C_1-C_{10})$alkyl. In another embodiment, the present invention relates to a compound of Formula (I), wherein $R^2$ is $(C_1-C_{10})$alkyl-O—. In yet another embodiment, the present invention relates to a compound of Formula (I), wherein $R^2$ is $CH_3$—O—, or $CH_3$—$CH_2$—O—.

In a preferred embodiment, the present invention relates to a compound of Formula (I), wherein $R^3$ and $R^4$ are each H.

In a preferred embodiment, the present invention relates to a compound of Formula (I), wherein $R^5$ and $R^6$ are each H.

In a preferred embodiment, present invention relates to a compound of Formula (I), with the structure of Formula (II):

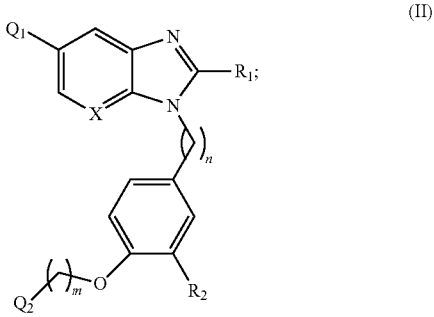

(II)

or a pharmaceutically acceptable salt thereof.

In a preferred embodiment, the present invention relates to a compound of Formula (II), wherein n is 1, 2, or 3. In another embodiment, the present invention relates to a compound of Formula (II), wherein n is 1. In another embodiment, the present invention relates to a compound of Formula (II), wherein n is 2. In yet another embodiment, the present invention relates to a compound of Formula (II), wherein n is 3.

In a preferred embodiment, the present invention relates to a compound of Formula (II), wherein m is 0, 1, or 2. In another embodiment, the present invention relates to a compound of Formula (II), wherein m is 0. In another embodiment, the present invention relates to a compound of Formula (II), wherein m is 1. In yet another embodiment, the present invention relates to a compound of Formula (II), wherein m is 2.

In a preferred embodiment, the present invention relates to a compound of Formula (II), wherein n is 1 and m is 1.

In a preferred embodiment, the present invention further relates to a compound of Formula (II), wherein $Q^1$ is H or $(C_6-C_{14})$aryl or $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —$NH_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-$O_2$S—, $(C_3-C_{10})$cycloalkyl-$O_2$S—, $(C_6-C_{14})$aryl-$O_2$S—, $(C_2-C_9)$heteroalkyl-$O_2$S—, $(C_2-C_9)$heterocycloalkyl-$O_2$S—, $(C_2-C_9)$heteroaryl-$O_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In another embodiment, the present invention further relates to a compound of Formula (II), wherein $Q^1$ is H. In yet another embodiment, the present invention further relates to a compound of Formula (II), wherein $Q^1$ is $(C_6-C_{14})$aryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —$NH_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-$O_2$S—, $(C_3-C_{10})$cycloalkyl-$O_2$S—, $(C_6-C_{14})$aryl-$O_2$S—, $(C_2-C_9)$heteroalkyl-$O_2$S—, $(C_2-C_9)$heterocycloalkyl-$O_2$S—, $(C_2-C_9)$heteroaryl-$O_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In yet another embodiment, the present invention further relates to a compound of Formula (II), wherein $Q^1$ is $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —$NH_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-$O_2$S—, $(C_3-C_{10})$cycloalkyl-$O_2$S—, $(C_6-C_{14})$aryl-$O_2$S—, $(C_2-C_9)$heteroalkyl-$O_2$S—, $(C_2-C_9)$heterocycloalkyl-$O_2$S—, $(C_2-C_9)$heteroaryl-$O_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

In a preferred embodiment, the present invention further relates to a compound of Formula (II), wherein $Q^2$ is $(C_6-C_{14})$aryl or $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In another embodiment, the present invention further relates to a compound of Formula (II), wherein $Q^2$ is $(C_6-C_{14})$aryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl. In yet another embodiment, the present invention further relates to a compound of Formula (II), wherein $Q^2$ is $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8N$—, $R^7R^8N(O)C$—, $R^7(O)CR^8N$—, $F_3C$—, NC—, $(C_3-C_{10})$alkyl(O)P—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8NO_2S$—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl.

In a preferred embodiment, the present invention further relates to a compound of Formula (II), wherein X is CH or N. In another embodiment the present invention further relates to a compound of Formula (II), wherein X is CH. In yet another embodiment the present invention further relates to a compound of Formula (II), wherein X is N.

In a preferred embodiment, the present invention further relates to a compound of Formula (II), wherein $R^1$ is H, halo, NH$_2$, or $(C_1-C_{10})$alkyl. In another embodiment, the present invention further relates to a compound of Formula (II), wherein $R^1$ is H. In another embodiment, the present invention further relates to a compound of Formula (II), wherein $R^1$ is halo. In another embodiment, the present invention further relates to a compound of Formula (II), wherein $R^1$ is NH$_2$. In yet another embodiment, the present invention further relates to a compound of Formula (II), wherein $R^1$ is $(C_1-C_{10})$alkyl.

In a preferred embodiment, the present invention relates to a compound of Formula (II), wherein $R^2$ is H, halo, $(C_1-C_{10})$alkyl, or $(C_1-C_{10})$alkyl-O—. In another embodiment, the present invention relates to a compound of Formula (II), wherein $R^2$ is H. In another embodiment, the present invention relates to a compound of Formula (II), wherein $R^2$ is halo. In another embodiment, the present invention relates to a compound of Formula (II), wherein $R^2$ is $(C_1-C_{10})$alkyl. In another embodiment, the present invention relates to a compound of Formula (II), wherein $R^2$ is $(C_1-C_{10})$alkyl-O—. In yet another embodiment, the present invention relates to a compound of Formula (II), wherein $R^2$ is CH$_3$—O—, or CH$_3$—CH$_2$—O—.

In a preferred embodiment, the present invention further relates to a compound of Formula (I), wherein the compound is selected from:

1-(3-Methoxy-4-((4-methoxybenzyl)oxy)benzyl)-5-(1-methyl-1H-pyrazol-4-yl)-1H-benzo[d]imidazol-2-amine 1-(3-Methoxy-4-((4-methoxybenzyl)oxy)benzyl)-5-(pyrimidin-5-yl)-1H-benzo[d]imidazol-2-amine, 1-(3-Methoxy-4-((4-methoxybenzyl)oxy)benzyl)-5-(pyridine-4-yl)-1H-benzo[d]imidazol-2-amine, 1-(3-Methoxy-4-((4-methoxybenzyl)oxy)benzyl)-5-(1-(2-morpholinoethyl)-1H-pyrazol-4-yl)-1H-benzo[d]imidazol-2-amine, (5-(2-Amino-1-(3-methoxy-4-((4-methoxybenzyl)oxy)benzyl)-1H-benzo[d]imidazol-5-yl)pyridin-2-yl)dimethylphosphine oxide, 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine, 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine, 2-(1-(3-(3-Methoxy-4-((6-methoxypyridin-3-yl)methoxy)benzyl)-3H-imidazo[4,5-b]pyridin-6-yl)piperidin-4-yl)propan-2-amine, 4-(3-(3-Methoxy-4-((6-methoxypyridin-3-yl)methoxy)benzyl)-3H-imidazo[4,5-b]pyridin-6-yl)morpholine, 6-(4-Cyclopropylpiperazin-1-yl)-3-(3-methoxy-4-((6-methoxypyridin-3-yl)methoxy)benzyl)-3H-imidazo[4,5-b]pyridine, 3-(3-Methoxy-4-((6-methoxypyridin-3-yl)methoxy)benzyl)-6-(2,7-diazaspiro[3.5]nonan-2-yl)-3H-imidazo[4,5-b]pyridine
(S)-1-(3-(3-Methoxy-4-((6-methoxypyridin-3-yl)methoxy)benzyl)-3H-imidazo[4,5-b]pyridin-6-yl)pyrrolidine-2-carboxylic acid,
3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine
3-(3-Methoxy-4-((6-methylpyridin-3-yl)methoxy)benzyl)-6-(1-(piperidin-4-yl)-1H-pyrazol-4-yl)-3H-imidazo[4,5-b]pyridine,
3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole,
2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole,
2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and
3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to a pharmaceutical composition comprising a compound according to Formula (I). In yet another preferred embodiment, the present invention further relates to a pharmaceutical composition comprising a compound according to Formula (II). In another embodiment, the present invention further relates to a pharmaceutical composition comprising a compound according to Formula (I) wherein the compound is selected from:
1-(3-Methoxy-4-((4-methoxybenzyl)oxy)benzyl)-5-(1-methyl-1H-pyrazol-4-yl)-1H-benzo[d]imidazol-2-amine
1-(3-Methoxy-4-((4-methoxybenzyl)oxy)benzyl)-5-(pyrimidin-5-yl)-1H-benzo[d]imidazol-2-amine,
1-(3-Methoxy-4-((4-methoxybenzyl)oxy)benzyl)-5-(pyridine-4-yl)-1H-benzo[d]imidazol-2-amine,
1-(3-Methoxy-4-((4-methoxybenzyl)oxy)benzyl)-5-(1-(2-morpholinoethyl)-1H-pyrazol-4-yl)-1H-benzo[d]imidazol-2-amine,
(5-(2-Amino-1-(3-methoxy-4-((4-methoxybenzyl)oxy)benzyl)-1H-benzo[d]imidazol-5-yl)pyridin-2-yl)dimethylphosphine oxide,
3-(3-methoxy-4-((6-methoxypyridin-3-yl)methoxy)benzyl)-6-(1-(piperidin-4-yl)-1H-pyrazol-4-yl)-3H-imidazo[4,5-b]pyridine,
1-(3-Methoxy-4-((6-methoxypyridin-3-yl)methoxy)benzyl)-5-(4-(piperidin-3-yl)-1H-1,2,3-triazol-1-yl)-1H-benzo[d]imidazole,
3-(3-Methoxy-4-((4-methoxybenzyl)oxy)benzyl)-6-(1-methyl-1H-pyrazol-4-yl)-3H-imidazo[4,5-b]pyridin-2-amine,
(5-(2-Amino-3-(3-methoxy-4-((4-methoxybenzyl)oxy)benzyl)-3H-imidazo[4,5-b]pyridin-6-yl)pyridin-2-yl)dimethylphosphine oxide,
3-(3-Methoxy-4-((6-methoxypyridin-3-yl)methoxy)benzyl)-6-(4-methylpiperazin-1-yl)-3H-imidazo[4,5-b]pyridine,
2-(1-(3-(3-Methoxy-4-((6-methoxypyridin-3-yl)methoxy)benzyl)-3H-imidazo[4,5-b]pyridin-6-yl)piperidin-4-yl)propan-2-amine,
4-(3-(3-Methoxy-4-((6-methoxypyridin-3-yl)methoxy)benzyl)-3H-imidazo[4,5-b]pyridin-6-yl)morpholine,
6-(4-Cyclopropylpiperazin-1-yl)-3-(3-methoxy-4-((6-methoxypyridin-3-yl)methoxy)benzyl)-3H-imidazo[4,5-b]pyridine,
3-(3-Methoxy-4-((6-methoxypyridin-3-yl)methoxy)benzyl)-6-(2,7-diazaspiro[3.5]nonan-2-yl)-3H-imidazo[4,5-b]pyridine
(S)-1-(3-(3-Methoxy-4-((6-methoxypyridin-3-yl)methoxy)benzyl)-3H-imidazo[4,5-b]pyridin-6-yl)pyrrolidine-2-carboxylic acid,
3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine
3-(3-Methoxy-4-((6-methylpyridin-3-yl)methoxy)benzyl)-6-(1-(piperidin-4-yl)-1H-pyrazol-4-yl)-3H-imidazo[4,5-b]pyridine,
3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole,
2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole,
2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and
3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of treating inflammatory diseases, autoimmune disease, defects of bone metabolism or cancer comprising administering to the patient a compound according to Formula (I). In yet another preferred embodiment, the present invention further relates to methods of treating inflammatory diseases, autoimmune disease, defects of bone metabolism or cancer comprising administering to the patient a compound according to Formula (II). In another embodiment, the present invention further relates to methods of treating inflammatory diseases, autoimmune disease, defects of bone metabolism or cancer comprising administering to the patient a compound according to Formula (I) wherein the compound is selected from:
1-(3-Methoxy-4-((4-methoxybenzyl)oxy)benzyl)-5-(1-methyl-1H-pyrazol-4-yl)-1H-benzo[d]imidazol-2-amine
1-(3-Methoxy-4-((4-methoxybenzyl)oxy)benzyl)-5-(pyrimidin-5-yl)-1H-benzo[d]imidazol-2-amine,
1-(3-Methoxy-4-((4-methoxybenzyl)oxy)benzyl)-5-(pyridine-4-yl)-1H-benzo[d]imidazol-2-amine,
1-(3-Methoxy-4-((4-methoxybenzyl)oxy)benzyl)-5-(1-(2-morpholinoethyl)-1H-pyrazol-4-yl)-1H-benzo[d]imidazol-2-amine,
(5-(2-Amino-1-(3-methoxy-4-((4-methoxybenzyl)oxy)benzyl)-1H-benzo[d]imidazol-5-yl)pyridin-2-yl)dimethylphosphine oxide,
3-(3-methoxy-4-((6-methoxypyridin-3-yl)methoxy)benzyl)-6-(1-(piperidin-4-yl)-1H-pyrazol-4-yl)-3H-imidazo[4,5-b]pyridine,
1-(3-Methoxy-4-((6-methoxypyridin-3-yl)methoxy)benzyl)-5-(4-(piperidin-3-yl)-1H-1,2,3-triazol-1-yl)-1H-benzo[d]imidazole,
3-(3-Methoxy-4-((4-methoxybenzyl)oxy)benzyl)-6-(1-methyl-1H-pyrazol-4-yl)-3H-imidazo[4,5-b]pyridin-2-amine,
(5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine,
2-(1-(3-(3-Methoxy-4-((6-methoxypyridin-3-yl)methoxy)benzyl)-3H-imidazo[4,5-b]pyridin-6-yl)piperidin-4-yl)propan-2-amine,
4-(3-(3-Methoxy-4-((6-methoxypyridin-3-yl)methoxy)benzyl)-3H-imidazo[4,5-b]pyridin-6-yl)morpholine,
6-(4-Cyclopropylpiperazin-1-yl)-3-(3-methoxy-4-((6-methoxypyridin-3-yl)methoxy)benzyl)-3H-imidazo[4,5-b]pyridine,
3-(3-Methoxy-4-((6-methoxypyridin-3-yl)methoxy)benzyl)-6-(2,7-diazaspiro[3.5]nonan-2-yl)-3H-imidazo[4,5-b]pyridine
(S)-1-(3-(3-Methoxy-4-((6-methoxypyridin-3-yl)methoxy)benzyl)-3H-imidazo[4,5-b]pyridin-6-yl)pyrrolidine-2-carboxylic acid,
3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine
3-(3-Methoxy-4-((6-methylpyridin-3-yl)methoxy)benzyl)-6-(1-(piperidin-4-yl)-1H-pyrazol-4-yl)-3H-imidazo[4,5-b]pyridine,
3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole,
2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole,
2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and
3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of treating osteoarthritis comprising administering to the patient a compound according to Formula (I). In yet another preferred embodiment, the present invention further relates to methods of treating osteoarthritis comprising administering to the patient a compound according to Formula (II). In another embodiment, the present invention further relates to methods of treating osteoarthritis comprising administering to the patient a compound according to Formula (I) wherein the compound is selected from:
1-(3-Methoxy-4-((4-methoxybenzyl)oxy)benzyl)-5-(1-methyl-1H-pyrazol-4-yl)-1H-benzo[d]imidazol-2-amine
1-(3-Methoxy-4-((4-methoxybenzyl)oxy)benzyl)-5-(pyrimidin-5-yl)-1H-benzo[d]imidazol-2-amine,
1-(3-Methoxy-4-((4-methoxybenzyl)oxy)benzyl)-5-(pyridine-4-yl)-1H-benzo[d]imidazol-2-amine,
1-(3-Methoxy-4-((4-methoxybenzyl)oxy)benzyl)-5-(1-(2-morpholinoethyl)-1H-pyrazol-4-yl)-1H-benzo[d]imidazol-2-amine,
(5-(2-Amino-1-(3-methoxy-4-((4-methoxybenzyl)oxy)benzyl)-1H-benzo[d]imidazol-5-yl)pyridin-2-yl)dimethylphosphine oxide,
3-(3-methoxy-4-((6-methoxypyridin-3-yl)methoxy)benzyl)-6-(1-(piperidin-4-yl)-1H-pyrazol-4-yl)-3H-imidazo[4,5-b]pyridine,
1-(3-Methoxy-4-((6-methoxypyridin-3-yl)methoxy)benzyl)-5-(4-(piperidin-3-yl)-1H-1,2,3-triazol-1-yl)-1H-benzo[d]imidazole,
3-(3-(4-methoxybenzyl)oxy)benzyl)-6-(1-methyl-1H-pyrazol-4-yl)-3H-imidazo[4,5-b]pyridin-2-amine,
(5-(2-Amino-3-(3-methoxy-4-((4-methoxybenzyl)oxy)benzyl)-3H-imidazo[4,5-b]pyridin-6-yl)pyridin-2-yl)dimethylphosphine oxide,
3-(3-Methoxy-4-((6-methoxypyridin-3-yl)methoxy)benzyl)-6-(4-methylpiperazin-1-yl)-3H-imidazo[4,5-b]pyridine,
2-(1-(3-(3-Methoxy-4-((6-methoxypyridin-3-yl)methoxy)benzyl)-3H-imidazo[4,5-b]pyridin-6-yl)piperidin-4-yl)propan-2-amine,
4-(3-(3-Methoxy-4-((6-methoxypyridin-3-yl)methoxy)benzyl)-3H-imidazo[4,5-b]pyridin-6-yl)morpholine,
6-(4-Cyclopropylpiperazin-1-yl)-3-(3-methoxy-4-((6-methoxypyridin-3-yl)methoxy)benzyl)-3H-imidazo[4,5-b]pyridine,
3-(3-Methoxy-4-((6-methoxypyridin-3-yl)methoxy)benzyl)-6-(2,7-diazaspiro[3.5]nonan-2-yl)-3H-imidazo[4,5-b]pyridine
(S)-1-(3-(3-Methoxy-4-((6-methoxypyridin-3-yl)methoxy)benzyl)-3H-imidazo[4,5-b]pyridin-6-yl)pyrrolidine-2-carboxylic acid,
3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine
3-(3-Methoxy-4-((6-methylpyridin-3-yl)methoxy)benzyl)-6-(1-(piperidin-4-yl)-1H-pyrazol-4-yl)-3H-imidazo[4,5-b]pyridine,
3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole,
2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole,
2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and
3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of treating pain comprising administering to the patient a compound according to Formula (I). In an embodiment, the pain treated by the compound according to Formula (I) is post-operative pain. In yet another preferred embodiment, the present invention further relates to methods of treating pain comprising administering to the patient a compound according to Formula (II). In another embodiment, the pain treated by the compound according to Formula (II) is post-operative pain. In another embodiment, the present invention further relates to methods of treating pain and methods of treating post-operative pain comprising administering to the patient a compound according to Formula (I) wherein the compound is selected from:
1-(3-Methoxy-4-((4-methoxybenzyl)oxy)benzyl)-5-(1-methyl-1H-pyrazol-4-yl)-1H-benzo[d]imidazol-2-amine,
3-(3-Methoxy-4-((4-methoxybenzyl)oxy)benzyl)-6-(1-methyl-1H-pyrazol-4-yl)-3H-imidazo[4,5-b]pyridin-2-amine,
(5-(2-Amino-3-(3-methoxy-4-((4-methoxybenzyl)oxy)benzyl)-3H-imidazo[4,5-b]pyridin-6-yl)pyridin-2-yl)dimethylphosphine oxide,
3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, and
3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine.

In a preferred embodiment, the present invention further relates to methods of treating pain associated with osteoarthritis comprising administering to the patient a compound according to Formula (I). In yet another preferred embodiment, the present invention further relates to methods of treating pain associated with osteoarthritis comprising administering to the patient a compound according to Formula (II). In another embodiment, the present invention further relates to methods of treating pain associated with osteoarthritis comprising administering to the patient a compound according to Formula (I) wherein the compound is selected from:

1-(3-Methoxy-4-((4-methoxybenzyl)oxy)benzyl)-5-(1-methyl-1H-pyrazol-4-yl)-1H-benzo[d]imidazol-2-amine 1-(3-Methoxy-4-((4-methoxybenzyl)oxy)benzyl)-5-(pyrimidin-5-yl)-1H-benzo[d]imidazol-2-amine, 1-(3-Methoxy-4-((4-methoxybenzyl)oxy)benzyl)-5-(pyridine-4-yl)-1H-benzo[d]imidazol-2-amine, 1-(3-Methoxy-4-((4-methoxybenzyl)oxy)benzyl)-5-(1-(2-morpholinoethyl)-1H-pyrazol-4-yl)-1H-benzo[d]imidazol-2-amine, (5-(2-Amino-1-(3-methoxy-4-((4-methoxybenzyl)oxy)benzyl)-1H-benzo[d]imidazol-5-yl)pyridin-2-yl)dimethylphosphine oxide, 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine, 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine, 2-(1-(3-(3-Methoxy-4-((6-methoxypyridin-3-yl)methoxy)benzyl)-3H-imidazo[4,5-b]pyridin-6-yl)piperidin-4-yl)propan-2-amine, 4-(3-(3-Methoxy-4-((6-methoxypyridin-3-yl)methoxy)benzyl)-3H-imidazo[4,5-b]pyridin-6-yl)morpholine, 6-(4-Cyclopropylpiperazin-1-yl)-3-(3-methoxy-4-((6-methoxypyridin-3-yl)methoxy)benzyl)-3H-imidazo[4,5-b]pyridine, 3-(3-Methoxy-4-((6-methoxypyridin-3-yl)methoxy)benzyl)-6-(2,7-diazaspiro[3.5]nonan-2-yl)-3H-imidazo[4,5-b]pyridine (S)-1-(3-(3-Methoxy-4-((6-methoxypyridin-3-yl)methoxy)benzyl)-3H-imidazo[4,5-b]pyridin-6-yl)pyrrolidine-2-carboxylic acid, 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, 3-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole, 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole, 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of inhibiting tropomyosin-related kinase A comprising administering to the patient a compound according to Formula (I). In yet another preferred embodiment, the present invention further relates to methods of inhibiting tropomyosin-related kinase A comprising administering to the patient a compound according to Formula (II). In another embodiment, the present invention further relates to methods of inhibiting tropomyosin-related kinase A comprising administering to the patient a compound according to Formula (I) wherein the compound is selected from:

1-(3-Methoxy-4-((4-methoxybenzyl)oxy)benzyl)-5-(1-methyl-1H-pyrazol-4-yl)-1H-benzo[d]imidazol-2-amine 1-(3-Methoxy-4-((4-methoxybenzyl)oxy)benzyl)-5-(pyrimidin-5-yl)-1H-benzo[d]imidazol-2-amine, 1-(3-Methoxy-4-((4-methoxybenzyl)oxy)benzyl)-5-(pyridine-4-yl)-1H-benzo[d]imidazol-2-amine, 1-(3-Methoxy-4-((4-methoxybenzyl)oxy)benzyl)-5-(1-(2-morpholinoethyl)-1H-pyrazol-4-yl)-1H-benzo[d]imidazol-2-amine, (5-(2-Amino-1-(3-methoxy-4-((4-methoxybenzyl)oxy)benzyl)-1H-benzo[d]imidazol-5-yl)pyridin-2-yl)dimethylphosphine oxide, 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine, 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine, 2-(1-(3-(3-Methoxy-4-((6-methoxypyridin-3-yl)methoxy)benzyl)-3H-imidazo[4,5-b]pyridin-6-yl)piperidin-4-yl)propan-2-amine, 4-(3-(3-Methoxy-4-((6-methoxypyridin-3-yl)methoxy)benzyl)-3H-imidazo[4,5-b]pyridin-6-yl)morpholine, 6-(4-Cyclopropylpiperazin-1-yl)-3-(3-methoxy-4-((6-methoxypyridin-3-yl)methoxy)benzyl)-3H-imidazo[4,5-b]pyridine, 3-(3-Methoxy-4-((6-methoxypyridin-3-yl)methoxy)benzyl)-6-(2,7-diazaspiro[3.5]nonan-2-yl)-3H-imidazo[4,5-b]pyridine (S)-1-(3-(3-Methoxy-4-((6-methoxypyridin-3-yl)methoxy)benzyl)-3H-imidazo[4,5-b]pyridin-6-yl)pyrrolidine-2-carboxylic acid, 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole, 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole, 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of inhibiting tropomyosin-related kinase B comprising administering to the patient a compound according to Formula (I). In yet another preferred embodiment, the present invention further relates to methods of inhibiting tropomyosin-related kinase B comprising administering to the patient a compound according to Formula (II). In another embodiment, the present invention further relates to methods of inhibiting tropomyosin-related kinase B comprising administering to the patient a compound according to Formula (I) wherein the compound is selected from:

1-(3-Methoxy-4-((4-methoxybenzyl)oxy)benzyl)-5-(1-methyl-1H-pyrazol-4-yl)-1H-benzo[d]imidazol-2-amine 1-(3-Methoxy-4-((4-methoxybenzyl)oxy)benzyl)-5-(pyrimidin-5-yl)-1H-benzo[d]imidazol-2-amine, 1-(3-Methoxy-4-((4-methoxybenzyl)oxy)benzyl)-5-(pyridine-4-yl)-1H-benzo[d]imidazol-2-amine, 1-(3-Methoxy-4-((4-methoxybenzyl)oxy)benzyl)-5-(1-(2-morpholinoethyl)-1H-pyrazol-4-yl)-1H-benzo[d]imidazol-2-amine, (5-(2-Amino-1-(3-methoxy-4-((4-methoxybenzyl)oxy)benzyl)-1H-benzo[d]imidazol-5-yl)pyridin-2-yl)dimethylphosphine oxide, 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine, 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine, 2-(1-(3-(3-Methoxy-4-((6-methoxypyridin-3-yl)methoxy)benzyl)-3H-imidazo[4,5-b]pyridin-6-yl)piperidin-4-yl)propan-2-amine, 4-(3-(3-Methoxy-4-((6-methoxypyridin-3-yl)methoxy)benzyl)-3H-imidazo[4,5-b]pyridin-6-yl)morpholine, 6-(4-Cyclopropylpiperazin-1-yl)-3-(3-methoxy-4-((6-methoxypyridin-3-yl)methoxy)benzyl)-3H-imidazo[4,5-b]pyridine, 3-(3-Methoxy-4-((6-methoxypyridin-3-yl)methoxy)benzyl)-6-(2,7-diazaspiro[3.5]nonan-2-yl)-3H-imidazo[4,5-b]pyridine (S)-1-(3-(3-Methoxy-4-((6-methoxypyridin-3-yl)methoxy)benzyl)-3H-imidazo[4,5-b]pyridin-6-yl)pyrrolidine-2-carboxylic acid, 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole, 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole, 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of inhibiting tropomyosin-related kinase C comprising administering to the patient a compound according to Formula (I). In yet another preferred embodiment, the present invention further relates to methods of inhibiting tropomyosin-related kinase C comprising administering to the patient a compound according to Formula (II). In another embodiment, the present invention further relates to methods of inhibiting tropomyosin-related kinase C comprising administering to the patient a compound according to Formula (I) wherein the compound is selected from:

1-(3-Methoxy-4-((4-methoxybenzyl)oxy)benzyl)-5-(1-methyl-1H-pyrazol-4-yl)-1H-benzo[d]imidazol-2-amine 1-(3-Methoxy-4-((4-methoxybenzyl)oxy)benzyl)-5-(pyrimidin-5-yl)-1H-benzo[d]imidazol-2-amine, 1-(3-Methoxy-4-((4-methoxybenzyl)oxy)benzyl)-5-(pyridine-4-yl)-1H-benzo[d]imidazol-2-amine, 1-(3-Methoxy-4-((4-methoxybenzyl)oxy)benzyl)-5-(1-(2-morpholinoethyl)-1H-pyrazol-4-yl)-1H-benzo[d]imidazol-2-amine, (5-(2-Amino-1-(3-methoxy-4-((4-methoxybenzyl)oxy)benzyl)-1H-benzo[d]imidazol-5-yl)pyridin-2-yl)dimethylphosphine oxide, 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine, 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methoxypyridin-3-yl)methoxy)benzyl)-6-(4-methylpiperazin-1-yl)-3H-imidazo[4,5-b]pyridine, 2-(1-(3-(3-Methoxy-4-((6-methoxypyridin-3-yl)methoxy)benzyl)-3H-imidazo[4,5-b]pyridin-6-yl)piperidin-4-yl)propan-2-amine, 4-(3-(3-Methoxy-4-((6-methoxypyridin-3-yl)methoxy)benzyl)-3H-imidazo[4,5-b]pyridin-6-yl)morpholine, 6-(4-Cyclopropylpiperazin-1-yl)-3-(3-methoxy-4-((6-methoxypyridin-3-yl)methoxy)benzyl)-3H-imidazo[4,5-b]pyridine, 3-(3-Methoxy-4-((6-methoxypyridin-3-yl)methoxy)benzyl)-6-(2,7-diazaspiro[3.5]nonan-2-yl)-3H-imidazo[4,5-b]pyridine (S)-1-(3-(3-Methoxy-4-((6-methoxypyridin-3-yl)methoxy)benzyl)-3H-imidazo[4,5-b]pyridin-6-yl)pyrrolidine-2-carboxylic acid, 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole, 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole, 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine, and 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine.

In a preferred embodiment, the present invention further relates to methods of inhibiting c-FMS comprising administering to the patient a compound according to Formula (I). In yet another preferred embodiment, the present invention further relates to methods of inhibiting c-FMS comprising administering to the patient a compound according to Formula (II). In another embodiment, the present invention further relates to methods of inhibiting c-FMS comprising administering to the patient a compound according to Formula (I) wherein the compound is selected from:

1-(3-Methoxy-4-((4-methoxybenzyl)oxy)benzyl)-5-(1-methyl-1H-pyrazol-4-yl)-1H-benzo[d]imidazol-2-amine, 3-(3-Methoxy-4-((4-methoxybenzyl)oxy)benzyl)-6-(1-methyl-1H-pyrazol-4-yl)-3H-imidazo[4,5-b]pyridin-2-amine, (5-(2-Amino-3-(3-methoxy-4-((4-methoxybenzyl)oxy)benzyl)-3H-imidazo[4,5-b]pyridin-6-yl)pyridin-2-yl)dimethylphosphine oxide, 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine, and 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine.

Non-limiting examples of suitable Trk inhibitors according to Formula (I) are presented in Table 1. It is understood that any the structures presented in Table 1 also include pharmaceutically acceptable salts thereof. Preferred pharmaceutically acceptable anions include but are not limited to halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate. Most preferred pharmaceutically acceptable anions include chloride, carbonate, and bicarbonate.

TABLE 1

| | Trk Inhibitors | |
| --- | --- | --- |
| Example No. | Compound Name | Compound Structure |
| Ex. 3-1 | 1-(3-Methoxy-4-((4-methoxybenzyl)oxy)benzyl)-5-(1-methyl-1H-pyrazol-4-yl)-1H-benzo[d]imidazol-2-amine | |

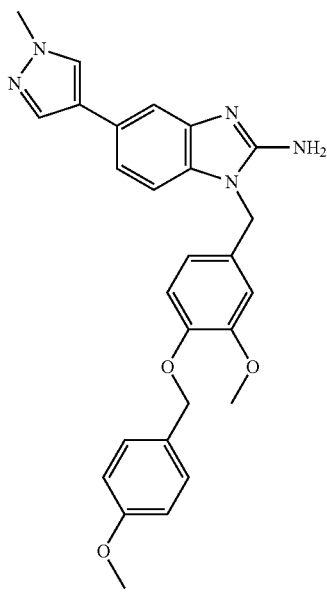 [SMILES: COc1ccc(COc2ccc(Cn3c(N)nc4cc(-c5cnn(C)c5)ccc43)cc2OC)cc1]

TABLE 1-continued

| | Trk Inhibitors | |
|---|---|---|
| Example No. | Compound Name | Compound Structure |
| Ex. 3-2-1 | 1-(3-Methoxy-4-((4-methoxybenzyl)oxy)benzyl)-5-(pyrimidin-5-yl)-1H-benzo[d]imidazol-2-amine | |
| Ex. 3-2-2 | 1-(3-Methoxy-4-((4-methoxybenzyl)oxy)benzyl)-5-(pyridine-4-yl)-1H-benzo[d]imidazol-2-amine | |

TABLE 1-continued
| | Trk Inhibitors | |
|---|---|---|
| Example No. | Compound Name | Compound Structure |
| Ex. 3-2-3 | 1-(3-Methoxy-4-((4-methoxybenzyl)oxy)benzyl)-5-(1-(2-morpholinoethyl)-1H-pyrazol-4-yl)-1H-benzo[d]imidazol-2-amine | |
| Ex. 3-3 | (5-(2-Amino-1-(3-methoxy-4-((4-methoxybenzyl)oxy)benzyl)-1H-benzo[d]imidazol-5-yl)pyridin-2-yl)dimethylphosphine oxide | 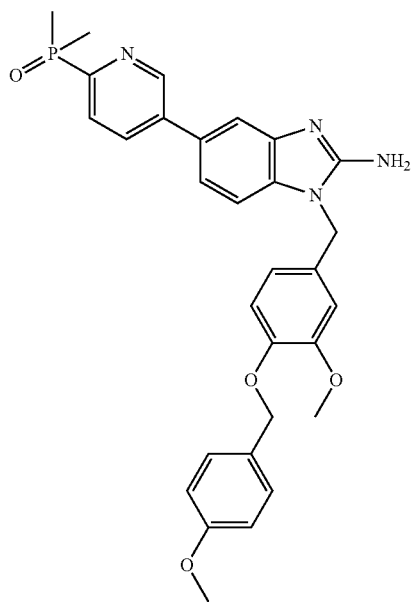 [SMILES: COc1ccc(COc2ccc(Cn3c(N)nc4cc(-c5ccc(P(C)(C)=O)nc5)ccc43)cc2OC)cc1] |

TABLE 1-continued
| | Trk Inhibitors | |
|---|---|---|
| Example No. | Compound Name | Compound Structure |
| Ex. 3-4 | 1-(3-Methoxy-4-((6-methoxypyridin-3-yl)methoxy)benzyl)-5-(pyrimidin-5-yl)-1H-benzo[d]imidazole | 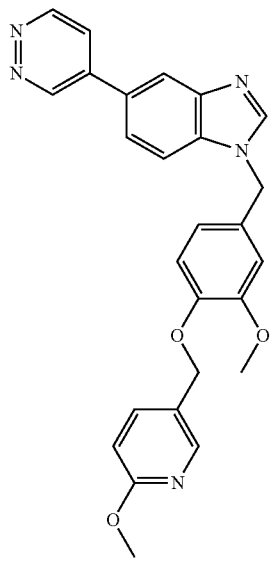 [SMILES: COc1ccc(COc2ccc(Cn3cnc4cc(-c5ccnnc5)ccc43)cc2OC)cn1] |
| Ex. 3-5 | 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine | 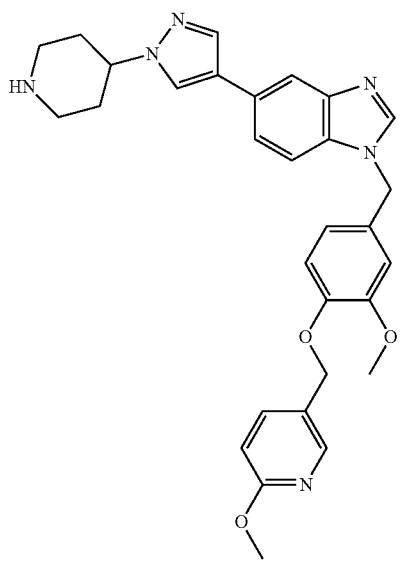 [SMILES: COc1ccc(COc2ccc(Cn3cnc4cc(-c5cnn(C6CCNCC6)c5)ccc43)cc2OC)cn1] |

TABLE 1-continued

Trk Inhibitors

| Example No. | Compound Name | Compound Structure |
|---|---|---|
| Ex. 3-6 | 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole | 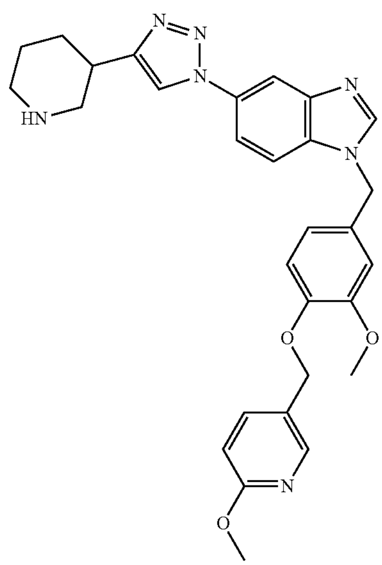 [SMILES: COc1ccc(COc2ccc(Cn3cnc4cc(-n5cc(C6CCCNC6)nn5)ccc43)cc2OC)cn1] |
| Ex. 3-7 | 2-(1-(3-Methoxy-4-((6-methoxypyridin-3-yl)methoxy)benzyl)-1H-benzo[d]imidazol-5-yl)-5-(piperidin-4-yl)-1,3,4-oxadiazole | 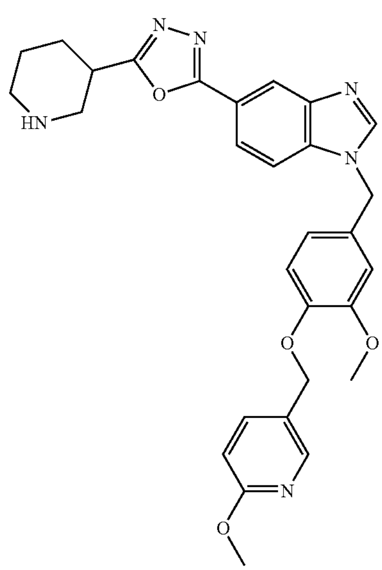 [SMILES: COc1ccc(COc2ccc(Cn3cnc4cc(-c5nnc(C6CCCNC6)o5)ccc43)cc2OC)cn1] |

TABLE 1-continued
Trk Inhibitors
| Example No. | Compound Name | Compound Structure |
|---|---|---|
| Ex. 3-8 | 1-(3-Methoxy-4-((6-methoxypyridin-3-yl)methoxy)benzyl)-5-(piperidin-4-yl)-1H-benzo[d]imidazole | 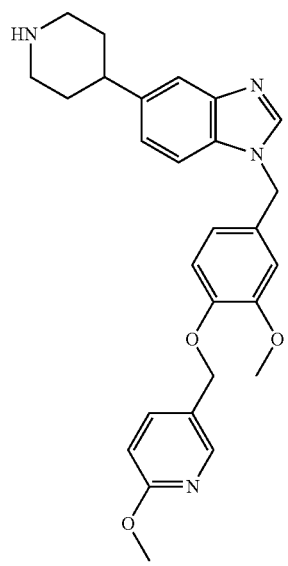 [SMILES: COc1ccc(COc2ccc(Cn3cnc4cc(C5CCNCC5)ccc43)cc2OC)cn1] |
| Ex. 3-9 | 4-(1-(3-Methoxy-4-((6-methoxypyridin-3-yl)methoxy)benzyl)-1H-benzo[d]imidazol-5-yl)morpholine | 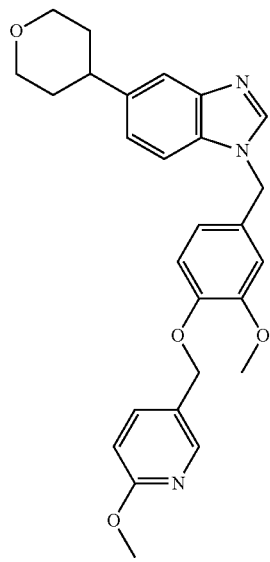 [SMILES: COc1ccc(COc2ccc(Cn3cnc4cc(C5CCOCC5)ccc43)cc2OC)cn1] |

TABLE 1-continued

| | Trk Inhibitors | |
|---|---|---|
| Example No. | Compound Name | Compound Structure |
| Ex. 3-10 | 2-(1-(1-(3-Methoxy-4-((6-methoxypyridin-3-yl)methoxy)benzyl)-1H-benzo[d]imidazol-5-yl)piperidin-4-yl)propan-2-amine | |
| Ex. 3-11 | 1-(3-methoxy-4-((6-methoxypyridin-3-yl)methoxy)benzyl)-5-(2,7-diazaspiro[3.5]nonan-2-yl)-1H-benzo[d]imidazole | |

TABLE 1-continued
| | Trk Inhibitors | |
|---|---|---|
| Example No. | Compound Name | Compound Structure |
| Ex. 3-12 | 1-(1-(3-Methoxy-4-((6-methoxypyridin-3-yl)methoxy)benzyl)-1H-benzo[d]imidazol-5-yl)piperidin-4-amine | 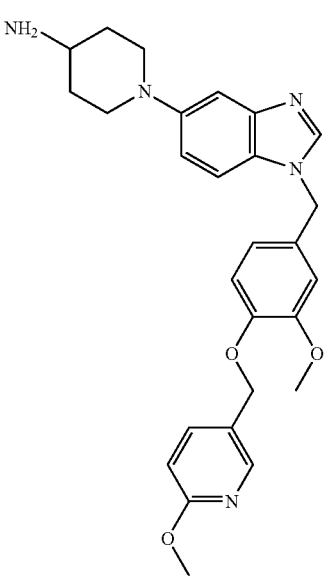 [SMILES: COc1ccc(COc2ccc(Cn3cnc4cc(N5CCC(N)CC5)ccc43)cc2OC)cn1] |
| Ex. 3-13 | 1-(3-Methoxy-4-((6-methoxypyridin-3-yl)methoxy)benzyl)-5-(4-methylpiperazin-1-yl)-1H-benzo[d]imidazole | 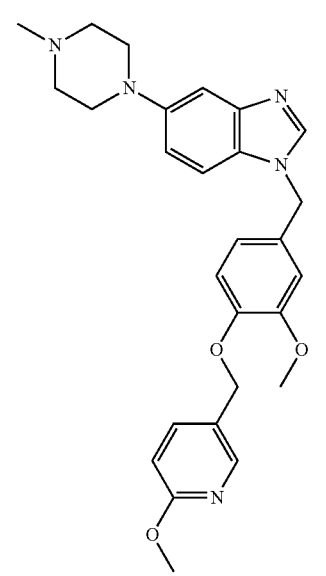 [SMILES: COc1ccc(COc2ccc(Cn3cnc4cc(N5CCN(C)CC5)ccc43)cc2OC)cn1] |

TABLE 1-continued
| Example No. | Compound Name | Compound Structure |
|---|---|---|
| Ex. 3-14 | 1-(2-Amino-1-(3-methoxy-4-((6-methoxypyridin-3-yl)methoxy)benzyl)-1H-benzo[d]imidazol-5-yl)-4-methylpiperazin-2-one | 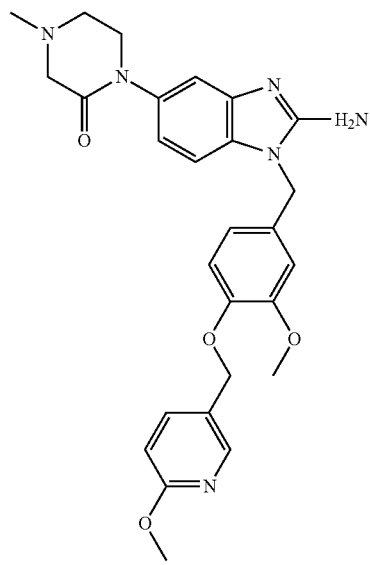 [SMILES: COc1ccc(COc2ccc(Cn3c(N)nc4cc(N5CCN(C)CC5=O)ccc43)cc2OC)cn1] |
| Ex. 3-15 | 3-(3-Methoxy-4-((4-methoxybenzyl)oxy)benzyl)-6-(1-methyl-1H-pyrazol-4-yl)-3H-imidazo[4,5-b]pyridin-2-amine | 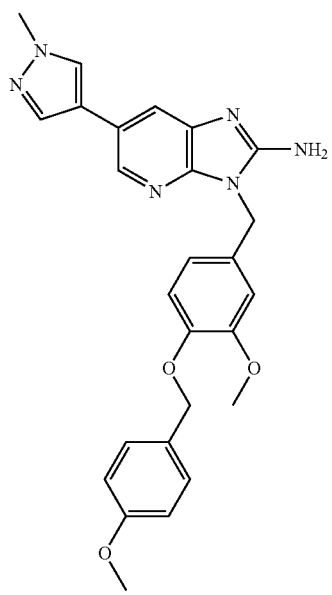 [SMILES: COc1ccc(COc2ccc(Cn3c(N)nc4cc(-c5cnn(C)c5)cnc43)cc2OC)cc1] |

TABLE 1-continued
| | Trk Inhibitors | |
|---|---|---|
| Example No. | Compound Name | Compound Structure |
| Ex. 3-16 | (5-(2-Amino-3-(3-methoxy-4-((4-methoxybenzyl)oxy)benzyl)-3H-imidazo[4,5-b]pyridin-6-yl)pyridin-2-yl)dimethylphosphine oxide | 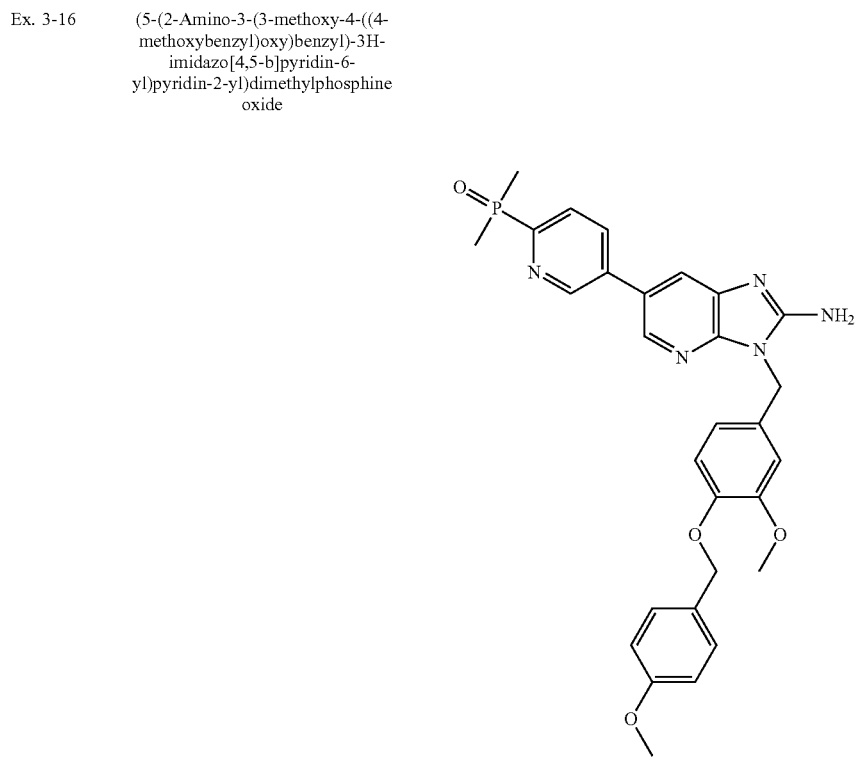 |
| Ex. 3-17 | 3-(3-Methoxy-4-((6-methoxypyridin-3-yl)methoxy)benzyl)-6-(4-methylpiperazin-1-yl)-3H-imidazo[4,5-b]pyridine | 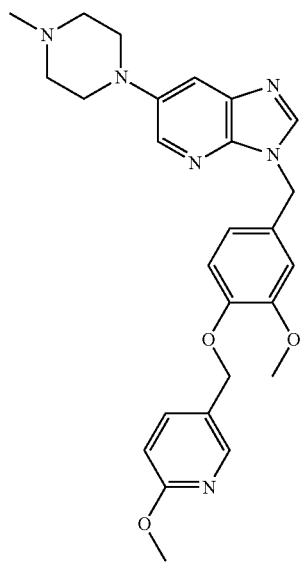 |

TABLE 1-continued
| | Trk Inhibitors | |
|---|---|---|
| Example No. | Compound Name | Compound Structure |
| Ex. 3-18-1 | 2-(1-(3-(3-Methoxy-4-((6-methoxypyridin-3-yl)methoxy)benzyl)-3H-imidazo[4,5-b]pyridin-6-yl)piperidin-4-yl)propan-2-amine | 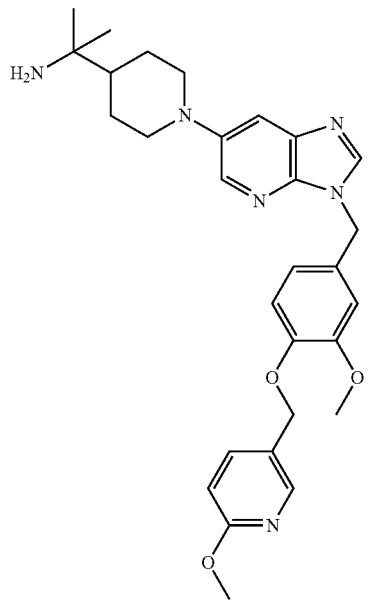 [SMILES: COc1ccc(COc2ccc(Cn3cnc4cc(N5CCC(C(C)(C)N)CC5)cnc43)cc2OC)cn1] |
| Ex. 3-18-2 | 4-(3-(3-Methoxy-4-((6-methoxypyridin-3-yl)methoxy)benzyl)-3H-imidazo[4,5-b]pyridin-6-yl)morpholine | 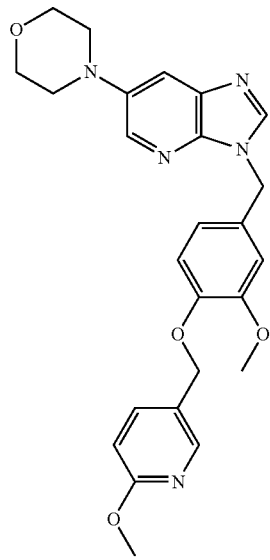 [SMILES: COc1ccc(COc2ccc(Cn3cnc4cc(N5CCOCC5)cnc43)cc2OC)cn1] |

TABLE 1-continued
| Trk Inhibitors | | |
|---|---|---|
| Example No. | Compound Name | Compound Structure |
| Ex. 3-18-3 | 6-(4-Cyclopropylpiperazin-1-yl)-3-(3-methoxy-4-((6-methoxypyridin-3-yl)methoxy)benzyl)-3H-imidazo[4,5-b]pyridine | 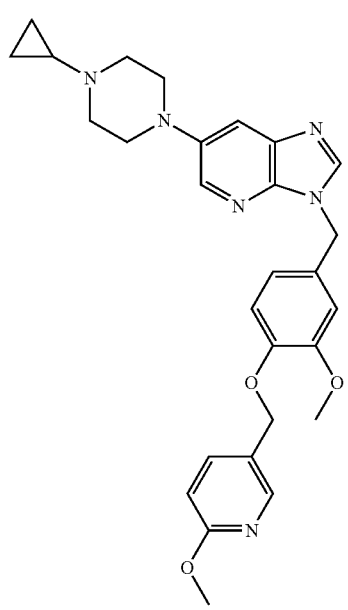 [SMILES: COc1ccc(COc2ccc(Cn3cnc4cc(N5CCN(C6CC6)CC5)cnc43)cc2OC)cn1] |
| Ex. 3-18-4 | 4-(3-(3-Methoxy-4-((6-methoxypyridin-3-yl)methoxy)benzyl)-3H-imidazo[4,5-b]pyridin-6-yl)-1,4-diazabicyclo[3.2.2]nonane | 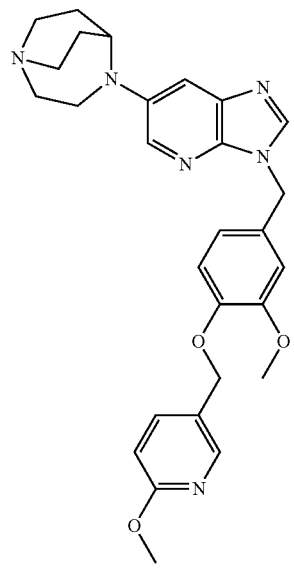 [SMILES: COc1ccc(COc2ccc(Cn3cnc4cc(N5CCN6CCC5CC6)cnc43)cc2OC)cn1] |

TABLE 1-continued
| | Trk Inhibitors | |
|---|---|---|
| Example No. | Compound Name | Compound Structure |
| Ex. 3-18-5 | 3-(3-Methoxy-4-((6-methoxypyridin-3-yl)methoxy)benzyl)-6-(2,7-diazaspiro[3.5]nonan-2-yl)-3H-imidazo[4,5-b]pyridine | 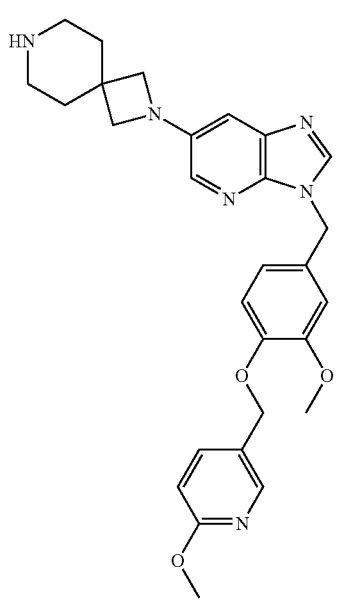 [SMILES: COc1ccc(COc2ccc(Cn3cnc4cc(N5CC6(CCNCC6)C5)cnc43)cc2OC)cn1] |
| Ex. 3-18-6 | 1-(3-(3-Methoxy-4-((6-methoxypyridin-3-yl)methoxy)benzyl)-3H-imidazo[4,5-b]pyridin-6-yl)piperidin-4-amine | 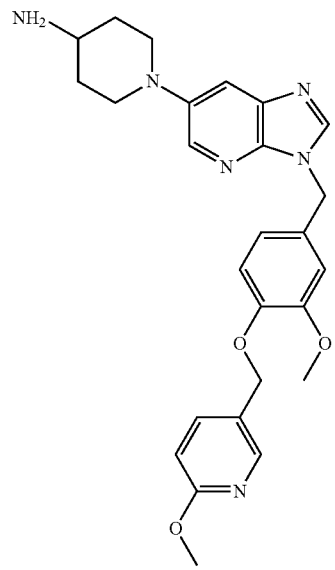 [SMILES: COc1ccc(COc2ccc(Cn3cnc4cc(N5CCC(N)CC5)cnc43)cc2OC)cn1] |

TABLE 1-continued
Trk Inhibitors
| Example No. | Compound Name | Compound Structure |
|---|---|---|
| Ex. 3-18-7 | (S)-1-(3-(3-Methoxy-4-((6-methoxypyridin-3-yl)methoxy)benzyl)-3H-imidazo[4,5-b]pyridin-6-yl)pyrrolidine-2-carboxylic acid | 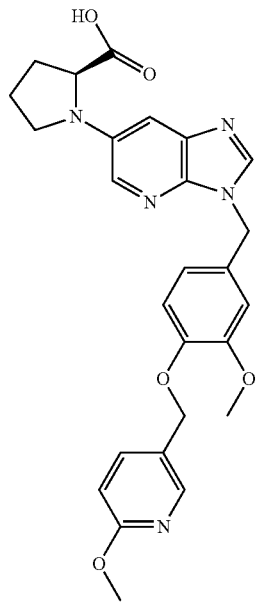 [SMILES: COc1ccc(COc2ccc(Cn3cnc4cc(N5CCC[C@H]5C(=O)O)cnc43)cc2OC)cn1] |
| Ex. 3-19 | 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine | 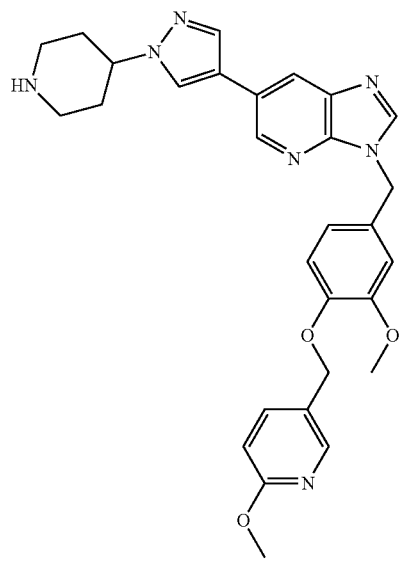 |

TABLE 1-continued
| | Trk Inhibitors | |
|---|---|---|
| Example No. | Compound Name | Compound Structure |
| Ex. 3-20 | 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine | |
| Ex. 3-21 | 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole | 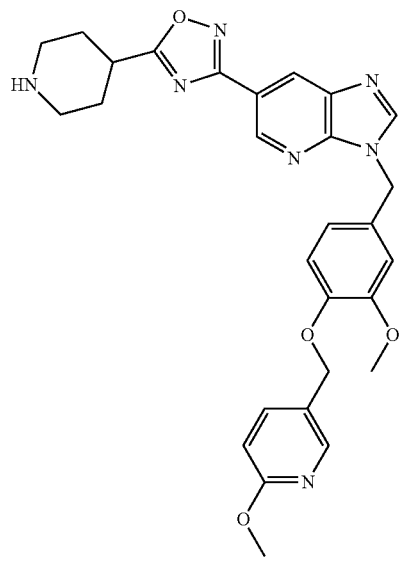 [SMILES: COc1ccc(COc2ccc(Cn3cnc4cc(-c5noc(C6CCNCC6)n5)cnc43)cc2OC)cn1] |

TABLE 1-continued

| | Trk Inhibitors | |
|---|---|---|
| Example No. | Compound Name | Compound Structure |
| Ex. 3-22 | 3-(1-(3-Methoxy-4-((6-methoxypyridin-3-yl)methoxy)benzyl)-1H-benzo[d]imidazol-5-yl)-5-(piperidin-4-yl)-1,2,4-oxadiazole | |
| Ex. 3-23 | 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole | |

TABLE 1-continued
Trk Inhibitors
| Example No. | Compound Name | Compound Structure |
|---|---|---|
| Ex. 3-24 | 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine | 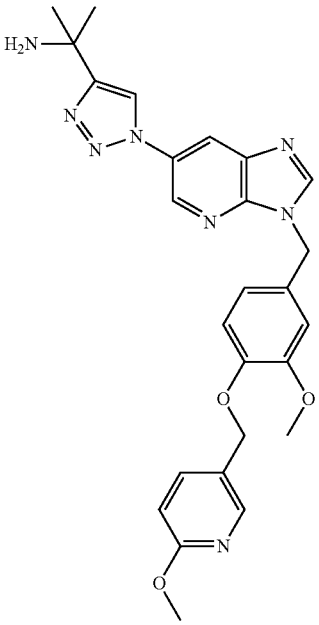 [SMILES: COc1ccc(COc2ccc(Cn3cnc4cc(-n5cc(C(C)(C)N)nn5)cnc43)cc2OC)cn1] |
| Ex. 3-25 | 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine | 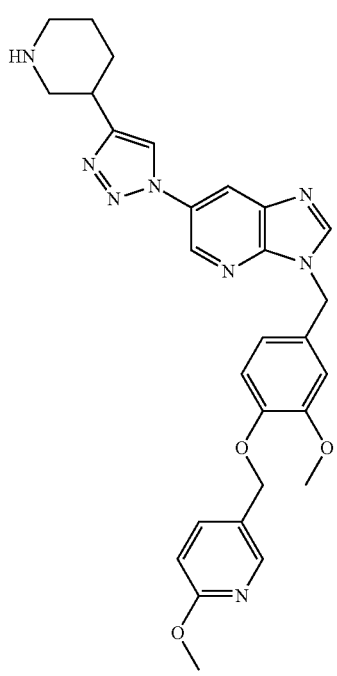 [SMILES: COc1ccc(COc2ccc(Cn3cnc4cc(-n5cc(C6CCCNC6)nn5)cnc43)cc2OC)cn1] |

TABLE 1-continued

Trk Inhibitors

| Example No. | Compound Name | Compound Structure |
|---|---|---|
| Ex. 3-26 | 1-(3-methoxy-4-((6-methoxypyridin-3-yl)methoxy)benzyl)-5-(4-methylpiperazin-1-yl)-1H-benzo[d]imidazol-2-amine | 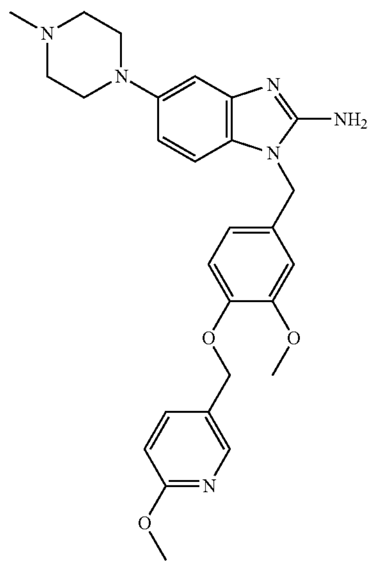 [SMILES: COc1ccc(COc2ccc(Cn3c(N)nc4cc(N5CCN(C)CC5)ccc43)cc2OC)cn1] |
| Ex. 3-27 | 1-(2-fluoro-5-methoxy-4-((6-methoxypyridin-3-yl)methoxy)benzyl)-5-(4-methylpiperazin-1-yl)-1H-benzo[d]imidazole | 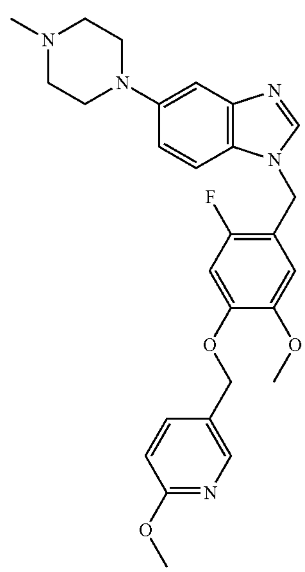 [SMILES: COc1ccc(COc2cc(F)c(Cn3cnc4cc(N5CCN(C)CC5)ccc43)cc2OC)cn1] |

TABLE 1-continued

| | Trk Inhibitors | |
|---|---|---|
| Example No. | Compound Name | Compound Structure |
| Ex. 3-28 | 3-(3-Ethoxy-4-((6-methoxypyridin-3-yl)methoxy)benzyl)-6-(4-methylpiperazin-1-yl)-3H-imidazo[4,5-b]pyridine | |
| Ex. 3-29 | 1-(1-(3-Methoxy-4-((6-methoxypyridin-3-yl)methoxy)benzyl)-1H-benzo[d]imidazol-5-yl)-4-methylpiperazin-2-one | |

TABLE 1-continued
Trk Inhibitors
| Example No. | Compound Name | Compound Structure |
|---|---|---|
| Ex. 3-30 | 3-(3-Methoxy-4-((6-methoxypyridin-3-yl)methoxy)benzyl)-6-(5-methyl-1-azabicyclo[3.2.1]oct-6-en-7-yl)-3H-imidazo[4,5-b]pyridine | 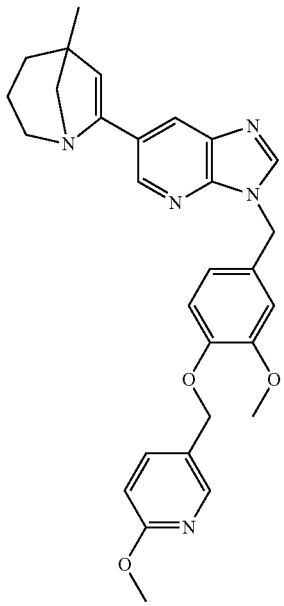 [SMILES: COc1ccc(COc2ccc(Cn3cnc4cc(C5=CC6(C)CCCN5C6)cnc43)cc2OC)cn1] |
| Ex. 3-31 | 1-(3-methoxy-4-((6-methoxypyridin-3-yl)methoxy)benzyl)-5-(5-methyl-1-azabicyclo[3.2.1]oct-6-en-7-yl)-1H-benzo[d]imidazole | 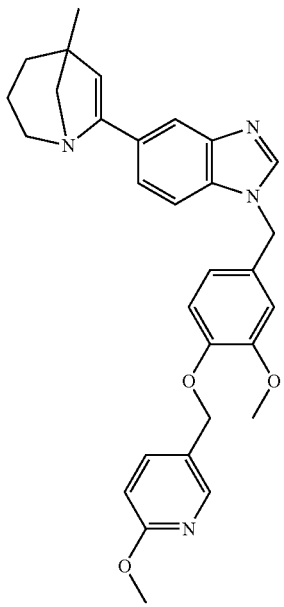 |

TABLE 1-continued
Trk Inhibitors
| Example No. | Compound Name | Compound Structure |
|---|---|---|
| Ex. 3-32 | 7-(3-(3-methoxy-4-((6-methoxypyridin-3-yl)methoxy)benzyl)-3H-imidazo[4,5-b]pyridin-6-yl)-1-azabicyclo[3.2.1]oct-6-en-5-ol | 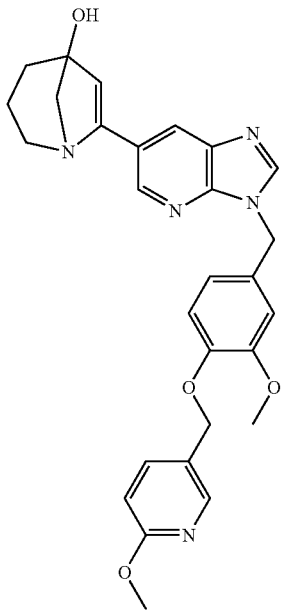 [SMILES: COc1ccc(COc2ccc(Cn3cnc4cc(C5=CC6(O)CCCN5C6)cnc43)cc2OC)cn1] |
| Ex. 3-33 | 7-(1-(3-Methoxy-4-((6-methoxypyridin-3-yl)methoxy)benzyl)-1H-benzo[d]imidazol-5-yl)-1-azabicyclo[3.2.1]oct-6-en-5-ol | 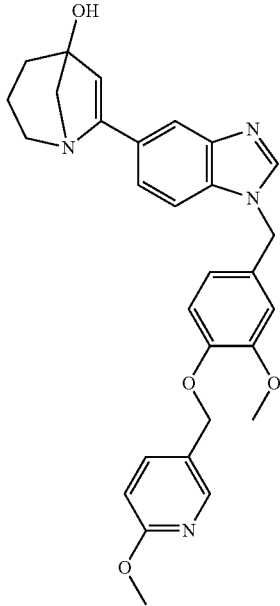 |

TABLE 1-continued

| | Trk Inhibitors | |
|---|---|---|
| Example No. | Compound Name | Compound Structure |
| Ex. 3-34 | 3-(3-methoxy-4-(1-(6-methoxypyridin-3-yl)propoxy)benzyl)-6-(1-methyl-1H-pyrazol-4-yl)-3H-imidazo[4,5-b]pyridin-2-amine | |
| Ex. 3-35-1 | 3-(3-methoxy-4-((6-methoxypyridin-3-yl)methoxy)benzyl)-6-(1-methyl-1H-pyrazol-4-yl)-3H-imidazo[4,5-b]pyridin-2-amine | |
| Ex. 3-35-2 | 3-(3-methoxy-4-((6-(trifluoromethyl)pyridin-3-yl)methoxy)benzyl)-6-(1-methyl-1H-pyrazol-4-yl)-3H-imidazo[4,5-b]pyridin-2-amine | |

TABLE 1-continued

Trk Inhibitors

| Example No. | Compound Name | Compound Structure |
|---|---|---|
| Ex. 3-35-3 | 3-(3-methoxy-4-((4-(trifluoromethyl)benzyl)oxy)benzyl)-6-(1-methyl-1H-pyrazol-4-yl)-3H-imidazo[4,5-b]pyridin-2-amine | 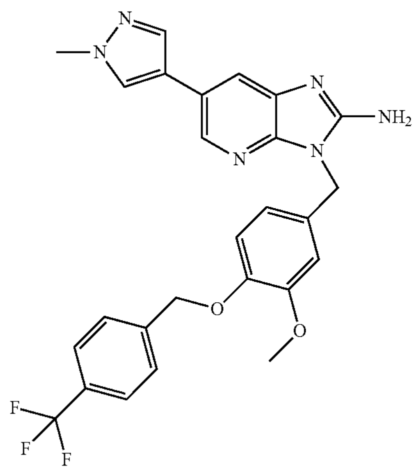 [SMILES: COc1cc(Cn2c(N)nc3cc(-c4cnn(C)c4)cnc32)ccc1OCc1ccc(C(F)(F)F)cc1] |
| Ex. 3-35-4 | 3-(4-((6-cyclopropylpyridin-3-yl)methoxy)-3-methoxybenzyl)-6-(1-methyl-1H-pyrazol-4-yl)-3H-imidazo[4,5-b]pyridin-2-amine | 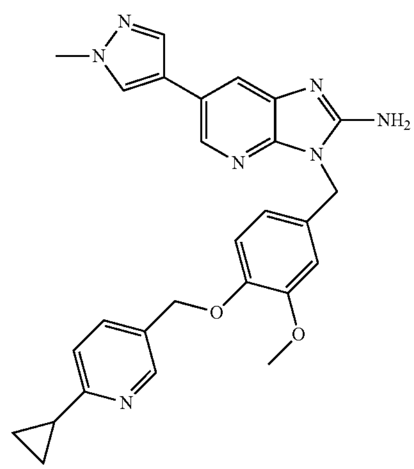 [SMILES: COc1cc(Cn2c(N)nc3cc(-c4cnn(C)c4)cnc32)ccc1OCc1ccc(C2CC2)nc1] |
| Ex. 3-35-5 | 3-(3-methoxy-4-((2-methylthiazol-4-yl)methoxy)benzyl)-6-(1-methyl-1H-pyrazol-4-yl)-3H-imidazo[4,5-b]pyridin-2-amine | 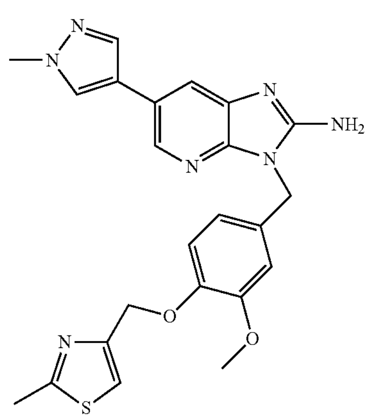 [SMILES: COc1cc(Cn2c(N)nc3cc(-c4cnn(C)c4)cnc32)ccc1OCc1csc(C)n1] |

TABLE 1-continued

| Trk Inhibitors | | |
|---|---|---|
| Example No. | Compound Name | Compound Structure |
| Ex. 3-36 | 3-(3-methoxy-4-((6-methoxypyridin-3-yl)methoxy)benzyl)-6-phenyl-3H-imidazo[4,5-b]pyridin-2-amine | |
| Ex. 3-37-1 | 6-(4-fluorophenyl)-3-(3-methoxy-4-((6-methoxypyridin-3-yl)methoxy)benzyl)-3H-imidazo[4,5-b]pyridin-2-amine | |
| Ex. 3-37-2 | 3-(3-methoxy-4-((6-methoxypyridin-3-yl)methoxy)benzyl)-6-(1-methyl-1H-pyrazol-3-yl)-3H-imidazo[4,5-b]pyridin-2-amine | |

TABLE 1-continued

| | Trk Inhibitors | |
|---|---|---|
| Example No. | Compound Name | Compound Structure |
| Ex. 3-37-3 | 3-(3-methoxy-4-((6-methoxypyridin-3-yl)methoxy)benzyl)-6-(pyrimidin-5-yl)-3H-imidazo[4,5-b]pyridin-2-amine | |
| Ex. 3-37-4 | 3-(3-methoxy-4-((6-methoxypyridin-3-yl)methoxy)benzyl)-6-(1,3,5-trimethyl-1H-pyrazol-4-yl)-3H-imidazo[4,5-b]pyridin-2-amine | |
| Ex. 3-37-5 | 3-(3-methoxy-4-((6-methoxypyridin-3-yl)methoxy)benzyl)-6-(pyridin-4-yl)-3H-imidazo[4,5-b]pyridin-2-amine | |

TABLE 1-continued

| | Trk Inhibitors | |
|---|---|---|
| Example No. | Compound Name | Compound Structure |
| Ex. 3-37-6 | 3-(3-methoxy-4-((6-methoxypyridin-3-yl)methoxy)benzyl)-6-(pyridin-3-yl)-3H-imidazo[4,5-b]pyridin-2-amine | |
| Ex. 3-38 | 3-(3-methoxy-4-((6-methoxypyridin-3-yl)methoxy)benzyl)-6-(pyridin-2-yl)-3H-imidazo[4,5-b]pyridin-2-amine | |
| Ex. 3-39 | 3-(3-methoxy-4-((4-(perfluoroethyl)benzyl)oxy)benzyl)-6-(1-methyl-1H-pyrazol-4-yl)-3H-imidazo[4,5-b]pyridin-2-amine | |

TABLE 1-continued
| | Trk Inhibitors | |
|---|---|---|
| Example No. | Compound Name | Compound Structure |
| Ex. 3-40-1 | 3-(3-methoxy-4-((4-(trifluoromethoxy)benzyl)oxy)benzyl)-6-(1-methyl-1H-pyrazol-4-yl)-3H-imidazo[4,5-b]pyridin-2-amine | 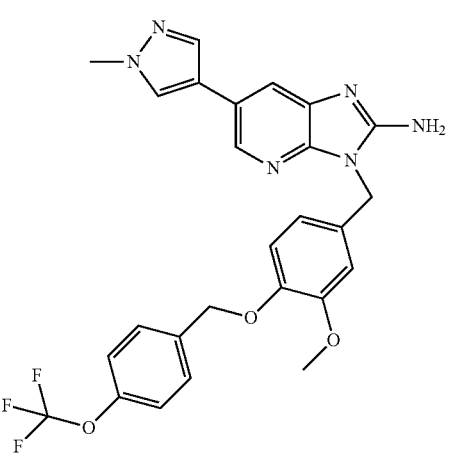 |
| Ex. 3-40-2 | 3-(3-methoxy-4-((4-((trifluoromethyl)thio)benzyl)oxy)benzyl)-6-(1-methyl-1H-pyrazol-4-yl)-3H-imidazo[4,5-b]pyridin-2-amine | 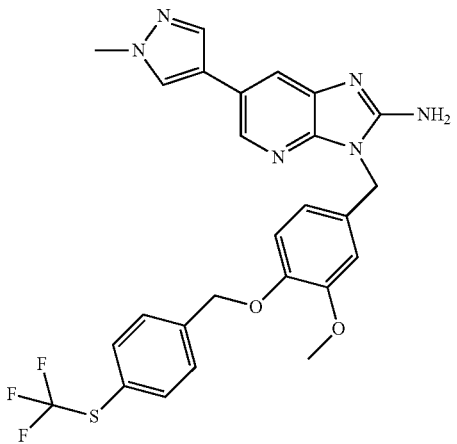 |
| Ex. 3-40-3 | 3-(4-((6-isopropylpyridin-3-yl)methoxy)-3-methoxybenzyl)-6-(1-methyl-1H-pyrazol-4-yl)-3H-imidazo[4,5-b]pyridin-2-amine | 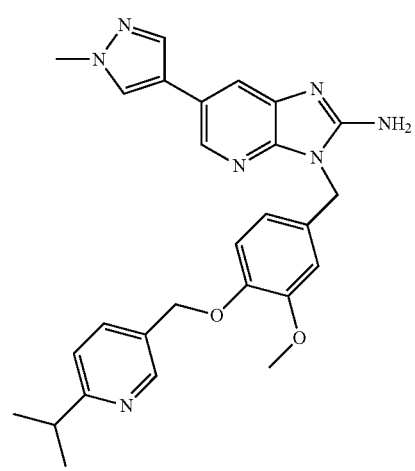 [SMILES: COc1cc(Cn2c(N)nc3cc(-c4cnn(C)c4)cnc32)ccc1OCc1ccc(C(C)C)nc1] |

TABLE 1-continued

Trk Inhibitors

| Example No. | Compound Name | Compound Structure |
|---|---|---|
| Ex. 3-40-4 | 3-(3-methoxy-4-((4-(2,2,2-trifluoroethyl)benzyl)oxy)benzyl)-6-(1-methyl-1H-pyrazol-4-yl)-3H-imidazo[4,5-b]pyridin-2-amine | 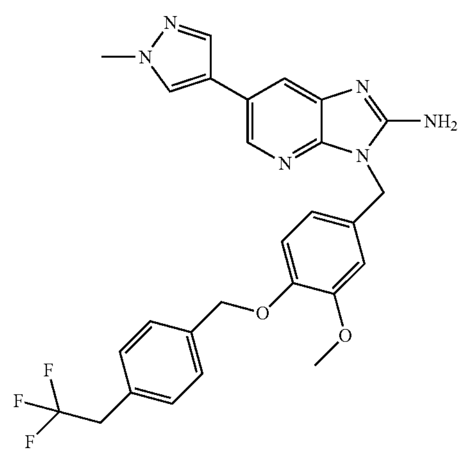 [SMILES: COc1cc(Cn2c(N)nc3cc(-c4cnn(C)c4)cnc32)ccc1OCc1ccc(CC(F)(F)F)cc1] |
| Ex. 3-40-5 | 3-(3-methoxy-4-((2-(trifluoromethyl)thiazol-4-yl)methoxy)benzyl)-6-(1-methyl-1H-pyrazol-4-yl)-3H-imidazo[4,5-b]pyridin-2-amine | 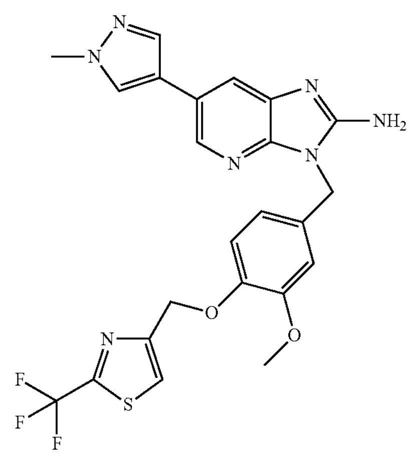 [SMILES: COc1cc(Cn2c(N)nc3cc(-c4cnn(C)c4)cnc32)ccc1OCc1csc(C(F)(F)F)n1] |
| Ex. 3-41 | 6-(cyclohexylethynyl)-3-(3-methoxy-4-((6-methoxypyridin-3-yl)methoxy)benzyl)-3H-imidazo[4,5-b]pyridin-2-amine | 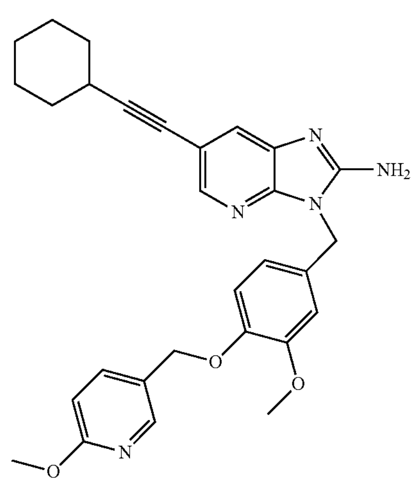 [SMILES: COc1ccc(COc2ccc(Cn3c(N)nc4cc(C#CC5CCCCC5)cnc43)cc2OC)cn1] |

TABLE 1-continued

Trk Inhibitors

| Example No. | Compound Name | Compound Structure |
|---|---|---|
| Ex. 3-42 | 4-(2-amino-3-(3-methoxy-4-((6-methoxypyridin-3-yl)methoxy)benzyl)-3H-imidazo[4,5-b]pyridin-6-yl)but-3-yn-1-ol | 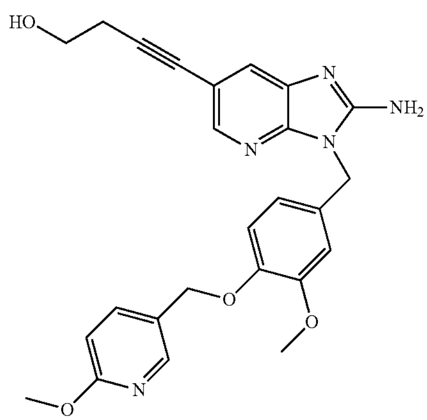 [SMILES: COc1ccc(COc2ccc(Cn3c(N)nc4cc(C#CCCO)cnc43)cc2OC)cn1] |
| Ex. 3-43 | 3-(4-(cyclopropyl(6-methoxypyridin-3-yl)methoxy)-3-methoxybenzyl)-6-(1-methyl-1H-pyrazol-4-yl)-3H-imidazo[4,5-b]pyridin-2-amine | 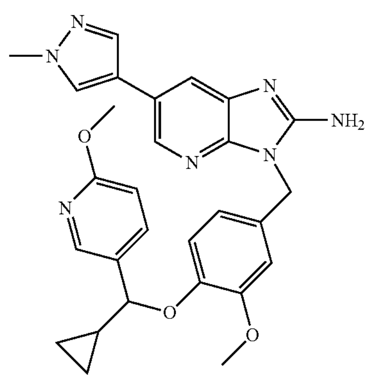 [SMILES: COc1ccc(C(Oc2ccc(Cn3c(N)nc4cc(-c5cnn(C)c5)cnc43)cc2OC)C2CC2)cn1] |
| Ex. 3-44 | 3-(3-methoxy-4-((3-methoxy-5,6,7,8-tetrahydroisoquinolin-8-yl)oxy)benzyl)-6-(1-methyl-1H-pyrazol-4-yl)-3H-imidazo[4,5-b]pyridin-2-amine | 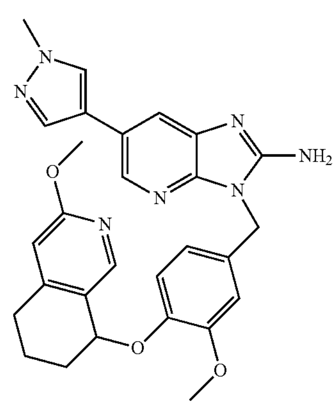 [SMILES: COc1cc2c(cn1)C(Oc1ccc(Cn3c(N)nc4cc(-c5cnn(C)c5)cnc43)cc1OC)CCC2] |

TABLE 1-continued

Trk Inhibitors

| Example No. | Compound Name | Compound Structure |
|---|---|---|
| Ex. 3-45 | 1-(1-(3-methoxy-4-((6-methoxypyridin-3-yl)methoxy)phenyl)ethyl)-5-(1-methyl-1H-pyrazol-4-yl)-1H-benzo[d]imidazol-2-amine | 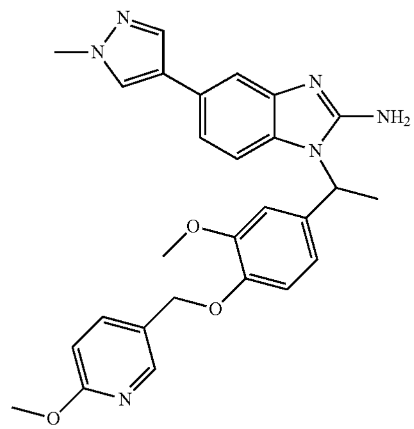 [SMILES: COc1ccc(COc2ccc(C(C)n3c(N)nc4cc(-c5cnn(C)c5)ccc43)cc2OC)cn1] |
| Ex. 3-46 | 5-(4-fluorophenyl)-1-(1-(3-methoxy-4-((6-methoxypyridin-3-yl)methoxy)phenyl)ethyl)-1H-benzo[d]imidazol-2-amine | 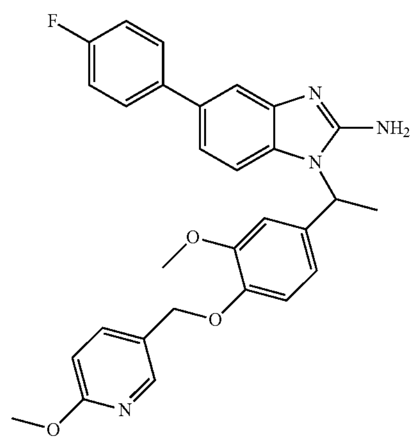 [SMILES: COc1ccc(COc2ccc(C(C)n3c(N)nc4cc(-c5ccc(F)cc5)ccc43)cc2OC)cn1] |
| Ex. 3-47 | 5-(4-fluorophenyl)-1-(1-(3-methoxy-4-((6-(trifluoromethyl)pyridin-3-yl)methoxy)phenyl)ethyl)-1H-benzo[d]imidazole | 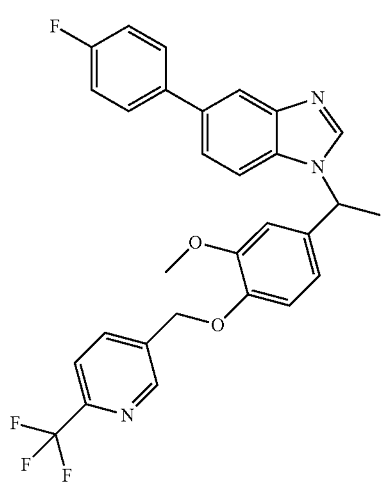 [SMILES: COc1cc(C(C)n2cnc3cc(-c4ccc(F)cc4)ccc32)ccc1OCc1ccc(C(F)(F)F)nc1] |

TABLE 1-continued

Trk Inhibitors

| Example No. | Compound Name | Compound Structure |
|---|---|---|
| Ex. 3-48-1 | 1-(1-(3-methoxy-4-((6-(trifluoromethyl)pyridin-3-yl)methoxy)phenyl)ethyl)-5-(1-methyl-1H-pyrazol-4-yl)-1H-benzo[d]imidazole | 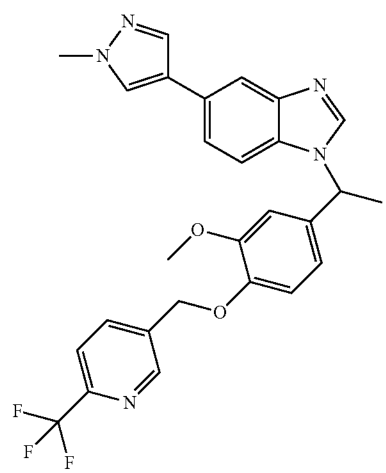 [SMILES: COc1cc(C(C)n2cnc3cc(-c4cnn(C)c4)ccc32)ccc1OCc1ccc(C(F)(F)F)nc1] |
| Ex. 3-48-2 | 4-(1-(1-(3-methoxy-4-((6-(trifluoromethyl)pyridin-3-yl)methoxy)phenyl)ethyl)-1H-benzo[d]imidazol-5-yl)but-3-yn-1-ol | 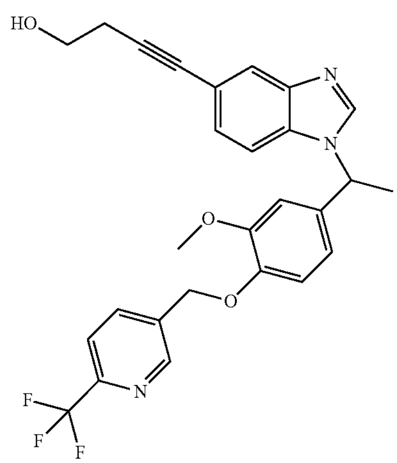 [SMILES: COc1cc(C(C)n2cnc3cc(C#CCCO)ccc32)ccc1OCc1ccc(C(F)(F)F)nc1] |
| Ex. 3-49 | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine | 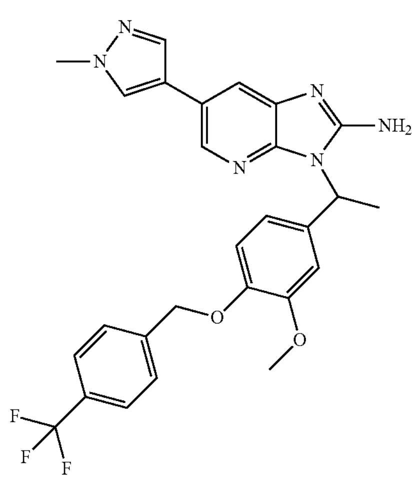 [SMILES: COc1cc(C(C)n2c(N)nc3cc(-c4cnn(C)c4)cnc32)ccc1OCc1ccc(C(F)(F)F)cc1] |

TABLE 1-continued

Trk Inhibitors

| Example No. | Compound Name | Compound Structure |
|---|---|---|
| Ex. 3-49-6a | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine (enantiomer a) | 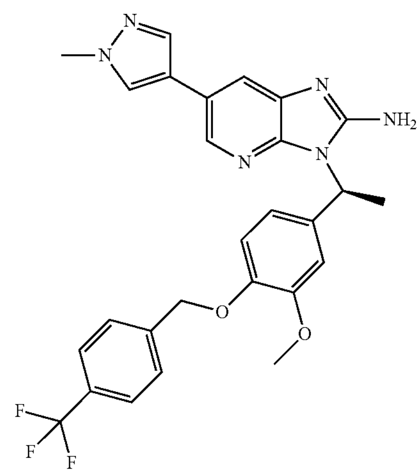 [SMILES: COc1cc([C@H](C)n2c(N)nc3cc(-c4cnn(C)c4)cnc32)ccc1OCc1ccc(C(F)(F)F)cc1] |
| Ex. 3-49-6b | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine (enantiomer b) | 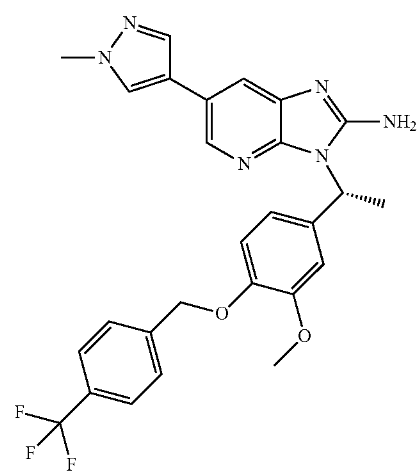 |
| Ex. 3-50-1 | 2-(4-(2-Amino-3-(1-(3-methoxy-4-((4-(trifluoromethyl)benzyl)oxy)phenyl)ethyl)-3H-imidazo[4,5-b]pyridin-6-yl)-1H-pyrazol-1-yl)ethan-1-ol | 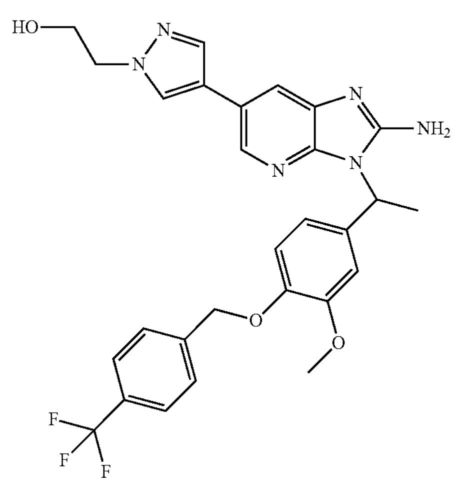 [SMILES: COc1cc(C(C)n2c(N)nc3cc(-c4cnn(CCO)c4)cnc32)ccc1OCc1ccc(C(F)(F)F)cc1] |

TABLE 1-continued

Trk Inhibitors

| Example No. | Compound Name | Compound Structure |
|---|---|---|
| Ex. 3-50-2 | 3-(1-(3-Methoxy-4-((4-(trifluoromethyl)benzyl)oxy)phenyl)ethyl)-6-(1H-pyrazol-4-yl)-3H-imidazo[4,5-b]pyridin-2-amine | 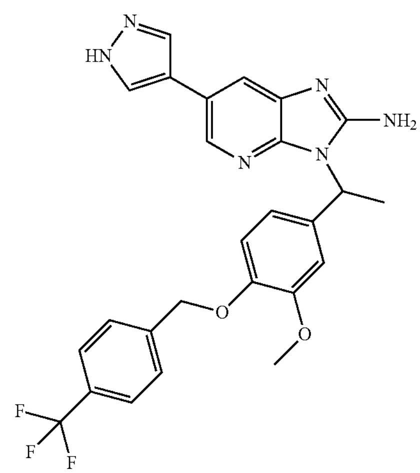 [SMILES: COc1cc(C(C)n2c(N)nc3cc(-c4cn[nH]c4)cnc32)ccc1OCc1ccc(C(F)(F)F)cc1] |
| Ex. 3-51 | 3-(1-(3-methoxy-4-((6-(trifluoromethyl)pyridin-3-yl)methoxy)phenyl)propyl)-6-(1-methyl-1H-pyrazol-4-yl)-3H-imidazo[4,5-b]pyridin-2-amine | 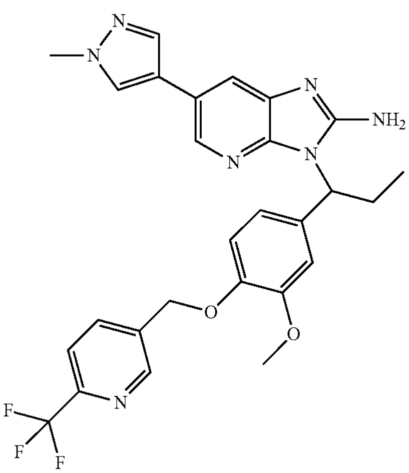 [SMILES: CCC(c1ccc(OCc2ccc(C(F)(F)F)nc2)c(OC)c1)n1c(N)nc2cc(-c3cnn(C)c3)cnc21] |
| Ex. 3-52 | 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridine | 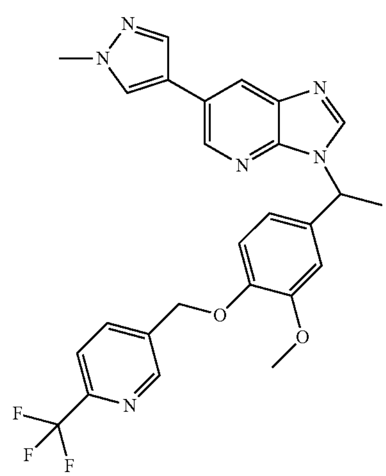 [SMILES: COc1cc(C(C)n2cnc3cc(-c4cnn(C)c4)cnc32)ccc1OCc1ccc(C(F)(F)F)nc1] |

TABLE 1-continued

Trk Inhibitors

| Example No. | Compound Name | Compound Structure |
|---|---|---|
| Ex. 3-53 | 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridin-2-amine | 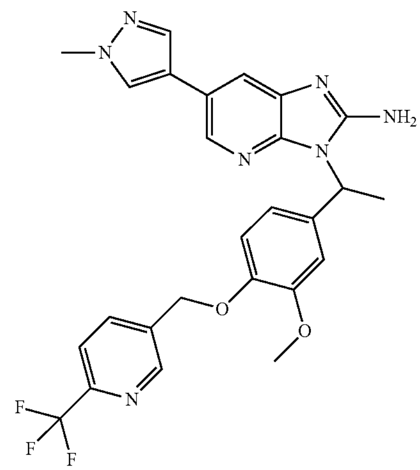 [SMILES: COc1cc(C(C)n2c(N)nc3cc(-c4cnn(C)c4)cnc32)ccc1OCc1ccc(C(F)(F)F)nc1] |
| Ex. 3-54 | 2-(4-(2-amino-3-(1-(3-methoxy-4-((6-(trifluoromethyl)pyridin-3-yl)methoxy)phenyl)ethyl)-3H-imidazo[4,5-b]pyridin-6-yl)-1H-pyrazol-1-yl)ethan-1-ol | 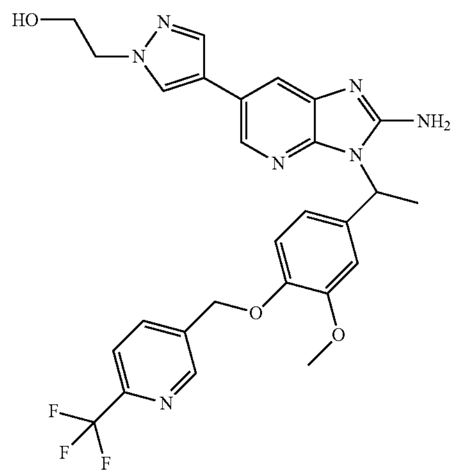 [SMILES: COc1cc(C(C)n2c(N)nc3cc(-c4cnn(CCO)c4)cnc32)ccc1OCc1ccc(C(F)(F)F)nc1] |
| Ex. 3-55 | 4-(2-amino-3-(1-(3-methoxy-4-((6-(trifluoromethyl)pyridin-3-yl)methoxy)phenyl)ethyl)-3H-imidazo[4,5-b]pyridin-6-yl)but-3-yn-1-ol | 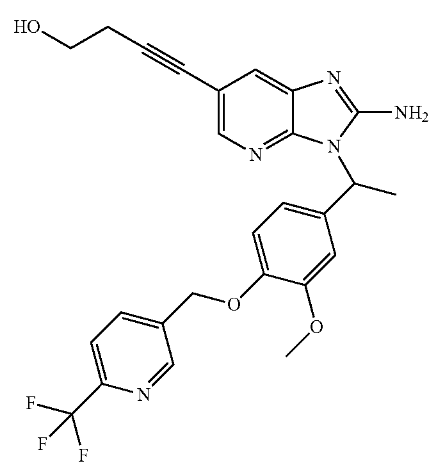 [SMILES: COc1cc(C(C)n2c(N)nc3cc(C#CCCO)cnc32)ccc1OCc1ccc(C(F)(F)F)nc1] |

TABLE 1-continued

Trk Inhibitors

| Example No. | Compound Name | Compound Structure |
|---|---|---|
| Ex. 3-56 | 4-(3-(4-((6-(difluoromethyl)pyridin-3-yl)methoxy)-3-methoxybenzyl)-3H-imidazo[4,5-b]pyridin-6-yl)but-3-yn-1-ol | 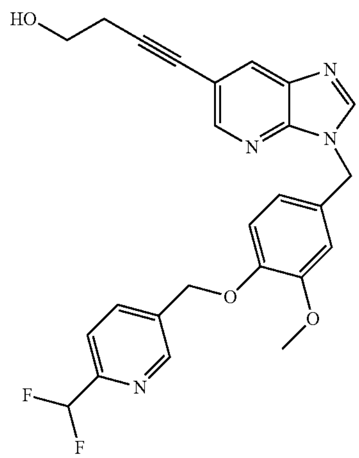 [SMILES: COc1cc(Cn2cnc3cc(C#CCCO)cnc32)ccc1OCc1ccc(C(F)F)nc1] |
| Ex. 3-57 | 3-(3-methoxy-4-(1-(6-methoxypyridin-3-yl)ethoxy)benzyl)-6-(1-methyl-1H-pyrazol-4-yl)-3H-imidazo[4,5-b]pyridine formate | 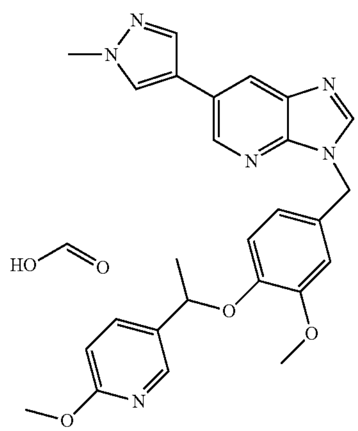 |
| Ex. 3-58-1 | 3-(3-methoxy-4-(1-(6-methoxypyridin-3-yl)ethoxy)benzyl)-6-(1-methyl-1H-pyrazol-5-yl)-3H-imidazo[4,5-b]pyridine formate | 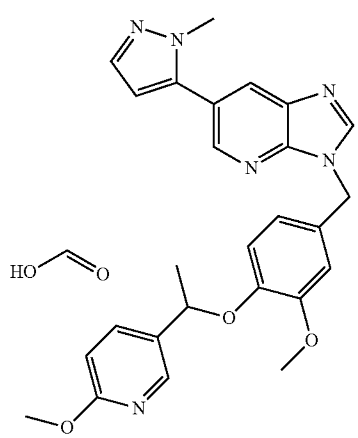 |

TABLE 1-continued

Trk Inhibitors

| Example No. | Compound Name | Compound Structure |
|---|---|---|
| Ex. 3-58-2 | 3-(3-methoxy-4-(1-(6-methoxypyridin-3-yl)ethoxy)benzyl)-6-(6-methoxypyridin-3-yl)-3H-imidazo[4,5-b]pyridine formate | 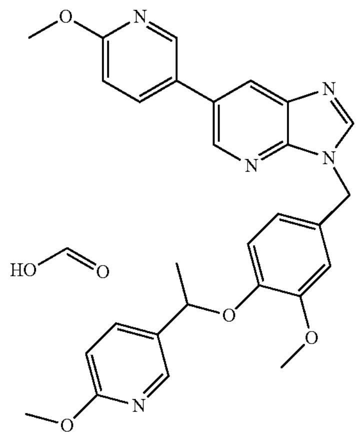 |
| Ex. 3-58-3 | 6-(2-fluoropyridin-4-yl)-3-(3-methoxy-4-(1-(6-methoxypyridin-3-yl)ethoxy)benzyl)-3H-imidazo[4,5-b]pyridine formate | 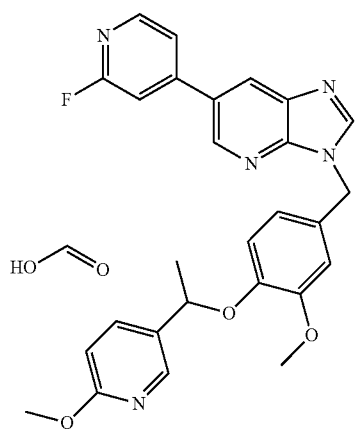 |

In one embodiment, the invention relates to a pharmaceutical composition comprising Trk inhibitors of Formula (I). In another embodiment of the invention, the pharmaceutical composition comprising Trk inhibitors of Formula (I) are administered in an effective amount to achieve the desired therapeutic effect. The skilled artisan will be able to determine the effective amount of the pharmaceutical composition comprising Trk inhibitors of Formula (I) depending on the individual and the condition being treated.

In one embodiment of the invention, the Trk inhibitors and pharmaceutical compositions comprising Trk inhibitors can be for use in treating pain. In another embodiment of the invention, the Trk inhibitors and pharmaceutical compositions comprising Trk inhibitors can be for use in treating pain associated with osteoarthritis. In yet another embodiment of the invention, the Trk inhibitors and pharmaceutical compositions comprising Trk inhibitors can be for use in treating osteoarthritis.

In one embodiment of the invention, the Trk inhibitors and pharmaceutical compositions comprising Trk inhibitors can be for use in inhibiting tropomyosin-related kinase. In another embodiment of the invention, the Trk inhibitors and pharmaceutical compositions comprising Trk inhibitors can be for use in inhibiting TrkA. In another embodiment of the invention, the Trk inhibitors and pharmaceutical compositions comprising Trk inhibitors can be for use in inhibiting TrkB In yet another embodiment of the invention, the Trk inhibitors and pharmaceutical compositions comprising Trk inhibitors can be for use in inhibiting TrkC The Trk inhibitors of the present invention may be administered alone or in a pharmaceutical composition comprising a Trk inhibitor or multiple Trk inhibitors. Suitable pharmaceutical compositions may comprise a Trk inhibitor and one or more pharmaceutically acceptable excipients. The form in which the Trk inhibitors are administered, for example, powder, tablet, capsule, solution, suspension or emulsion, depends in part on the route by which it is administered. The Trk inhibitors can be administered, for example, orally or by injection. Suitable excipients include, but are not limited to, are inorganic or organic materials such as gelatin, albumin, lactose, starch, stabilizers, melting agents, emulsifying agents, salts and buffers. Suitable pharmaceutically acceptable excipients for intra-articular formulations such as solutions or suspensions include, but are not limited to, commercially available inert gels or liquids.

The Trk inhibitors and pharmaceutical compositions comprising Trk inhibitors can be administered alone or in combination with one or more additional drugs. Additional drugs administered in combination with the Trk inhibitors and pharmaceutical compositions comprising Trk inhibitors of the present invention include therapies for the treatment of pain and osteoarthritis. The additional drugs may be administered concomitantly with the Trk inhibitors and pharmaceutical compositions comprising Trk inhibitors. The additional drugs may also be administered in series with the Trk inhibitors and pharmaceutical compositions comprising Trk inhibitors.

In vitro and in vivo effects of Trk inhibitors and methods of preparing the preferred Trk inhibitors of the invention are described in the Examples.

EXAMPLES

Example 1: In Vitro Studies

Example 1-1: TrkA Activity

Reagents and consumables were purchased from Sigma Aldrich, Carna Biosciences, or Caliper Life Sciences. All assay reaction conditions for $IC_{50}$ determinations were within the linear range with respect to time and enzyme concentration. In a 384 well polypropylene plate, TrkA (0.4 nM, Carna 08-186) was pre-incubated in a 100 mM Hepes-NaOH pH 7.5 buffer containing 0.01% Triton X-100, 10 mM $MgCl_2$, 0.1% BSA, 1 mM DTT, 10 μM sodium orthovanadate and 10 μM beta-glycerophosphate and compound with a concentration of 2.5% DMSO for 15 minutes at room temperature. The reaction was initiated with an equal volume of peptide substrate (Caliper Life Sciences catalog no. 760430) and ATP in the aforementioned buffer. The final concentrations in the reaction were 200 pM TrkA, 1.5 μM peptide substrate and 55 μM ATP (ATP Km). The reaction was incubated at room temperature for 180 minutes and terminated with a buffer containing excess EDTA (100 mM Hepes-NaOH pH 7.5, 0.02% Brij, 0.1% CR-3, 0.36% DMSO and 100 mM EDTA). The plate was run for one cycle on a LabChip 3000 (Caliper Life Sciences, Hopkinton, Mass.) in an off-chip mobility shift type assay with an upstream voltage of −2250 volts, a downstream voltage of −500 volts and a vacuum pressure of −1.6 psi. The LabChip 3000 separates and measures the fluorescent signal of fluorescein labeled peptide substrate and fluorescein labeled peptide product present in each well. Results are expressed as percent conversion by measuring peak height for both the substrate and product and dividing the product peak height by the sum of peak heights for both substrate and product. On every plate 100% inhibition (with a saturating concentration of staurosporine) and 0% inhibition (substrate with enzyme and DMSO) controls were used to calculate percent inhibition of tested compounds and a Z' prime value.

Table 2 displays the TrkA $IC_{50}$ for selected compounds.

Example 1-2: TrkB Activity

Reagents and consumables were purchased from Sigma Aldrich, Carna Biosciences, or Caliper Life Sciences. All assay reaction conditions for $IC_{50}$ determinations were within the linear range with respect to time and enzyme concentration. In a 384 well polypropylene plate, TrkB (0.6 nM, Carna 08-187) was pre-incubated in a 100 mM Hepes-NaOH pH 7.5 buffer containing 0.01% Triton X-100, 10 mM $MgCl_2$, 0.1% BSA, 1 mM DTT, 10 uM sodium orthovanadate and 10 μM beta-glycerophosphate and compound with a concentration of 2.5% DMSO for 15 minutes at room temperature. The reaction was initiated with an equal volume of peptide substrate (Caliper Life Sciences catalog no. 760430) and ATP in the aforementioned buffer. The final concentrations in the reaction were 300 pM TrkB, 1.5 μM peptide substrate and 70 μM ATP (ATP Km). The reaction was incubated at room temperature for 180 minutes and terminated with a buffer containing excess EDTA (100 mM Hepes-NaOH pH 7.5, 0.02% Brij, 0.1% CR-3, 0.36% DMSO and 100 mM EDTA). The plate was run for one cycle on a LabChip 3000 (Caliper Life Sciences, Hopkinton, Mass.) in an off-chip mobility shift type assay with an upstream voltage of −2250 volts, a downstream voltage of −500 volts and a vacuum pressure of −1.6 psi. The LabChip 3000 separates and measures the fluorescent signal of fluorescein labeled peptide substrate and fluorescein labeled peptide product present in each well. Results are expressed as percent conversion by measuring peak height for both the substrate and product and dividing the product peak height by the sum of peak heights for both substrate and product. On every plate 100% inhibition (with a saturating concentration of staurosporine) and 0% inhibition (substrate with enzyme and DMSO) controls were used to calculate percent inhibition of tested compounds and a Z' prime value.

Table 2 displays the TrkB $IC_{50}$ for selected compounds.

Example 1-3: TrkC Activity

Human TrkC, catalytic domain [456-825 (end) amino acids of accession number NP_002521.2] was expressed as N-terminal GST-fusion protein (69 kDa) using baculovirus expression system. GST-TRKC was purified by using glutathione sepharose chromatography and stored in 50 mM Tris-HCl, 150 mM NaCl, 0.05% Brij35, 1 mM DTT, 10% glycerol, pH7.5 at −80 C. The kinase activity was measured by off-chip mobility shift assay. The enzyme was incubated with fluorecence-labeled substrate, Srctide, in the presence of 100 uM of ATP (Mg/or Mn)/ATP). The phosphorylated and unphosphorylated substrates were separated and detected by LabChip™ 3000.

Table 2 displays the TrkC $IC_{50}$ for selected compounds.

Example 1-4: c-FMS Activity

Reagents and consumables were purchased from Sigma Aldrich, Carna Biosciences, or Caliper Life Sciences. All assay reaction conditions for $IC_{50}$ determinations were within the linear range with respect to time and enzyme concentration. In a 384 well polypropylene plate, c-FMS (0.14 nM, Carna 08-155) was pre-incubated in a 100 mM Hepes-NaOH pH 7.5 buffer containing 0.01% Triton X-100, 10 mM $MgCl_2$, 0.1% BSA, 1 mM DTT, 10 uM sodium orthovanadate and 10 μM beta-glycerophosphate and compound with a concentration of 2.5% DMSO for 15 minutes at room temperature. The reaction was initiated with an equal volume of peptide substrate (Caliper Life Sciences catalog no. 760430) and ATP in the aforementioned buffer. The final concentrations in the reaction were 70 pM c-FMS, 1.5 μM peptide substrate and 500 μM ATP (ATP Km). The reaction was incubated at room temperature for 120 minutes and terminated with a buffer containing excess EDTA (100 mM Hepes-NaOH pH 7.5, 0.02% Brij, 0.1% CR-3, 0.36% DMSO and 100 mM EDTA). The plate was run for one cycle on a LabChip 3000 (Caliper Life Sciences, Hopkinton, Mass.) in an off-chip mobility shift type assay with an upstream voltage of −2250 volts, a downstream voltage of −500 volts and a vacuum pressure of −1.6 psi. The LabChip 3000 separates and measures the fluorescent signal of fluorescein labeled peptide substrate and fluorescein labeled peptide product present in each well. Results are expressed as percent conversion by measuring peak height for both the substrate and product and dividing the product peak height by the sum of peak heights for both substrate and product. On every plate 100% inhibition (with a saturating concentration of staurosporine) and 0% inhibition (substrate with enzyme and DMSO) controls were used to calculate percent inhibition of tested compounds and a Z' prime value.

Table 2 displays the c-FMS IC$_{50}$ for selected compounds.

TABLE 2

In vitro Results of Representative Trk Inhibitors
[TrkA, TrkB and c-FMS IC$_{50}$]

| Example No. | Compound Name | IC$_{50}$ TrkA (μM) | IC$_{50}$ TrkB (μM) | IC$_{50}$ TrkC (nM) | IC$_{50}$ c-FMS (μM) |
|---|---|---|---|---|---|
| Ex. 3-1 | 1-(3-Methoxy-4-((4-methoxybenzyl)oxy)benzyl)-5-(1-methyl-1H-pyrazol-4-yl)-1H-benzo[d]imidazol-2-amine | 0.001 | 0.0005 | — | 0.002 |
| Ex. 3-2-1 | 1-(3-Methoxy-4-((4-methoxybenzyl)oxy)benzyl)-5-(pyrimidin-5-yl)-1H-benzo[d]imidazol-2-amine | 0.086 | 0.023 | — | 0.004 |
| Ex. 3-2-2 | 1-(3-Methoxy-4-((4-methoxybenzyl)oxy)benzyl)-5-(pyridine-4-yl)-1H-benzo[d]imidazol-2-amine | 0.008 | 0.004 | — | 0.002 |
| Ex. 3-2-3 | 1-(3-Methoxy-4-((4-methoxybenzyl)oxy)benzyl)-5-(1-(2-morpholinoethyl)-1H-pyrazol-4-yl)-1H-benzo[d]imidazol-2-amine | 0.003 | 0.001 | — | 0.004 |
| Ex. 3-3 | (5-(2-Amino-1-(3-methoxy-4-((4-methoxybenzyl)oxy)benzyl)-1H-benzo[d]imidazol-5-yl)pyridin-2-yl)dimethylphosphine oxide | 0.007 | 0.006 | — | 0.001 |
| Ex. 3-4 | 1-(3-Methoxy-4-((6-methoxypyridin-3-yl)methoxy)benzyl)-5-(pyrimidin-5-yl)-1H-benzo[d]imidazole | 0.836 | 0.252 | — | 0.03 |
| Ex. 3-5 | 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine | 0.006 | 0.005 | — | 0.002 |
| Ex. 3-6 | 1-(3-Methoxy-4-((6-methoxypyridin-3-yl)methoxy)benzyl)-5-(4-(piperidin-3-yl)-1H-1,2,3-triazol-1-yl)-1H-benzo[d]imidazol | 0.175 | 0.086 | — | 0.006 |
| Ex. 3-7 | 2-(1-(3-Methoxy-4-((6-methoxypyridin-3-yl)methoxy)benzyl)-1H-benzo[d]imidazol-5-yl)-5-(piperidin-4-yl)-1,3,4-oxadiazole | 0.434 | 0.439 | — | 0.028 |
| Ex. 3-8 | 1-(3-Methoxy-4-((6-methoxypyridin-3-yl)methoxy)benzyl)-5-(piperidin-4-yl)-1H-benzo[d]imidazole | 11.1 | 3.46 | — | 0.359 |
| Ex. 3-9 | 4-(1-(3-Methoxy-4-((6-methoxypyridin-3-yl)methoxy)benzyl)-1H-benzo[d]imidazol-5-yl)morpholine | 0.793 | 0.257 | — | 0.027 |
| Ex. 3-10 | 2-(1-(1-(3-Methoxy-4-((6-methoxypyridin-3-yl)methoxy)benzyl)-1H-benzo[d]imidazol-5-yl)piperidin-4-yl)propan-2-amine | 0.652 | 0.574 | — | 0.013 |
| Ex. 3-11 | 1-(3-methoxy-4-((6-methoxypyridin-3-yl)methoxy)benzyl)-5-(2,7-diazaspiro[3.5]nonan-2-yl)-1H-benzo[d]imidazole | 0.135 | 0.12 | — | 0.012 |
| Ex. 3-12 | 1-(1-(3-Methoxy-4-((6-methoxypyridin-3-yl)methoxy)benzyl)-1H-benzo[d]imidazol-5-yl)piperidin-4-amine | 1.03 | 0.637 | — | 0.031 |
| Ex. 3-13 | 1-(3-Methoxy-4-((6-methoxypyridin-3-yl)methoxy)benzyl)-5-(4-methylpiperazin-1-yl)-1H-benzo[d]imidazole | 1.13 | 0.443 | — | 0.032 |
| Ex. 3-14 | 1-(2-Amino-1-(3-methoxy-4-((6-methoxypyridin-3-yl)methoxy)benzyl)-1H-benzo[d]imidazol-5-yl)-4-methylpiperazin-2-one | 8.98 | 4.37 | — | 0.33 |
| Ex. 3-15 | 3-(3-Methoxy-4-((4-methoxybenzyl)oxy)benzyl)-6-(1-methyl-1H-pyrazol-4-yl)-3H-imidazo[4,5-b]pyridin-2-amine | 0.0003 | 0.0001 | 0.503 | 0.002 |
| Ex. 3-16 | (5-(2-Amino-3-(3-methoxy-4-((4-methoxybenzyl)oxy)benzyl)-3H-imidazo[4,5-6]pyridin-6-yl)pyridin-2-yl)dimethylphosphine oxide | 0.0005 | 0.0002 | — | 0.002 |
| Ex. 3-17 | 3-(3-Methoxy-4-((6-methoxypyridin-3-yl)methoxy)benzyl)-6-(4-methylpiperazin-1-yl)-3H-imidazo[4,5-b]pyridine | 0.179 | 0.066 | — | 0.016 |
| Ex. 3-18-1 | 2-(1-(3-(3-Methoxy-4-((6-methoxypyridin-3-yl)methoxy)benzyl)-3H-imidazo[4,5-b]pyridin-6-yl)piperidin-4-yl)propan-2-amine | 0.054 | 0.057 | — | 0.005 |
| Ex. 3-18-2 | 4-(3-(3-Methoxy-4-((6-methoxypyridin-3-yl)methoxy)benzyl)-3H-imidazo[4,5-b]pyridin-6-yl)morpholine | 0.09 | 0.031 | — | 0.008 |
| Ex. 3-18-3 | 6-(4-Cyclopropylpiperazin-1-yl)-3-(3-methoxy-4-((6-methoxypyridin-3-yl)methoxy)benzyl)-3H-imidazo[4,5-b]pyridine | 0.113 | 0.052 | — | 0.016 |
| Ex. 3-18-4 | 4-(3-(3-Methoxy-4-((6-methoxypyridin-3-yl)methoxy)benzyl)-3H-imidazo[4,5-b]pyridin-6-yl)-1,4-diazabicyclo[3.2.2]nonane | 0.47 | 0.349 | — | 0.036 |
| Ex. 3-18-5 | 3-(3-Methoxy-4-((6-methoxypyridin-3-yl)methoxy)benzyl)-6-(2,7-diazaspiro[3.5]nonan-2-yl)-3H-imidazo[4,5-b]pyridine | 0.025 | 0.021 | — | 0.007 |

TABLE 2-continued

In vitro Results of Representative Trk Inhibitors
[TrkA, TrkB and c-FMS IC$_{50}$]

| Example No. | Compound Name | IC$_{50}$ TrkA (μM) | IC$_{50}$ TrkB (μM) | IC$_{50}$ TrkC (nM) | IC$_{50}$ c-FMS (μM) |
|---|---|---|---|---|---|
| Ex. 3-18-6 | 1-(3-(3-Methoxy-4-((6-methoxypyridin-3-yl)methoxy)benzyl)-3H-imidazo[4,5-b]pyridin-6-yl)piperidin-4-amine | 0.232 | 0.133 | — | 0.012 |
| Ex. 3-18-7 | (S)-1-(3-(3-Methoxy-4-((6-methoxypyridin-3-yl)methoxy)benzyl)-3H-imidazo[4,5-b]pyridin-6-yl)pyrrolidine-2-carboxylicacid | 0.008 | 0.013 | — | 0.032 |
| Ex. 3-19 | 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine | 0.001 | 0.0009 | — | 0.002 |
| Ex. 3-20 | 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine | 0.0009 | 0.0006 | — | 0.003 |
| Ex. 3-21 | 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole | 0.026 | 0.024 | — | 0.007 |
| Ex. 3-22 | 3-(1-(3-Methoxy-4-((6-methoxypyridin-3-yl)methoxy)benzyl)-1H-benzo[d]imidazol-5-yl)-5-(piperidin-4-yl)-1,2,4-oxadiazole | 0.306 | 0.317 | — | 0.015 |
| Ex. 3-23 | 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole | 0.051 | 0.057 | — | 0.013 |
| Ex. 3-24 | 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine | 0.088 | 0.043 | — | 0.007 |
| Ex. 3-25 | 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine | 0.032 | 0.018 | — | 0.003 |
| Ex. 3-26 | 1-(3-methoxy-4-((6-methoxypyridin-3-yl)methoxy)benzyl)-5-(4-methylpiperazin-1-yl)-1H-benzo[d]imidazol-2-amine | 0.59 | 0.315 | — | 0.03 |
| Ex. 3-27 | 1-(2-fluoro-5-methoxy-4-((6-methoxypyridin-3-yl)methoxy)benzyl)-5-(4-methylpiperazin-1-yl)-1H-benzo[d]imidazole | 0.852 | 0.305 | — | 0.379 |
| Ex. 3-28 | 3-(3-Ethoxy-4-((6-methoxypyridin-3-yl)methoxy)benzyl)-6-(4-methylpiperazin-1-yl)-3H-imidazo[4,5-b]pyridine | 0.337 | 0.179 | — | 0.012 |
| Ex. 3-29 | 1-(1-(3-Methoxy-4-((6-methoxypyridin-3-yl)methoxy)benzyl)-1H-benzo[d]imidazol-5-yl)-4-methylpiperazin-2-one | 6.02 | 4.28 | — | 0.431 |
| Ex. 3-30 | 3-(3-Methoxy-4-((6-methoxypyridin-3-yl)methoxy)benzyl)-6-(5-methyl-1-azabicyclo[3.2.1]oct-6-en-7-yl)-3H-imidazo[4,5-b]pyridine | 0.201 | 0.118 | — | 0.015 |
| Ex. 3-31 | 1-(3-methoxy-4-((6-methoxypyridin-3-yl)methoxy)benzyl)-5-(5-methyl-1-azabicyclo[3.2.1]oct-6-en-7-yl)-1H-benzo[d]imidazole | 1.48 | 0.889 | — | 0.161 |
| Ex. 3-32 | 7-(3-(3-methoxy-4-((6-methoxypyridin-3-yl)methoxy)benzyl)-3H-imidazo[4,5-b]pyridin-6-yl)-1-azabicyclo[3.2.1]oct-6-en-5-ol | 0.36 | 0.15 | — | 0.041 |
| Ex. 3-33 | 7-(1-(3-Methoxy-4-((6-methoxypyridin-3-yl)methoxy)benzyl)-1H-benzo[d]imidazol-5-yl)-1-azabicyclo[3.2.1]oct-6-en-5-ol | 1.16 | 0.372 | — | 0.151 |
| Ex. 3-34 | 3-(3-methoxy-4-(1-(6-methoxypyridin-3-yl)propoxy)benzyl)-6-(1-methyl-1H-pyrazol-4-yl)-3H-imidazo[4,5-b]pyridin-2-amine | 0.032 | 0.026 | — | 0.059 |
| Ex. 3-35-1 | 3-(3-methoxy-4-((6-methoxypyridin-3-yl)methoxy)benzyl)-6-(1-methyl-1H-pyrazol-4-yl)-3H-imidazo[4,5-b]pyridin-2-amine | 0.0006 | 0.0003 | — | 0.003 |
| Ex. 3-35-2 | 3-(3-methoxy-4-((6-(trifluoromethyl)pyridin-3-yl)methoxy)benzyl)-6-(1-methyl-1H-pyrazol-4-yl)-3H-imidazo[4,5-b]pyridin-2-amine | 0.0002 | 0.0002 | — | 0.005 |
| Ex. 3-35-3 | 3-(3-methoxy-4-((4-(trifluoromethyl)benzyl)oxy)benzyl)-6-(1-methyl-1H-pyrazol-4-yl)-3H-imidazo[4,5-b]pyridin-2-amine | 0.0002 | 0.0003 | — | 0.005 |
| Ex. 3-35-4 | 3-(4-((6-cyclopropylpyridin-3-yl)methoxy)-3-methoxybenzyl)-6-(1-methyl-1H-pyrazol-4-yl)-3H-imidazo[4,5-b]pyridin-2-amine | 0.0002 | 0.0002 | — | 0.003 |
| Ex. 3-35-5 | 3-(3-methoxy-4-((2-methylthiazol-4-yl)methoxy)benzyl)-6-(1-methyl-1H-pyrazol-4-yl)-3H-imidazo[4,5-b]pyridin-2-amine | 0.0005 | 0.0002 | — | 0.005 |

TABLE 2-continued

In vitro Results of Representative Trk Inhibitors
[TrkA, TrkB and c-FMS IC$_{50}$]

| Example No. | Compound Name | IC$_{50}$ TrkA (μM) | IC$_{50}$ TrkB (μM) | IC$_{50}$ TrkC (nM) | IC$_{50}$ c-FMS (μM) |
|---|---|---|---|---|---|
| Ex. 3-36 | 3-(3-methoxy-4-((6-methoxypyridin-3-yl)methoxy)benzyl)-6-phenyl-3H-imidazo[4,5-b]pyridin-2-amine | 0.006 | 0.004 | — | 0.007 |
| Ex. 3-37-1 | 6-(4-fluorophenyl)-3-(3-methoxy-4-((6-methoxypyridin-3-yl)methoxy)benzyl)-3H-imidazo[4,5-b]pyridin-2-amine | 0.009 | 0.004 | — | 0.009 |
| Ex. 3-37-2 | 3-(3-methoxy-4-((6-methoxypyridin-3-yl)methoxy)benzyl)-6-(1-methyl-1H-pyrazol-3-yl)-3H-imidazo[4,5-b]pyridin-2-amine | 0.003 | 0.002 | — | 0.005 |
| Ex. 3-37-3 | 3-(3-methoxy-4-((6-methoxypyridin-3-yl)methoxy)benzyl)-6-(pyrimidin-5-yl)-3H-imidazo[4,5-b]pyridin-2-amine | 0.051 | 0.016 | — | 0.011 |
| Ex. 3-37-4 | 3-(3-methoxy-4-((6-methoxypyridin-3-yl)methoxy)benzyl)-6-(1,3,5-trimethyl-1H-pyrazol-4-yl)-3H-imidazo[4,5-b]pyridin-2-amine | 0.014 | 0.013 | — | 0.005 |
| Ex. 3-37-5 | 3-(3-methoxy-4-((6-methoxypyridin-3-yl)methoxy)benzyl)-6-(pyridin-4-yl)-3H-imidazo[4,5-b]pyridin-2-amine | 0.002 | 0.0007 | — | 0.002 |
| Ex. 3-37-6 | 3-(3-methoxy-4-((6-methoxypyridin-3-yl)methoxy)benzyl)-6-(pyridin-3-yl)-3H-imidazo[4,5-b]pyridin-2-amine | 0.005 | 0.002 | — | 0.006 |
| Ex. 3-38 | 3-(3-methoxy-4-((6-methoxypyridin-3-yl)methoxy)benzyl)-6-(pyridin-2-yl)-3H-imidazo[4,5-b]pyridin-2-amine | 0.004 | 0.002 | — | 0.005 |
| Ex. 3-39 | 3-(3-methoxy-4-((4-(perfluoroethyl)benzyl)oxy)benzyl)-6-(1-methyl-1H-pyrazol-4-yl)-3H-imidazo[4,5-b]pyridin-2-amine | 0.0003 | 0.0006 | — | 0.028 |
| Ex. 3-40-1 | 3-(3-methoxy-4-((4-(trifluoromethoxy)benzyl)oxy)benzyl)-6-(1-methyl-1H-pyrazol-4-yl)-3H-imidazo[4,5-b]pyridin-2-amine | 0.0002 | 0.0002 | — | 0.008 |
| Ex. 3-40-2 | 3-(3-methoxy-4-((4-((trifluoromethyl)thio)benzyl)oxy)benzyl)-6-(1-methyl-1H-pyrazol-4-yl)-3H-imidazo[4,5-b]pyridin-2-amine | 0.0002 | 0.0006 | — | 0.018 |
| Ex. 3-40-3 | 3-(4-((6-isopropylpyridin-3-yl)methoxy)-3-methoxybenzyl)-6-(1-methyl-1H-pyrazol-4-yl)-3H-imidazo[4,5-b]pyridin-2-amine | 0.0002 | 0.0002 | — | 0.005 |
| Ex. 3-40-4 | 3-(3-methoxy-4-((4-(2,2,2-trifluoroethyl)benzyl)oxy)benzyl)-6-(1-methyl-1H-pyrazol-4-yl)-3H-imidazo[4,5-b]pyridin-2-amine | 0.0002 | 0.0003 | — | 0.01 |
| Ex. 3-40-5 | 3-(3-methoxy-4-((2-(trifluoromethyl)thiazol-4-yl)methoxy)benzyl)-6-(1-methyl-1H-pyrazol-4-yl)-3H-imidazo[4,5-b]pyridin-2-amine | 0.0002 | 0.0002 | — | 0.007 |
| Ex. 3-41 | 6-(cyclohexylethynyl)-3-(3-methoxy-4-((6-methoxypyridin-3-yl)methoxy)benzyl)-3H-imidazo[4,5-b]pyridin-2-amine | 0.065 | 0.08 | — | 0.213 |
| Ex. 3-42 | 4-(2-amino-3-(3-methoxy-4-((6-methoxypyridin-3-yl)methoxy)benzyl)-3H-imidazo[4,5-b]pyridin-6-yl)but-3-yn-1-ol | 0.007 | 0.003 | — | 0.013 |
| Ex. 3-43 | 3-(4-(cyclopropyl(6-methoxypyridin-3-yl)methoxy)-3-methoxybenzyl)-6-(1-methyl-1H-pyrazol-4-yl)-3H-imidazo[4,5-b]pyridin-2-amine | 0.058 | 0.051 | — | 0.794 |
| Ex. 3-44 | 3-(3-methoxy-4-((3-methoxy-5,6,7,8-tetrahydroisoquinolin-8-yl)oxy)benzyl)-6-(1-methyl-1H-pyrazol-4-yl)-3H-imidazo[4,5-b]pyridin-2-amine | 0.039 | 0.041 | — | 0.765 |
| Ex. 3-45 | 1-(1-(3-methoxy-4-((6-methoxypyridin-3-yl)methoxy)phenyl)ethyl)-5-(1-methyl-1H-pyrazol-4-yl)-1H-benzo[d]imidazol-2-amine | 0.003 | 0.001 | — | 0.073 |
| Ex. 3-46 | 5-(4-fluorophenyl)-1-(1-(3-methoxy-4-((6-methoxypyridin-3-yl)methoxy)phenyl)ethyl)-1H-benzo[d]imidazol-2-amine | 0.085 | 0.037 | — | 0.686 |
| Ex. 3-47 | 5-(4-fluorophenyl)-1-(1-(3-methoxy-4-((6-(trifluoromethyl)pyridin-3-yl)methoxy)phenyl)ethyl)-1H-benzo[d]imidazole | 1.24 | 0.427 | — | 4.13 |

TABLE 2-continued

In vitro Results of Representative Trk Inhibitors
[TrkA, TrkB and c-FMS $IC_{50}$]

| Example No. | Compound Name | $IC_{50}$ TrkA (μM) | $IC_{50}$ TrkB (μM) | $IC_{50}$ TrkC (nM) | $IC_{50}$ c-FMS (μM) |
|---|---|---|---|---|---|
| Ex. 3-48-1 | 1-(1-(3-methoxy-4-((6-(trifluoromethyl)pyridin-3-yl)methoxy)phenyl)ethyl)-5-(1-methyl-1H-pyrazol-4-yl)-1H-benzo[d]imidazole | 0.102 | 0.014 | — | 0.16 |
| Ex. 3-48-2 | 4-(1-(1-(3-methoxy-4-((6-(trifluoromethyl)pyridin-3-yl)methoxy)phenyl)ethyl)-1H-benzo[d]imidazol-5-yl)but-3-yn-1-ol | 0.692 | 0.127 | — | 4.68 |
| Ex. 3-49 | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine | n/d | n/d | — | n/d |
| Ex. 3-49-6a | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine (enantiomer a) | 0.0003 | 0.0006 | — | 0.019 |
| Ex. 3-49-6b | 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine (enantiomer b) | 0.005 | 0.003 | — | 0.096 |
| Ex. 3-50-1 | 2-(4-(2-Amino-3-(1-(3-methoxy-4-((4-(trifluoromethyl)benzyl)oxy)phenyl)ethyl)-3H-imidazo[4,5-b]pyridin-6-yl)-1H-pyrazol-1-yl)ethan-1-ol | n/d | n/d | — | n/d |
| Ex. 3-50-2 | 3-(1-(3-Methoxy-4-((4-(trifluoromethyl)benzyl)oxy)phenyl)ethyl)-6-(1H-pyrazol-4-yl)-3H-imidazo[4,5-b]pyridin-2-amine | n/d | n/d | — | n/d |
| Ex. 3-51 | 3-(1-(3-methoxy-4-((6-(trifluoromethyl)pyridin-3-yl)methoxy)phenyl)propyl)-6-(1-methyl-1H-pyrazol-4-yl)-3H-imidazo[4,5-b]pyridin-2-amine | n/d | n/d | — | n/d |
| Ex. 3-52 | 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridine | 0.007 | 0.001 | — | 0.056 |
| Ex. 3-53 | 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridin-2-amine | 0.0004 | 0.0006 | — | 0.019 |
| Ex. 3-54 | 2-(4-amino-3-(1-(3-methoxy-4-((6-(trifluoromethyl)pyridin-3-yl)methoxy)phenyl)ethyl)-3H-imidazo[4,5-b]pyridin-6-yl)-1H-pyrazol-1-yl)ethan-1-ol | n/d | n/d | — | n/d |
| Ex. 3-55 | 4-(2-amino-3-(1-(3-methoxy-4-((6-(trifluoromethyl)pyridin-3-yl)methoxy)phenyl)ethyl)-3H-imidazo[4,5-b]pyridin-6-yl)but-3-yn-1-ol | 0.001 | 0.001 | — | 0.137 |
| Ex. 3-56 | 4-(3-(4-((6-(difluoromethyl)pyridin-3-yl)methoxy)-3-methoxybenyl)-3H-imidazo[4,5-b]pyridin-6-yl)but-3-yn-1-ol | 0.017 | 0.004 | — | 0.025 |
| Ex. 3-57 | 3-(3-methoxy-4-(1-(6-methoxypyridin-3-yl)ethoxy)benzyl)-6-(1-methyl-1H-pyrazol-4-yl)-3H-imidazo[4,5-b]pyridine formate | 0.035 | 0.013 | — | 0.058 |
| Ex. 3-58-1 | 3-(3-methoxy-4-(1-(6-methoxypyridin-3-yl)ethoxy)benzyl)-6-(1-methyl-1H-pyrazol-5-yl)-3H-imidazo[4,5-b]pyridine formate | 0.449 | 0.219 | — | 0.082 |
| Ex. 3-58-2 | 3-(3-methoxy-4-(1-(6-methoxypyridin-3-yl)ethoxy)benzyl)-6-(6-methoxypyridin-3-yl)-3H-imidazo[4,5-b]pyridine formate | 0.16 | 0.61 | — | 0.103 |
| Ex. 3-58-3 | 6-(2-fluoropyridin-4-yl)-3-(3-methoxy-4-(1-(6-methoxypyridin-3-yl)ethoxy)benzyl)-3H-imidazo[4,5-b]pyridine formate | 0.215 | 0.068 | — | 0.102 | n/d indicates none detected
— indicates not tested

Example 2: In Vivo Studies

Example 2-1: Effect of Trk Inhibitors on Reactivated Peptidoglycan-Polysaccharide Knee Arthritis Male Lewis rats were acclimated to the testing facility for 7 days. The rats were housed in 5 per cage in shoe-box polycarbonate cages with wire tops, wood chip bedding and suspended food and water bottles.

On day −21, the male Lewis rats were randomized into treatment groups by body weight. The rats were anesthetized and injected with peptidoglycan-polysaccharide (PGPS) into the right knee to induce PGPS arthritis. Arthritis was reactivated on days 0 and 14 by an IV tail injection of PGPS. The animals were dosed intra-articularly with vehicle, triamcinolone and test compound on day −7. The treatment groups are presented in Table 3 below.

TABLE 3

PGPS Knee Arthritis Treatment Groups

| Group | Treatment | Dose |
|---|---|---|
| 1 | Vehicle (No reactivation) | N/A |
| 2 | Vehicle | N/A |
| 3 | Triamcinolone | 0.06 mg |
| 4 | 3-(3-Methoxy-4-((4-methoxybenzyl)oxy)benzyl)-6-(1-methyl-1H-pyrazol-4-yl)-3H-imidazo[4,5-b]pyridin-2-amine | 1 mg |

The rats were weighed at baseline on days 0, 4, 14 and 18. Knee thickness was measured by caliper at baseline and on days 0, 2, 4, 14, 16 and 18. Gait analysis occurred on days 0-4 and 14-18, with video recording of selected animals on days 3 and 17. Gait analysis was performed by applying ink to the ventral surface of the foot and documenting weight bearing during movement across paper.

The animals were terminated at day 18. Right knees were removed, trimmed of extraneous tissue, and collected into 10% neutral buffered formalin. After two days in the formalin buffer and three days in 10% formic acid decalcifier, the knees were cut into two approximately equal halves in the frontal plane and processed for paraffin embedding and stained with T. Blue. Histological examinations were subsequently performed for bone resorption, inflammation, pannus and cartilage damage.

Body weights, gait deficiency and caliper measurements were analyzed using a one-way analysis of variance (1-way ANOVA) with Dunnett's multiple comparison post-test. Gait scores were analyzed using a Kruskal-Wallis test (non-parametric ANOVA) with Dunn's multiple comparison post-test. Histopathology scores were analyzed using a Kruskal-Wallis test (non-parametric ANOVA) with Dunn's multiple comparison post-test.

Vehicle control animals gained an average of approximately 96 grams of body weight over the course of the study, which was a significant reduction from the non-reactivated controls. There were no significant differences compared to any of the treatment groups. Following the second reactivation, several animals developed systemic PGPS inflammation that affected the ankles and compromised the pain measurement. Gait scores and deficiency for the vehicle controls peaked two days after the first reactivation and one day after the second reactivation, and were significantly increased over the non-reactivated controls at all time points except for the two pre-reactivation time points (days 0 and 14). The first reactivation peaked higher, but dropped off more sharply. The pattern was reversed for knee caliper measurements, with a much higher peak and sharper drop-off after the second reactivation. Histopathology sections had marked to severe inflammation with minimal to mild pannus and cartilage damage and minimal to moderate bone resorption. All parameters were significantly increased over the non-reactivated controls, which had minimal lesions, except for bone resorption, which ranged from minimal to marked.

Animals treated with 0.06 mg of Triamcinolone had significantly reduced gait scores and deficiency throughout the first reactivation (days 1-4) and on day 15, 17, and 18 of the second reactivation. AUC values were also significantly reduced, whether each reactivation was calculated separately (74-99%) or summed (88-92%). Knee caliper measurements were significantly reduced on days 2, 4, 16, and 18, as well as prior to the first reactivation on day 0, with corresponding 53-106% reductions in the AUC. Histopathology sections had significant 61-88% reductions in all parameters, with a significant 74% reduction in summed scores.

Animals treated with 1 mg of 3-(3-Methoxy-4-((4-methoxybenzyl)oxy)benzyl)-6-(1-methyl-1H-pyrazol-4-yl)-3H-imidazo[4,5-b]pyridin-2-amine had significant reductions in gait scores and deficiency throughout the first reactivation. Scores were significantly reduced throughout the second reactivation, and reductions in deficiency were significant on days 15, 17, and 18. AUC values for the first (92-93%) and second (85-86%) reactivations were significantly reduced for both scores and deficiency, and the summed AUC was significantly reduced for deficiency (84%). Knee caliper measurements were significantly reduced on day 14 (just prior to the second reactivation). AUC values were generally unaffected by treatment. Histopathology sections had significant 49-94% reductions in all parameters, with a significant 70% reduction in summed scores.

Example 2-2: Effect of Trk Inhibitors on Monosodium Iodoacetate Induced Osteoarthritis Male Wistar rats were acclimated to the testing facility for 5 days. The rats were individually housed in micro-isolator shoe-box polycarbonate cages with cob bedding and water bottles. Dry pelleted food of known composition and nutritional components was provided ad libitum Animals were randomized by treatment type using an online random number generator. Each treatment group was assigned a number, entered into the random number generator, recorded then translated back to the associated treatment. All injections were given in the left leg unless the treatment indicated "Contralateral" in which case the injection was given in the right leg. Both legs were shaved on all animals at the time of the treatment injections to blind the test administrator.

The rats were weighed the day prior to injection with monosodium iodoacetate (MIA), the agent used to induce osteoarthritis in the animals. The day of injection, rats from groups 2-8 received a subcutaneous (SC) dose of buprenorphine at least one hour prior to induction. Anesthesia induction was achieved for all groups. Naïve animals were then placed in recovery. All other animals received an injection of MIA. In animals receiving MIA, the hind leg was flexed and an injection of MIA (25 µL) was injected into the intra-articular space using a 27 gauge ½ Inch Needle. Standard postoperative care was performed (twice daily for 48 hours).

| Group | Treatment | Animals/Group | Animals/Time Point |
|---|---|---|---|
| 1 | Naïve | 8 | 8 |
| 2 | MIA/LRS* | 8 | 8 |

| Group | Treatment | Animals/Group | Animals/Time Point |
|---|---|---|---|
| 3 | MIA/3-(3-Methoxy-4-((4-methoxybenzyl)oxy)benzyl)-6-(1-methyl-1H-pyrazol-4-yl)-3H-imidazo[4,5-b]pyridin-2-amine (100 µg) Ipsilateral | 8 | 8 |
| 4 | MIA/3-(3-Methoxy-4-((4-methoxybenzyl)oxy)benzyl)-6-(1-methyl-1H-pyrazol-4-yl)-3H-imidazo[4,5-b]pyridin-2-amine (100 µg) Contralateral | 8 | 8 |
| 5 | MIA/3-(3-Methoxy-4-((4-methoxybenzyl)oxy)benzyl)-6-(1-methyl-1H-pyrazol-4-yl)-3H-imidazo[4,5-b]pyridin-2-amine (30 µg) Ipsilateral | 8 | 8 |
| 6 | MIA/3-(3-Methoxy-4-((4-methoxybenzyl)oxy)benzyl)-6-(1-methyl-1H-pyrazol-4-yl)-3H-imidazo[4,5-b]pyridin-2-amine (30 µg) Contralateral | 8 | 8 |
| 7 | MIA/3-(3-Methoxy-4-((4-methoxybenzyl)oxy)benzyl)-6-(1-methyl-1H-pyrazol-4-yl)-3H-imidazo[4,5-b]pyridin-2-amine (10 µg) Ipsilateral | 8 | 8 |
| 8 | MIA/3-(3-Methoxy-4-((4-methoxybenzyl)oxy)benzyl)-6-(1-methyl-1H-pyrazol-4-yl)-3H-imidazo[4,5-b]pyridin-2-amine (10 µg) Contralateral | 8 | 8 |

*Lactated Ringer's Solution: injection control/placebo.

On Day 8 the test article was administered as described above. On Days −1, 7, 14, 21, 28, and 35 post-induction, weight bearing was assessed. A weight bearing scale was utilized using a plexiglass chamber to assess the amount of weight distributed in each hind limb. The animals were acclimated to the chamber for at least 5 minutes prior to testing and the weight distribution was recorded 5 times.

No adverse observations were found in body weight results due to treatment. MIA/LRS was significantly worse than MA/3-(3-Methoxy-4-((4-methoxybenzyl)oxy)benzyl)-6-(1-methyl-1H-pyrazol-4-yl)-3H-imidazo[4,5-b]pyridin-2-amine Ipsilateral 100 µg and 30 µg at day 35 ($p<0.05$).

3-(3-Methoxy-4-((4-methoxybenzyl)oxy)benzyl)-6-(1-methyl-1H-pyrazol-4-yl)-3H-imidazo[4,5-b]pyridin-2-amine 100 and 30 µg Ipsilateral injections were effective throughout the four weeks following administration. The 3-(3-methoxy-4-((4-methoxybenzyl)oxy)benzyl)-6-(1-methyl-1H-pyrazol-4-yl)-3H-imidazo[4,5-b]pyridin-2-amine 10 µg Ipsilateral efficacy was observed at 2 through 4 weeks following administration. 3-(3-Methoxy-4-((4-methoxybenzyl)oxy)benzyl)-6-(1-methyl-1H-pyrazol-4-yl)-3H-imidazo[4,5-b]pyridin-2-amine 100 µg Contralateral did not show systemic pain relief at any timepoint throughout the study (1-4 weeks), whereas 3-(3-methoxy-4-((4-methoxybenzyl)oxy)benzyl)-6-(1-methyl-1H-pyrazol-4-yl)-3H-imidazo[4,5-b]pyridin-2-amine 30 µg Contralateral administration resulted in efficacy at only the 3 week timepoint and 3-(3-methoxy-4-((4-methoxybenzyl)oxy)benzyl)-6-(1-methyl-1H-pyrazol-4-yl)-3H-imidazo[4,5-b]pyridin-2-amine 10 µg Contralateral administration resulted in efficacy at 3 and 4 weeks following administration.

The animals were terminated at day 36. Both stifles were collected from each animal; the skin was removed from the joint and the patella was removed while leaving as much of the fat pad intact with the joint. The stifle was placed in the appropriate cassette with rolled gauze to secure the stifle in the cassette and then placed into 4% Paraformaldehyde. These samples were examined histologically. Histopathology revealed no adverse changes attributable to 3-(3-methoxy-4-((4-methoxybenzyl)oxy)benzyl)-6-(1-methyl-1H-pyrazol-4-yl)-3H-imidazo[4,5-b]pyridin-2-amine in the knee joint.

Example 3: Synthesis of Trk Inhibitors

Example 3-1: Synthesis of 1-(3-Methoxy-4-((4-methoxybenzyl)oxy)benzyl)-5-(1-methyl-1H-pyrazol-4-yl)-1H-benzo[d]imidazol-2-amine Example 3-1-1: Preparation of 3-Methoxy-4-((4-methoxybenzyl)oxy)benzonitrile To a stirred solution of 4-hydroxy-3-methoxybenzonitrile (2.43 g, 16.29 mmol) in acetonitrile (75 mL) was added cesium carbonate (6.68 g, 20.50 mmol) and p-methoxybenzyl chloride (2.81 g, 17.92 mmol). The reaction mixture was heated to reflux and stirred. After 1 h, the mixture was allowed to cool to room temperature and was filtered. The filtrate was concentrated to provide 4.56 g (>100%) 3-methoxy-4-((4-methoxybenzyl)oxy)benzonitrile as an off-white solid. The crude material was used without purification in the next reaction.

Example 3-1-2: Preparation of (3-Methoxy-4-((4-methoxybenzyl)oxy)phenyl)methanamine To a stirred solution of crude 3-methoxy-4-((4-methoxybenzyl)oxy)benzonitrile (4.39 g, 16.29 mmol) in tetrahydrofuran (50 mL) was added lithium aluminum hydride (0.93 g, 24.44 mmol Caution: gas evolution and moderate exotherm). The resulting mixture was allowed to stir at room temperature. After 1 h, the reaction mixture was cooled to 0°

C. while water (930 µL) was added slowly (gas evolution). The mixture was then treated with 1N sodium hydroxide solution (930 µL) and additional water (2.8 mL). The mixture was allowed to stir for 15 min, and then it was filtered through Celite with the aid of ethyl acetate. The filtrate was dried over magnesium sulfate, filtered, and concentrated to provide 3.90 g (86% for 2 steps) of 3-methoxy-4-((4-methoxybenzyl)oxy)phenyl)methanamine as an off-white solid.

Example 3-1-3: Preparation of 4-bromo-N-(3-methoxy-4-((4-methoxybenzyl)oxy)benzyl)-2-nitroaniline To a stirred solution of 3-methoxy-4-((4-methoxybenzyl)oxy)phenyl)methanamine (4.48 g, 16.39 mmol) in acetonitrile (75 mL) was added 4-bromo-1-fluoro-2-nitrobenzene (3.43 g, 15.61 mmol) and diisopropylethylamine (2.52 g, 19.51 mmol). The resulting bright yellow solution was heated to reflux. After 16 h, the orange mixture was allowed to cool to room temperature and was diluted with water. The mixture was extracted with dichloromethane (2×150 mL). The combined organic phases were dried over magnesium sulfate, filtered, and concentrated to provide 7.71 g (99%) of 4-bromo-N-(3-methoxy-4-((4-methoxybenzyl)oxy)benzyl)-2-nitroaniline as an orange semi-solid.

Example 3-1-4: Preparation of 4-bromo-$N^1$-(3-methoxy-4-((4-methoxybenzyl)oxy)benzyl)benzene-1,2-diamine To a stirred suspension of 4-bromo-N-(3-methoxy-4-((4-methoxybenzyl)oxy)benzyl)-2-nitroaniline (7.71 g, 16.30 mmol) in tetrahydrofuran (100 mL), ethanol (25 mL), and water (25 mL) was added ammonium chloride (0.44 g, 8.15 mmol) and iron powder (9.10 g, 163 mmol). The mixture was heated to reflux. After 5 h, the reaction mixture was allowed to cool to room temperature and was filtered through Celite with the aid of ethanol. The filtrate was concentrated, and the residue partitioned between dichloromethane and water. The organic phase was separated, dried over magnesium sulfate, filtered, and concentrated to provide 6.73 g (95%) of 4-bromo-$N^1$-(3-methoxy-4-((4-methoxybenzyl)oxy)benzyl)benzene-1,2-diamine as a brown solid.

Example 3-1-5: Preparation of 5-bromo-1-(3-methoxy-4-((4-methoxybenzyl)oxy)benzyl)-1H-benzo[d]imidazol-2-amine To a stirred solution of cyanogen bromide (5.0 M in acetonitrile, 5.0 mL, 25.0 mmol) in water (75 mL) was added a solution of 4-bromo-N-(3-methoxy-4-((4-methoxybenzyl)oxy)benzyl)benzene-1,2-diamine (3.40 g, 7.67 mmol) in methanol (75 mL), acetonitrile (75 mL), and dichloromethane (25 mL). The addition of the diamine solution was conducted over 45 min. The resulting brown solution was allowed to stir at room temperature. After 16 h, the reaction mixture was concentrated, and the residue was dissolved in dichloromethane. The solution was washed with 1N sodium hydroxide solution, dried over magnesium sulfate, filtered, and concentrated to provide 2.46 g of an orange-brown solid. Trituration of the crude material with diethyl ether afforded 1.54 g of 5-bromo-1-(3-methoxy-4-((4-methoxybenzyl)oxy)benzyl)-1H-benzo[d]imidazol-2-amine as an off-white solid.

Example 3-1-6: Preparation of 1-(3-Methoxy-4-((4-methoxybenzyl)oxy)benzyl)-5-(1-methyl-1H-pyrazol-4-yl)-1H-benzo[d]imidazol-2-amine To a stirred suspension of 5-bromo-1-(3-methoxy-4-((4-methoxybenzyl)oxy)benzyl)-1H-benzo[d]imidazol-2-amine (0.28 g, 0.59 mmol) in 1,4-dioxane (8 mL) and water (6 mL) was added 1-methyl-4-(4,4,5,5-tetramethyl-1,3,2-dioxaborolan-2-yl)-1H-pyrazole (0.15 g, 0.73 mmol), potassium phosphate (0.44 g, 2.06 mmol), tricyclohexylphosphine (0.016 g, 0.059 mmol), and palladium(II)acetate (0.007 g, 0.029 mmol). The reaction mixture was heated to 125° C. in a microwave reactor. After 15 min, the reaction mixture was diluted with water. The mixture was extracted with ethyl acetate (×3), and the combined organic phases were washed with brine, dried over magnesium sulfate, filtered, and concentrated to provide 0.33 g of a light green solid. Chromatographic purification (Combi-Flash, 12 g $SiO_2$ gold column, 1-5% 2 M ammonia in methanol/dichloromethane elute) afforded 0.13 g (48%) of the product as an off-white solid: $^1$H NMR (400 MHz, DMSO-d6) δ 7.96 (s, 1H), 7.71 (s, 1H), 7.34-7.24 (m, 3H), 7.05-6.87 (m, 6H), 6.65-6.60 (m, 1H), 6.50 (s, 2H), 5.11 (s, 2H), 4.90 (s, 2H), 3.81 (s, 3H), 3.72 (s, 3H), 3.69 (s, 3H) ppm; (M+1) 470.

Example 3-2: Synthesis of Additional Compounds from 5-bromo-1-(3-methoxy-4-((4-methoxybenzyl)oxy)benzyl)-1H-benzo[d]imidazol-2-amine The following compounds were prepared using the procedure described in Example 3-1 by employing the appropriate boronic acid/boronate ester coupling partner:

Example 3-2-1: 1-(3-Methoxy-4-((4-methoxybenzyl)oxy)benzyl)-5-(pyrimidin-5-yl)-1H-benzo[d]imidazol-2-amine $^1$H NMR (400 MHz, DMSO-d6) δ 9.09-9.07 (m, 3H), 7.57-7.54 (m, 1H), 7.34-7.30 (m, 2H), 7.28-7.20 (m, 2H), 7.01 (d, J=1.9 Hz, 1H), 6.98-6.89 (m, 3H), 6.71 (br s, 2H), 6.66 (dd, J=8.3, 1.9 Hz, 1H), 5.20 (s, 2H), 4.93 (s, 2H), 3.74 (s, 3H), 3.72 (s, 3H) ppm; (M+1) 468.

Example 3-2-2: 1-(3-Methoxy-4-((4-methoxybenzyl)oxy)benzyl)-5-(pyridine-4-yl)-1H-benzo[d]imidazol-2-amine $^1$H NMR (400 MHz, DMSO-d6) δ 8.54 (dd, J=4.6, 1.5 Hz, 2H), 7.66 (dd, J=4.6, 1.6 Hz, 2H), 7.56 (d, J=1.4 Hz, 1H), 7.36-7.27 (m, 3H), 7.21 (d, J=8.2 Hz, 1H), 7.01 (d, J=1.8 Hz, 1H), 6.98-6.88 (m, 3H), 6.72-6.64 (m, 3H), 5.20 (s, 2H), 4.93 (s, 2H), 3.74 (s, 3H), 3.72 (s, 3H) ppm; (M+1) 467.

Example 3-2-3: 1-(3-Methoxy-4-((4-methoxybenzyl)oxy)benzyl)-5-(1-(2-morpholinoethyl)-1H-pyrazol-4-yl)-1H-benzo[d]imidazol-2-amine $^1$H NMR (400 MHz, DMSO-d6) δ 8.03 (s, 1H), 7.74 (s, 1H), 7.36-7.27 (m, 3H), 7.07-7.01 (m, 2H), 6.98 (d, J=1.9 Hz, 1H), 6.96-6.89 (m, 3H), 6.65 (dd, J=8.3, 1.9 Hz, 1H), 6.54 (br s, 2H), 5.14 (s, 2H), 4.92 (s, 2H), 4.20 (t, J=6.6 Hz, 2H), 3.74 (s, 3H), 3.71 (s, 3H), 3.59-3.50 (m, 4H), 2.72 (t, J=6.6 Hz, 2H), 2.44-2.36 (m, 4H) ppm; (M+1) 569.

Example 3-3: Synthesis of (5-(2-Amino-1-(3-methoxy-4-((4-methoxybenzyl)oxy)benzyl)-1H-benzo[d]imidazol-5-yl)pyridin-2-yl)dimethylphosphine oxide

Example 3-3-1: Preparation of 4-iodo-N-(3-methoxy-4-((4-methoxybenzyl)oxy)benzyl)-2-nitroaniline To a stirred solution of 3-methoxy-4-((4-methoxybenzyl)oxy)phenyl)methanamine (5.02 g, 18.37 mmol) in acetonitrile (75 mL) was added 1-fluoro-4-iodo-2-nitrobenzene (4.67 g, 17.49 mmol) and diisopropylethylamine (2.83 g, 21.86 mmol). The resulting bright yellow solution was heated to reflux. After 17 h, the orange mixture was allowed to cool to room temperature and was diluted with water. The mixture was extracted with dichloromethane (3×100 mL). The combined organic phases were dried over magnesium sulfate, filtered, and concentrated to provide 9.49 g (>100%) of 4-iodo-N-(3-methoxy-4-((4-methoxybenzyl)oxy)benzyl)-2-nitroaniline as an orange semi-solid.

Example 3-3-2: Preparation of 4-iodo-$N^1$-(3-methoxy-4-((4-methoxybenzyl)oxy)benzyl)benzene-1,2-diamine To a stirred solution of 4-iodo-N-(3-methoxy-4-((4-methoxybenzyl)oxy)benzyl)-2-nitroaniline (9.10 g, 17.49 mmol) in tetrahydrofuran (50 mL), ethanol (50 mL), and water (10 mL) was added ammonium chloride (7.48 g, 139.9 mmol) and iron (II) sulfate heptahydrate (14.59 g, 52.47 mmol). The bright orange suspension was treated with zinc (3.43 g, 52.47 mmol). The mixture was gradually warmed to reflux. After 3.5 h, the color of the reaction mixture had turned from orange to olive-green. At this point the reaction mixture was allowed to cool to room temperature. The mixture was filtered through Celite, and the filtercake was washed with methanol. The filtrate concentrated, the residue was suspended in water. The aqueous mixture was extracted with chloroform (×3). The combined organic phases were dried over magnesium sulfate, filtered, and concentrated to afford 8.32 g (97%) of 4-iodo-$N^1$-(3-methoxy-4-((4-methoxybenzyl)oxy)benzyl)benzene-1,2-diamine as a tan solid.

Example 3-3-3: Preparation of 5-iodo-1-(3-methoxy-4-((4-methoxybenzyl)oxy)benzyl)-1H-benzo[d]imidazol-2-amine To a stirred suspension of 4-iodo-$N^1$-(3-methoxy-4-((4-methoxybenzyl)oxy)benzyl)benzene-1,2-diamine (8.32 g, 16.97 mmol) in dichloromethane (100 mL) and methanol (50 mL) was added cyanogen bromide solution (5.0 M in acetonitrile, 17.0 mL, 85.00 mmol). The resulting brown reaction mixture was allowed to stir at room temperature. After 16 h, the mixture was treated with 1 N sodium hydroxide solution (250 mL) and was allowed to stir at room temperature. After 15 min, a precipitate formed. The solids were isolated by filtration, washed with water, and dried to afford 4.42 g (51%) of 5-iodo-1-(3-methoxy-4-((4-methoxybenzyl)oxy)benzyl)-1H-benzo[d]imidazol-2-amine as a tan solid.

Example 3-3-4: Preparation of 5-(6-chloropyridin-3-yl)-1-(3-methoxy-4-((4-methoxybenzyl)oxy)benzyl)-1H-benzo[d]imidazol-2-amine To a stirred suspension of 5-iodo-1-(3-methoxy-4-((4-methoxybenzyl)oxy)benzyl)-1H-benzo[d]imidazol-2-amine (0.40 g, 0.78 mmol) in 1,4-dioxane (10 mL) and water (4 mL) was added (6-chloropyridin-3-yl)boronic acid (0.14 g, 0.89 mmol), potassium phosphate (0.58 g, 2.72 mmol), tricyclohexylphosphine (0.044 g, 0.16 mmol), and palladium(II)acetate (0.017 g, 0.078 mmol). The reaction mixture was heated to 125° C. in a microwave reactor. After 15 min, the reaction mixture was diluted with water. The mixture was extracted with chloroform (×3). The combined organic phases were dried over magnesium sulfate, filtered, and concentrated to provide 0.43 g of a brown solid. Chromatographic purification (Combi-Flash, 24 g $SiO_2$ gold column, 5-10% methanol/dichloromethane elute) afforded 0.23 g (58%) of 5-(6-chloropyridin-3-yl)-1-(3-methoxy-4-((4-methoxybenzyl)oxy)benzyl)-1H-benzo[d]imidazol-2-amine as a light yellow solid.

Example 3-3-5: Preparation of (5-(2-Amino-1-(3-methoxy-4-((4-methoxybenzyl)oxy)benzyl)-1H-benzo[d]imidazol-5-yl)pyridin-2-yl)dimethylphosphine oxide To a stirred suspension of 5-(6-chloropyridin-3-yl)-1-(3-methoxy-4-((4-methoxybenzyl)oxy)benzyl)-1H-benzo[d]imidazol-2-amine (0.15 g, 0.30 mmol) in 1,4-dioxane (4 mL) was added dimethylphosphine oxide (0.029 g, 0.37 mmol), 4,5-bis(diphenylphosphino)-9,9-dimethylxanthene (0.035 g, 0.060 mmol), palladium(II) acetate (0.007 g, 0.030 mmol), and cesium carbonate (0.20 g, 0.60 mmol). The reaction mixture was heated to 150° C. in a microwave reactor. After 45 min, additional portions of dimethylphosphine oxide (0.029 g, 0.37 mmol), 4,5-bis(diphenylphosphino)-9,9-dimethylxanthene (0.035 g, 0.060 mmol), and palladium(II) acetate (0.007 g, 0.030 mmol) were added. The reaction mixture was subjected to a second round of heating in the microwave reactor (45 min, 150° C.). After the second heating cycle, the reaction mixture was diluted with water and was extracted with chloroform (×3). The combined organic phases were dried over magnesium sulfate, filtered, and concentrated to provide 0.24 g of a bright yellow solid. Chromatographic purification (Combi-Flash, 12 g SiO2 gold column, 5-10% 2M ammonia in methanol/dichloromethane elute) afforded 0.052 g (32%) of the product as a yellow solid: $^1$H NMR (400 MHz, DMSO-d6) δ $^1$H NMR (400 MHz, DMSO) δ 9.03 (d, J=1.9 Hz, 1H), 8.22-8.14 (m, 1H), 7.95 (dd, J=8.2, 4.9 Hz, 1H), 7.52 (s, 1H), 7.32 (d, J=8.6 Hz, 2H), 7.28-7.19 (m, 2H), 7.02 (d, J=1.9 Hz, 1H), 6.96 (d, J=8.2 Hz, 1H), 6.91 (d, J=8.6 Hz, 2H), 6.71-6.64 (m, 3H), 5.20 (s, 2H), 4.93 (s, 2H), 3.74 (s, 3H), 3.72 (s, 3H), 1.68 (d, J=13.5 Hz, 6H) ppm; (M+1)=543.

Example 3-4: Synthesis of 1-(3-Methoxy-4-((6-methoxypyridin-3-yl)methoxy)benzyl)-5-(pyrimidin-5-yl)-1H-benzo[d]imidazole

Example 3-4-1: Preparation of tert-butyl 3-methoxy-4-((6-methoxypyridin-3-yl)methoxy)benzylcarbamate To a stirred solution of tert-butyl 4-hydroxy-3-methoxybenzylcarbamate (22.44 g, 88.59 mmol) in acetonitrile (250 mL) was added potassium carbonate (30.61 g, 221.5 mmol) and 5-(chloromethyl)-2-methoxypyridine hydrochloride (18.33 g, 94.46 mmol). The resulting mixture was heated to reflux and stirred. After 23 h, the light green suspension was allowed to cool to room temperature and was diluted with water (600 mL), resulting in the formation of a precipitate. The solids were isolated by filtration and washed with water.

The moist solids were dissolved in dichloromethane (300 mL), and a small amount of water separated and was removed. The organic phase was dried over magnesium sulfate, filtered, and concentrated to provide 31.92 g (96%) of tert-butyl 3-methoxy-4-((6-methoxypyridin-3-yl)methoxy)benzylcarbamate as an off-white solid.

Example 3-4-2: Preparation of (3-methoxy-4-((6-methoxypyridin-3-yl)methoxy)phenyl)methanamine To a stirred solution of tert-butyl 3-methoxy-4-((6-methoxypyridin-3-yl)methoxy)benzylcarbamate (31.92 g, 85.25 mmol) in dichloromethane (100 mL) was added trifluoroacetic acid (75 mL, 973.5 mmol). The resulting yellow solution was allowed to stir at room temperature. After 2 h, the reaction mixture was concentrated to dryness, and the residue was dissolved in water (250 mL). The acidic solution was extracted with diethyl ether (2×125 mL; organic phases discarded). The aqueous phase was then made basic with concentrated ammonium hydroxide. The basic aqueous phase was then extracted with dichloromethane (2×200 mL). The combined organic phases were dried over magnesium sulfate, filtered, and concentrated to provide 21.46 g (92%) of (3-methoxy-4-((6-methoxypyridin-3-yl)methoxy)phenyl)methanamine as an off-white solid.

Example 3-4-3: Preparation of 4-iodo-N-(3-methoxy-4-((6-methoxypyridin-3-yl)methoxy)benzyl)-2-nitroaniline To a stirred solution of (3-methoxy-4-((6-methoxypyridin-3-yl)methoxy)phenyl)methanamine (5.00 g, 18.23 mmol) in acetonitrile (75 mL) was added 1-fluoro-4-iodo-2-nitrobenzene (4.55 g, 17.04 mmol) and diisopropylethylamine (3.30 g, 25.56 mmol). The yellow solution was heated to reflux and stirred. After 4 h, the orange-brown mixture was allowed to cool to room temperature and was diluted with water (150 mL). The resulting bright orange precipitate was isolated by filtration and washed with water. The moist solids were dissolved in dichloromethane, and a small amount of water separated and was removed. The organic phase was dried over magnesium sulfate, filtered, and concentrated to provide 7.10 g (80%) of 4-iodo-N-(3-methoxy-4-((6-methoxypyridin-3-yl)methoxy)benzyl)-2-nitroaniline as a bright orange solid.

Example 3-4-4: Preparation of 4-iodo-N$^1$-(3-methoxy-4-((6-methoxypyridin-3-yl)methoxy)benzyl)benzene-1,2-diamine To a stirred solution of 4-iodo-N-(3-methoxy-4-((6-methoxypyridin-3-yl)methoxy)benzyl)-2-nitroaniline (7.10 g, 13.62 mmol) in tetrahydrofuran (100 mL), methanol (50 mL), and water (10 mL) was added ammonium chloride (5.83 g, 109.0 mmol) and iron (II) sulfate heptahydrate (13.25 g, 47.67 mmol). The bright orange suspension was treated with zinc (3.12 g, 47.67 mmol). The mixture was gradually warmed to reflux. After 20 min, the color of the reaction mixture had turned from orange to ollie-green. At this point the reaction mixture was allowed to cool to room temperature. The mixture was filtered through Celite, and the filtercake was washed with chloroform. The filtrate was then washed with 5N ammonium hydroxide solution (75 mL). The organic phase was dried over magnesium sulfate, filtered, and concentrated to provide 6.49 g of 4-iodo-N$^1$-(3-methoxy-4-((6-methoxypyridin-3-yl)methoxy)benzyl)benzene-1,2-diamine as a tan solid.

Example 3-4-5: Preparation of 5-iodo-1-(3-methoxy-4-((6-methoxypyridin-3-yl)methoxy)benzyl)-1H-benzo[d]imidazole To a stirred suspension of 4-iodo-N-(3-methoxy-4-((6-methoxypyridin-3-yl)methoxy)benzyl)benzene-1,2-diamine in ethanol (100 mL) was added triethyl orthoformate (4.45 g, 30.03 mmol) and p-toluenesulfonic acid monohydrate (0.075 g, 0.39 mmol). As the resulting mixture was warmed to reflux, the solids gradually dissolved to provide an orange solution. After 45 min, the reaction mixture was allowed to cool to room temperature, resulting in the formation of a precipitate. Water (250 mL) was added to the mixture, and the solids were isolated by filtration. The moist solids were dissolved in ethyl acetate (250 mL), and this solution was washed with brine, dried over magnesium sulfate, filtered, and concentrated to provide 5.99 g (91%) of 5-iodo-1-(3-methoxy-4-((6-methoxypyridin-3-yl)methoxy)benzyl)-1H-benzo[d]imidazole as a tan solid.

Example 3-4-6: Preparation of 1-(3-Methoxy-4-((6-methoxypyridin-3-yl)methoxy)benzyl)-5-(pyrimidin-5-yl)-1H-benzo[d]imidazole To a suspension of 5-iodo-1-(3-methoxy-4-((6-methoxypyridin-3-yl)methoxy)benzyl)-1H-benzo[d]imidazole (0.37 g, 0.74 mmol) in 1,4-dioxane (10 mL) and water (4 mL) was added 5-(4,4,5,5-tetramethyl-1,3,2-dioxaborolan-2-yl)pyrimidine (0.19 g, 0.93 mmol), potassium phosphate (0.55 g, 2.60 mmol), tricyclohexylphosphine (0.021 g, 0.074 mmol), and palladium(II)acetate (0.008 g, 0.037 mmol). The reaction mixture was heated to 125° C. in a microwave reactor. After 15 min, the reaction mixture was diluted with water. The mixture was extracted with chloroform (×3), and the combined organic phases were dried over magnesium sulfate, filtered, and concentrated to provide 0.45 g of a light green solid. Chromatographic purification (Combi-Flash, 12 g SiO$_2$ gold column, 1-5% methanol/dichloromethane elute) afforded 0.14 g (40%) of the product as an off-white solid: $^1$H NMR (400 MHz, DMSO-d$_6$) δ 9.17-9.14 (m, 3H), 8.50 (s, 1H), 8.20 (d, J=2.5, 1H), 8.12 (d, J=1.7, 1H), 7.77-7.70 (m, 2H), 7.65 (dd, J=8.4, 1.7 Hz, 1H), 7.12 (d, J=2.0 Hz, 1H), 7.02 (d, J=8.4 Hz, 1H), 6.87-6.80 (m, 2H), 5.45 (s, 2H), 4.97 (s, 2H), 3.84 (s, 3H), 3.74 (s, 3H) ppm; (M+1)=454.

Example 3-5: Synthesis of 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine 3-(3-methoxy-4-((6-methoxypyridin-3-yl)methoxy)benzyl)-6-(1-(piperidin-4-yl)-1H-pyrazol-4-yl)-3H-imidazo[4,5-b]pyridine was prepared from 5-iodo-1-(3-methoxy-4-((6-methoxypyridin-3-yl)methoxy)benzyl)-1H-benzo[d]imidazole and tert-butyl 4-(4-(4,4,5,5-tetramethyl-1,3,2-dioxaborolan-2-yl)-1H-pyrazol-1-yl)piperidine-1-carboxylate according to the procedure described in Example 3-4-6 for the synthesis of Example 3-4. The final product was obtained after removal of the carbamate protecting under acidic conditions: $^1$H NMR (500 MHz, CDCl$_3$) δ 8.20 (d, J=2.0 Hz, 1H), 7.93 (s, 1H), 7.92 (s, 1H), 7.82 (s, 1H), 7.72 (s, 1H), 7.68 (dd, J=8.5, 2.0 Hz, 1H), 7.41 (d, J=8.0 Hz, 1H), 7.29 (d, J=8.0 Hz, 1H), 6.89 (d, J=8.0 Hz, 1H), 6.76 (d, J=8.5 Hz, 1H), 6.74 (d, J=8.5 Hz, 2H), 5.29 (s, 2H), 5.04 (s, 2H), 4.29-4.25 (m, 1H), 3.95 (s, 3H), 3.79 (s, 3H), 3.29-3.27 (m, 2H), 2.83-2.78 (m, 2H), 2.23-2.21 (m, 2H), 1.99-1.85 (m, 2H) ppm; (M+1)=525.

Example 3-6: Synthesis of 1-(3-Methoxy-4-((6-methoxypyridin-3-yl)methoxy)benzyl)-5-(4-(piperidin-3-yl)-1H-1,2,3-triazol-1-yl)-1H-benzo[d]imidazole To a suspension of 5-iodo-1-(3-methoxy-4-((6-methoxypyridin-3-yl)methoxy)benzyl)-1H-benzo[d]imidazole (0.32 g, 0.63 mmol) in dimethyl sulfoxide (4 mL) and water (1 mL) was added 3-ethynylpiperidine hydrochloride (0.11 g, 0.75 mmol), sodium azide (0.051 g, 0.79 mmol), L-ascorbic acid sodium salt (0.025 g, 0.13 mmol), trans-N,N'-dimethylcyclohexane-1,2-diamine (0.023 mg, 0.158 mmol), potassium carbonate (0.13 g, 0.95 mmol), and copper(I) iodide (0.024 g, 0.13 mmol). The resulting blue mixture was allowed to stir at room temperature. After 16 h, the yellow mixture was diluted with 5N ammonium hydroxide solution and extracted with chloroform (2×30 mL). The combined organic phases were dried over magnesium sulfate, filtered, and concentrated to provide 0.53 g of a yellow oil. Chromatographic purification (Combi-Flash, 24 g $SiO_2$ gold column, 1-10% 2M ammonia in methanol/dichloromethane elute) afforded 0.15 g (45%) of the product as a white foamy solid: $^1$H NMR (400 MHz, DMSO-$d_6$) δ 8.61-8.53 (m, 2H), 8.20 (d, J=2.4 Hz, 1H), 8.11 (d, J=1.9 Hz, 1H), 7.79-7.71 (m, 3H), 7.12 (d, J=1.9 Hz, 1H), 7.03 (d, J=8.2 Hz, 1H), 6.89-6.80 (m, 2H), 5.46 (s, 2H), 4.97 (s, 2H), 3.84 (s, 3H), 3.73 (s, 3H), 3.25-3.16 (m, 1H), 3.01-2.91 (m, 1H), 2.90-2.80 (m, 1H), 2.68-2.51 (m, 2H), 2.12-2.03 (m, 1H), 1.72-1.44 (m, 3H) ppm; (M+1)=526.

Example 3-7: Synthesis of 2-(1-(3-Methoxy-4-((6-methoxypyridin-3-yl)methoxy)benzyl)-1H-benzo[d]imidazol-5-yl)-5-(piperidin-4-yl)-1,3,4-oxadiazole Example 3-7-1: Preparation of 1-(3-methoxy-4-((6-methoxypyridin-3-yl)methoxy)benzyl)-1H-benzo[d]imidazole-5-carbonitrile To a stirred solution of 5-iodo-1-(3-methoxy-4-((6-methoxypyridin-3-yl)methoxy)benzyl)-1H-benzo[d]imidazole (1.00 g, 1.99 mmol) in N,N-dimethylformamide (20 mL) was added zinc(II) cyanide (0.64 g, 3.52 mmol), tetrakis(triphenylphosphine)palladium(O) (0.46 g, 0.40 mmol) and potassium carbonate (0.63 g, 4.54 mmol). The mixture was heated to 150° C. After 4 h, the mixture was allowed to cool to room temperature and was concentrated. The residue was purified by silica gel chromatography (2% methanol/dichloromethane elute) to give 0.70 g (87%) of 1-(3-methoxy-4-((6-methoxypyridin-3-yl)methoxy)benzyl)-1H-benzo[d]imidazole-5-carbonitrile as a yellow solid.

Example 3-7-2: Preparation of 1-(3-methoxy-4-((6-methoxypyridin-3-yl)methoxy)benzyl)-1H-benzo[d]imidazole-5-carboxylic acid To a solution of 1-(3-methoxy-4-((6-methoxypyridin-3-yl)methoxy)benzyl)-1H-benzo[d]imidazole-5-carbonitrile (0.70 g, 1.75 mmol) in 1,4-dioxane (10 mL) was added 50% sodium hydroxide solution (20 mL). The resulting mixture was heated to reflux and stirred. After 48 h, the reaction mixture was allowed to cool to room temperature and was extracted with 10% methanol in dichloromethane. The extracts were washed with brine, dried and concentrated. The residue was purified by Prep-HPLC to afford 0.50 g (68%) of 1-(3-methoxy-4-((6-methoxypyridin-3-yl)methoxy)benzyl)-1H-benzo[d]imidazole-5-carboxylic acid as a light yellow solid.

Example 3-7-3: Preparation of tert-butyl 4-(2-(1-(3-methoxy-4-((6-methoxypyridin-3-yl)methoxy)benzyl)-1H-benzo[d]imidazole-5-carbonyl)hydrazinecarbonyl)piperidine-1-carboxylate To a solution of 1-(3-methoxy-4-((6-methoxypyridin-3-yl)methoxy)benzyl)-1H-benzo[d]imidazole-5-carboxylic acid (0.30 g, 0.72 mmol) in dichloromethane was added tert-butyl 4-(hydrazinecarbonyl)piperidine-1-carboxylate (0.24 g, 0.98 mmol), 1-[bis(dimethylamino)methylene]-1H-1,2,3-triazolo[4,5-b]pyridinium 3-oxid hexafluorophosphate (0.34 g, 0.89 mmol), diisopropylamine (0.19 g, 1.47 mmol). The resulting mixture was allowed to stir at room temperature. After 16 h, the mixture was concentracted and the residue was purified by silica gel chromatography (2% methanol/dichloromethane elute) to afford 0.30 g (65%) tert-butyl 4-(2-(1-(3-methoxy-4-((6-methoxypyridin-3-yl)methoxy)benzyl)-1H-benzo[d]imidazole-5-carbonyl)hydrazinecarbonyl)piperidine-1-carboxylate as a yellow solid.

Example 3-7-4: Preparation of tert-butyl 4-(5-(1-(3-methoxy-4-((6-methoxypyridin-3-yl)methoxy)benzyl)-1H-benzo[d]imidazol-5-yl)-1,3,4-oxadiazol-2-yl)piperidine-1-carboxylate To a stirred mixture of tert-butyl 4-(2-(1-(3-methoxy-4-((6-methoxypyridin-3-yl)methoxy)benzyl)-1H-benzo[d]imidazole-5-carbonyl)hydrazinecarbonyl)piperidine-1-carboxylate (0.18 g, 0.28 mmol) in 2,4,6-tripropyl-1,3,5,2,4,6-trioxatriphosphinane 2,4,6-trioxide ($T_3P$) (2.70 g, 8.49 mmol) was added triethylamine (0.42 g, 4.20 mmol). The resulting mixture was heated 120° C. and stirred. After 16 h, the mixture was extracted with dichloromethane. The extracts were washed with brine, dried and concentrated. The residue was purified by silica gel chromatography (1% methanol/dichloromethane elute) to afford 0.14 g (70%) of tert-butyl 4-(5-(1-(3-methoxy-4-((6-methoxypyridin-3-yl)methoxy)benzyl)-1H-benzo[d]imidazol-5-yl)-1,3,4-oxadiazol-2-yl)piperidine-1-carboxylate as a yellow solid.

Example 3-7-5: Preparation of 2-(1-(3-Methoxy-4-((6-methoxypyridin-3-yl)methoxy)benzyl)-1H-benzo[d]imidazol-5-yl)-5-(piperidin-4-yl)-1,3,4-oxadiazol To a −20° C. solution of tert-butyl 4-(5-(1-(3-methoxy-4-((6-methoxypyridin-3-yl)methoxy)benzyl)-1H-benzo[d]imidazol-5-yl)-1,3,4-oxadiazol-2-yl)piperidine-1-carboxylate (0.090 mg, 0.14 mmol) in dichloromethane (10 mL) was added trifluoroacetic acid (1.0 mL). The resulting mixture was stirred at −20° C. After 1 h, the mixture was concentrated. The residue was purified by Prep-HPLC to afford 0.010 g (14%) of the product as a yellow solid: $^1$H NMR (500 MHz, CDCl$_3$) δ 8.43 (s, 1H), 8.19 (d, J=1.0 Hz, 1H), 8.02-8.01 (m, 2H), 7.67 (dd, J=8.5, 2.0 Hz, 1H), 7.42 (d, J=8.5 Hz, 1H), 6.89 (d, J=8.5 Hz, 1H), 6.76-6.72 (m, 3H), 5.32 (s, 2H), 5.03 (s, 2H), 3.93 (s, 3H), 3.78 (s, 3H), 3.31-3.29 (m, 2H), 3.23-3.21 (m, 1H), 2.92-2.88 (m, 2H), 2.23-2.21 (m, 2H), 2.02-1.98 (m, 2H) ppm; (M+1)=527.

Example 3-8: Synthesis of 1-(3-Methoxy-4-((6-methoxypyridin-3-yl)methoxy)benzyl)-5-(piperidin-4-yl)-1H-benzo[d]imidazole

Example 3-8-1: Preparation of tert-butyl 4-(1-(3-methoxy-4-((6-methoxypyridin-3-yl)methoxy)benzyl)-1H-benzo[d]imidazol-5-yl)-5,6-dihydropyridine-1(2H)-carboxylate To a stirred solution of 5-iodo-1-(3-methoxy-4-((6-methoxypyridin-3-yl)methoxy)benzyl)-1H-benzo[d]imidazole (0.801 g, 1.60 mmol) in 1,4-dioxane (10 mL) and 2 M sodium carbonate solution (3.2 mL) was added 4-(4, 4, 5, 5-tetramethyl-1, 3, 2-dioxaborolan-2-yl)-5, 6-dihydropyridine-1(2H)-carboxylate (0.65 mg, 2.10 mmol). The mixture was treated with [1,1'-bis(diphenylphosphino)ferrocene]dichloropalladium(II) (0.12 mg, 0.16 mmol) and heated to 100° C. After 16 h, the reaction mixture was allowed to cool to room temperature and filtered. The filtrate was diluted with water (30 mL) and extracted with dichloromethane (3×50 mL). The combined organic layers were washed with brine (30 mL×2), dried over sodium sulfate, and concentrated. The residue was purified by silica gel chromatography (5% methanol/dichloromethane elute) to afford 0.79 mg (89%) of tert-butyl 4-(1-(3-methoxy-4-((6-methoxypyridin-3-yl)methoxy)benzyl)-1H-benzo[d]imidazol-5-yl)-5,6-dihydropyridine-1(2H)-carboxylate as a light yellow solid.

Example 3-8-2: Preparation of tert-butyl 4-(1-(4-hydroxy-3-methoxybenzyl)-1H-benzo[d]imidazol-5-yl)piperidine-1-carboxylate To a stirred solution of tert-butyl 4-(1-(3-methoxy-4-((6-methoxypyridin-3-yl)methoxy)benzyl)-1H-benzo[d]imidazol-5-yl)-5,6-dihydropyridine-1(2H)-carboxylate (0.56 g, 1.00 mmol) in methanol (15 mL) was added ammonium formate (0.63 g, 10 mmol) and palladium on carbon (0.30 g). The reaction mixture was heated to 60° C. under $H_2$. After 16 h, the reaction mixture was allowed to cool to room temperature and was filtered through Celite. The filtrate was concentrated. The residue was purified by silica gel chromatography (5% methanol/dichloromethane elute) to afford 0.42 g (96%) of tert-butyl 4-(1-(4-hydroxy-3-methoxybenzyl)-1H-benzo[d]imidazol-5-yl)piperidine-1-carboxylate as a light yellow solid.

Example 3-8-3: Preparation of tert-butyl 4-(1-(3-methoxy-4-((6-methoxypyridin-3-yl)methoxy)benzyl)-1H-benzo[d]imidazol-5-yl)piperidine-1-carboxylate To a stirred solution of tert-butyl 4-(1-(4-hydroxy-3-methoxybenzyl)-1H-benzo[d]imidazol-5-yl)piperidine-1-carboxylate (0.51 g, 1.16 mmol) in N,N-dimethylformamide (5 mL) was added potassium carbonate (0.32 g, 2.32 mmol). The mixture was treated with a solution of 5-(chloromethyl)-2-methoxypyridine (219 mg, 1.39 mmol) in N,N-dimethylformamide (2 mL) added dropwise. The mixture was stirred at room temperature. After 16 h, the mixture was diluted with saturated ammonium chloride solution (20 mL) and extracted with ethyl acetate (3×30 mL). The combined organic layers were washed with brine (3×10 mL), dried over sodium sulfate, filtered and concentrated to afford 0.53 g (82%) of tert-butyl 4-(1-(3-methoxy-4-((6-methoxypyridin-3-yl)methoxy)benzyl)-1H-benzo[d]imidazol-5-yl)piperidine-1-carboxylate as a light yellow solid.

Example 3-8-4: Preparation of 1-(3-Methoxy-4-((6-methoxypyridin-3-yl)methoxy)benzyl)-5-(piperidin-4-yl)-1H-benzo[d]imidazole To a stirred and cooled (5° C.) solution of tert-butyl 4-(1-(3-methoxy-4-((6-methoxypyridin-3-yl)methoxy)benzyl)-1H-benzo[d]imidazol-5-yl)piperidine-1-carboxylate (0.28 g, 0.51 mmol) in dichloromethane (1 mL) was added trifluoroacetic acid (1 mL). The resulting mixture was allowed to warm room temperature and stir. After 2 h, the mixture was treated with 1 N sodium hydroxide solution to achieve a pH 10 and was extracted with dichloromethane (3×10 mL). The combined organic layers were washed with brine (3×10 mL), dried over sodium sulfate, concentrated. The residue was purified by prep-HPLC to afford 0.018 g (8%) of the product as a white solid: $^1$H NMR (500 MHz, MeOD-$d_4$) δ 8.25 (s, 1H), 8.16 (d, J=2.5 Hz, 1H), 7.76 (dd, J=8.5, 2.5 Hz, 1H), 7.55 (s, 1H), 7.40 (d, J=8.5 Hz, 1H), 7.20 (dd, J=8.5, 1.0 Hz, 1H), 7.00-6.97 (m, 2H), 6.82-6.79 (m, 2H), 5.41 (s, 2H), 5.01 (s, 2H), 3.91 (s, 3H), 3.79 (s, 3H), 3.24-3.21 (m, 2H), 2.86-2.81 (m, 3H), 1.93-1.90 (m, 2H), 1.78-1.75 (m, 2H) ppm; (M+1)=459.

Example 3-9: Synthesis of 4-(1-(3-Methoxy-4-((6-methoxypyridin-3-yl)methoxy)benzyl)-1H-benzo[d]imidazol-5-yl)morpholine To a suspension of 5-iodo-1-(3-methoxy-4-((6-methoxypyridin-3-yl)methoxy)benzyl)-1H-benzo[d]imidazole (0.32 g, 0.64 mmol) in dimethyl sulfoxide (4 mL) was added morpholine (0.067 g, 0.77 mmol), copper(I) iodide (0.015 g, 0.076 mmol), potassium carbonate (0.22 g, 1.54 mmol), and L-proline (0.018 g, 0.15 mmol). The light yellow reaction mixture was heated to 120° C. After 16 h, the reaction mixture was allowed to cool to room temperature and was diluted with 3 N ammonium hydroxide solution (20 mL). The mixture was extracted with dichloromethane (×3). The combined organic phases were washed with water (×2), brine, dried over magnesium sulfate, filtered, and concentrated. Chromatographic purification (CombiFlash, 40 g SiO2 column, 1-5% methanol/dichloromethane elute) afforded 0.076 g (26%) of the product as an off-white solid: $^1$H NMR (400 MHz, CDCl$_3$) δ 8.18 (d, J=1.9 Hz, 1H), 7.85 (s, 1H), 7.66 (dd, J=8.5, 2.5 Hz, 1H), 7.35-7.13 (m, 2H), 6.98 (dd, J=8.8, 2.2 Hz, 1H), 6.90-6.82 (m, 1H), 6.78-6.67 (m, 3H), 5.23 (s, 2H), 5.02 (s, 2H), 3.93 (s, 3H), 3.95-3.85 (m, 4H), 3.76 (s, 3H), 3.18-3.12 (m, 4H) ppm; (M+1)=461.

Example 3-10: Synthesis of 2-(1-(1-(3-Methoxy-4-((6-methoxypyridin-3-yl)methoxy)benzyl)-1H-benzo[d]imidazol-5-yl)piperidin-4-yl)propan-2-amine

Example 3-10-1: Preparation of 2-(piperidin-4-yl)propan-2-amine Dihydrochloride A stirred suspension of cesium(III) chloride (5.27 g, 21.40 mmol) in tetrahydrofuran (50 mL) was heated to 60° C. After 2 h, the mixture was allowed to cool to room temperature and was treated with tert-butyl 4-cyanopiperidine-1-carboxylate (2.25 g, 10.70 mmol). The mixture was cooled to −20° C. while a 1.5 M solution of methyllithium lithium bromide complex (21.4 mL, 32.10 mmol) was added. After 1 h at −20° C., the mixture was quenched with saturated ammonium chloride solution and diluted with ethyl acetate. The biphasic mixture was filtered to remove the undissolved solid material, and the layers of the filtrate were separated. The organic phase was washed with brine, dried over magnesium sulfate, filtered, and concentrated. The residue was treated with Dowex 50-WX8-200 acidic resin in methanol (1.1 eq/mL, 20 mL added). After 2 h at room temperature, the mixture was filtered. The filtercake was washed with methanol followed by ammonia in methanol (3 M to 6 M). The filtrate was concentrated to provide a waxy solid (containing both the free diamine and the carbamate-protected monoamine). This crude mixture was dissolved in methanol and was treated with hydrogen chloride (2.0 M in diethyl ether). The mixture was allowed to stir at room temperature. After 20 h, the mixture was concentrated. The residue was suspended in toluene and reconcentrated to afford 0.96 g (42%) of 2-(piperidin-4-yl)propan-2-amine dihydrochloride as a white solid.

Example 3-10-2: Preparation of 2-(1-(1-(3-Methoxy-4-((6-methoxypyridin-3-yl)methoxy)benzyl)-1H-benzo[d]imidazol-5-yl)piperidin-4-yl)propan-2-amine To a stirred suspension of 5-iodo-1-(3-methoxy-4-((6-methoxypyridin-3-yl)methoxy)benzyl)-1H-benzo[d]imidazole (0.15 g, 0.30 mmol) in dimethyl sulfoxide (5 mL) was added 2-(piperidin-4-yl)propan-2-amine dihydrochloride (0.19 g, 0.90 mmol), copper(I) iodide (0.005 g, 0.030 mmol), potassium carbonate (0.25 g, 1.80 mmol), and L-proline (0.007 g, 0.057 mmol). The light yellow reaction mixture was heated to 100° C. After 24 h, an additional portion of L-proline (0.007 g, 0.057 mmol) was added and heating continued. After an additional 5 h, the reaction mixture was allowed to cool to room temperature and was diluted with ammonium hydroxide solution and ethyl acetate. The organic phase was separated and washed with saturated sodium bicarbonate solution (×2), brine, dried over magnesium sulfate, filtered, and concentrated. Chromatographic purification (Biotage, 10 g SiO2 column, 10% methanol/dichloromethane to 3 M ammonia in methanol/dichloromethane elute) provided an oil. The oil was dissolved in aqueous acetonitrile and lyophilized to afford 0.070 g (45%) of the product as tan solid: $^1$H NMR (400 MHz, CDCl$_3$) 8.20 (s, 1H), 7.85 (s, 1H), 7.67 (d, J=8.0 Hz, 1H), 7.35 (s, 1H), 7.17 (d, J=8.0 Hz, 1H), 7.03 (d, J=8.0 Hz, 1H), 6.87 (d, J=8.0 Hz, 1H), 6.77-6.72 (m, 2H), 6.71 (s, 1H), 5.23 (s, 2H), 5.03 (s, 2H), 3.94 (s, 3H), 3.77 (s, 3H), 3.72-3.68 (m, 2H), 2.67 (t, J=12.0 Hz, 2H), 1.89 (dd, J=12.0, 4.0 Hz, 2H), 1.53-1.50 (m, 2H), 1.35-1.25 (m, 1H), 1.15 (s, 6H) ppm; (M+1)=516.

Example 3-11: Synthesis of 1-(3-methoxy-4-((6-methoxypyridin-3-yl)methoxy)benzyl)-5-(2,7-diazaspiro[3.5]nonan-2-yl)-1H-benzo[d]imidazole Example 3-11-1: Preparation of tert-butyl 2-(1-(3-methoxy-4-((6-methoxypyridin-3-yl)methoxy)benzyl)-1H-benzo[d]imidazol-5-yl)-2,7-diazaspiro[3.5]nonane-7-carboxylate To a stirred suspension of 5-iodo-1-(3-methoxy-4-((6-methoxypyridin-3-yl)methoxy)benzyl)-1H-benzo[d]imidazole (0.61 g, 1.22 mmol) in dimethyl sulfoxide (4 mL) was added tert-butyl 2,7-diazaspiro[3.5]nonane-7-carboxylate (0.30 g, 1.34 mmol), copper(I) iodide (0.028 g, 0.15 mmol), potassium carbonate (0.41 g, 2.94 mmol), and L-proline (0.034 g, 0.29 mmol). The light yellow reaction mixture was heated to 120° C. After 16 h, the reaction mixture was allowed to cool to room temperature and was diluted with 3 N ammonium hydroxide solution (20 mL). The mixture was extracted with dichloromethane, resulting in a thick emulsion. The emulsion was filtered through Celite to remove any insoluble material. The organic phase was washed with water, brine, dried over magnesium sulfate, filtered, and concentrated. Chromatographic purification (CombiFlash, 40 g SiO2 column, 1-5% methanol/dichloromethane elute) afforded 0.53 g (72%) of tert-butyl 2-(1-(3-methoxy-4-((6-methoxypyridin-3-yl)methoxy)benzyl)-1H-benzo[d]imidazol-5-yl)-2,7-diazaspiro[3.5]nonane-7-carboxylate.

Example 3-11-2: Preparation of 1-(3-methoxy-4-((6-methoxypyridin-3-yl)methoxy)benzyl)-5-(2,7-diazaspiro[3.5]nonan-2-yl)-1H-benzo[d]imidazole To a stirred solution of tert-butyl 2-(1-(3-methoxy-4-((6-methoxypyridin-3-yl)methoxy)benzyl)-1H-benzo[d]imidazol-5-yl)-2,7-diazaspiro[3.5]nonane-7-carboxylate (0.53 g, 0.88 mmol) in dichloromethane (10 mL) was added trifluoroacetic acid (5.0 mL. 64.90 mmol). The reaction mixture was allowed to stir at room temperature. After 1 h, the mixture was concentrated, and the residue partitioned between 3 M ammonium hydroxide solution and dichloromethane. The phases were separated, and the aqueous phase was extracted with dichloromethane. The combined organic phases were washed with brine, dried over magnesium sulfate, filtered, and concentrated. Chromatographic purification (Combi-Flash, 40 g SiO$_2$ gold column, 1-15% methanol/dichloromethane elute) afforded 0.28 g (64%) of the product as a solid: $^1$H NMR (400 MHz, CDCl$_3$) δ 8.18 (d, J=2.1 Hz, 1H), 7.80 (s, 1H), 7.65 (dd, J=8.5, 2.4 Hz, 1H), 7.10 (d, J=8.6 Hz, 1H), 6.88-6.79 (m, 2H), 6.78-6.65 (m, 3H), 6.47 (dd, J=8.6, 2.1 Hz, 1H), 5.18 (s, 2H), 5.00 (s, 2H), 3.92 (s, 3H), 3.75 (s, 3H), 3.61 (s, 4H), 2.86-2.78 (m, 4H), 2.54 (b, 1H), 1.82-1.74 (m, 4H) ppm; (M+1)=500.

Example 3-12: Synthesis of 1-(1-(3-Methoxy-4-((6-methoxypyridin-3-yl)methoxy)benzyl)-1H-benzo[d]imidazol-5-yl)piperidin-4-amine Example 3-12-1: Preparation of tert-butyl (1-(1-(3-methoxy-4-((6-methoxypyridin-3-yl)methoxy)benzyl)-1H-benzo[d]imidazol-5-yl)piperidin-4-yl)carbamate To a suspension of 5-iodo-1-(3-methoxy-4-((6-methoxypyridin-3-yl)methoxy)benzyl)-1H-benzo[d]imidazole (0.48 g, 0.96 mmol) in dimethyl sulfoxide (4 mL) was added tert-butyl piperidin-4-ylcarbamate (0.22 g, 1.05 mmol), copper(I) iodide (0.022 g, 0.11 mmol), potassium carbonate (0.32 g, 2.32 mmol), and L-proline (0.026 g, 0.23 mmol). The light yellow reaction mixture was heated to 120° C. After 16 h, additional portions tert-butyl piperidin-4-ylcarbamate (0.048 g, 0.47 mmol), copper(I) iodide (0.018 g, 0.095 mmol), and L-proline (0.022 g, 0.19 mmol) were added. Heating was continued for an additional 4 h. After a total of 20 h, the reaction mixture was allowed to cool to room temperature and was diluted with 3 N ammonium hydroxide solution (25 mL). The mixture was extracted with dichloromethane (×3). The combined organic phases were washed with water (×2), brine, dried over magnesium sulfate, filtered, and concentrated. Chromatographic purification (CombiFlash, 40 g SiO2 column, 1-10% methanol/dichloromethane elute) afforded 0.33 g (60%) of tert-butyl (1-(1-(3-methoxy-4-((6-methoxypyridin-3-yl)methoxy)benzyl)-1H-benzo[d]imidazol-5-yl)piperidin-4-yl)carbamate as an impure solid.

Example 3-12-2: Preparation of 1-(1-(3-Methoxy-4-((6-methoxypyridin-3-yl)methoxy)benzyl)-1H-benzo[d]imidazol-5-yl)piperidin-4-amine To a stirred solution of tert-butyl (1-(1-(3-methoxy-4-((6-methoxypyridin-3-yl)methoxy)benzyl)-1H-benzo[d]imidazol-5-yl)piperidin-4-yl)carbamate (0.33 g, 0.58 mmol) in dichloromethane (10 mL) was added trifluoroacetic acid (5.0 mL. 64.90 mmol). The reaction mixture was allowed to stir at room temperature. After 2 h, the mixture was concentrated, and the residue partitioned between 3 M ammonium hydroxide solution and dichloromethane. The phases were separated, and the aqueous phase was extracted with dichloromethane. The combined organic phases were washed with brine, dried over magnesium sulfate, filtered, and concentrated. Chromatographic purification (Combi-Flash, 40 g SiO$_2$ gold column, 1-15% methanol/dichloromethane elute) afforded 0.19 g (62%) of the product as a solid: $^1$H NMR (400 MHz, CDCl$_3$) δ 8.18 (d, J=2.0 Hz, 1H), 7.83 (s, 1H), 7.65 (dd, J=8.5, 2.4 Hz, 1H), 7.36-7.26 (m, 1H), 7.15 (d, J=8.8 Hz, 1H), 7.01 (dd, J=8.8, 2.2 Hz, 1H), 6.89-6.82 (m, 1H), 6.78-6.67 (m, 3H), 5.21 (s, 2H), 5.01 (s, 2H), 3.93 (s, 3H), 3.76 (s, 3H), 3.60-3.52 (m, 2H), 2.85-2.72 (m, 3H), 1.98-1.90 (m, 2H), 1.80 (b, 2H), 1.62-1.50 (m, 2H) ppm; (M+1)=474.

Example 3-13: Synthesis of 1-(3-Methoxy-4-((6-methoxypyridin-3-yl)methoxy)benzyl)-5-(4-methylpiperazin-1-yl)-1H-benzo[d]imidazole To a stirred suspension of 5-iodo-1-(3-methoxy-4-((6-methoxypyridin-3-yl)methoxy)benzyl)-1H-benzo[d]imidazole (0.25 g, 0.50 mmol) in dimethyl sulfoxide (5 mL) was added 1-methylpiperazine (0.28 g, 1.50 mmol), copper(I) iodide (0.029 g, 0.15 mmol), sodium carbonate (0.32 g, 2.60 mmol), and L-proline (0.035 g, 0.30 mmol). The mixture was heated to 90° C. in a microwave reactor. After 1 h, the reaction mixture was allowed to cool to room temperature and was filtered through Celite. The filtrate was concentrated, and the residue purified via prep-HPLC to afford 0.045 g (19%) of the product as a white solid: $^1$H NMR (500 MHz, CDCl$_3$) δ 8.20 (d, J=2.5 Hz, 1H), 7.87 (s, 1H), 7.68 (dd, J=8.5, 2.0 Hz, 1H), 7.36 (d, J=1.0 Hz, 1H), 7.18 (d, J=9.0 Hz, 1H), 7.02 (dd, J=9.0, 2.0 Hz, 1H), 6.88 (d, J=8.5 Hz, 1H), 6.77 (d, J=8.5 Hz, 1H), 6.73-6.72 (m, 2H), 5.25 (s, 2H), 5.04 (s, 2H), 3.95 (s, 3H), 3.78 (s, 3H), 3.24-3.18 (m, 4H), 2.67-2.62 (m, 4H), 2.39 (s, 3H) ppm; (M+1)=474.

Example 3-14: Synthesis of 1-(2-Amino-1-(3-methoxy-4-((6-methoxypyridin-3-yl)methoxy)benzyl)-1H-benzo[d]imidazol-5-yl)-4-methylpiperazin-2-one

Example 3-14-1: Preparation of 5-iodo-1-(3-methoxy-4-((6-methoxypyridin-3-yl)methoxy)benzyl)-1H-benzo[d]imidazol-2-amine To a stirred suspension of 4-iodo-N-(3-methoxy-4-((6-methoxypyridin-3-yl)methoxy)benzyl)benzene-1,2-diamine (3.82 g, 7.77 mmol) in dichloromethane (40 mL) and methanol (20 mL) was added cyanogen bromide solution (5.0 M in acetonitrile, 7.8 mL, 38.87 mmol). The resulting brown reaction mixture was allowed to stir at room temperature. After 18 h, the mixture was treated with 1N sodium hydroxide solution (50 mL) and allowed to stir. After 30 min, the phases were separated, and the aqueous phase was extracted with chloroform. The combined organic phases were dried over magnesium sulfate, filtered, and concentrated to provide 5.26 g of a brown semi solid. Chromatographic purification (Combi-Flash, 80 g SiO2 column, 5-10% methanol/dichloromethane elute) afforded 2.78 g (69%) of 5-iodo-1-(3-methoxy-4-((6-methoxypyridin-3-yl)methoxy)benzyl)-1H-benzo[d]imidazol-2-amine as a brown solid.

Example 3-14-2: Preparation of 1-(2-Amino-1-(3-methoxy-4-((6-methoxypyridin-3-yl)methoxy)benzyl)-1H-benzo[d]imidazol-5-yl)-4-methylpiperazin-2-one To a stirred suspension of 5-iodo-1-(3-methoxy-4-((6-methoxypyridin-3-yl)methoxy)benzyl)-1H-benzo[d]imidazol-2-amine (0.25 g, 0.48 mmol) in 1,4-dioxane (8 mL) was added 4-methylpiperazin-2-one (0.11 g, 0.96 mmol), CuI (0.036 mg, 0.19 mmol), trans-N,N-dimethylcyclohexane-1,2-diamine (0.044 g, 0.38 mmol), and tribasic potassium phosphate (0.32 g, 1.52 mmol). The mixture was heated to 145° C. in a microwave reactor. After 3 h, the mixture was allowed to cool to room temperature and was filtrated through Celite. The filtrate was concentrated, and the residue was purified by silica gel chromatography (2-5% methanol/dichloromethane elute) followed by prep-HPLC to afford 0.030 g (12%) of the product as a white solid: $^1$H NMR (500 MHz, CDCl$_3$) δ 8.17 (s, 1H), 7.66 (dd, J=8.0, 2.0 Hz, 1H), 7.25 (s, 1H), 7.01 (d, J=8.0 Hz, 1H), 6.86 (d, J=8.0 Hz, 1H), 6.79 (d, J=8.0 Hz, 1H), 6.76-6.74 (m, 2H), 6.64 (d, J=7.5 Hz, 1H), 4.99 (s, 2H), 4.89 (br s, 2H), 4.81 (s, 2H), 3.94 (s, 3H), 3.79 (s, 3H), 3.72 (t, J=5.0 Hz, 2H), 3.30 (s, 2H), 2.82 (t, J=5.0 Hz, 2H), 2.44 (s, 3H) ppm; (M+1)=503.

Example 3-15: Synthesis of 3-(3-Methoxy-4-((4-methoxybenzyl)oxy)benzyl)-6-(1-methyl-1H-pyrazol-4-yl)-3H-imidazo[4,5-b]pyridin-2-amine

Example 3-15-1: Preparation of 5-bromo-N-(3-methoxy-4-(4-methoxybenzyloxy)benzyl)-3-nitropyridin-2-amine To a stirred solution of 3-methoxy-4-(4-methoxybenzyloxy)phenyl)methanamine (2.00 g, 7.32 mmol) and 5-bromo-2-chloro-3-nitropyridine (1.66 g, 6.97 mmol) in acetonitrile (50 mL) was added N,N-diisopropylethylamine (1.13 g, 8.71 mmol). The resulting mixture was heated to reflux and allowed to stir. After 64 h, the reaction mixture was allowed to cool to room temperature and was diluted with water. The mixture was extracted twice with dichloromethane. The combined organic phases were dried over magnesium sulfate, filtered, and concentrated to provide 3.34 g (>100%) of 5-bromo-N-(3-methoxy-4-(4-methoxybenzyloxy)benzyl)-3-nitropyridin-2-amine as a yellow-brown solid.

Example 3-15-2: Preparation of 5-bromo-N$^2$-(3-methoxy-4-(4-methoxybenzyloxy)benzyl)pyridine-2,3-diamine To a stirred solution of 5-bromo-N-(3-methoxy-4-(4-methoxybenzyloxy)benzyl)-3-nitropyridin-2-amine in tetrahydrofuran (40 mL), ethanol (40 mL), and water (40 mL) was added sodium hydrosulfite (6.09 g, 34.99 mmol). The resulting mixture was heated to reflux and allowed to stir. After 4 h, the reaction mixture was allowed to cool to room temperature and was diluted with water. The yellow mixture was extracted three times with dichloromethane. The combined organic phases were washed with brine, dried (magnesium sulfate), filtered, and concentrated to provide 3.10 g of a yellow-brown solid. Chromatographic purification (Combi-Flash 40 g SiO$_2$ gold column, 1-2.5% methanol/dichloromethane) afforded 1.28 g (51%) of 5-bromo-N$^2$-(3-methoxy-4-(4-methoxybenzyloxy)benzyl)pyridine-2,3-diamine as a yellow solid.

Example 3-15-3: Preparation of 6-bromo-3-(3-methoxy-4-(4-methoxybenzyloxy)benzyl)-3H-imidazo[4,5-b]pyridin-2-amine To a stirred solution of 5-bromo-N$^2$-(3-methoxy-4-(4-methoxybenzyloxy)benzyl)pyridine-2,3-diamine (0.850 g, 1.91 mmol) in dichloromethane (30 mL) and methanol (30 mL) was added cyanogen bromide (5.0 M in acetontitrile, 573 µL, 2.87 mmol). The resulting solution was allowed to stir at room temperature. After 24 h, a second aliquot of cyanogen bromide solution was added (600 µL) and stirring continued. After 48 h, a third aliquot of cyanogen bromide solution (600 µL) was added and stirring continued. After a total of 72 h, the reaction mixture was concentrated, and the residue was dissolved in dichloromethane. The solution was washed with 1N sodium hydroxide solution, dried over magnesium sulfate, filtered, and concentrated to provide 1.17 g of a brown solid. Chromatographic purification (Combi-Flash, 40 g SiO$_2$ gold column, 1-10% 2M ammonia in methanol/dichloromethane) afforded 0.28 g (32%) of 6-bromo-3-(3-methoxy-4-(4-methoxybenzyloxy)benzyl)-3H-imidazo[4,5-b]pyridin-2-amine as a brown solid.

Example 3-15-4: Preparation of 3-(3-Methoxy-4-((4-methoxybenzyl)oxy)benzyl)-6-(1-methyl-1H-pyrazol-4-yl)-3H-imidazo[4,5-b]pyridin-2-amine To a stirred solution of 6-bromo-3-(3-methoxy-4-(4-methoxybenzyloxy)benzyl)-3H-imidazo[4,5-b]pyridin-2-amine (0.25 g, 0.53 mmol) in 1,4-dioxane (10 mL) and water (4 mL) was added 1-methyl-4-(4,4,5,5-tetramethyl-1,3,2-dioxaborolan-2-yl)-1H-pyrazole (0.14 g, 0.66 mmol), potassium phosphate tribasic (0.39 g, 1.84 mmol), tricyclohexylphosphine (0.015 g, 0.052 mmol), palladium(II) acetate (0.005 g, 0.026 mmol). The reaction mixture heated to 125° C. in a microwave reactor. After 15 min, the reaction mixture was allowed to cool to room temperature and was diluted with water. The mixture was extracted twice with ethyl acetate. The combined organic phases were washed with brine, dried over magnesium sulfate, filtered, and concentrated to provide 0.36 g of a greenish brown solid. Chromatographic purification (Combi-Flash, 12 g SiO$_2$ gold column, 1-10% 2M ammonia in methanol/dichloromethane) afforded 0.10 g (41%) of the product as a light green solid: $^1$H NMR (400 MHz, DMSO-d6) δ 8.12-8.08 (m, 2H), 7.83 (d, J=0.6 Hz, 1H), 7.58 (d, J=1.9 Hz, 1H), 7.32 (d, J=8.7 Hz, 2H), 7.08 (d, J=1.9 Hz, 1H), 6.96-6.85 (m, 5H), 6.72 (dd, J=8.3, 1.9 Hz, 1H), 5.18 (s, 2H), 4.92 (s, 2H), 3.85 (s, 3H), 3.74 (s, 3H), 3.70 (s, 3H) ppm, (M+1)=471.

Example 3-16: Synthesis of (5-(2-Amino-3-(3-methoxy-4-((4-methoxybenzyl)oxy)benzyl)-3H-imidazo[4,5-b]pyridin-6-yl)pyridin-2-yl)dimethylphosphine oxide Example 3-16-1: Preparation of 5-iodo-N-(3-methoxy-4-((4-methoxybenzyl)oxy)benzyl)-3-nitropyridin-2-amine To a stirred solution of 3-methoxy-4-(4-methoxybenzyloxy)phenyl)methanamine (3.80 g, 13.92 mmol) and 2-chloro-5-iodo-3-nitropyridine (3.77 g, 13.25 mmol) in acetonitrile (50 mL) was added potassium carbonate (2.29 g, 16.57 mmol). The resulting bright yellow mixture was heated to reflux and allowed to stir. After 16 h, the brown reaction mixture was allowed to cool to room temperature and was diluted with water. The mixture was extracted with chloroform (×3). The combined organic phases were dried over magnesium sulfate, filtered, and concentrated to provide 6.88 g (>100%) of 5-iodo-N-(3-methoxy-4-((4-methoxybenzyl)oxy)benzyl)-3-nitropyridin-2-amine as a yellow-brown solid.

Example 3-16-2: Preparation of 5-iodo-N$^2$-(3-methoxy-4-((4-methoxybenzyl)oxy)benzyl)pyridine-2,3-diamine To a stirred suspension of 5-iodo-N-(3-methoxy-4-((4-methoxybenzyl)oxy)benzyl)-3-nitropyridin-2-amine (6.72 g, 13.25 mmol) in tetrahydrofuran (75 mL), methanol (25 mL), and water (25 ml) was added ammonium chloride (5.68 g, 106.0 mmol) and iron(II) sulfate heptahydrate (11.05 g, 39.76 mmol). The yellow mixture was treated with zinc (2.60 g, 39.76 mmol), and the resulting dark mixture was heated to reflux. After 3 h, the reaction mixture was allowed to cool to room temperature and was filtered through Celite with the aid of methanol. The filtrate was concentrated, and the residue was dissolved in chloroform. The solution was washed with water, filtered through Celite, dried over magnesium sulfate, filtered, and concentrated to provide 6.67 g (>100%) of 5-iodo-N$^2$-(3-methoxy-4-((4-methoxybenzyl)oxy)benzyl)pyridine-2,3-diamine as a brown solid.

Example 3-16-3: Preparation of 6-iodo-3-(3-methoxy-4-((4-methoxybenzyl)oxy)benzyl)-3H-imidazo[4,5-b]pyridin-2-amine To a stirred suspension of 5-iodo-N$^2$-(3-methoxy-4-((4-methoxybenzyl)oxy)benzyl)pyridine-2,3-diamine (6.33 g, 13.25 mmol) in dichloromethane (100 mL) and methanol (50 mL) was added cyanogen bromide solution (5.0M in acetonitrile, 13.3 mL, 66.27 mmol). The resulting dark brown reaction mixture was allowed to stir at room temperature. After 68 h, the now black reaction mixture was treated with 1N sodium hydroxide solution (75 mL) and stirred at room temperature. After 30 min, the mixture was diluted with water, and the phases were separated. The organic phase was dried over magnesium sulfate, filtered, and concentrated to provide 6.43 g of a brown oil. Chromatographic purification (Combi-Flash, 120 g SiO2 column, 1-5% 2M ammonia in methanol/dichloromethane elute) provided 2.40 g of a black oil. A second chromatographic purification (Combi-Flash, 80 g SiO2 column, 1-5% 2M ammonia in methanol/dichloromethane elute) afforded 0.98 g (14%) of 6-iodo-3-(3-methoxy-4-((4-methoxybenzyl)oxy)benzyl)-3H-imidazo[4,5-b]pyridin-2-amine as a gray solid.

Example 3-16-4: Preparation of 6-(6-chloropyridin-3-yl)-3-(3-methoxy-4-((4-methoxybenzyl)oxy)benzyl)-3H-imidazo[4,5-b]pyridin-2-amine To a stirred suspension of 6-iodo-3-(3-methoxy-4-((4-methoxybenzyl)oxy)benzyl)-3H-imidazo[4,5-b]pyridin-2-amine (0.34 g, 0.66 mol) in 1,4-dioxane (10 mL) and water (4 mL) was added (6-chloropyridin-3-yl)boronic acid (0.12 g, 0.76 mmol), potassium phosphate tribasic (0.49 g, 2.33 mmol), tricyclohexylphosphine (0.037 g, 0.13 mmol), and palladium(II) acetate (0.015 g, 0.066 mmol). The reaction mixture was heated to 125° C. in a microwave reactor. After 30 min, the reaction mixture was diluted with water. The mixture was extracted with chloroform (×3). The combined organic phases were dried over magnesium sulfate, filtered, and concentrated to provide 0.44 g of a brown solid. Chromatographic purification (Combi-Flash, 24 g SiO$_2$ gold column, 5-10% methanol/dichloromethane elute) afforded 0.20 g (60%) of 6-(6-chloropyridin-3-yl)-3-(3-methoxy-4-((4-methoxybenzyl)oxy)benzyl)-3H-imidazo[4,5-b]pyridin-2-amine as a tan solid.

Example 3-16-5: Preparation of (5-(2-Amino-3-(3-methoxy-4-((4-methoxybenzyl)oxy)benzyl)-3H-imidazo[4,5-b]pyridin-6-yl)pyridin-2-yl)dimethylphosphine oxide To a stirred suspension of 6-(6-chloropyridin-3-yl)-3-(3-methoxy-4-((4-methoxybenzyl)oxy)benzyl)-3H-imidazo[4,5-b]pyridin-2-amine (0.17 g, 0.34 mmol) in 1,4-dioxane (12 mL) was added dimethylphosphine oxide (0.053 g, 0.69 mmol), 4,5-bis(diphenylphosphino)-9,9-dimethylxanthene (0.079 g, 0.14 mmol), palladium(II) acetate (0.015 g, 0.069 mmol), and cesium carbonate (0.22 g, 0.69 mmol). The reaction mixture was heated to 150° C. in a microwave reactor. After 1 h, the reaction mixture was allowed to cool to room temperature. The mixture was diluted with water and extracted with chloroform (×2). The combined organic phases were dried over magnesium sulfate, filtered, and concentrated to provide 0.27 g of a yellow solid. Chromatographic purification (Combi-Flash, 12 g SiO2 column, 5-10% 2M ammonia in methanol/dichloromethane elute) afforded 0.078 g (42%) of the product as a tan solid: $^1$H NMR (400 MHz, DMSO-d6) δ 9.10 (d, J=1.8 Hz, 1H), 8.32-8.21 (m, 2H), 7.99 (dd, J=7.9, 5.1 Hz, 1H), 7.82 (d, J=1.8 Hz, 1H), 7.32 (d, J=8.6 Hz, 2H), 7.11 (d, J=1.7 Hz, 1H), 7.05 (s, 2H), 6.98-6.87 (m, 3H), 6.72 (dd, J=8.2, 1.7 Hz, 1H), 5.24 (s, 2H), 4.93 (s, 2H), 3.74 (s, 3H), 3.72 (s, 3H), 1.69 (d, J=13.5 Hz, 6H) ppm; (M+1)=544.

Example 3-17: Synthesis of 3-(3-Methoxy-4-((6-methoxypyridin-3-yl)methoxy)benzyl)-6-(4-methylpiperazin-1-yl)-3H-imidazo[4,5-b]pyridine Example 3-17-1: Preparation of 5-iodo-N-(3-methoxy-4-((6-methoxypyridin-3-yl)methoxy)benzyl)-3-nitropyridin-2-amine To a stirred solution of (3-methoxy-4-((6-methoxypyridin-3-yl)methoxy)phenyl)methanamine (9.11 g, 33.21 mmol) in acetonitrile (150 mL) was added 2-chloro-5-iodo-3-nitropyridine (9.90 g, 34.81 mmol) and N,N-diisopropylethylamine (6.44 g, 49.81 mmol). The yellow solution was heated to reflux and stirred. After 3 h, the red-brown mixture was cooled to 0° C. resulting in the formation of a precipitate. The precipitate was isolated by filtration and washed with acetonitrile (50 mL) and water (200 mL). The moist solids were dissolved in dichloromethane, and a small amount of water separated and was removed. The organic phase was dried over magnesium sulfate, filtered, and concentrated to provide 14.67 g (85%) of 5-iodo-N-(3-methoxy-4-((6-methoxypyridin-3-yl)methoxy)benzyl)-3-nitropyridin-2-amine as a yellow-brown solid.

Example 3-17-2: Preparation of 5-iodo-N$^2$-(3-methoxy-4-((6-methoxypyridin-3-yl)methoxy)benzyl)pyridine-2,3-diamine To a stirred suspension of 5-iodo-N-(3-methoxy-4-((6-methoxypyridin-3-yl)methoxy)benzyl)-3-nitropyridin-2-amine (14.67 g, 28.09 mmol) in acetic acid (130 mL) was added iron powder (10.98 g, 196.6 mmol). The bright yellow mixture was warmed to ~85° C. After 15 min of heating, the reaction mixture became a gray-brown suspension and was allowed to cool to room temperature. The mixture was diluted with ethyl acetate (400 mL), and the thick mixture was filtered through Celite with the aid of additional ethyl acetate (100 mL). The filtrate was washed with water (2×150 mL) and 5N ammonium hydroxide solution (4×125 mL). The organic phase was dried over magnesium sulfate, filtered, and concentrated to provide 11.67 g (84%) of 5-iodo-N$^2$-(3-methoxy-4-((6-methoxypyridin-3-yl)methoxy)benzyl)pyridine-2,3-diamine as a tan solid.

Example 3-17-3: Preparation of 6-iodo-3-(3-methoxy-4-((6-methoxypyridin-3-yl)methoxy)benzyl)-3H-imidazo[4,5-b]pyridine To a stirred suspension of 5-iodo-N$^2$-(3-methoxy-4-((6-methoxypyridin-3-yl)methoxy)benzyl)pyridine-2,3-diamine (11.67 g, 23.70 mmol) in ethanol (175 mL) was added triethyl orthoformate (8.90 g, 60.05 mmol) and p-toluenesulfonic acid monohydrate (0.23 g, 1.19 mmol). As the mixture was warmed to reflux, the solids dissolved to provide a brown solution. After 30 min, the reaction mixture was cooled to 0° C., resulting in the formation of a precipitate. The solids were isolated by filtration, washed with a small amount of cold ethanol, and dried to provide 10.34 g (87%) of 6-iodo-3-(3-methoxy-4-((6-methoxypyridin-3-yl)methoxy)benzyl)-3H-imidazo[4,5-b]pyridine as an off-white solid.

Example 3-17-4: Preparation of 3-(3-Methoxy-4-((6-methoxypyridin-3-yl)methoxy)benzyl)-6-(4-methylpiperazin-1-yl)-3H-imidazo[4,5-b]pyridine To a stirred suspension of 6-iodo-3-(3-methoxy-4-((6-methoxypyridin-3-yl)methoxy)benzyl)-3H-imidazo[4,5-b]pyridine (1.40 g, 2.79 mmol) in dimethylsulfoxide (15 mL) was added 1-methylpiperazine (0.44 g, 4.40 mmol), copper (I) iodide (0.16 g, 0.84 mmol), L-proline (0.19 g, 1.67 mmol), and potassium carbonate (0.96 g, 6.97 mmol). The mixture was degassed under vacuum/backfilled with N2 (×3), and then it was heated to 120° C. As the mixture warmed, it became dark blue/black in color. After 19 h, the brown mixture was allowed to cool to room temperature and was diluted with 5N ammonium hydroxide solution (100 mL). The mixture was extracted with dichloromethane (3×50 mL). The combined organic phases were dried over magnesium sulfate, filtered, and concentrated to provide 1.78 g of a brown oil. Chromatographic purification (Combi-Flash, 40 g SiO2 gold column, 1-10% 2M ammonia in methanol/dichloromethane elute) afforded 0.60 g (45%) of the product as a tan solid: $^1$H NMR (400 MHz, CDCl$_3$) δ 8.26 (d, J=2.4 Hz, 1H), 8.18 (d, J=2.4 Hz, 1H), 7.92 (s, 1H), 7.69-7.61 (m, 2H), 6.91-6.84 (m, 2H), 6.80 (dd, J=8.2, 2.0 Hz, 1H), 6.74 (dd, J=8.5 Hz, 1H), 5.34 (s, 2H), 5.02 (s, 2H), 3.93 (s, 3H), 3.80 (s, 3H), 3.25-3.18 (m, 4H), 2.68-2.61 (m, 4H), 2.38 (s, 3H) ppm; (M+1)=475.

Example 3-18: Synthesis of Additional Compounds from 6-iodo-3-(3-methoxy-4-((6-methoxypyridin-3-yl)methoxy)benzyl)-3H-imidazo[4,5-b]pyridine The following compounds 6-iodo-3-(3-methoxy-4-((6-methoxypyridin-3-yl)methoxy)benzyl)-3H-imidazo[4,5-b]

pyridine using the procedure described in Example 3-17-4 by employing the appropriate amine coupling partner:

Example 3-18-1: 2-(1-(3-(3-Methoxy-4-((6-methoxypyridin-3-yl)methoxy)benzyl)-3H-imidazo[4,5-b]pyridin-6-yl)piperidin-4-yl)propan-2-amine $^1$H NMR (400 MHz, CDCl$_3$): 8.20 (s, 1H), 8.11 (s, 1H), 7.85 (s, 1H), 7.58-7.56 (m, 2H), 6.81 (d, J=8.0 Hz, 1H), 6.78 (s, 1H), 6.74 (dd, J=8.0, 4.0 Hz, 1H), 6.67 (d, J=8.0 Hz, 1H), 5.27 (s, 2H), 4.95 (s, 2H), 3.85 (s, 3H), 3.72 (s, 3H), 3.62-3.57 (m, 2H), 2.65 (t, J=12.0 Hz, 2H), 1.83 (dd, J=12.0, 4.0 Hz, 2H), 1.52-1.48 (m, 2H), 1.26-1.24 (m, 1H), 1.06 (s, 6H) ppm; (M+1) 517.

Example 3-18-2: 4-(3-(3-Methoxy-4-((6-methoxypyridin-3-yl)methoxy)benzyl)-3H-imidazo[4,5-b]pyridin-6-yl)morpholine $^1$H NMR (400 MHz, CDCl$_3$) δ 8.24 (d, J=2.5 Hz, 1H), 8.18 (d, J=2.0 Hz, 1H), 7.95 (s, 1H), 7.70-7.59 (m, 2H), 6.92-6.71 (m, 4H), 5.35 (s, 2H), 5.02 (s, 2H), 3.95-3.88 (m, 7H), 3.80 (s, 3H), 3.21-3.13 (m, 4H) ppm; (M+1) 462.

Example 3-18-3: 6-(4-Cyclopropylpiperazin-1-yl)-3-(3-methoxy-4-((6-methoxypyridin-3-yl)methoxy)benzyl)-3H-imidazo[4,5-b]pyridine $^1$H NMR (400 MHz, DMSO-d$_6$) δ 8.43 (s, 1H), 8.24-8.18 (m, 2H), 7.73 (dd, J=8.4, 2.5 Hz, 1H), 7.58 (d, J=2.5 Hz, 1H), 7.10 (d, J=2.0 Hz, 1H), 6.99 (d, J=8.4 Hz, 1H), 6.85-6.78 (m, 2H), 5.34 (s, 2H), 4.96 (s, 2H), 3.84 (s, 3H), 3.72 (s, 3H), 3.13-3.05 (m, 4H), 2.75-2.67 (m, 4H), 1.70-1.63 (m, 1H), 0.48-0.41 (m, 2H), 0.37-0.30 (m, 2H) ppm; (M+1) 501

Example 3-18-4: 4-(3-(3-Methoxy-4-((6-methoxypyridin-3-yl)methoxy)benzyl)-3H-imidazo[4,5-b]pyridin-6-yl)-1,4-diazabicyclo[3.2.2]nonane $^1$H NMR (400 MHz, CDCl$_3$) δ 8.18 (d, J=2.6, 1H), 8.14 (d, J=2.6 Hz, 1H), 7.89 (s, 1H), 7.66 (dd, J=8.5, 2.5 Hz, 1H), 7.49 (d, J=2.5 Hz, 1H), 6.92-6.83 (m, 2H), 6.81 (d, J=8.2, 2.0 Hz, 1H), 6.74 (d, J=8.5 Hz, 1H), 5.32 (s, 2H), 5.02 (s, 2H), 3.93 (s, 3H), 3.80 (s, 3H), 3.54-3.46 (m, 2H), 3.24-2.99 (m, 7H), 2.21-2.09 (m, 2H), 1.81-1.69 (m, 2H) ppm; (M+1) 501.

Example 3-18-5: 3-(3-Methoxy-4-((6-methoxypyridin-3-yl)methoxy)benzyl)-6-(2,7-diazaspiro[3.5]nonan-2-yl)-3H-imidazo[4,5-b]pyridine Synthesis is a two-step process including coupling followed by carbamate deprotection as described for Example 3-11.

$^1$H NMR (400 MHz, CDCl$_3$) δ 8.21-8.16 (m, 1H), 7.93-7.88 (m, 1H), 7.79-7.73 (m, 1H), 7.70-7.62 (m, 1H), 7.14-7.09 (m, 1H), 6.91-6.71 (m, 4H), 5.32 (s, 2H), 5.02 (s, 2H), 3.93 (s, 3H), 3.80 (s, 3H), 3.72-3.67 (m, 4H), 3.10 (b, 1H) 2.90 (s, 4H), 1.90-1.84 (m, 4H) ppm; (M+1) 501.

Example 3-18-6: 1-(3-(3-Methoxy-4-((6-methoxypyridin-3-yl)methoxy)benzyl)-3H-imidazo[4,5-b]pyridin-6-yl)piperidin-4-amine Synthesis is a two-step process including coupling followed by carbamate deprotection as described for Example 3-12.

$^1$H NMR (400 MHz, CDCl$_3$) δ 8.26 (d, J=2.5 Hz, 1H), 8.18 (d, J=2.1 Hz, 1H), 7.93 (s, 1H), 7.70-7.60 (m, 2H), 6.93-6.71 (m, 4H), 5.34 (s, 2H), 5.01 (s, 2H), 3.92 (s, 3H), 3.80 (s, 3H), 3.59-3.51 (m, 2H), 2.88-2.77 (m, 3H), 2.42 (b, 2H), 2.01-1.94 (m, 2H), 1.66-1.51 (m, 2H) ppm; (M+1) 475.

Example 3-18-7: (S)-1-(3-(3-Methoxy-4-((6-methoxypyridin-3-yl)methoxy)benzyl)-3H-imidazo[4,5-b]pyridin-6-yl)pyrrolidine-2-carboxylic acid $^1$H NMR (500 MHz, CD$_3$D) δ 8.31-8.19 (m, 1H), 8.17-8.13 (m, 1H), 7.87 (br s, 1H), 7.64 (dd, J=8.5, 2.5 Hz, 1H), 7.22-7.11 (m, 1H), 7.04 (s, 1H), 6.95 (d, J=8.0 Hz, 1H), 6.84 (d, J=8.0 Hz, 1H), 6.79 (d, J=8.5 Hz, 1H), 5.38 (s, 2H), 4.98 (s, 2H), 4.22-4.12 (m, 1H), 3.90 (s, 3H), 3.78 (s, 3H), 3.68-3.58 (m, 1H), 3.42-3.39 (m, 1H), 2.37-2.08 (m, 4H) ppm; (M+1) 490.

Example 3-19: Synthesis of 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine Example 3-19-1: Preparation of tert-butyl 4-(4-(3-(3-methoxy-4-((6-methoxypyridin-3-yl)methoxy)benzyl)-3H-imidazo[4,5-b]pyridin-6-yl)-1H-pyrazol-1-yl)piperidine-1-carboxylate To a stirred suspension of 6-iodo-3-(3-methoxy-4-((6-methoxypyridin-3-yl)methoxy)benzyl)-3H-imidazo[4,5-b]pyridine (0.20 g, 0.40 mmol) in N,N-dimethylformamide (8 mL) and water (2 mL) was added tert-butyl 4-(4-(4,4,5,5-tetramethyl-1,3,2-dioxaborolan-2-yl)-1H-pyrazol-1-yl)piperidine-1-carboxylate (0.15 g, 0.40 mmol), potassium carbonate (0.22 g, 1.59 mmol), and tetrakis(triphenylphosphino)palladium(O) (0.021 g, 0.018 mmol). The mixture was heated to 100° C. After 1 h, the reaction mixture was allowed to cool to room temperature and was filtered through Celite. The filtrate was concentrated, and the residue purified via silica gel chromatography (5% methanol/dichloromethane elute) to provide 0.15 g (60%) of tert-butyl 4-(4-(3-(3-methoxy-4-((6-methoxypyridin-3-yl)methoxy)benzyl)-3H-imidazo[4,5-b]pyridin-6-yl)-1H-pyrazol-1-yl)piperidine-1-carboxylate as a yellow solid.

Example 3-19-2: Preparation of 3-(3-Methoxy-4-((6-methoxypyridin-3-yl)methoxy)benzyl)-6-(1-(piperidin-4-yl)-1H-pyrazol-4-yl)-3H-imidazo[4,5-b]pyridine To a stirred solution of tert-butyl 4-(4-(3-(3-methoxy-4-((6-methoxypyridin-3-yl)methoxy)benzyl)-3H-imidazo[4,5-b]pyridin-6-yl)-1H-pyrazol-1-yl)piperidine-1-carboxylate (0.15 g, 0.24 mmol) in dichloromethane (10 mL) was added trifluoroacetic acid (0.5 mL). The resulting mixture was stirred at room temperature. After 1 h, the reaction mixture was concentrated, and the residue was diluted with 1M potassium carbonate solution (20 mL) and extracted with dichloromethane (3×10 mL). The combined organic phases were washed with brine (3×20 mL), dried over sodium sulfate, filtered, and concentrated. The residue was purified by Prep-HPLC to afford 0.065 g (52%) of the product as a white solid: $^1$H NMR (500 MHz, CDCl$_3$) δ 8.59 (s, 1H), 8.19 (s, 1H), 8.13 (s, 1H), 8.02 (s, 1H), 7.83 (s, 1H), 7.75 (s, 1H), 7.67 (d, J=8.0 Hz, 1H), 6.93 (s, 1H), 6.89 (d, J=8.0 Hz, 1H), 6.85 (d, J=8.5 Hz, 1H), 6.75 (d, J=8.5 Hz, 1H), 5.40 (s, 2H), 5.03 (s, 2H), 4.30 (m, 1H), 3.94 (s, 3H), 3.82 (s, 3H), 3.31-3.28 (m, 2H), 2.84-2.80 (m, 2H), 2.24-2.22 (m, 2H), 2.04-1.97 (m, 2H) ppm; (M+1)=526.

Example 3-20: Synthesis of 3-(3-Methoxy-4-((6-methylpyridin-3-yl)methoxy)benzyl)-6-(1-(piperidin-4-yl)-1H-pyrazol-4-yl)-3H-imidazo[4,5-b]pyridine

Example 3-20-1: Preparation of Tert-butyl 3-methoxy-4-((6-methylpyridin-3-yl)methoxy)benzylcarbamate To a stirred solution of tert-butyl 4-hydroxy-3-methoxybenzylcarbamate (21.02 g, 82.99 mmol) in acetonitrile (250 mL) was added potassium carbonate (30.61 g, 221.5 mmol) and 5-(chloromethyl)-2-methylpyridine hydrochloride (16.25 g, 91.29 mmol). The resulting mixture was heated to reflux. After 63 h, the brown suspension was allowed to cool to room temperature and was diluted with water (1000 mL). The mixture was extracted with dichloromethane (3×250 mL). The combined organic phases were dried over magnesium sulfate, filtered, and concentrated to provide 31.59 g (>100%) of tert-butyl 3-methoxy-4-((6-methylpyridin-3-yl)methoxy)benzylcarbamate as a brown oil.

Example 3-20-2: Preparation of (3-methoxy-4-((6-methylpyridin-3-yl)methoxy)phenyl)methanamine To a stirred solution of tert-butyl 3-methoxy-4-((6-methylpyridin-3-yl)methoxy)benzylcarbamate (29.74 g, 82.97 mmol) in dichloromethane (100 mL) was added trifluoroacetic acid (50 mL, 649.0 mmol). The resulting brown solution was allowed to stir at room temperature. After 2 h, the reaction mixture was concentrated to dryness, and the residue was dissolved in water (250 mL). The acidic solution was extracted with diethyl ether (2×125 mL; organic phases discarded). The aqueous phase was then made basic with concentrated ammonium hydroxide. The basic aqueous phase was then extracted with dichloromethane (3×100 mL). The combined organic phases were dried over magnesium sulfate, filtered, and concentrated to provide 19.22 g (90%) of (3-methoxy-4-((6-methylpyridin-3-yl)methoxy)phenyl)methanamine as brown solid.

Example 3-20-3: Preparation of 5-iodo-N-(3-methoxy-4-((6-methylpyridin-3-yl)methoxy)benzyl)-3-nitropyridin-2-amine To a stirred solution of (3-methoxy-4-((6-methylpyridin-3-yl)methoxy)phenyl)methanamine (7.30 g, 28.26 mmol) in acetonitrile (200 mL) was added 2-chloro-5-iodo-3-nitropyridine (8.44 g, 29.67 mmol) and N,N-diisopropylethylamine (5.48 g, 42.39 mmol). The brown mixture was heated to reflux. After 5 h, the brown mixture was allowed to cool to room temperature and was diluted with water (600 mL). The resulting precipitate was isolated by filtration and washed with water (200 mL). The moist solids were dissolved in ethyl acetate (300 mL), and this solution was washed with water (100 mL). The organic phase was dried over magnesium sulfate, filtered, and concentrated to provide 13.57 g (95%) of 5-iodo-N-(3-methoxy-4-((6-methylpyridin-3-yl)methoxy)benzyl)-3-nitropyridin-2-amine as a bright yellow solid.

Example 3-20-4: Preparation of 5-iodo-N2-(3-methoxy-4-((6-methylpyridin-3-yl)methoxy)benzyl)pyridine-2,3-diamine To a stirred suspension of 5-iodo-N-(3-methoxy-4-((6-methylpyridin-3-yl)methoxy)benzyl)-3-nitropyridin-2-amine (13.57 g, 26.80 mmol) in acetic acid (100 mL) was added iron powder (8.10 g, 145.0 mmol). The bright yellow suspension was gradually warmed to 90° C. After 30 min of heating, the dark brown reaction mixture was allowed to cool to room temperature and was diluted with ethyl acetate (400 mL). The mixture was filtered through Celite with the aid of additional ethyl acetate (100 mL). The filtrate was then washed with water (2×150 mL) and 1N sodium hydroxide solution (2×200 mL). The organic phase was dried over magnesium sulfate, filtered, and concentrated to provide 6.97 g (55%) of 5-iodo-N2-(3-methoxy-4-((6-methylpyridin-3-yl)methoxy)benzyl)pyridine-2,3-diamine as a brown solid.

Example 3-20-5: Preparation of 6-iodo-3-(3-methoxy-4-((6-methylpyridin-3-yl)methoxy)benzyl)-3H-imidazo[4,5-b]pyridine To a stirred suspension of 5-iodo-N2-(3-methoxy-4-((6-methylpyridin-3-yl)methoxy)benzyl)pyridine-2,3-diamine (6.98 g, 14.65 mmol) in ethanol (100 mL) was added triethyl orthoformate (3.56 g, 24.02 mmol) and p-toluenesulfonic acid monohydrate (0.050 g, 0.26 mmol). As the resulting mixture was warmed to reflux, the solids gradually dissolved to provide a brown solution. After 90 min, the reaction mixture was allowed to cool to room temperature, and the mixture was concentrated to provide 7.91 g of a brown oil. Chromatographic purification (Combi-Flash, 220 g SiO2 gold column, 1-5% methanol/dichloromethane elute) afforded 5.22 g (73%) of 6-iodo-3-(3-methoxy-4-((6-methylpyridin-3-yl)methoxy)benzyl)-3H-imidazo[4,5-b]pyridine as a tan solid.

A portion of this material was used to prepare Example 3-20 using the procedure outlined for the synthesis of Example 3-19: $^1$H NMR (500 MHz, CDCl$_3$) δ 8.58 (d, J=1.5 Hz, 1H), 8.53 (d, J=2.0 Hz, 1H), 8.12 (d, J=2.0 Hz, 1H), 8.00 (s, 1H), 7.83 (s, 1H), 7.74 (s, 1H), 7.66 (dd, J=8.0, 2.0 Hz, 1H), 7.15 (d, J=8.5 Hz, 1H), 6.92 (d, J=1.0 Hz, 1H), 6.86-6.83 (m, 2H), 5.39 (s, 2H), 5.08 (s, 2H), 4.31-4.26 (m, 1H), 3.81 (s, 3H), 3.29-3.26 (m, 2H), 2.82-2.77 (m, 2H), 2.55 (s, 3H), 2.23-2.22 (m, 2H), 2.01-1.92 (m, 2H) ppm; (M+1)=510.

Example 3-21: Synthesis of 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole

Example 3-21-1: Preparation of 3-(3-methoxy-4-((6-methoxypyridin-3-yl)methoxy)benzyl)-3H-imidazo[4,5-b]pyridine-6-carbonitrile To a stirred solution of 6-iodo-3-(3-methoxy-4-((6-methoxypyridin-3-yl)methoxy)benzyl)-3H-imidazo[4,5-b]pyridine (1.00 g, 1.99 mmol) in N,N-dimethylformamide (15 mL) was added copper(I) cyanide (0.53 g, 6.00 mmol). The mixture was heated to 150° C. After 5 h, the mixture was allowed to cool to room temperature and was concentrated. The residue was purified by silica gel chromatography (2% methanol/dichloromethane elute) to give 0.53 g (66%) of 3-(3-methoxy-4-((6-methoxypyridin-3-yl)methoxy)benzyl)-3H-imidazo[4,5-b]pyridine-6-carbonitrile as a yellow solid.

Example 3-21-2: Preparation of N'-hydroxy-3-(3-methoxy-4-((6-methoxypyridin-3-yl)methoxy)benzyl)-3H-imidazo[4,5-b]pyridine-6-carboximidamide To a stirred solution of 3-(3-methoxy-4-((6-methoxypyridin-3-yl)methoxy)benzyl)-3H-imidazo[4,5-b]pyridine-6- carbonitrile (0.53 g, 1.32 mmol) in ethanol was added hydroxylamine solution (50% weight in water, 0.1 mL). The mixture was heated to 100° C. After 1 h, the mixture was concentrated to provide 0.66 g (>100%) of N-hydroxy-3-(3-methoxy-4-((6-methoxypyridin-3-yl)methoxy)benzyl)-3H-imidazo[4,5-b]pyridine-6-carboximidamide as a white solid.

Example 3-21-3: Preparation of tert-butyl 4-(3-(3-(3-methoxy-4-((6-methoxypyridin-3-yl)methoxy) benzyl)-3H-imidazo[4,5-b]pyridin-6-yl)-1,2,4-oxadiazol-5-yl)piperidine-1-carboxylate To a stirred solution of N-hydroxy-3-(3-methoxy-4-((6-methoxypyridin-3-yl)methoxy)benzyl)-3H-imidazo[4,5-b]pyridine-6-carboximidamide (0.38 g, 0.75 mmol) in N,N-dimethylformamide (10 mL) was added 1-(tert-butoxycarbonyl)piperidine-4-carboxylic acid (0.21 g, 0.92 mmol), 1-[bis(dimethylamino)methylene]-1H-1,2,3-triazolo[4,5-b]pyridinium 3-oxide hexafluorophosphate (0.35 g, 0.92 mmol) and N,N-diisopropylethylamine (0.19 g, 1.50 mmol). The reaction mixture was stirred at room temperature. After 1 h, the mixture was diluted with ethyl acetate and brine. The organic phase was separated, dried over magnesium sulfate, filtered, and concentrated. The residue was dissolved in 1,4-dioxane (20 mL) and heated to 85° C. After 16 h, the reaction mixture was allowed to cool to room temperature and was concentrated. The crude product was purified by silica gel chromatography (2% methanol/dichloromethane elute) to provide 0.14 g (25%) of tert-butyl 4-(3-(3-(3-methoxy-4-((6-methoxypyridin-3-yl)methoxy)benzyl)-3H-imidazo[4,5-b]pyridin-6-yl)-1,2,4-oxadiazol-5-yl)piperidine-1-carboxylate as a yellow solid.

Example 3-21-4: Preparation of 3-(3-(3-Methoxy-4-((6-methoxypyridin-3-yl)methoxy)benzyl)-3H-imidazo[4,5-b]pyridin-6-yl)-5-(piperidin-4-yl)-1,2,4-oxadiazole To a stirred solution of tert-butyl 4-(3-(3-(3-methoxy-4-((6-methoxypyridin-3-yl)methoxy)benzyl)-3H-imidazo[4,5-b]pyridin-6-yl)-1,2,4-oxadiazol-5-yl)piperidine-1-carboxylate (0.14 g, 0.22 mmol) in dichloromethane (20 mL) was added trifluoroacetic acid (0.20 g, 1.79 mmol). The reaction mixture was allowed to stir at room temperature. After 1 h, the mixture was diluted with cold saturated sodium carbonate solution. The phases were separated, and the aqueous phase extracted with dichloromethane. The combined organic phases were washed with brine, dried over magnesium sulfate, filtered, and concentrated. The residue was purified by Prep-HPLC to provide 0.067 g (57%) of the product as a white solid: $^1$H NMR (500 MHz, DMSO-d$_6$) δ 9.02 (d, J=1.5 Hz, 1H), 8.75 (s, 1H), 8.58 (d, J=2.0 Hz, 1H), 8.21 (d, J=2.0 Hz, 1H), 7.75 (dd, J=8.5, 2.0 Hz, 1H), 7.16 (d, J=1.5 Hz, 1H), 7.03 (d, J=8.0 Hz, 1H), 6.89 (dd, J=8.0, 2.0 Hz, 1H), 6.83 (d, J=8.5 Hz, 1H), 5.48 (s, 2H), 4.98 (s, 2H), 3.84 (s, 3H), 3.74 (s, 3H), 3.26-3.21 (m, 1H), 3.02-3.00 (m, 2H), 2.65-2.61 (m, 2H), 2.02-2.00 (m, 2H), 1.75-1.67 (m, 2H) ppm; (M+1)=528.

Example 3-22: Synthesis of 3-(1-(3-Methoxy-4-((6-methoxypyridin-3-yl)methoxy)benzyl)-1H-benzo[d]imidazol-5-yl)-5-(piperidin-4-yl)-1,2,4-oxadiazole 3-(1-(3-Methoxy-4-((6-methoxypyridin-3-yl)methoxy)benzyl)-1H-benzo[d]imidazol-5-yl)-5-(piperidin-4-yl)-1,2,4-oxadiazole was prepared from 5-iodo-1-(3-methoxy-4-((6-methoxypyridin-3-yl)methoxy)benzyl)-1H-benzo[d]imidazole using the procedure outlined for Example 3-21: $^1$H NMR (500 MHz, DMSO-d$_6$) δ 8.55 (s, 1H), 8.26 (s, 1H), 8.21 (d, J=2.0 Hz, 1H), 7.89 (d, J=8.5 Hz, 1H), 7.77-7.73 (m, 2H), 7.12 (d, J=1.5 Hz, 1H), 7.03 (d, J=8.0 Hz, 1H), 6.87-6.83 (m, 2H), 5.46 (s, 2H), 4.98 (s, 2H), 3.85 (s, 3H), 3.74 (s, 3H), 3.22-3.17 (m, 1H), 3.02-3.00 (m, 2H), 2.65-2.61 (m, 2H), 2.01-1.99 (m, 2H), 1.73-1.68 (m, 2H) ppm; (M+1)=527.

Example 3-23: Synthesis of 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole 2-(3-(3-Methoxy-4-((6-methoxypyridin-3-yl)methoxy)benzyl)-3H-imidazo[4,5-b]pyridin-6-yl)-5-(piperidin-4-yl)-1,3,4-oxadiazole was prepared from 6-iodo-3-(3-methoxy-4-((6-methylpyridin-3-yl)methoxy)benzyl)-3H-imidazo[4,5-b]pyridine according to the procedure outlined for the synthesis of Example 3-7: $^1$H NMR (500 MHz, CD$_3$D) δ 9.13 (d, J=1.5 Hz, 1H), 8.67-8.62 (m, 2H), 8.15 (d, J=1.5 Hz, 1H), 7.76 (dd, J=8.5, 2.0 Hz, 1H), 7.15 (d, J=1.5 Hz, 1H), 7.01-6.95 (m, 2H), 6.80 (d, J=9.0 Hz, 1H), 5.53 (s, 2H), 5.01 (s, 2H), 3.90 (s, 3H), 3.82 (s, 3H), 3.51-3.46 (m, 3H), 3.21-3.16 (m, 2H), 2.44-2.41 (m, 2H), 2.18-2.09 (m, 2H) ppm; (M+1)=528.

Example 3-24: Synthesis of 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine 2-(1-(3-(3-Methoxy-4-((6-methoxypyridin-3-yl)methoxy)benzyl)-3H-imidazo[4,5-b]pyridin-6-yl)-1H-1,2,3-triazol-4-yl)propan-2-amine was prepared from 6-iodo-3-(3-methoxy-4-((6-methoxypyridin-3-yl)methoxy)benzyl)-3H-imidazo[4,5-b]pyridine and 2-methylbut-3-yn-2-amine according to the procedure described for the synthesis of Example 3-6: $^1$H NMR (400 MHz, DMSO-d$_6$) δ 8.92 (d, J=2.3 Hz, 1H), 8.76 (s, 1H), 8.65 (s, 1H), 8.56 (d, J=2.3 Hz, 1H), 8.21 (d, J=2.5, 1H), 7.74 (dd, J=8.5, 2.5 Hz, 1H), 7.16 (d, J=2.0 Hz, 1H), 7.02 (d, J=8.2 Hz, 1H), 6.88 (dd, J=8.2, 2.0 Hz, 1H), 6.83 (d, J=8.5 Hz, 1H), 5.48 (s, 2H), 4.98 (s, 2H), 3.84 (s, 3H), 3.74 (s, 3H), 1.98 (br s, 2H), 1.46 (s, 6H) ppm; (M+1)=501.

Example 3-25: Synthesis of 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine 3-(3-Methoxy-4-((6-methoxypyridin-3-yl)methoxy)benzyl)-6-(4-(piperidin-3-yl)-1H-1,2,3-triazol-1-yl)-3H-imidazo[4,5-b]pyridine was prepared from 6-iodo-3-(3-methoxy-4-((6-methoxypyridin-3-yl)methoxy)benzyl)-3H-imidazo[4,5-b]pyridine according to the procedure described for the synthesis of Example 3-6: $^1$H NMR (400 MHz, DMSO-d$_6$) δ 8.91 (d, J=2.3 Hz, 1H), 8.76 (s, 1H), 8.64 (s, 1H), 8.56 (d, J=2.3 Hz, 1H), 8.20 (d, J=1.7 Hz, 1H), 7.74 (dd, J=8.5, 2.4 Hz, 1H), 7.16 (d, J=2.0 Hz, 1H), 7.02 (d, J=8.3 Hz, 1H), 6.87 (dd, J=8.3, 2.0 Hz, 1H), 6.83 (d, J=8.5 Hz, 1H), 5.48 (s, 2H), 4.97 (s, 2H), 3.84 (s, 3H), 3.73 (s, 3H), 3.22-3.16 (m, 1H), 2.98-2.79 (m, 2H), 2.65-2.52 (m, 2H), 2.14-2.03 (m, 1H), 1.71-1.43 (m, 3H) ppm; (M+1)=527.

Example 3-26: Synthesis of 1-(3-methoxy-4-((6-methoxypyridin-3-yl)methoxy)benzyl)-5-(4-methylpiperazin-1-yl)-1H-benzo[d]imidazol-2-amine 1-(3-methoxy-4-((6-methoxypyridin-3-yl)methoxy)benzyl)-5-(4-methylpiperazin-1-yl)-1H-benzo[d]imidazol-2-amine was prepared from 5-iodo-1-(3-methoxy-4-((6-methoxypyridin-3-yl)methoxy)benzyl)-1H-benzo[d]imidazol-2-amine and 1-methylpiperazine according to the procedure described for the synthesis of Example 3-13: $^1$H NMR (500 MHz, CDCl$_3$) δ 8.19 (d, J=2.0 Hz, 1H), 7.67 (dd, J=8.5, 3.0 Hz, 1H), 7.09 (d, J=1.5 Hz, 1H), 6.99 (d, J=8.5 Hz, 1H), 6.85 (d, J=8.0 Hz, 1H), 6.79-6.75 (m, 2H), 6.72 (s, 1H), 6.67 (d, J=8.5 Hz, 1H), 5.03 (s, 2H), 5.02 (s, 2H), 3.94 (s, 3H), 3.77 (s, 3H), 3.22-3.17 (m, 4H), 2.65-2.59 (m, 4H), 2.37 (s, 3H) ppm; (M+1)=489.

Example 3-27: Synthesis of 1-(2-fluoro-5-methoxy-4-((6-methoxypyridin-3-yl)methoxy)benzyl)-5-(4-methylpiperazin-1-yl)-1H-benzo[d]imidazole

Example 3-27-1: Preparation of 5-((4-bromo-5-fluoro-2-methoxyphenoxy)methyl)-2-methoxypyridine To a stirred solution of 4-bromo-5-fluoro-2-methoxyphenol (2.82 g, 12.25 mmol) in N,N-dimethylformamide (50 mL) was added 5-(chloromethyl)-2-methoxypyridine hydrochloride (2.50 g, 12.86 mmol) and potassium carbonate (5.08 g, 36.75 mmol). The reaction mixture was heated to 100° C. After 2 h, the mixture was allowed to cool to room temperature and was diluted with water. The mixture was extracted with ethyl acetate (3×25 mL). The combined organic phases were washed with brine, dried over magnesium sulfate, filtered, and concentrated. Chromatographic purification (0-33% ethyl acetate/hexanes elute) afforded 2.76 g (66%) of 5-((4-bromo-5-fluoro-2-methoxyphenoxy)methyl)-2-methoxypyridine as an oil.

Example 3-27-2: Preparation of 2-fluoro-5-methoxy-4-((6-methoxypyridin-3-yl)methoxy)benzonitrile To a stirred solution of 5-((4-bromo-5-fluoro-2-methoxyphenoxy)methyl)-2-methoxypyridine (4.57 g, 13.36 mmol) in N,N-dimethylformamide (50 mL) was added copper(I) cyanide (3.59 g, 40.07 mmol). The mixture was heated to 150° C. After 16 h, the mixture was allowed to cool to room temperature and was diluted with dichloromethane. The mixture was filtered through Celite. The filtrate was washed with water and brine, dried over magnesium sulfate, filtered, and concentrated. Chromatographic purification (Combi-Flash, 80 g SiO2 column, 1-5% methanol/dichloromethane elute) afforded 3.25 g (84%) of 2-fluoro-5-methoxy-4-((6-methoxypyridin-3-yl)methoxy)benzonitrile as an off-white solid.

Example 3-27-3: Preparation of (2-fluoro-5-methoxy-4-((6-methoxypyridin-3-yl)methoxy)phenyl)methanamine To a 0° C. stirred solution of 2-fluoro-5-methoxy-4-((6-methoxypyridin-3-yl)methoxy)benzonitrile (3.25 g, 11.27 mmol) in tetrahydrofuran (50 mL) was added (in three portions) lithium aluminum hydride (0.86 g, 22.55 mmol). Mild gas evolution was noted upon each addition, and the color of the reaction mixture became olive-green. After 1.5 h, the mixture was quenched by the slow addition of water (1.0 mL), 15% sodium hydroxide solution (1.0 mL), and water (3.0 mL). The resulting off-white suspension was allowed to stir at 0° C. After 15 min, the mixture was filtered through Celite with the aid of ethyl acetate. The filtrate was concentrated to provide 1.91 g (58%) of (2-fluoro-5-methoxy-4-((6-methoxypyridin-3-yl)methoxy)phenyl)methanamine as a crude oil.

Example 3-27-4: Preparation of N$^1$-(2-fluoro-5-methoxy-4-((6-methoxypyridin-3-yl)methoxy)benzyl)-4-iodo-2-nitroaniline To a stirred solution of (2-fluoro-5-methoxy-4-((6-methoxypyridin-3-yl)methoxy)phenyl)methanamine (0.89 g, 3.04 mmol) in acetonitrile (15 mL) was added 1-fluoro-4-iodo-2-nitrobenzene (0.89 g, 3.35 mmol) and N,N-diisopropylethylamine. The resulting yellow solution was heated to reflux. After 16 h, the mixture was allowed to cool to room temperature and was diluted with water. The mixture was extracted with ethyl acetate (3×25 mL). The combined organic phases were washed with brine, dried over magnesium sulfate, filtered, and concentrated. Chromatographic purification (Combi-Flash, 40 g SiO2 column, 0-33% ethyl acetate/hexanes elute) afforded 0.38 g (23%) of N-(2-fluoro-5-methoxy-4-((6-methoxypyridin-3-yl)methoxy)benzyl)-4-iodo-2-nitroaniline as a solid.

Example 3-27-5: Preparation of N-(2-fluoro-5-methoxy-4-((6-methoxypyridin-3-yl)methoxy)benzyl)-4-iodobenzene-1,2-diamine To a stirred solution of N-(2-fluoro-5-methoxy-4-((6-methoxypyridin-3-yl)methoxy)benzyl)-4-iodo-2-nitroaniline (0.38 g, 0.70 mmol) in tetrahydrofuran (10 mL), methanol (5 mL), and water (1 mL) was added ammonium chloride (0.30 g, 5.64 mmol) and iron (II) sulfate heptahydrate (0.69 g, 2.47 mmol). The bright orange suspension was treated with zinc (0.16 g, 2.47 mmol). The mixture was gradually warmed to reflux. After 3.5 h, the color of the reaction mixture had turned from orange to olive-green. At this point the reaction mixture was allowed to cool to room temperature. The mixture was filtered through Celite, and the filtercake was washed with chloroform (250 mL). The filtrate was washed with 5N ammonium hydroxide solution (75 mL). The organic phase was dried over magnesium sulfate, filtered, and concentrated to afford 0.36 g (100%) of N$^1$-(2-fluoro-5-methoxy-4-((6-methoxypyridin-3-yl)methoxy)benzyl)-4-iodobenzene-1,2-diamine as a tan solid.

Example 3-27-6: Preparation of 1-(2-fluoro-5-methoxy-4-((6-methoxypyridin-3-yl)methoxy)benzyl)-5-iodo-1H-benzo[d]imidazole To a stirred solution of N$^1$-(2-fluoro-5-methoxy-4-((6-methoxypyridin-3-yl)methoxy)benzyl)-4-iodobenzene-1,2-diamine (0.36 g, 0.70 mmol) in ethanol (10 mL) was added triethyl orthoformate (0.31 g, 2.11 mmol) and p-toluenesulfonic acid (0.007 g, 0.035 mmol). The reaction mixture was heated to reflux. After 30 min, the brown solution was allowed to cool to room temperature and was concentrated. The residue was partitioned between water and dichloromethane. The phases were separated, and the aqueous phase extracted with dichloromethane. The combined organic phases were washed with water and brine, dried over magnesium sulfate, filtered, and concentrated. Chromatographic purification (Combi-Flash, 12 g SiO$_2$ column, 1-5% methanol/dichloromethane elute) afforded 0.25 g (68%) of 1-(2-fluoro-5-methoxy-4-((6-methoxypyridin-3-yl) methoxy)benzyl)-5-iodo-1H-benzo[d]imidazole as a tan solid.

Example 3-27-7: Preparation of 1-(2-fluoro-5-methoxy-4-((6-methoxypyridin-3-yl)methoxy)benzyl)-5-(4-methylpiperazin-1-yl)-1H-benzo[d]imidazole To a stirred suspension of 1-(2-fluoro-5-methoxy-4-((6-methoxypyridin-3-yl)methoxy)benzyl)-5-iodo-1H-benzo[d] imidazole (0.20 g, 0.39 mmol) in dimethyl sulfoxide (4 mL) was added 1-methylpiperazine (0.039 g, 0.39 mmol), copper (I) iodide (0.009 g, 0.046 mmol), potassium carbonate (0.19 g, 1.35 mmol), and L-proline (0.010 g, 0.092 mmol). The light yellow reaction mixture was heated to 120° C. After 16 h, the reaction mixture was allowed to cool to room temperature and was diluted with 3 N ammonium hydroxide solution (20 mL). The mixture was extracted with dichloromethane. The organic phase was washed with water (2×15 mL), brine, dried over magnesium sulfate, filtered, and concentrated. Chromatographic purification (CombiFlash, 40 g SiO$_2$ column, 1-5% methanol/dichloromethane elute) provided 0.062 g of impure material. Subsequent re-purification via Prep-HPLC afforded 0.030 g (16%) of the product as a solid: $^1$H NMR (400 MHz, CDCl$_3$) δ 8.19 (d, J=2.0 Hz, 1H), 7.88 (s, 1H), 7.65 (dd, J=8.5, 2.5 Hz, 1H) 7.33 (d, J=2.1 Hz, 1H), 7.29-7.22 (m, 2H), 7.07-6.99 (m, 1H), 6.78-6.69 (m, 2H), 6.56 (d, J=7.1 Hz, 1H), 5.30 (s, 2H), 5.00 (s, 2H), 3.94 (s, 3H), 3.69 (s, 3H), 3.25-3.18 (m, 4H), 2.71-2.59 (m, 4H), 2.39 (s, 3H) ppm; (M+1)=492.

Example 3-28: Synthesis of 3-(3-Ethoxy-4-((6-methoxypyridin-3-yl)methoxy)benzyl)-6-(4-methylpiperazin-1-yl)-3H-imidazo[4,5-b]pyridine Example 3-28-1: Preparation of 3-ethoxy-4-((6-methoxypyridin-3-yl)methoxy)benzaldehyde To a stirred solution of 3-ethoxy-4-hydroxybenzaldehyde (2.75 g, 16.55 mmol) in acetonitrile (75 mL) was added 5-(chloromethyl)-2-methoxypyridine hydrochloride (3.37 g, 17.38 mmol) and potassium carbonate (9.15 g, 66.20 mmol). The mixture was heated to reflux. After 3 h, the yellow mixture was allowed to cool to room temperature and was diluted with water (400 mL), resulting in the formation of a precipitate. The solids were isolated by filtration and washed with water (50 mL). The filtrate was extracted with chloroform (2×100 mL). The organic phases were combined with the previously isolated solids. The resulting solution was dried over magnesium sulfate, filtered, and concentrated to provide 3.40 g (72%) of 3-ethoxy-4-((6-methoxypyridin-3-yl)methoxy)benzaldehyde as a yellow solid.

Example 3-28-2: Preparation of 3-ethoxy-4-((6-methoxypyridin-3-yl)methoxy)benzaldehyde oxime To a stirred solution of 3-ethoxy-4-((6-methoxypyridin-3-yl)methoxy)benzaldehyde (3.40 g, 11.83 mmol) in methanol (50 mL), pyridine (1.5 mL), and water (5 mL) was added hydroxylamine hydrochloride (1.23 g, 17.75 mmol). The reaction mixture was heated to reflux. After 2 h, the colorless solution was allowed to cool to room temperature and was concentrated. The residue was suspended in water (50 mL) and filtered. The solids were washed with water and then dissolved in ethyl acetate (150 mL). The solution was dried over magnesium sulfate, filtered, and concentrated to provide 3.05 g (85%) of 3-ethoxy-4-((6-methoxypyridin-3-yl) methoxy)benzaldehyde oxime as an off-white solid.

Example 3-28-3: Preparation of (3-ethoxy-4-((6-methoxypyridin-3-yl)methoxy)phenyl)methanamine To a stirred solution of 3-ethoxy-4-((6-methoxypyridin-3-yl)methoxy)benzaldehyde oxime (3.05 g, 10.09 mmol) in acetic acid (25 mL) was added zinc (3.30 g, 50.44 mmol). The resulting mixture was heated to 65° C. After 2 h, the gray suspension was allowed to cool to room temperature and was diluted with ethyl acetate (150 mL). The mixture was filtered through Celite with the aid of additional ethyl acetate (50 mL). The filtrate was diluted with water (50 mL) and made basic by the addition of concentrated ammonium hydroxide solution (~30 mL). The phases were separated, and the aqueous phase was extracted with ethyl acetate (50 mL). The combined organic phases were dried over magnesium sulfate, filtered, and concentrated to provide 2.75 g (95%) of (3-ethoxy-4-((6-methoxypyridin-3-yl)methoxy) phenyl)methanamine as a yellow oil.

Example 3-28-4: Preparation of N-(3-ethoxy-4-((6-methoxypyridin-3-yl)methoxy)benzyl)-5-iodo-3-nitropyridin-2-amine To a stirred solution of (3-ethoxy-4-((6-methoxypyridin-3-yl)methoxy)phenyl)methanamine (2.75 g, 9.54 mmol) in acetonitrile (50 mL) was added 2-chloro-5-iodo-3-nitropyridine (2.85 g, 10.01 mmol) and N,N-diisopropylethylamine (1.85 g, 14.31 mmol). The resulting yellow mixture was heated to reflux. After 3 h, the red-brown solution was allowed to cool to room temperature, resulting in the formation of a precipitate. The solids were isolated by filtration and washed with water (200 mL). The moist solids were dissolved in dichloromethane (100 mL), and a small amount of water separated and was removed. The solution was dried over magnesium sulfate, filtered, and concentrated to provide 4.34 g (85%) of N-(3-ethoxy-4-((6-methoxypyridin-3-yl)methoxy)benzyl)-5-iodo-3-nitropyridin-2-amine as an orange solid.

Example 3-28-5: Preparation of N$^2$-(3-ethoxy-4-((6-methoxypyridin-3-yl)methoxy)benzyl)-5-iodopyridine-2,3-diamine To a stirred suspension of N-(3-ethoxy-4-((6-methoxypyridin-3-yl)methoxy)benzyl)-5-iodo-3-nitropyridin-2-amine (4.34 g, 8.09 mmol) in acetic acid (25 mL) was added iron powder (2.26 g, 40.46 mmol). The reaction mixture was heated to 90° C. After 15 min, the reaction mixture became a gray-brown suspension. The mixture was allowed to cool to room temperature and was diluted with ethyl acetate (200 mL). The mixture was filtered through Celite with the aid of additional ethyl acetate (50 mL). The filtrate was washed with water (2×50 mL) and then with 1N sodium hydroxide solution (3×50 mL). The organic phase was dried over magnesium sulfate, filtered, and concentrated to provide 3.99 g (97%) of N$^2$-(3-ethoxy-4-((6-methoxypyridin-3-yl) methoxy)benzyl)-5-iodopyridine-2,3-diamine as a tan solid.

Example 3-28-6: Preparation of 3-(3-ethoxy-4-((6-methoxypyridin-3-yl)methoxy)benzyl)-6-iodo-3H-imidazo[4,5-b]pyridine To a stirred suspension of N$^2$-(3-ethoxy-4-((6-methoxypyridin-3-yl)methoxy)benzyl)-5-iodopyridine-2,3-diamine (3.99 g, 7.88 mmol) in ethanol (50 mL) was added triethyl orthoformate (2.67 g, 18.02 mmol) and p-toluenesulfonic acid monohydrate (0.075 g, 0.39 mmol). As the mixture was heated to reflux, a brown solution was obtained. After 30 min, the mixture was allowed to cool to room temperature, resulting in the formation of a precipitate. The solids were isolated by filtration, washed with ethanol, and dried to provide 2.50 g (61%) of 3-(3-ethoxy-4-((6-methoxypyridin-3-yl)methoxy)benzyl)-6-iodo-3H-imidazo[4,5-b]pyridine as a tan solid.

Example 3-28-7: Preparation of 3-(3-Ethoxy-4-((6-methoxypyridin-3-yl)methoxy)benzyl)-6-(4-methylpiperazin-1-yl)-3H-imidazo[4,5-b]pyridine To a stirred suspension of 3-(3-ethoxy-4-((6-methoxypyridin-3-yl)methoxy)benzyl)-6-iodo-3H-imidazo[4,5-b]pyridine (0.37 g, 0.71 mmol) in dimethylsulfoxide was added 1-methylpiperazine (0.086 g, 0.85 mmol), copper(I) iodide (0.033 g, 0.18 mmol), L-proline (0.041 g, 0.35 mmol), and potassium carbonate (0.24 g, 1.77 mmol). The mixture was degassed under vacuum/backfilled with $N_2$ (×3) and then heated to 120° C. After 16 h, the dark brown mixture was allowed to cool to room temperature and was diluted with 5N ammonium hydroxide solution (50 mL). The mixture was extracted with dichloromethane (3×50 mL). The combined organic phases were dried over magnesium sulfate, filtered, and concentrated to provide 0.36 g of a brown oil. Chromatographic purification (Combi-Flash, 12 g $SiO_2$ gold column, 5-10% 2M ammonia in methanol/dichloromethane elute) afforded 0.14 g (41%) of the product as an orange solid: $^1$H NMR (400 MHz, DMSO-$d_6$) δ 8.43 (s, 1H), 8.22-8.19 (m, 2H), 7.73 (dd, J=8.5, 2.4 Hz, 1H), 7.59 (d, J=2.4 Hz, 1H), 7.08 (d, J=2.0 Hz, 1H), 6.99 (d, J=8.2 Hz, 1H), 6.86-6.76 (m, 2H), 5.33 (s, 2H), 4.97 (s, 2H), 3.97 (q, J=6.9 Hz, 2H), 3.84 (s, 3H), 3.17-3.08 (m, 4H), 2.53-2.45 (m, 4H), 2.23 (s, 3H), 1.28 (t, J=6.9 Hz, 3H); (M+1)=489.

Example 3-29: Synthesis of 1-(1-(3-Methoxy-4-((6-methoxypyridin-3-yl)methoxy)benzyl)-1H-benzo[d]imidazol-5-yl)-4-methylpiperazin-2-one 1-(1-(3-Methoxy-4-((6-methoxypyridin-3-yl)methoxy)benzyl)-1H-benzo[d]imidazol-5-yl)-4-methylpiperazin-2-one was prepared from 5-iodo-1-(3-methoxy-4-((6-methoxypyridin-3-yl)methoxy)benzyl)-1H-benzo[d]imidazole (Step 5, Example 6) and 4-methylpiperazin-2-one using the procedure outlined for Example 3-14: $^1$H NMR (500 MHz, CDCl$_3$) δ 8.21 (d, J=2.0 Hz, 1H), 7.97 (s, 1H), 7.70-7.68 (m, 2H), 7.34 (d, J=8.5 Hz, 1H), 7.22 (dd, J=8.5, 1.5 Hz, 1H), 6.90-6.89 (m, 1H), 6.78-6.74 (m, 3H), 5.29 (s, 2H), 5.05 (s, 2H), 3.95 (s, 3H), 3.81 (s, 3H), 3.79 (t, J=5.5 Hz, 2H), 3.35 (s, 2H), 2.86 (t, J=5.5 Hz, 2H), 2.46 (s, 3H) ppm; (M+1)=488.

Example 3-30: Synthesis of 3-(3-Methoxy-4-((6-methoxypyridin-3-yl)methoxy)benzyl)-6-(5-methyl-1-azabicyclo[3.2.1]oct-6-en-7-yl)-3H-imidazo[4,5-b]pyridine

Example 3-30-1: Preparation of tert-butyl 3-ethynyl-3-methylpiperidine-1-carboxylate To a stirred solution of tert-butyl 3-formyl-3-methylpiperidine-1-carboxylate (2.10 g, 9.25 mmol) in methanol (40 mL) was added potassium carbonate (2.76 g, 20.00 mmol). The mixture was treated with dimethyl 1-diazo-2-oxopropylphosphonate (2.11 g, 11.00 mmol), and the resulting mixture was allowed to stir at room temperature. After 2 h, the mixture was concentrated, diluted with water, and extracted with ethyl acetate. The organic phase was washed with brine, dried over magnesium sulfate, filtered, and concentrated. The residue was purified by silica gel chromatography (6% ethyl acetate/petroleum ether elute) to afford 1.50 g (73%) of tert-butyl 3-ethynyl-3-methylpiperidine-1-carboxylate as a pale yellow oil.

Example 3-30-2: Preparation of 3-ethynyl-3-methylpiperidine hydrochloride

To a stirred solution of tert-butyl 3-ethynyl-3-methylpiperidine-1-carboxylate (0.50 g, 2.24 mmol) in dichloromethane (10 mL) was added a solution of hydrogen chloride in 1,4-dioxane (3.0M, 5.0 mL, 15.00 mmol). The resulting solution was allowed to stir at room temperature. After 2 h, the mixture was concentrated to provide 0.34 g (95%) of 3-ethynyl-3-methylpiperidine hydrochloride (340 mg, 95%) as a white solid.

Example 3-30-3: Preparation of 3-(3-Methoxy-4-((6-methoxypyridin-3-yl)methoxy)benzyl)-6-(5-methyl-1-azabicyclo[3.2.1]oct-6-en-7-yl)-3H-imidazo[4,5-b]pyridine To a stirred suspension of 6-iodo-3-(3-methoxy-4-((6-methoxypyridin-3-yl)methoxy)benzyl)-3H-imidazo[4,5-b]pyridine (Step 3, Example 19, 0.20 g, 0.40 mmol) in tetrahydrofuran (3.0 mL) was added 3-ethynyl-3-methylpiperidine hydrochloride (0.13 g, 1.00 mmol), bis(triphenylphosphine)palladium(II) chloride (0.055 g, 0.078 mmol), copper(I) iodide (0.030 g, 0.16 mmol), and piperidine (0.17 g, 2.00 mmol). The mixture was heated to 60° C. in a microwave reactor. After 30 min, the mixture was allowed to cool to room temperature and was filtered through Celite. The filtrate was concentrated, and the residue was purified by Prep-HPLC to afford 0.020 g (10%) of the product as a yellow solid: $^1$H NMR (500 MHz, CDCl$_3$) δ 8.77 (d, J=2.0 Hz, 1H), 8.29 (d, J=2.0 Hz, 1H), 8.20 (d, J=2.0 Hz, 1H), 8.01 (s, 1H), 7.68 (dd, J=8.0, 2.0 Hz, 1H), 6.94-6.76 (m, 4H), 6.02 (s, 1H), 5.40 (s, 2H), 5.04 (s, 2H), 3.95 (s, 3H), 3.82 (s, 3H), 3.22 (d, J=8.5 Hz, 1H), 2.94-2.86 (m, 2H), 2.80 (d, J=9.5 Hz, 1H), 1.91-1.85 (m, 1H), 1.60-1.46 (m, 3H), 1.16 (s, 3H) ppm; (M+1)=498.

Example 3-31: Synthesis of 1-(3-methoxy-4-((6-methoxypyridin-3-yl)methoxy)benzyl)-5-(5-methyl-1-azabicyclo[3.2.1]oct-6-en-7-yl)-1H-benzo[d]imidazole 1-(3-methoxy-4-((6-methoxypyridin-3-yl)methoxy)benzyl)-5-(5-methyl-1-azabicyclo[3.2.1]oct-6-en-7-yl)-1H-benzo[d]imidazole was prepared from 5-iodo-1-(3-methoxy-4-((6-methoxypyridin-3-yl)methoxy)benzyl)-1H-benzo[d]imidazole and 3-ethynyl-3-methylpiperidine hydrochloride using the procedure outlined for the synthesis of Example 3-30: $^1$H NMR (500 MHz, CDCl$_3$) δ 8.22-8.21 (m, 1H), 8.09 (s, 1H), 7.93 (s, 1H), 7.69 (dd, J=8.5, 2.5 Hz, 1H), 7.60 (d, J=8.5 Hz, 1H), 7.28-7.26 (m, 1H, partially obscured by CHCl$_3$), 6.89 (d, J=8.5 Hz, 1H), 6.77 (d, J=8.5 Hz, 1H), 6.75-6.73 (m, 2H), 5.93 (s, 1H), 5.28 (s, 2H), 5.04 (s, 2H), 3.95 (s, 3H), 3.80 (s, 3H), 3.21 (dd, J=9.5, 1.5 Hz, 1H), 2.92-2.90 (m, 2H), 2.79 (d, J=10.0 Hz, 1H), 1.87-1.83 (m, 1H), 1.57-1.43 (m, 3H), 1.14 (s, 3H) ppm; (M+1)=497.

Example 3-32: Synthesis of 7-(3-(3-methoxy-4-((6-methoxypyridin-3-yl)methoxy)benzyl)-3H-imidazo[4,5-b]pyridin-6-yl)-1-azabicyclo[3.2.1]oct-6-en-5-ol

Example 3-32-1: Preparation of 3-ethynylpiperidin-3-ol Hydrochloride

3-Ethynylpiperidin-3-ol hydrochloride was prepared from tert-butyl 3-ethynyl-3-hydroxypiperidine-1-carboxylate and hydrogen chloride using the procedure outlined in Example 3-30.

Example 3-32-2: Preparation of 7-(3-(3-methoxy-4-((6-methoxypyridin-3-yl)methoxy)benzyl)-3H-imidazo[4,5-b]pyridin-6-yl)-1-azabicyclo[3.2.1]oct-6-en-5-ol 7-(3-(3-methoxy-4-((6-methoxypyridin-3-yl)methoxy)benzyl)-3H-imidazo[4,5-b]pyridin-6-yl)-1-azabicyclo[3.2.1]oct-6-en-5-ol was prepared from 6-iodo-3-(3-methoxy-4-((6-methoxypyridin-3-yl)methoxy)benzyl)-3H-imidazo[4,5-b]pyridine and 3-ethynylpiperidin-3-ol hydrochloride using the procedure outlined for the synthesis of Example 3-30: $^1$H NMR (500 MHz, CDCl$_3$) δ 8.76 (d, J=2.0 Hz, 1H), 8.29 (d, J=1.5 Hz, 1H), 8.20 (d, J=2.7 Hz, 1H), 8.04 (s, 1H), 7.68 (dd, J=8.5, 2.7 Hz, 1H), 6.93 (d, J=2.0 Hz, 1H), 6.89 (d, J=8.0 Hz, 1H), 6.85 (dd, J=8.0, 1.5 Hz, 1H), 6.77 (d, J=8.5 Hz, 1H), 6.19 (s, 1H), 5.41 (s, 2H), 5.05 (s, 2H), 3.95 (s, 3H), 3.83 (s, 3H), 3.43-3.41 (m, 1H), 2.94-2.91 (m, 1H), 2.85-2.81 (m, 2H), 1.91-1.84 (m, 2H), 1.74-1.71 (m, 2H) ppm; (M+1)=500.

Example 3-33: Synthesis of 7-(1-(3-Methoxy-4-((6-methoxypyridin-3-yl)methoxy)benzyl)-1H-benzo[d]imidazol-5-yl)-1-azabicyclo[3.2.1]oct-6-en-5-ol 7-(1-(3-Methoxy-4-((6-methoxypyridin-3-yl)methoxy)benzyl)-1H-benzo[d]imidazol-5-yl)-1-azabicyclo[3.2.1]oct-6-en-5-ol was prepared from 5-iodo-1-(3-methoxy-4-((6-methoxypyridin-3-yl)methoxy)benzyl)-1H-benzo[d]imidazole and 3-ethynylpiperidin-3-ol hydrochloride using the procedure outlined for the synthesis of Example 3-30: $^1$H NMR (500 MHz, CDCl$_3$) δ 8.21 (d, J=2.5 Hz, 1H), 8.09 (s, 1H), 7.95 (s, 1H), 7.69 (dd, J=8.5, 2.5 Hz, 1H), 7.59 (dd, J=8.5, 1.0 Hz, 1H), 7.29-7.26 (m, 1H, partially obscured by CHCl$_3$), 6.89 (d, J=9.0 Hz, 1H), 6.77 (d, J=8.5 Hz, 1H), 6.75-6.73 (m, 2H), 6.09 (s, 1H), 5.29 (s, 2H), 5.05 (s, 2H), 3.95 (s, 3H), 3.80 (s, 3H), 3.41-3.39 (m, 1H), 2.92-2.83 (m, 3H), 1.89-1.81 (m, 3H), 1.71-1.67 (m, 1H) ppm; (M+1)=499.

Example 3-34: Synthesis of 3-(3-methoxy-4-(1-(6-methoxypyridin-3-yl)propoxy)benzyl)-6-(1-methyl-1H-pyrazol-4-yl)-3H-imidazo[4,5-b]pyridin-2-amine

Example 3-34-1: Preparation of Ethyl N—({5-iodo-2-[({3-methoxy-4-[(4-methoxyphenyl)methoxy]phenyl}methyl)amino]pyridin-3-yl}carbamothioyl)carbamate To a stirred solution of 5-iodo-N$^2$-(3-methoxy-4-((4-methoxybenzyl)oxy)benzyl)pyridine-2,3-diamine (Example 3-16-2) (2.00 g, 4.07 mmol) and triethylamine (1.30 g, 1.8 mL, 12.85 mmol) in tetrahydrofuran (20 mL) was added O-ethyl carbonisothiocyanatidate (1.07 g, 8.20 mmol). The reaction mixture was allowed to stir at room temperature. After 3 h, the mixture was filtered, and the filtrate was concentrated to provide 2.30 g of ethyl N—({5-iodo-2-[({3-methoxy-4-[(4-methoxyphenyl)methoxy]phenyl}methyl)amino]pyridin-3-yl}carbamothioyl)carbamate as a yellow oil.

Example 3-34-2: Preparation of Ethyl (6-iodo-3-(3-methoxy-4-((4-methoxybenzyl)oxy)benzyl)-3H-imidazo[4,5-b]pyridin-2-yl)carbamate To a stirred solution of ethyl N—({5-iodo-2-[({3-methoxy-4-[(4-methoxyphenyl)methoxy]phenyl}methyl)amino]pyridin-3-yl}carbamothioyl)carbamate (2.30 g, 3.69 mmol) and triethylamine (1.30 g, 1.8 mL, 12.85 mmol) in tetrahydrofuran (20 mL) was added benzenesulfonyl chloride (0.93 g, 5.27 mmol). The resulting mixture was allowed to stir at room temperature. After 12 h, a precipitate had formed. The mixture was filtered, and the filtercake was washed with water (2×10 mL) and methanol (10 mL). The solids were dried to provide 1.50 g (69%) of ethyl (6-iodo-3-(3-methoxy-4-((4-methoxybenzyl)oxy)benzyl)-3H-imidazo[4,5-b]pyridin-2-yl)carbamate as a brown solid.

Example 3-34-3: Preparation of Ethyl (3-(3-methoxy-4-((4-methoxybenzyl)oxy)benzyl)-6-(1-methyl-1H-pyrazol-4-yl)-3H-imidazo[4,5-b]pyridin-2-yl)carbamate To a stirred solution of ethyl (6-iodo-3-(3-methoxy-4-((4-methoxybenzyl)oxy)benzyl)-3H-imidazo[4,5-b]pyridin-2-yl)carbamate (11.80 g, 20.05 mmol) and 1-methyl-4-(4,4,5,5-tetramethyl-1,3,2-dioxaborolan-2-yl)-1H-pyrazole (5.00 g, 24.03 mmol) in N,N-dimethylformamide (100 mL) and 2M aqueous sodium carbonate solution (10 mL) was added (1,1'-bis(diphenylphosphino)ferrocene)palladium(II) dichloride (0.87 g, 1.19 mmol). The resulting mixture was heated to 80° C. under a nitrogen atmosphere. After 4 h, the mixture was allowed to cool to room temperature and was filtered through Celite. The filtrate was diluted with water (150 mL) and extracted with ethyl acetate (3×200 mL). The combined organic phases were washed with water (300 mL) and brine (2×300 mL), dried over sodium sulfate, filtered, and concentrated. Chromatographic purification (silica gel, 5% methanol in dichloromethane elute) afforded 2.50 g (23%) of ethyl (3-(3-methoxy-4-((4-methoxybenzyl)oxy)benzyl)-6-(1-methyl-1H-pyrazol-4-yl)-3H-imidazo[4,5-b]pyridin-2-yl)carbamate as a gray solid.

Example 3-34-4: Preparation of Ethyl (3-(4-hydroxy-3-methoxybenzyl)-6-(1-methyl-1H-pyrazol-4-yl)-3H-imidazo[4,5-b]pyridin-2-yl)carbamate To a stirred solution of ethyl (3-(3-methoxy-4-((4-methoxybenzyl)oxy)benzyl)-6-(1-methyl-1H-pyrazol-4-yl)-3H-imidazo[4,5-b]pyridin-2-yl)carbamate (2.50 g, 4.61 mmol) in dichloromethane (100 mL) at 0° C. was added trifluoroacetic acid (4.47 g, 3.0 mL, 39.18 mmol). The resulting mixture was allowed to stir at 0° C. After 2 h, the mixture was treated with 2M potassium carbonate solution to adjust the pH to ~9. The basic mixture was extracted with 1:1 methanol/dichloromethane solution (2×50 mL). The combined organic phases were washed with brine (2×50 mL), dried over sodium sulfate, filtered, and concentrated to provide 1.80 g (93%) of ethyl (3-(4-hydroxy-3-methoxybenzyl)-6-(1-methyl-1H-pyrazol-4-yl)-3H-imidazo[4,5-b]pyridin-2-yl)carbamate as a white solid.

Example 3-34-5: Preparation of 5-(1-chloropropyl)-2-methoxypyridine

To a stirred solution of 1-(6-methoxypyridin-3-yl)propan-1-ol (1.67 g, 9.99 mmol) in dichloromethane (30 mL) at 0° C. was added thionyl chloride (2.46 g, 1.5 mL, 20.68 mmol). The cooling bath was removed, and the mixture was allowed to warm to room temperature. After 1 h, the reaction was quenched by the addition of saturated aqueous sodium bicarbonate solution. The phases were separated, and the organic phase was washed with brine (20 mL), dried over sodium sulfate, filtered, and concentrated to provide 1.50 g (81%) of 5-(1-chloropropyl)-2-methoxypyridine as a yellow oil.

Example 3-34-6: Preparation of 3-(3-methoxy-4-(1-(6-methoxypyridin-3-yl)propoxy)benzyl)-6-(1-methyl-1H-pyrazol-4-yl)-3H-imidazo[4,5-b]pyridin-2-amine To a stirred solution of ethyl (3-(4-hydroxy-3-methoxybenzyl)-6-(1-methyl-1H-pyrazol-4-yl)-3H-imidazo[4,5-b]pyridin-2-yl)carbamate (0.300 g, 0.710 mmol) in tetrahydrofuran (20 mL) was added 5M aqueous sodium hydroxide solution (0.72 mL, 3.60 mmol). The resulting mixture was allowed to stir at room temperature. After 2 h, the mixture was concentrated, and the residue was dissolved in N,N-dimethylformamide (10 mL). The solution was treated with 5-(1-chloropropyl)-2-methoxypyridine (0.263 g, 1.42 mmol), and the resulting mixture was heated to 80° C. After 3 h, the mixture was allowed to cool to room temperature and was diluted with water (20 mL). The mixture was extracted with ethyl acetate (3×40 mL). The combined organic phases were dried over sodium sulfate, filtered, and concentrated to provide 0.26 g of a brown solid. The crude solid was dissolved in ethylene glycol (6 mL) and water (2 mL). The solution was treated with potassium hydroxide (0.13 g, 2.32 mmol) and heated to 100° C. After 12 h, the mixture was allowed to cool to room temperature and was filtered through Celite. The filtrate was concentrated, and the residue was purified by prep-HPLC to afford 0.070 g (30%) of the product as a white solid: $^1$H NMR (500 MHz, DMSO-$d_6$) δ 8.10-8.07 (m, 3H), 7.83 (s, 1H), 7.66-7.64 (m, 1H), 7.57 (d, J=1.5 Hz, 1H), 7.04 (d, J=1.5 Hz, 1H), 6.86 (s, 2H), 6.77-6.74 (m, 2H), 6.58-6.57 (m, 1H), 5.15-5.12 (m, 3H), 3.85 (s, 3H), 3.79 (s, 3H), 3.72 (s, 3H), 1.95-1.90 (m, 1H), 1.78-1.74 (m, 1H), 0.85 (t, J=7.5 Hz, 3H) ppm; (M+1)=500.

Example 3-35: Synthesis of Additional Compounds from Ethyl (3-(4-hydroxy-3-methoxybenzyl)-6-(1-methyl-1H-pyrazol-4-yl)-3H-imidazo[4,5-b]pyridin-2-yl)carbamate The following compounds were prepared from ethyl (3-(4-hydroxy-3-methoxybenzyl)-6-(1-methyl-1H-pyrazol-4-yl)-3H-imidazo[4,5-b]pyridin-2-yl)carbamate using the procedure described in Example 3-34-6 by employing the appropriate alkylating agent:

Example 3-35-1: 3-(3-methoxy-4-((6-methoxypyridin-3-yl)methoxy)benzyl)-6-(1-methyl-1H-pyrazol-4-yl)-3H-imidazo[4,5-b]pyridin-2-amine $^1$H NMR (500 MHz, DMSO-$d_6$) δ 8.21 (d, J=2.5 Hz, 1H), 8.12-8.11 (m, 2H), 7.85 (s, 1H), 7.74 (dd, J=8.5, 2.0 Hz, 1H), 7.59 (d, J=1.5 Hz, 1H), 7.10 (d, J=1.5 Hz, 1H), 6.98 (d, J=8.5 Hz, 1H), 6.89 (s, 2H), 6.83 (d, J=8.5 Hz, 1H), 6.74 (dd, J=8.0, 1.5 Hz, 1H), 5.19 (s, 2H), 4.96 (s, 2H), 3.86 (s, 3H), 3.84 (s, 3H), 3.71 (s, 3H) ppm; (M+1)=472.

Example 3-35-2: 3-(3-methoxy-4-((6-(trifluoromethyl)pyridin-3-yl)methoxy)benzyl)-6-(1-methyl-1H-pyrazol-4-yl)-3H-imidazo[4,5-b]pyridin-2-amine $^1$H NMR (400 MHz, DMSO-$d_6$) δ 8.81 (s, 1H), 8.11-8.09 (m, 3H), 7.93 (d, J=8.0 Hz, 1H), 7.85 (s, 1H), 7.59 (d, J=2.0 Hz, 1H), 7.14 (d, J=1.6 Hz, 1H), 7.00-6.98 (m, 1H), 6.91 (s, 2H), 6.75-6.72 (m, 1H), 5.21-5.20 (m, 4H), 3.86 (s, 3H), 3.74 (s, 3H) ppm; (M+1)=510.

Example 3-35-3: 3-(3-methoxy-4-((4-(trifluoromethyl)benzyl)oxy)benzyl)-6-(1-methyl-1H-pyrazol-4-yl)-3H-imidazo[4,5-b]pyridin-2-amine (RA09651030)

$^1$H NMR (500 MHz, MeOD-$d_4$) δ 8.17 (s, 1H), 7.98 (s, 1H), 7.83 (s, 1H), 7.68-7.61 (m, 5H), 7.00 (d, J=1.5 Hz, 1H), 6.92 (d, J=8.0 Hz, 1H), 6.75-6.74 (m, 1H), 5.29 (s, 2H), 5.15 (s, 2H), 3.95 (s, 3H), 3.80 (s, 3H) ppm; (M+1)=509.

Example 3-35-4: 3-(4-((6-cyclopropylpyridin-3-yl)methoxy)-3-methoxybenzyl)-6-(1-methyl-1H-pyrazol-4-yl)-3H-imidazo[4,5-b]pyridin-2-amine (RA09677155)

$^1$H NMR (500 MHz, DMSO-$d_6$) δ 8.42 (d, J=1.5 Hz, 1H), 8.11 (d, J=2.0 Hz, 1H), 8.10 (s, 1H), 7.85 (s, 1H), 7.66 (dd, J=8.0, 2.5 Hz, 1H), 7.59 (d, J=2.5 Hz, 1H), 7.28 (d, J=8.0 Hz, 1H), 7.10 (d, J=2.0 Hz, 1H), 6.97 (d, J=8.5 Hz, 1H), 6.89 (s, 2H), 6.73 (dd, J=8.0, 1.0 Hz, 1H), 5.19 (s, 2H), 4.98 (s, 2H), 3.86 (s, 3H), 3.71 (s, 3H), 2.10-2.07 (m, 1H), 0.95-0.89 (m, 4H) ppm; (M+1)=482.

Example 3-35-5: 3-(3-methoxy-4-((2-methylthiazol-4-yl)methoxy)benzyl)-6-(1-methyl-1H-pyrazol-4-yl)-3H-imidazo[4,5-b]pyridin-2-amine $^1$H NMR (500 MHz, DMSO-$d_6$) δ 8.11-8.10 (m, 2H), 7.85 (s, 1H), 7.59 (d, J=1.5 Hz, 1H), 7.48 (s, 1H), 7.11 (d, J=1.5 Hz, 1H), 7.00 (d, J=8.0 Hz, 1H), 6.90 (s, 2H), 6.74-6.72 (m, 1H), 5.19 (s, 2H), 5.01 (s, 2H), 3.86 (s, 3H), 3.72 (s, 3H) 2.64 (s, 3H) ppm; (M+1)=462.

Example 3-36: Synthesis of 3-(3-methoxy-4-((6-methoxypyridin-3-yl)methoxy)benzyl)-6-phenyl-3H-imidazo[4,5-b]pyridin-2-amine

Example 3-36-1: Preparation of Ethyl (3-(4-hydroxy-3-methoxybenzyl)-6-iodo-3H-imidazo[4,5-b]pyridin-2-yl)carbamate To a stirred solution of ethyl (6-iodo-3-(3-methoxy-4-((4-methoxybenzyl)oxy)benzyl)-3H-imidazo[4,5-b]pyridin-2-yl)carbamate (Example 3-34-2) (2.40 g, 4.08 mmol) in dichloromethane (50 mL) at 0° C. was added trifluoroacetic acid (4.47 g, 3.0 mL, 39.18 mmol). The resulting mixture was allowed to stir at 0° C. After 2 h, the mixture was treated with 2M potassium carbonate solution to adjust the pH to 9. The basic mixture was extracted with 1:1 methanol/dichloromethane solution (3×50 mL). The combined organic phases were washed with brine (50 mL), dried over sodium sulfate, filtered, and concentrated to provide 1.30 g (70%) of ethyl (3-(4-hydroxy-3-methoxybenzyl)-6-iodo-3H-imidazo[4,5-b]pyridin-2-yl)carbamate as a light yellow solid.

Example 3-36-2: Preparation of Ethyl (6-iodo-3-(3-methoxy-4-((6-methoxypyridin-3-yl)methoxy)benzyl)-3H-imidazo[4,5-b]pyridin-2-yl)carbamate To a stirred solution of ethyl (3-(4-hydroxy-3-methoxybenzyl)-6-iodo-3H-imidazo[4,5-b]pyridin-2-yl)carbamate( ) (1.30 g, 2.78 mmol) and 5M aqueous sodium hydroxide solution (0.8 mL, 4.00 mmol) in N,N-dimethylformamide (10 mL) and tetrahydrofuran (10 mL) was added 5-(chloromethyl)-2-methoxypyridine (0.567 g, 3.60 mmol). The resulting mixture was allowed to stir at room temperature. After 2 h, the mixture was diluted with brine (40 mL) and extracted with ethyl acetate (3×40 mL). The combined organic phases were dried over sodium sulfate, filtered, and concentrated to provide 1.10 g (71%) of ethyl (6-iodo-3-(3-methoxy-4-((6-methoxypyridin-3-yl)methoxy)benzyl)-3H-imidazo[4,5-b]pyridin-2-yl)carbamate as a white solid.

Example 3-36-3: Preparation of Ethyl (3-(3-methoxy-4-((6-methoxypyridin-3-yl)methoxy)benzyl)-6-phenyl-3H-imidazo[4,5-b]pyridin-2-yl)carbamate To a stirred solution of ethyl (6-iodo-3-(3-methoxy-4-((6-methoxypyridin-3-yl)methoxy)benzyl)-3H-imidazo[4,5-b]pyridin-2-yl)carbamate (0.300 g, 0.51 mmol), phenylboronic acid (0.093 g, 0.76 mmol), and sodium carbonate (0.108 g, 1.20 mmol) in 1,4-dioxane (8 mL) and water (3 mL) was added (1,1'-bis(diphenylphosphino)ferrocene)palladium(II) dichloride (0.080 g, 0.11 mmol). The mixture was heated to 60° C. under a nitrogen atmosphere. After 4 h, the reaction mixture was allowed to cool to room temperature and was filtered through Celite. The filtrate was diluted with water (40 mL) and extracted with ethyl acetate (3×20 mL). The combined organic phases were washed with brine (2×20 mL), dried over sodium sulfate, filtered, and concentrated. Chromatographic purification of the residue (silica gel, 2% methanol in dichloromethane elute) afforded 0.100 g (40%) of ethyl (3-(3-methoxy-4-((6-methoxypyridin-3-yl)methoxy)benzyl)-6-phenyl-3H-imidazo[4,5-b]pyridin-2-yl)carbamate as a white solid.

Example 3-36-4: Preparation of 3-(3-methoxy-4-((6-methoxypyridin-3-yl)methoxy)benzyl)-6-phenyl-3H-imidazo[4,5-b]pyridin-2-amine To a stirred solution of ethyl (3-(3-methoxy-4-((6-methoxypyridin-3-yl)methoxy)benzyl)-6-phenyl-3H-imidazo[4,5-b]pyridin-2-yl)carbamate (0.090 g, 0.17 mmol) in ethylene glycol (10 mL) and water (10 mL) was added potassium hydroxide (1.00 g, 17.82 mmol). The mixture was heated to 100° C. After 48 h, the mixture was allowed to cool to room temperature and was diluted with water (30 mL). The mixture was extracted with dichloromethane (3×10 mL). The combined organic phases were dried over sodium sulfate, filtered, and concentrated. The residue was purified by prep-HPLC to afford 0.027 g (34%) of the product as a yellow solid: $^1$H NMR (500 MHz, CDCl$_3$) δ 8.36 (s, 1H), 8.21 (s, 1H), 7.87 (s, 1H), 7.70-7.68 (m, 3H), 7.50 (s, 2H), 7.40 (s, 1H), 6.90-6.77 (m, 4H), 5.31 (s, 2H), 5.05 (s, 2H), 4.77 (s, 2H), 3.95 (s, 3H), 3.81 (s, 3H) ppm; (M+1)=468.

Example 3-37: Synthesis of Additional Compounds from Ethyl (6-iodo-3-(3-methoxy-4-((6-methoxypyridin-3-yl)methoxy)benzyl)-3H-imidazo[4,5-b]pyridin-2-yl)carbamate The following compounds were prepared from ethyl (6-iodo-3-(3-methoxy-4-((6-methoxypyridin-3-yl)methoxy)benzyl)-3H-imidazo[4,5-b]pyridin-2-yl)carbamate using a modification of the procedure described in Example 3-36-3 by employing the appropriate boronic acid/boronate ester coupling partner. For these compounds, the reactions were conducted under microwave irradiation (140° C. for 1.5 h). Under these conditions, both the Suzuki coupling and hydrolysis of the carbamate were accomplished in one step:

Example 3-37-1: 6-(4-fluorophenyl)-3-(3-methoxy-4-((6-methoxypyridin-3-yl)methoxy)benzyl)-3H-imidazo[4,5-b]pyridin-2-amine $^1$H NMR (500 MHz, DMSO-d$_6$) δ 8.21 (d, J=2.0 Hz, 1H), 8.14 (d, J=1.5 Hz, 1H), 7.75-7.69 (m, 3H), 7.66 (d, J=2.0 Hz, 1H), 7.30-7.26 (m, 2H), 7.12 (d, J=2.0 Hz, 1H), 7.00-6.98 (m, 3H), 6.83 (d, J=8.5 Hz, 1H), 6.73 (dd, J=8.0 Hz & 1.5 Hz, 1H), 5.23 (s, 2H), 4.96 (s, 2H), 3.84 (s, 3H), 3.72 (s, 3H) ppm; (M+1)=486.

Example 3-37-2: 3-(3-methoxy-4-((6-methoxypyridin-3-yl)methoxy)benzyl)-6-(1-methyl-1H-pyrazol-3-yl)-3H-imidazo[4,5-b]pyridin-2-amine (RA09936946)

$^1$H NMR (500 MHz, CDCl$_3$) δ 8.55 (d, J=1.5 Hz, 1H), 8.18 (d, J=2.5 Hz, 1H), 8.03 (d, J=2.0 Hz, 1H), 7.66 (dd, J=6.5, 2.0 Hz, 1H), 7.41 (d, J=2.5 Hz, 1H), 6.87 (d, J=8.0 Hz, 1H), 6.83-6.81 (m, 1H), 6.77 (dd, J=6.5, 2.0 Hz, 1H), 6.75 (d, J=8.0 Hz, 1H), 6.55 (d, J=2.5 Hz, 1H), 5.26 (s, 2H), 5.03 (s, 2H), 4.74 (br s, 2H), 3.98 (s, 3H), 3.93 (s, 3H), 3.77 (s, 3H) ppm; (M+1)=472.

Example 3-37-3: 3-(3-methoxy-4-((6-methoxypyridin-3-yl)methoxy)benzyl)-6-(pyrimidin-5-yl)-3H-imidazo[4,5-b]pyridin-2-amine (RA09943893)

$^1$H NMR (500 MHz, DMSO-d$_6$) δ 9.17-9.15 (m, 3H), 8.29 (d, J=2.0 Hz, 1H), 8.20 (d, J=2.0 Hz, 1H), 7.86 (d, J=1.5 Hz, 1H), 7.74 (dd, J=8.5, 2.5 Hz, 1H), 7.12 (d, J=1.5 Hz, 1H), 7.08 (s, 2H), 6.99 (d, J=8.0 Hz, 1H), 6.83 (d, J=8.5 Hz, 1H), 6.74-6.72 (m, 1H), 5.25 (s, 2H), 4.97 (s, 2H), 3.84 (s, 3H), 3.72 (s, 3H) ppm; (M+1)=470.

Example 3-37-4: 3-(3-methoxy-4-((6-methoxypyridin-3-yl)methoxy)benzyl)-6-(1,3,5-trimethyl-1H-pyrazol-4-yl)-3H-imidazo[4,5-b]pyridin-2-amine $^1$H NMR (500 MHz, CDCl$_3$) δ 8.21 (d, J=2.5 Hz, 1H), 8.18 (d, J=1.5 Hz, 1H), 7.69 (dd, J=6.5, 2.0 Hz, 1H), 7.55 (d, J=2.0 Hz, 1H), 6.92-6.88 (m, 2H), 6.81 (dd, J=6.0, 2.0 Hz, 1H), 6.77 (d, J=8.0 Hz, 1H), 5.29 (s, 2H), 5.06 (s, 2H), 4.77 (br s, 2H), 3.95 (s, 3H), 3.83 (s, 3H), 3.82 (s, 3H), 2.28 (s, 3H), 2.27 (s, 3H) ppm; (M+1)=500.

Example 3-37-5: 3-(3-methoxy-4-((6-methoxypyridin-3-yl)methoxy)benzyl)-6-(pyridin-4-yl)-3H-imidazo[4,5-b]pyridin-2-amine $^1$H NMR (500 MHz, DMSO-d$_6$) δ 8.60-8.59 (m, 2H), 8.33 (d, J=1.5 Hz, 1H), 8.20 (d, J=2.0 Hz, 1H), 7.83 (d, J=1.5

Hz, 1H), 7.75-7.73 (m, 3H), 7.12 (d, J=2.0 Hz, 1H), 7.06 (s, 2H), 6.99 (d, J=8.0 Hz, 1H), 6.82 (d, J=8.5 Hz, 1H), 6.73 (dd, J=8.5, 1.5 Hz, 1H), 5.24 (s, 2H), 4.96 (s, 2H), 3.84 (s, 3H), 3.71 (s, 3H) ppm; (M+1)=469.

Example 3-37-6: 3-(3-methoxy-4-((6-methoxypyridin-3-yl)methoxy)benzyl)-6-(pyridin-3-yl)-3H-imidazo[4,5-b]pyridin-2-amine $^1$H NMR (500 MHz, DMSO-$d_6$) δ 8.90 (d, J=2.0 Hz, 1H), 8.55-8.54 (m, 1H), 8.21-8.20 (m, 2H), 8.09 (d, J=2.0 Hz, 1H), 7.75-7.72 (m, 2H), 7.47-7.42 (m, 1H), 7.11 (d, J=1.5 Hz, 1H), 7.03-6.98 (m, 3H), 6.82 (d, J=8.5 Hz, 1H), 6.74-6.72 (m, 1H), 5.24 (s, 2H), 4.96 (s, 2H), 3.83 (s, 3H), 3.71 (s, 3H); (M+1)=469.

Example 3-38: Synthesis of 3-(3-methoxy-4-((6-methoxypyridin-3-yl)methoxy)benzyl)-6-(pyridin-2-yl)-3H-imidazo[4,5-b]pyridin-2-amine To a stirred solution of ethyl (6-iodo-3-(3-methoxy-4-((6-methoxypyridin-3-yl)methoxy)benzyl)-3H-imidazo[4,5-b]pyridin-2-yl)carbamate (0.250 g, 0.42 mmol), 2-(tributylstannyl)pyridine (0.235 g, 0.63 mmol), copper(I) iodide (0.040 g, 0.21 mmol) and triethylamine (0.130 g, 1.26 mmol) in N,N-dimethylformamide (5 mL) was added bis(triphenylphosphine)palladium(II) dichloride (0.018 g, 0.042 mmol). The mixture was irradiated in a microwave reactor at 140° C. After 1.5 h, the mixture was allowed to cool to room temperature and was filtered through Celite. The filtrate was concentrated. The residue was purified by prep-HPLC to afford 0.025 g (13%) of the product as a white solid: $^1$H NMR (500 MHz, DMSO-$d_6$) δ 8.64 (d, J=4.0 Hz, 1H), 8.62 (d, J=2.0 Hz, 1H), 8.20 (d, J=2.5 Hz, 1H), 8.06 (d, J=2.0 Hz, 1H), 7.97 (d, J=7.5 Hz, 1H), 7.84-7.76 (m, 1H), 7.74-7.72 (m, 1H), 7.32-7.29 (m, 1H), 7.12 (d, J=6.0 Hz, 1H), 7.00-6.77 (m, 3H), 6.82 (d, J=8.5 Hz, 1H), 6.83-6.74 (m, 1H), 5.24 (s, 2H), 4.96 (s, 2H), 3.83 (s, 3H), 3.70 (s, 3H) ppm; (M+1)=469.

Example 3-39: Synthesis of 3-(3-methoxy-4-((4-(perfluoroethyl)benzyl)oxy)benzyl)-6-(1-methyl-1H-pyrazol-4-yl)-3H-imidazo[4,5-b]pyridin-2-amine Example 3-39-1: Preparation of 4-(perfluoroethyl)benzyl 4-methylbenzenesulfonate To a stirred solution of (4-(perfluoroethyl)phenyl)methanol (0.60 g, 2.65 mmol) and triethylamine (0.53 g, 5.30 mmol) in dichloromethane (30 mL) was added p-toluenesulfonyl chloride (1.00 g, 5.30 mmol). The resulting mixture was allowed to stir at room temperature. After 2 h, the mixture was concentrated. Chromatographic purification of the residue (silica gel, 10% ethyl acetate in petroleum ether elute) afforded 0.400 g (40%) of 4-(perfluoroethyl)benzyl 4-methylbenzenesulfonate as a yellow oil.

Example 3-39-2: Preparation of Ethyl (6-iodo-3-(3-methoxy-4-((4-(perfluoroethyl)benzyl)oxy)benzyl)-3H-imidazo[4,5-b]pyridin-2-yl)carbamate To a stirred solution of ethyl (3-(4-hydroxy-3-methoxybenzyl)-6-iodo-3H-imidazo[4,5-b]pyridin-2-yl)carbamate (Example 3-36-1) (0.24 g, 0.52 mmol) in tetrahydrofuran (20 mL) was added 5M aqueous sodium hydroxide solution (0.2 mLs, 1.00 mmol). The resulting mixture was allowed to stir at room temperature. After 2 h, the mixture was concentrated, and the residue was dissolved in N,N-dimethylformamide (10 mL). The mixture was treated with 4-(perfluoroethyl)benzyl 4-methylbenzenesulfonate (0.40 g, 1.04 mmol), and the mixture was warmed to 80° C. After 3 h, the mixture was allowed to cool to room temperature and was diluted with water (20 mL). The mixture was extracted with ethyl acetate (3×40 mL), and the combined organic phases were dried over sodium sulfate, filtered, and concentrated to provide 0.090 g of ethyl (6-iodo-3-(3-methoxy-4-((4-(perfluoroethyl)benzyl)oxy)benzyl)-3H-imidazo[4,5-b]pyridin-2-yl)carbamate as a brown solid.

Example 3-39-3: Preparation of 3-(3-methoxy-4-((4-(perfluoroethyl)benzyl)oxy)benzyl)-6-(1-methyl-1H-pyrazol-4-yl)-3H-imidazo[4,5-b]pyridin-2-amine To a stirred solution of ethyl (6-iodo-3-(3-methoxy-4-((4-(perfluoroethyl)benzyl)oxy)benzyl)-3H-imidazo[4,5-b]pyridin-2-yl)carbamate (0.090 g, 0.13 mmol) and 1-methyl-4-(4,4,5,5-tetramethyl-1,3,2-dioxaborolan-2-yl)-1H-pyrazole (0.054 g, 0.26 mmol) in N,N-dimethylformamide (3 mL) and 2M aqueous sodium carbonate solution (150 μL) was added (1,1'-bis(diphenylphosphino)ferrocene)palladium(II) dichloride (0.050 g, 0.06 mmol). The resulting mixture was heated to 80° C. under a nitrogen atmosphere. After 4 h, the mixture was allowed to cool to room temperature and was filtered through Celite. The filtrate was diluted with water (10 mL) and extracted with ethyl acetate (3×20 mL). The combined organic phases were dried over sodium sulfate, filtered, and concentrated. The residue was purified by prep-HPLC to afford 0.010 g (14%) of the product as a white solid: $^1$H NMR (400 MHz, DMSO-$d_6$) δ 8.10 (s, 2H), 7.84 (s, 1H), 7.72-7.70 (m, 2H), 7.66-7.64 (m, 2H), 7.58 (d, J=1.6 Hz, 1H), 7.12 (d, J=1.6 Hz, 1H), 6.95-6.89 (m, s3H), 6.72 (d, J=6.8 Hz, 1H), 5.19 (s, 2H), 5.15 (s, 2H), 3.85 (s, 3H), 3.73 (s, 3H) ppm; (M+1)=559.

Example 3-40: Synthesis of Additional Compounds from Ethyl (3-(4-hydroxy-3-methoxybenzyl)-6-iodo-3H-imidazo[4,5-b]pyridin-2-yl)carbamate The following compounds were prepared from ethyl (3-(4-hydroxy-3-methoxybenzyl)-6-iodo-3H-imidazo[4,5-b]pyridin-2-yl)carbamate using the procedures described in Example 3-39-2 and Example 3-39-3 by employing the appropriate alkylating agent:

Example 3-40-1: 3-(3-methoxy-4-((4-(trifluoromethoxy)benzyl)oxy)benzyl)-6-(1-methyl-1H-pyrazol-4-yl)-3H-imidazo[4,5-b]pyridin-2-amine (RA10502607)

$^1$H NMR (500 MHz, DMSO-$d_6$) δ 8.11 (s, 2H), 7.85 (s, 1H), 7.58 (d, J=2.5 Hz, 1H), 7.54-7.53 (m, 2H), 7.37 (d, J=8.0 Hz, 2H), 7.12 (s, 1H), 6.94 (d, J=8.0 Hz, 1H), 6.91-6.89 (m, 2H), 6.72 (d, J=7.5 Hz, 1H), 5.19 (s, 2H), 5.05 (s, 2H), 3.86 (s, 3H), 3.73 (s, 3H) ppm; (M+1)=525.

Example 3-40-2: 3-(3-methoxy-4-((4-((trifluoromethyl)thio)benzyl)oxy)benzyl)-6-(1-methyl-1H-pyrazol-4-yl)-3H-imidazo[4,5-b]pyridin-2-amine $^1$H NMR (400 MHz, CDCl$_3$) δ 8.26 (d, J=1.6 Hz, 1H), 7.77 (s, 1H), 7.71 (d, J=1.6 Hz, 1H), 7.67-7.64 (m, 3H), 7.49 (d, J=8.4 Hz, 2H), 6.87 (d, J=1.6 Hz, 1H), 6.83-6.78 (m, 2H), 5.27 (s, 2H), 5.15 (s, 2H), 3.98 (s, 3H), 3.82 (s, 3H) ppm (note: NH$_2$ portions not observed); (M+1)=541.

Example 3-40-3: 3-(4-((6-isopropylpyridin-3-yl)methoxy)-3-methoxybenzyl)-6-(1-methyl-1H-pyrazol-4-yl)-3H-imidazo[4,5-b]pyridin-2-amine $^1$H NMR (400 MHz, CDCl$_3$) δ 8.58 (d, J=2.0 Hz, 1H), 8.26 (d, J=1.6 Hz, 1H), 7.78 (s, 1H), 7.72-7.70 (m, 2H), 7.64 (s, 1H), 7.21 (d, J=8.0 Hz, 1H), 6.89-6.84 (m, 2H), 6.79 (dd, J=6.4, 1.6 Hz, 1H), 5.27 (s, 2H), 5.09 (m, 4H), 3.98 (s, 3H), 3.80 (s, 3H), 3.10-3.06 (m, 1H), 1.32 (d, J=6.8 Hz, 6H) ppm; (M+1)=484.

Example 3-40-4: 3-(3-methoxy-4-((4-(2,2,2-trifluoroethyl)benzyl)oxy)benzyl)-6-(1-methyl-1H-pyrazol-4-yl)-3H-imidazo[4,5-b]pyridin-2-amine $^1$H NMR (400 MHz, DMSO-d$_6$) δ 8.96 (s, 2H), 8.48 (s, 1H), 8.26 (s, 1H), 7.97 (s, 1H), 7.86 (s, 1H), 7.42-7.40 (m, 2H), 7.36-7.34 (m, 2H), 7.18 (s, 1H), 6.98-6.96 (m, 1H), 6.83-6.81 (m, 1H), 5.30 (s, 2H), 5.04 (s, 2H), 3.88 (s, 3H), 3.75 (s, 3H), 3.66 (q, J 9.6 Hz, 2H) ppm; (M+1)=523.

Example 3-40-5: 3-(3-methoxy-4-((2-(trifluoromethyl)thiazol-4-yl)methoxy)benzyl)-6-(1-methyl-1H-pyrazol-4-yl)-3H-imidazo[4,5-b]pyridin-2-amine $^1$H NMR (400 MHz, DMSO-d$_6$) δ 8.16 (s, 1H), 8.11 (s, 2H), 7.85 (s, 1H), 7.59 (s, 1H), 7.13 (s, 1H), 7.03 (d, J=8.4 Hz, 1H), 6.92 (s, 2H), 6.75 (d, J=8.4 Hz, 1H), 5.20-5.18 (m, 4H), 3.86 (s, 3H), 3.72 (s, 3H) ppm; (M+1)=516.

Example 3-41: Synthesis of 6-(cyclohexylethynyl)-3-(3-methoxy-4-((6-methoxypyridin-3-yl)methoxy)benzyl)-3H-imidazo[4,5-b]pyridin-2-amine Example 3-41-1: Preparation of 6-iodo-3-(3-methoxy-4-((6-methoxypyridin-3-yl)methoxy)benzyl)-3H-imidazo[4,5-b]pyridin-2-amine To a stirred solution of ethyl (6-iodo-3-(3-methoxy-4-((6-methoxypyridin-3-yl)methoxy)benzyl)-3H-imidazo[4,5-b]pyridin-2-yl)carbamate (Example 3-36-2) (0.42 g, 0.71 mmol) in ethylene glycol (6 mL) and water (1 mL) was added potassium hydroxide (0.197 g, 3.51 mmol). The resulting mixture was heated to 100° C. After 12 h, the mixture was allowed to cool to room temperature and was diluted with brine (40 mL). The mixture was extracted with ethyl acetate (3×40 mL). The combined organic phases were dried over sodium sulfate, filtered, and concentrated. Chromatographic purification of the residue (silica gel, 3% methanol in dichloromethane elute) afforded 0.206 g (56%) of 6-iodo-3-(3-methoxy-4-((6-methoxypyridin-3-yl)methoxy)benzyl)-3H-imidazo[4,5-b]pyridin-2-amine as a yellow solid.

Example 3-41-2: Preparation of 6-(cyclohexylethynyl)-3-(3-methoxy-4-((6-methoxypyridin-3-yl)methoxy)benzyl)-3H-imidazo[4,5-b]pyridin-2-amine To a stirred suspension of 6-iodo-3-(3-methoxy-4-((6-methoxypyridin-3-yl)methoxy)benzyl)-3H-imidazo[4,5-b]pyridin-2-amine (0.14 g, 0.27 mmol), ethylnylcyclohexane (0.044 g, 0.41 mmol) in piperidine (3 mL) was added bis(triphenylphosphine)palladium(II) dichloride (0.038 g, 0.054 mmol) and copper(I) iodide (0.021 g, 0.11 mmol). The mixture was irradiated in a microwave reactor at 60° C. After 30 min, the reaction mixture was allowed to cool to room temperature and was filtered through Celite. The filtrate was concentrated, and the residue was purified by prep-HPLC to provide 0.032 g (23%) of the product as a white solid: $^1$H NMR (500 MHz, DMSO-d$_6$) δ 8.20 (s, 1H), 7.91 (s, 1H), 7.74 (dd, J=8.5, 1.5 Hz, 1H), 7.42-7.32 (m, 1H), 7.07-6.97 (m, 4H), 6.83 (d, J=8.5 Hz, 1H), 6.71 (d, J=7.5 Hz, 1H), 5.20 (s, 2H), 4.96 (s, 2H), 3.84 (s, 3H), 3.69 (s, 3H), 2.65-2.58 (m, 1H), 1.88-1.78 (m, 2H), 1.75-1.62 (m, 2H), 1.50-1.46 (m, 3H), 1.35-1.32 (m, 3H) ppm; (M+1)=498.

Example 3-42: Synthesis of 4-(2-amino-3-(3-methoxy-4-((6-methoxypyridin-3-yl)methoxy)benzyl)-3H-imidazo[4,5-b]pyridin-6-yl)but-3-yn-1-ol This compound was prepared from 6-iodo-3-(3-methoxy-4-((6-methoxypyridin-3-yl)methoxy)benzyl)-3H-imidazo[4,5-b]pyridin-2-amine and but-3-yn-1-ol using the procedure described in Example 3-41-2: $^1$H NMR (500 MHz, DMSO-d$_6$) δ 8.21 (s, 1H), 7.93 (s, 1H), 7.74 (dd, J=8.5, 2.0 Hz, 1H), 7.41 (s, 1H), 7.08-6.97 (m, 4H), 6.83 (d, J=8.5 Hz, 1H), 6.71 (d, J=8.0 Hz, 1H), 5.20 (s, 2H), 4.96 (s, 2H), 4.91 (t, J=5.5 Hz, 1H), 3.84 (s, 3H), 3.69 (s, 3H), 3.61-3.57 (m, 2H), 2.56 (t, J=6.5 Hz, 2H) ppm; (M+1)=460.

Example 3-43: Synthesis of 3-(4-(cyclopropyl(6-methoxypyridin-3-yl)methoxy)-3-methoxybenzyl)-6-(1-methyl-1H-pyrazol-4-yl)-3H-imidazo[4,5-b]pyridin-2-amine Example 3-43-1: Preparation of cyclopropyl(6-methoxypyridin-3-yl)methanol To a stirred −78° C. solution of 5-bromo-2-methoxypyridine (3.70 g, 19.79 mmol) in tetrahydrofuran (10 mL) was added 2.6 M n-butyllithium solution in hexane (8.4 mL, 21.84 mmol). The mixture was allowed to stir at −78° C. for 30 min, and then cyclopropanecarboxaldehye (1.70 g, 23.74 mmol) was added in one portion. The cooling bath was removed, and the mixture was allowed to warm to room temperature. After 2 h, the mixture was quenched by the addition of saturated aqueous ammonium chloride solution (100 mL). The resulting mixture was extracted with ethyl acetate (3×100 mL). The combined organic phases were dried over sodium sulfate, filtered, and concentrated. Chromatographic purification of the residue (silica gel, 20% ethyl acetate in petroleum ether elute) afforded 2.90 g (80%) of cyclopropyl(6-methoxypyridin-3-yl)methanol as a yellow oil.

Example 3-43-2: Preparation of 4-(cyclopropyl(6-methoxypyridin-3-yl)methoxy)-3-methoxybenzonitrile To a stirred 0° C. solution of cyclopropyl(6-methoxypyridin-3-yl)methanol (3.80 g, 21.20 mmol), 4-hydroxy-3-methoxybenzonitrile (1.60 g, 10.73 mmol), and triphenylphosphine (5.60 g, 21.35 mmol) in tetrahydrofuran (10 mL) was added diethyl azodicarboxylate (3.70 g, 21.25 mmol) dropwise. The resulting mixture was allowed to warm to room temperature. After 2 h, the mixture was concentrated. Chromatographic purification of the residue (silica gel, 10% ethyl acetate in petroleum ether elute) afforded 2.70 g (80%) of 4-(cyclopropyl(6-methoxypyridin-3-yl)methoxy)-3-methoxybenzonitrile as a light yellow oil.

Example 3-43-3: Preparation of (4-(cyclopropyl(6-methoxypyridin-3-yl)methoxy)-3-methoxyphenyl) methanamine To a stirred 0° C. solution of 4-(cyclopropyl(6-methoxypyridin-3-yl)methoxy)-3-methoxybenzonitrile (2.50 g, 8.06 mmol) in ethanol (20 mL) was added cobalt(II) chloride hexahydrate (2.20 g, 9.25 mmol) in small portions. The resulting mixture was allowed to stir at 0° C. After 30 min, the mixture was treated with sodium borohydride (1.80 g, 47.58 mmol) added in small portions. The mixture was allowed to warm to room temperature. After 30 min, the mixture was filtered through Celite, and the filtercake was washed with ethanol (20 mL). The filtrate was concentrated to provide 2.50 g (99%) of (4-(cyclopropyl(6-methoxypyridin-3-yl)methoxy)-3-methoxyphenyl)methanamine as a colorless oil.

Example 3-43-4: Preparation of N-(4-(cyclopropyl (6-methoxypyridin-3-yl)methoxy)-3-methoxybenzyl)-5-iodo-3-nitropyridin-2-amine To a stirred solution of (4-(cyclopropyl(6-methoxypyridin-3-yl)methoxy)-3-methoxyphenyl)methanamine (2.50 g, 7.95 mmol) and potassium carbonate (1.41 g, 10.20 mmol) in acetonitrile (10 mL) was added 2-chloro-5-iodo-3-nitropyridine (2.90 g, 10.20 mmol). The resulting mixture was heated to 80° C. After 2 h, the mixture was filtered, and the filtrate was concentrated. Chromatographic purification of the residue (silica gel, 20% ethyl acetate in petroleum ether elute) afforded 2.60 g (58%) of N-(4-(cyclopropyl(6-methoxypyridin-3-yl)methoxy)-3-methoxybenzyl)-5-iodo-3-nitropyridin-2-amine as a yellow oil.

Example 3-43-5: Preparation of N-(4-(cyclopropyl (6-methoxypyridin-3-yl)methoxy)-3-methoxybenzyl)-5-(1-methyl-1H-pyrazol-4-yl)-3-nitropyridin-2-amine To a stirred solution of N-(4-(cyclopropyl(6-methoxypyridin-3-yl)methoxy)-3-methoxybenzyl)-5-iodo-3-nitropyridin-2-amine (2.20 g, 3.91 mmol), 1-methyl-4-(4,4,5,5-tetramethyl-1,3,2-dioxaborolan-2-yl)-1H-pyrazole (0.896 g, 4.30 mmol), and potassium carbonate (1.10 g, 7.95 mmol) in toluene (10 mL) and water (1 mL) was added (1,1'-bis (diphenylphosphino)ferrocene)palladium(II) dichloride (0.143 g, 0.20 mmol). The resulting mixture was heated to 100° C. and stirred under a nitrogen atmosphere. After 16 h, the mixture was allowed to cool to room temperature and was diluted with water (15 mL). The mixture was extracted with ethyl acetate (2×60 mL). The combined organic phases were dried over sodium sulfate, filtered, and concentrated. Chromatographic purification of the residue (silica gel, 33% ethyl acetate in petroleum ether elute) afforded 1.10 g (55%) of N-(4-(cyclopropyl(6-methoxypyridin-3-yl)methoxy)-3-methoxybenzyl)-5-(1-methyl-1H-pyrazol-4-yl)-3-nitropyridin-2-amine as a light brown solid.

Example 3-43-6: Preparation of $N^2$-(4-(cyclopropyl (6-methoxypyridin-3-yl)methoxy)-3-methoxybenzyl)-5-(1-methyl-1H-pyrazol-4-yl)pyridine-2,3-diamine To a stirred solution of N-(4-(cyclopropyl(6-methoxypyridin-3-yl)methoxy)-3-methoxybenzyl)-5-(1-methyl-1H-pyrazol-4-yl)-3-nitropyridin-2-amine (1.10 g, 2.13 mmol) and ammonium chloride (0.564 g, 10.54 mmol) in ethanol (8 mL) and water (2 mL) was added iron powder (0.596 g, 10.67 mmol). The mixture was heated to 80° C. After 2 h, the mixture was allowed to cool to room temperature and was filtered through Celite. The filtrate was concentrated. Chromatographic purification of the residue (neutral alumina, 2% methanol in dichloromethane elute) afforded 0.984 g (95%) of $N^2$-(4-(cyclopropyl(6-methoxypyridin-3-yl)methoxy)-3-methoxybenzyl)-5-(1-methyl-1H-pyrazol-4-yl)pyridine-2,3-diamine as a brown solid.

Example 3-43-7: Preparation of Ethyl (3-(4-(cyclopropyl(6-methoxypyridin-3-yl)methoxy)-3-methoxybenzyl)-6-(1-methyl-1H-pyrazol-4-yl)-3H-imidazo [4,5-b]pyridin-2-yl)carbamate To a stirred solution of $N^2$-(4-(cyclopropyl(6-methoxypyridin-3-yl)methoxy)-3-methoxybenzyl)-5-(1-methyl-1H-pyrazol-4-yl)pyridine-2,3-diamine (0.55 g, 1.13 mmol) in tetrahydrofuran (5 mL) was added triethylamine (0.799 g, 7.90 mmol). The resulting mixture was allowed to stir at room temperature. After 15 min, the mixture was treated with ethyl carbonisothiocyanatidate (0.444 g, 3.39 mmol), and the resulting mixture was allowed to stir at room temperature. After 30 min, the mixture was filtered, and the filtrate was concentrated. The residue was dissolved in tetrahydrofuran (5 mL) and was treated with triethylamine (0.799 g, 7.90 mmol) and benzenesulfonyl chloride (0.259 g, 1.43 mmol). The resulting mixture was allowed to stir at room temperature. After 16 h, the mixture was concentrated. Chromatographic purification of the residue (neutral alumina, 50% ethyl acetate in petroleum ether elute) afforded 0.45 g (68%) of ethyl (3-(4-(cyclopropyl(6-methoxypyridin-3-yl)methoxy)-3-methoxybenzyl)-6-(1-methyl-1H-pyrazol-4-yl)-3H-imidazo[4,5-b]pyridin-2-yl)carbamate as a brown oil.

Example 3-43-8: Preparation of 3-(4-(cyclopropyl (6-methoxypyridin-3-yl)methoxy)-3-methoxybenzyl)-6-(1-methyl-1H-pyrazol-4-yl)-3H-imidazo[4,5-b]pyridin-2-amine To a stirred solution of ethyl (3-(4-(cyclopropyl(6-methoxypyridin-3-yl)methoxy)-3-methoxybenzyl)-6-(1-methyl-1H-pyrazol-4-yl)-3H-imidazo[4,5-b]pyridin-2-yl) carbamate (0.44 g, 0.75 mmol) in n-butanol (4 mL) and water (4 mL) was added potassium hydroxide (0.42 g, 7.49 mmol). The mixture was heated to 130° C. After 16 h, the mixture was allowed to cool to room temperature and was diluted with water (15 mL). The mixture was extracted with ethyl acetate (2×60 mL). The combined organic phases were dried over sodium sulfate, filtered, and concentrated. The residue was purified via prep-HPLC to provide 0.058 g (15%) of the product as a white solid: $^1$H NMR (500 MHz, CDCl$_3$) δ 8.24 (d, J=1.5 Hz, 1H), 8.09 (d, J=3.0 Hz, 1H), 7.78 (s, 1H), 7.70-7.68 (m, 2H), 7.64 (s, 1H), 6.78-6.23 (m, 4H), 5.21 (s, 2H), 4.85 (s, 2H), 4.50 (d, J=8.5 Hz, 1H), 3.98 (s, 3H), 3.93 (s, 3H), 3.79 (s, 3H), 1.45-1.40 (m, 1H), 0.75-0.70 (m, 1H), 0.61-0.50 (m, 2H), 0.38-0.34 (m, 1H) ppm; (M+1)=512.

Example 3-44: Synthesis of 3-(3-methoxy-4-((3-methoxy-5,6,7,8-tetrahydroisoquinolin-8-yl)oxy) benzyl)-6-(1-methyl-1H-pyrazol-4-yl)-3H-imidazo [4,5-b]pyridin-2-amine

Example 3-44-1: Preparation of 3-methoxy-5,6,7,8-tetrahydroisoquinolin-8-ol

To a stirred 0° C. solution of 3-methoxy-6,7-dihydroisoquinolin-8(5H)-one (1.90 g, 10.72 mmol) in methanol (30 mL) was added sodium borohydride (1.10 g, 29.08 mmol) in small portions. The resulting mixture was allowed to warm to room temperature. After 2 h, the mixture was quenched with water (20 mL) and was extracted with ethyl acetate (3×100 mL). The combined organic phases were dried over sodium sulfate, filtered, and concentrated. Chromatographic purification of the residue (silica gel, 50% ethyl acetate in petroleum ether elute) afforded 1.60 g (85%) of 3-methoxy-5,6,7,8-tetrahydroisoquinolin-8-ol as a light yellow solid.

Example 3-44-2: Preparation of 3-(3-methoxy-4-((3-methoxy-5,6,7,8-tetrahydroisoquinolin-8-yl)oxy)benzyl)-6-(1-methyl-1H-pyrazol-4-yl)-3H-imidazo[4,5-b]pyridin-2-amine This compound was prepared from 3-methoxy-5,6,7,8-tetrahydroisoquinolin-8-ol using the procedures outlined in Example 3-43-2 through Example 3-43-8: $^1$H NMR (400 MHz, CDCl$_3$) δ 8.25 (d, J=1.6 Hz, 1H), 8.12 (s, 1H), 7.77 (s, 1H), 7.70 (d, J=2.0 Hz, 1H), 7.63 (s, 1H), 6.94 (d, J=8.4 Hz, 1H), 6.84 (d, J=1.6 Hz, 1H), 6.79 (dd, J=8.4, 1.6 Hz, 1H), 6.50 (s, 1H), 5.27-5.24 (m, 3H), 5.03 (s, 2H), 3.97 (s, 3H), 3.89 (s, 3H), 3.76 (s, 3H), 2.87-2.81 (m, 1H), 2.72-2.65 (m, 1H), 2.19-1.73 (m, 4H) ppm; (M+1)=512

Example 3-45: Synthesis of 1-(1-(3-methoxy-4-((6-methoxypyridin-3-yl)methoxy)phenyl)ethyl)-5-(1-methyl-1H-pyrazol-4-yl)-1H-benzo[d]imidazol-2-amine

Example 3-45-1: Preparation of 1-(3-methoxy-4-((6-methoxypyridin-3-yl)methoxy)phenyl)ethan-1-one To a stirred suspension of 1-(4-hydroxy-3-methoxyphenyl)ethan-1-one (3.96 g, 23.82 mmol) and potassium carbonate (13.17 g, 95.29 mmol) in acetonitrile (75 mL) was added 5-(chloromethyl)-2-methoxypyridine hydrochloride (4.85 g, 25.01 mmol). After 2 h, the mixture was diluted with water (150 mL) and extracted with dichloromethane (3×100 mL). The combined organic phases were dried over magnesium sulfate, filtered, and concentrated to provide a yellow oil. Trituration of the crude material with hexanes afforded 5.48 g (85%) of 1-(3-methoxy-4-((6-methoxypyridin-3-yl)methoxy)phenyl)ethan-1-one as a white solid.

Example 3-45-2: Preparation of 1-(3-methoxy-4-((6-methoxypyridin-3-yl)methoxy)phenyl)ethan-1-one Oxime To a stirred suspension of 1-(3-methoxy-4-((6-methoxypyridin-3-yl)methoxy)phenyl)ethan-1-one (5.48 g, 19.07 mmol) and potassium carbonate (10.54 g, 76.29 mmol) in methanol (100 mL) and water (10 mL) was added hydroxylamine sulfate (4.70 g, 28.61 mmol). The resulting mixture was heated to reflux. After 64 h, the mixture was allowed to cool to room temperature and was diluted with water (250 mL). The resulting suspension was filtered, and the filtercake was washed with water (50 mL) and dried to provide 5.55 g (96%) of 1-(3-methoxy-4-((6-methoxypyridin-3-yl)methoxy)phenyl)ethan-1-one oxime as a white solid.

Example 3-45-3: Preparation of 1-(3-methoxy-4-((6-methoxypyridin-3-yl)methoxy)phenyl)ethan-1-amine To a stirred solution of 1-(3-methoxy-4-((6-methoxypyridin-3-yl)methoxy)phenyl)ethan-1-one oxime (5.55 g, 18.36 mmol) in acetic acid (40 mL) was added zinc dust (6.00 g, 91.79 mmol). The resulting mixture was heated to 65° C. After 1 h, the mixture was allowed to cool to room temperature and was filtered through Celite. The filtercake was washed with methanol (100 mL). The filtrate was concentrated, and the residue dissolved in 5N ammonium hydroxide solution (75 mL). The mixture was extracted with chloroform (2×50 mL). The combined organic phases were dried over magnesium sulfate, filtered, and concentrated to provide 4.56 g (86%) of 1-(3-methoxy-4-((6-methoxypyridin-3-yl)methoxy)phenyl)ethan-1-amine as a yellow oil.

Example 3-45-4: Preparation of 4-iodo-N-(1-(3-methoxy-4-((6-methoxypyridin-3-yl)methoxy)phenyl)ethyl)-2-nitroaniline To a stirred solution of 1-(3-methoxy-4-((6-methoxypyridin-3-yl)methoxy)phenyl)ethan-1-amine (1.93 g, 6.68 mmol) and potassium carbonate (3.70 g, 26.75 mmol) in acetonitrile (75 mL) was added 1-fluoro-4-iodo-2-nitrobenzene (2.14 g, 8.02 mmol). The mixture was heated to reflux. After 16 h, the orange mixture was allowed to cool to room temperature and was diluted with water (150 mL). The mixture was extracted with dichloromethane (3×75 mL), and the combined organic phases were dried over magnesium sulfate, filtered, and concentrated to provide 3.82 g of an orange solid. Trituration of the crude material with hexanes afforded 3.17 g (89%) of 4-iodo-N-(1-(3-methoxy-4-((6-methoxypyridin-3-yl)methoxy)phenyl)ethyl)-2-nitroaniline as a bright orange solid.

Example 3-45-5: Preparation of 4-iodo-N1-(1-(3-methoxy-4-((6-methoxypyridin-3-yl)methoxy)phenyl)ethyl)benzene-1,2-diamine To a stirred suspension of 4-iodo-N-(1-(3-methoxy-4-((6-methoxypyridin-3-yl)methoxy)phenyl)ethyl)-2-nitroaniline (3.17 g, 5.92 mmol) and ammonium chloride (2.53 g, 47.37 mmol) in tetrahydrofuran (50 mL)/methanol (20 mL)/water (10 mL) was added iron(II) sulfate heptahydrate (5.76 g, 20.73 mmol) and zinc dust (1.35 g, 20.73 mmol). The resulting mixture was heated to reflux. After 1 h, the mixture was allowed to cool to room temperature and was filtered through Celite. The filtercake was washed with methanol (50 mL). The filtrate was concentrated, and the residue was diluted with 3N ammonium hydroxide solution (100 mL). The basic mixture was extracted with chloroform (3×50 mL), and the combined organic phases were dried over magnesium sulfate, filtered, and concentrated to provide 2.02 g (68%) of 4-iodo-N$^1$-(1-(3-methoxy-4-((6-methoxypyridin-3-yl)methoxy)phenyl)ethyl)benzene-1,2-diamine as a brown solid.

Example 3-45-6: Preparation of 5-iodo-1-(1-(3-methoxy-4-((6-methoxypyridin-3-yl)methoxy)phenyl)ethyl)-1H-benzo[d]imidazol-2-amine To a stirred solution of 4-iodo-N$^1$-(1-(3-methoxy-4-((6-methoxypyridin-3-yl)methoxy)phenyl)ethyl)benzene-1,2-diamine (2.02 g, 4.00 mmol) in dichloromethane (20 mL)/methanol (10 mL) was added cyanogen bromide solution (5.0M in acetonitrile, 4.0 mL, 20.00 mmol). The resulting dark brown solution was allowed to stir at room temperature. After 17 h, the mixture was diluted with 1N sodium hydroxide solution (20 mL), and the basic mixture was allowed to stir. After 30 min, the phases were separated, and the aqueous phase was extracted with chloroform (30 mL). The combined organic phases were dried over magnesium sulfate, filtered, and concentrated to provide 3.36 g of a brown oil. Chromatographic purification of the residue (CombiFlash, 120 g SiO$_2$ gold column, 1-5% methanol in dichloromethane elute) provided a brown semi-solid. Trituration of this material with 1:1 diethyl ether/dichloromethane afforded 0.801 g (38%) of 5-iodo-1-(1-(3-methoxy-4-((6-methoxypyridin-3-yl)methoxy)phenyl)ethyl)-1H-benzo[d]imidazol-2-amine as a tan solid.

Example 3-45-7: Preparation of 1-(1-(3-methoxy-4-((6-methoxypyridin-3-yl)methoxy)phenyl)ethyl)-5-(1-methyl-1H-pyrazol-4-yl)-1H-benzo[d]imidazol-2-amine To stirred mixture of 5-iodo-1-(1-(3-methoxy-4-((6-methoxypyridin-3-yl)methoxy)phenyl)ethyl)-1H-benzo[d]imidazol-2-amine (0.267 g, 0.50 mmol), 1-methyl-4-(4,4,5,5-tetramethyl-1,3,2-dioxaborolan-2-yl)-1H-pyrazole (0.138 g, 0.63 mmol), tricyclohexylphosphine (0.014 g, 0.050 mmol), potassium phosphate tribasic (0.381 g, 1.76 mmol) in 1,4-dioxane (3 mL) and water (1 mL) was added palladium(II) acetate (0.005 g, 0.025 mmol). The mixture was heated to 125° C. in a microwave reactor. After 30 min, additional portions of catalyst (0.005 g) and ligand (0.014 g) were added, and the mixture was reheated in a microwave reactor to 150° C. After 60 min of reaction time, the crude mixture was transferred to a 20 mL microwave reaction vial and was treated with an additional portions of boronate ester (0.050 g), catalyst (0.005 g), and ligand (0.014 g). The mixture was diluted with additional 1,4-dioxane (8 mL) and water (4 mL). The mixture was heated to 150° C. in a microwave reactor. After a total of 105 min, the reaction was complete. The mixture was diluted with water (30 mL) and extracted with dichloromethane (3×25 mL). The combined organic phases were dried over magnesium sulfate, filtered, and concentrated to provide 419 mgs of a brown oil. Chromatographic purification (CombiFlash, 12 g SiO$_2$ gold column, 1-5% 2M ammonia in methanol/dichloromethane elute) provided 109 mgs of an impure tan solid. A second chromatographic purification (CombiFlash, 12 g SiO$_2$ gold column, 1-5% 2M ammonia in methanol/dichloromethane elute) afforded 0.063 g (26%) of the product as as a yellow solid: $^1$H NMR (400 MHz, CDCl$_3$) δ 8.22-8.16 (m, 1H), 7.75 (d, J=0.8 Hz, 1H), 7.68 (dd, J=8.5, 2.4 Hz, 1H), 7.58 (d, J=0.8 Hz, 1H), 7.53 (d, J=1.5 Hz, 1H), 7.20-7.16 (m, 1H), 7.11-7.06 (m, 1H), 6.96-6.87 (m, 2H), 6.80-6.73 (m, 2H), 5.55 (q, J=7.1 Hz, 1H), 5.05 (s, 2H), 4.33 (br s, 2H), 3.95 (s, 3H), 3.94 (s, 3H), 3.76 (s, 3H), 1.87 (d, J=7.1 Hz, 3H) ppm; (M+1)=485.

Example 3-46: Synthesis of 5-(4-fluorophenyl)-1-(1-(3-methoxy-4-((6-methoxypyridin-3-yl)methoxy)phenyl)ethyl)-1H-benzo[d]imidazol-2-amine To a stirred solution of 5-iodo-1-(1-(3-methoxy-4-((6-methoxypyridin-3-yl)methoxy)phenyl)ethyl)-1H-benzo[d]imidazol-2-amine (Example 3-45-6) (0.195 g, 0.37 mmol), 4-fluorophenylboronic acid (0.064 g, 0.46 mmol), and potassium phosphate tribasic (0.413 g, 1.91 mmol) in tetrahydrofuran (5 mL)/water (4 mL) was added 2$^{nd}$ generation XPhos precatalyst (0.015 g, 0.018 mmol). The yellow solution was degassed under vacuum/backfilled with nitrogen (×3). The mixture was heated to 60° C. After 90 min, the mixture was treated with an additional portion of boronic acid (0.030 g) and precatalyst (0.014 g), and the temperature was increased to 75° C. After a total reaction time of 150 min, the brown mixture was allowed to cool to room temperature and was diluted with water (30 mL). The mixture was extracted with dichloromethane (3×25 mL). The combined organic phases were dried over magnesium sulfate, filtered, and concentrated to provide 0.282 g of a brown oil. Chromatographic purification (CombiFlash, 12 g SiO$_2$ gold column, 1-5% 2M ammonia in methanol/dichloromethane elute) afforded 0.142 g (78%) of the product as a yellow solid: $^1$H NMR (400 MHz, CDCl$_3$) δ 8.20 (dd, J=2.4, 0.8 Hz, 1H), 7.68 (dd, J=8.4, 2.5 Hz, 1H), 7.62-7.52 (m, 3H), 7.23 (dd, J=8.4, 1.7 Hz, 1H), 7.17-7.06 (m, 3H), 6.96-6.88 (m, 2H), 6.81-6.79 (m, 1H), 6.78-6.74 (m, 1H), 5.58 (q, J=7.0 Hz, 1H), 5.05 (s, 2H), 4.49 (s, 2H), 3.93 (s, 3H), 3.76 (s, 3H), 1.88 (d, J=7.0 Hz, 3H) ppm; (M+1)=499.

Example 3-47: Synthesis of 5-(4-fluorophenyl)-1-(1-(3-methoxy-4-((6-(trifluoromethyl)pyridin-3-yl)methoxy)phenyl)ethyl)-1H-benzo[d]imidazole Example 3-47-1: Preparation of 5-iodo-1-(1-(3-methoxy-4-((6-(trifluoromethyl)pyridin-3-yl)methoxy)phenyl)ethyl)-1H-benzo[d]imidazole To stirred solution of 4-iodo-N1-(1-(3-methoxy-4-((6-(trifluoromethyl)pyridin-3-yl)methoxy)phenyl)ethyl)benzene-1,2-diamine [prepared from 5-(chloromethyl)-2-(trifluoromethyl)pyridine using the procedures described in Example 3-45-1 through Example 3-45-5] (1.04 g, 1.91 mmol) in ethanol (30 mL) was added triethyl orthoformate (1.0 mL, 5.89 mmol) and p-toluenesulfonic acid monohydrate (0.025 g, 0.13 mmol). The yellow solution was heated to reflux. After 30 min, the mixture was allowed to cool to room temperature and was concentrated to provide a yellow oil. Chromatographic purification (CombiFlash, 24 g SiO$_2$ gold column, 1-5% methanol/dichloromethane elute) afforded 0.803 g (76%) of 5-iodo-1-(1-(3-methoxy-4-((6-(trifluoromethyl)pyridin-3-yl)methoxy)phenyl)ethyl)-1H-benzo[d]imidazole as a yellow solid.

Example 3-47-2 Preparation of 5-(4-fluorophenyl)-1-(1-(3-methoxy-4-((6-(trifluoromethyl)pyridin-3-yl)methoxy)phenyl)ethyl)-1H-benzo[d]imidazole To a stirred solution of 5-iodo-1-(1-(3-methoxy-4-((6-(trifluoromethyl)pyridin-3-yl)methoxy)phenyl)ethyl)-1H-benzo[d]imidazole (0.248 g, 0.45 mmol), (4-fluorophenyl)boronic acid (0.088 g, 0.63 mmol), and potassium phosphate tribasic (0.485 g, 2.24 mmol) in tetrahydrofuran (7 mL)/water (5 mL) was added 2$^{nd}$ generation XPhos precatalyst (0.024 g, 0.031 mmol). The yellow solution was degassed under vacuum/backfilled with nitrogen (×3). The mixture was heated to 75° C. After 45 min, the brown reaction mixture was allowed to cool to room temperature and was diluted with water (30 mL). The mixture was extracted with dichloromethane (2×25 mL). The combined organic phases were dried over magnesium sulfate, filtered, and concentrated to provide 0.271 g of a brown oil. Chromatographic purification (CombiFlash, 12 g SiO$_2$ gold column, 1-5% methanol/dichloromethane elute) afforded 0.200 g (86%) of the product as an off-white solid: $^1$H NMR (400 MHz, CDCl$_3$) δ 8.78 (d, J=2.0 Hz, 1H), 8.08 (s, 1H), 7.99-7.94 (m, 2H), 7.70 (dd, J=8.1, 0.8 Hz, 1H), 7.61-7.52 (m, 2H), 7.40 (dd, J=8.4, 1.7 Hz, 1H), 7.27-7.23 (m, 1H), 7.16-7.09 (m, 2H), 6.88-6.84 (m, 1H), 6.80-6.76 (m, 1H), 6.75-6.73 (m, 1H), 5.60 (q, J=7.0 Hz, 1H), 5.20 (s, 2H), 3.80 (s, 3H), 2.01 (d, J=7.0 Hz, 3H) ppm; (M+1)=522.

Example 3-48: Synthesis of Additional Compounds from 5-iodo-1-(1-(3-methoxy-4-((6-(trifluoromethyl)pyridin-3-yl)methoxy)phenyl)ethyl)-1H-benzo[d]imidazole The following compound was prepared from 5-iodo-1-(1-(3-methoxy-4-((6-(trifluoromethyl)pyridin-3-yl)methoxy)phenyl)ethyl)-1H-benzo[d]imidazole using the procedure described in Example 3-47-2 by employing the appropriate boronate ester coupling partner.

Example 3-48-1: 1-(1-(3-methoxy-4-((6-(trifluoromethyl)pyridin-3-yl)methoxy)phenyl)ethyl)-5-(1-methyl-1H-pyrazol-4-yl)-1H-benzo[d]imidazole $^1$H NMR (400 MHz, CDCl$_3$) δ 8.82-8.75 (m, 1H), 8.04 (s, 1H), 7.99-7.93 (m, 1H), 7.89 (dd, J=1.7, 0.7 Hz, 1H), 7.76 (d, J=0.8 Hz, 1H), 7.72-7.68 (m, 1H), 7.64-7.57 (m, 1H), 7.34 (dd, J=8.4, 1.6 Hz, 1H), 7.18 (dd, J=8.4, 0.7 Hz, 1H), 6.85 (d, J=8.2 Hz, 1H), 6.80-6.70 (m, 2H), 5.57 (q, J=7.0 Hz, 1H), 5.20 (s, 2H), 3.95 (s, 3H), 3.79 (s, 3H), 1.99 (d, J=7.0 Hz, 3H) ppm; (M+1)=508.

Example 3-48-2: 4-(1-(1-(3-methoxy-4-((6-(trifluoromethyl)pyridin-3-yl)methoxy)phenyl)ethyl)-1H-benzo[d]imidazol-5-yl)but-3-yn-1-ol To a stirred mixture of 5-iodo-1-(1-(3-methoxy-4-((6-(trifluoromethyl)pyridin-3-yl)methoxy)phenyl)ethyl)-1H-benzo[d]imidazole (0.210 g, 0.38 mmol), 3-butyn-1-ol (0.041 g, 0.57 mmol), copper(I) iodide (0.019 g, 0.10 mmol) in piperidine (4 mL) was added bis(triphenylphosphine)palladium(II) chloride (0.037 g, 0.053 mmol). The mixture heated to 100° C. in a microwave reactor. After 30 min, the reaction mixture was allowed to cool to room temperature and was diluted with 5N ammonium hydroxide solution (30 mL). The mixture was extracted with dichloromethane (3×25 mL). The combined organic phases were dried over magnesium sulfate, filtered, and concentrated to provide 0.386 g of a brown solid. Chromatographic purification (CombiFlash, 12 g SiO$_2$ gold column, 1-5% methanol/dichloromethane elute) afforded 0.157 g (84%) of the product as a light yellow solid: $^1$H NMR (400 MHz, CDCl$_3$) δ 8.78 (d, J=2.1 Hz, 1H), 8.04 (s, 1H), 8.00-7.93 (m, 1H), 7.90-7.84 (m, 1H), 7.72-7.68 (m, 1H), 7.28-7.23 (m, 1H), 7.13-7.08 (m, 1H), 6.87-6.82 (m, 1H), 6.76-6.64 (m, 2H), 5.55 (q, J=7.0 Hz, 1H), 5.19 (s, 2H), 3.83 (t, J=6.2 Hz, 2H), 3.77 (s, 3H), 2.71 (t, J=6.2 Hz, 2H), 2.00-1.92 (m, 4H) ppm; (M+1)=496.

Example 3-49: Synthesis of 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine Example 3-49-1: Preparation of 5-iodo-N-(1-(3-methoxy-4-((4-(trifluoromethyl)benzyl)oxy)phenyl)ethyl)-3-nitropyridin-2-amine To a stirred solution of 1-(3-methoxy-4-((4-(trifluoromethyl)benzyl)oxy)phenyl)ethanamine [prepared from 1-(chloromethyl)-4-(trifluoromethyl)benzene using the procedures described in Example 3-45-1 through Example 3-45-3] (2.52 g, 7.75 mmol) and N,N-diisopropylethylamine (2.7 mL, 15.18 mmol) in acetonitrile (30 mL) was added 2-chloro-5-iodo-3-nitropyridine (2.39 g, 8.13 mmol), The orange solution was heated to reflux. After 15 h, the brown reaction mixture was allowed to cool to room temperature and was diluted with water (60 mL). As the mixture was stirred, a yellow precipitate formed. The solids were isolated by filtration and washed with water (50 mL), and dried to provide 4.19 g (94%) of 5-iodo-N-(1-(3-methoxy-4-((4-(trifluoromethyl)benzyl)oxy)phenyl)ethyl)-3-nitropyridin-2-amine as a yellow solid.

Example 3-49-2: Preparation of 5-iodo-N$^2$-(1-(3-methoxy-4-((4-(trifluoromethyl)benzyl)oxy)phenyl)ethyl)pyridine-2,3-diamine To a stirred mixture of 5-iodo-N-(1-(3-methoxy-4-((4-(trifluoromethyl)benzyl)oxy)phenyl)ethyl)-3-nitropyridin-2-amine (4.19 g, 7.31 mmol), and ammonium chloride (3.14 g, 58.47 mmol) in tetrahydrofuran (40 mL)/methanol (40 mL)/water (20 mL) was added iron(II) sulfate heptahydrate (7.18 g, 25.58 mmol) and zinc dust (1.69 g, 25.58 mmol). The yellow mixture was heated to 60° C. As the mixture warmed, an olive green color developed. After 5 min, the warm reaction mixture was filtered through Celite with the aid of ethyl acetate (100 mL). The filtrate was diluted with 5N ammonium hydroxide solution (30 mL), and the phases were separated. The aqueous phase was extracted with ethyl acetate (2×50 mL). The combined organic phases were dried over magnesium sulfate, filtered, and concentrated to provide 3.72 g of a brown oil. Chromatographic purification (CombiFlash, 120 g SiO$_2$ gold column, 30-60% ethyl acetate/heptane elute) afforded 2.39 g (60%) of 5-iodo-N$^2$-(1-(3-methoxy-4-((4-(trifluoromethyl)benzyl)oxy)phenyl)ethyl)pyridine-2,3-diamine as an off-white solid.

Example 3-49-3: Preparation of Ethyl (6-iodo-3-(1-(3-methoxy-4-((4-(trifluoromethyl)benzyl)oxy)phenyl)ethyl)-3H-imidazo[4,5-b]pyridin-2-yl)carbamate To stirred solution of 5-iodo-N$^2$-(1-(3-methoxy-4-((4-(trifluoromethyl)benzyl)oxy)phenyl)ethyl)pyridine-2,3-diamine (2.39 g, 4.40 mmol) and triethylamine (0.92 ml, 6.60 mmol) in tetrahydrofuran (30 mL) was added with ethoxycarbonyl isothiocyanate (0.64 ml, 5.28 mmol). After 3 h, the mixture was diluted with brine (100 mL) and extracted with ethyl acetate (3×50 mL). The combined organic phases were dried over magnesium sulfate, filtered, and concentrated to provide 3.16 g of a brown foamy solid. The crude solid was dissolved in tetrahydrofuran (30 mL) and was treated with triethylamine (1.53 mL, 11.01 mmol) and benzenesulfonyl chloride (1.42 mL, 11.01 mmol). The yellow mixture was allowed to stir at room temperature. After 63 h, the mixture was diluted with water (100 mL) and allowed to stir at room temperature. After 2 h, the reaction mixture was extracted with dichloromethane (3×50 mL). The combined organic phases were washed with saturated potassium carbonate solution (50 mL), dried over magnesium sulfate, filtered, and concentrated to provide 3.62 g of a brown oil. Chromatographic purification (CombiFlash, 80 g SiO$_2$ gold column, 10-30% ethyl acetate/heptane elute) provided a tan solid. Trituration of this material with diethyl ether (50 mL) afforded 1.30 g (46%) of ethyl (6-iodo-3-(1-(3-methoxy-4-((4-(trifluoromethyl)benzyl)oxy)phenyl)ethyl)-3H-imidazo[4,5-b]pyridin-2-yl)carbamate as a white solid.

Example 3-49-4: Preparation of 6-iodo-3-(1-(3-methoxy-4-((4-(trifluoromethyl)benzyl)oxy)phenyl)ethyl)-3H-imidazo[4,5-b]pyridin-2-amine To a stirred solution of ethyl (6-iodo-3-(1-(3-methoxy-4-((4-(trifluoromethyl)benzyl)oxy)phenyl)ethyl)-3H-imidazo[4,5-b]pyridin-2-yl)carbamate (1.30 g, 2.03 mmol) in ethanol (8 mL)/water (6 mL) was added potassium phosphate tribasic (1.76 g, 8.12 mmol). The mixture was heated to 160° C. in a microwave reactor. After 1 h, the reaction mixture was diluted with water (100 mL), resulting in a precipitate. The solids were isolated by filtration, washed with water (25 mL), and dried to provide 1.02 g (88%) of 6-iodo-3-(1-(3-methoxy-4-((4-(trifluoromethyl)benzyl)oxy)phenyl)ethyl)-3H-imidazo[4,5-b]pyridin-2-amine as a white solid.

Example 3-49-5: Preparation of 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine To a stirred mixture of 6-iodo-3-(1-(3-methoxy-4-((4-(trifluoromethyl)benzyl)oxy)phenyl)ethyl)-3H-imidazo[4,5-b]pyridin-2-amine (0.253 g, 0.45 mmol), 1-methyl-4-(4,4,5,5-tetramethyl-1,3,2-dioxaborolan-2-yl)-1H-pyrazole (0.158 g, 0.76 mmol), potassium phosphate tribasic (0.495 g, 2.29 mmol) in tetrahydrofuran (5 mL)/water (4 mL) was added $2^{nd}$ generation XPhos precatalyst (0.032 g, 0.041 mmol). The yellow solution was degassed under vacuum/backfilled with nitrogen (×3). The mixture heated to 75° C. After 4 h, the mixture was allowed to cool to room temperature and was diluted with water (40 mL). The mixture was extracted with ethyl acetate (3×25 mL). The combined organic phases were dried over magnesium sulfate, filtered, and concentrated to provide 0.320 g of a brown oil. Chromatographic purification (CombiFlash, 12 g $SiO_2$ gold column, 1-5% 2M ammonia in methanol/dichloromethane elute) afforded 0.178 g (77%) of the product as a tan solid: $^1$H NMR (400 MHz, $CDCl_3$) δ 8.25 (d, J=1.9 Hz, 1H), 7.77 (d, J=0.8 Hz, 1H), 7.68 (d, J=1.9 Hz, 1H), 7.66-7.62 (m, 3H), 7.57-7.53 (m, 2H), 6.96-6.92 (m, 1H), 6.89-6.84 (m, 2H), 6.11 (q, J=7.1 Hz, 1H), 5.21 (s, 2H), 4.46 (br s, 2H), 3.98 (s, 3H), 3.80 (s, 3H), 1.87 (d, J=7.1 Hz, 3H) ppm; (M+1)=523.

Example 3-49-6 a and Example 3-49-6 b: Chiral Separation of 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine The racemic 3-(1-(3-methoxy-4-((4-(trifluoromethyl)benzyl)oxy)phenyl)ethyl)-6-(1-methyl-1H-pyrazol-4-yl)-3H-imidazo[4,5-b]pyridin-2-amine was subjected to chiral separation using SFC (21×250 mm AS column, 25% methanol/0.5% diethylamine, flow rate 50 g/min) to provide the two enantiomers. The absolute configuration has not been assigned.

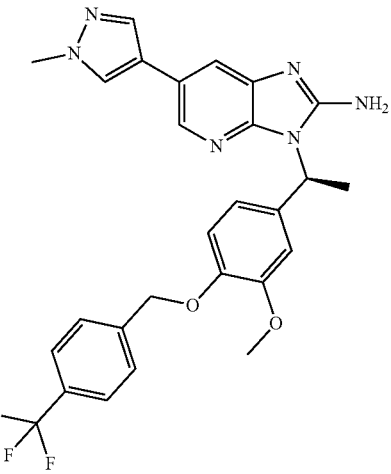

FIG. 2: Example 3-49-6a

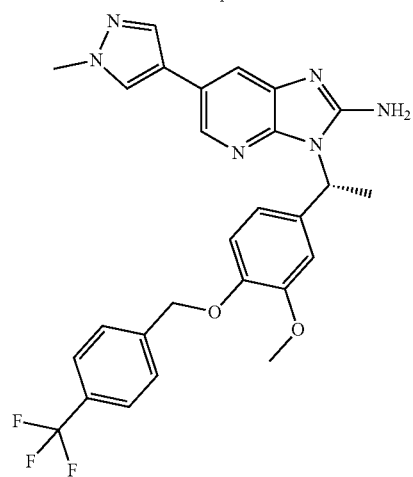

FIG. 2: Example 3-49-6b

Example 3-50: Synthesis of Additional Compounds from 6-iodo-3-(1-(3-methoxy-4-((4-(trifluoromethyl)benzyl)oxy)phenyl)ethyl)-3H-imidazo[4,5-b]pyridin-2-amine The following compounds were prepared from 6-iodo-3-(1-(3-methoxy-4-((4-(trifluoromethyl)benzyl)oxy)phenyl)ethyl)-3H-imidazo[4,5-b]pyridin-2-amine using the procedure described in Example 3-49-5 by employing the appropriate boronate ester coupling partner.

Example 3-50-1: 2-(4-(2-Amino-3-(1-(3-methoxy-4-((4-(trifluoromethyl)benzyl)oxy)phenyl)ethyl)-3H-imidazo[4,5-b]pyridin-6-yl)-1H-pyrazol-1-yl)ethan-1-ol (RA10074277)

$^1$H NMR (400 MHz, $CDCl_3$) δ 8.23 (d, J=1.9 Hz, 1H), 7.80 (d, J=0.8 Hz, 1H), 7.71 (d, J=0.8 Hz, 1H), 7.68-7.61 (m, 3H), 7.58-7.53 (m, 2H), 6.96-6.92 (m, 1H), 6.89-6.84 (m, 2H), 6.11 (q, J=7.1 Hz, 1H), 5.20 (s, 2H), 4.44 (br s, 2H), 4.35-4.27 (m, 2H), 4.11-4.02 (m, 2H), 3.80 (s, 3H), 1.87 (d, J=7.1 Hz, 3H), 1.68 (s, 1H) ppm; (M+1)=553.

Example 3-50-2: 3-(1-(3-Methoxy-4-((4-(trifluoromethyl)benzyl)oxy)phenyl)ethyl)-6-(1H-pyrazol-4-yl)-3H-imidazo[4,5-b]pyridin-2-amine (RA10161874)

$^1$H NMR (400 MHz, DMSO-d$_6$) δ 12.90 (s, 1H), 8.17 (d, J=2.0 Hz, 2H), 7.96-7.88 (m, 1H), 7.74 (d, J=8.1 Hz, 2H), 7.67-7.59 (m, 3H), 7.23 (d, J=1.3 Hz, 1H), 7.07-6.92 (m, 4H), 5.66 (q, J=7.0 Hz, 1H), 5.16 (s, 2H), 3.74 (s, 3H), 2.04 (d, J=7.0 Hz, 3H) ppm; (M+1)=509.

Example 3-51: Synthesis of 3-(1-(3-methoxy-4-((6-(trifluoromethyl)pyridin-3-yl)methoxy)phenyl)propyl)-6-(1-methyl-1H-pyrazol-4-yl)-3H-imidazo[4,5-b]pyridin-2-amine

Example 3-51-1: Preparation of 3-methoxy-4-((6-(trifluoromethyl)pyridin-3-yl)methoxy)benzonitrile To a stirred solution of (6-(trifluoromethyl)pyridin-3-yl)methanol (2.70 g, 15.25 mmol) in dimethylsulfoxide (25 mL) was added 60% sodium hydride dispersion (0.639 g, 15.98 mmol; gas evolution and mild exotherm noted upon addition). After 30 min, the dark brown reaction mixture was treated with 4-fluoro-3-methoxybenzonitrile (2.24 g, 14.52 mmol) and allowed to stir. 45 min after the addition, the orange-brown mixture was diluted with water (150 mL) and extracted with ethyl acetate (3×50 mL). The combined organic phases were washed with brine (50 mL), dried over magnesium sulfate, filtered, and concentrated to provide 4.50 g of an orange solid. Chromatographic purification (CombiFlash, 120 g SiO$_2$ gold column, 10-25% ethyl acetate/heptane elute) afforded 1.93 g (43%) of 3-methoxy-4-((6-(trifluoromethyl)pyridin-3-yl)methoxy)benzonitrile as an off-white solid.

Example 3-51-2: Preparation of 1-(3-methoxy-4-((6-(trifluoromethyl)pyridin-3-yl)methoxy)phenyl)propan-1-one To a stirred 0° C. solution of 3-methoxy-4-((6-(trifluoromethyl)pyridin-3-yl)methoxy)benzonitrile (1.69 g, 5.48 mmol) in tetrahydrofuran (15 mL) was added ethylmagnesium bromide solution (1.0 M in tetrahydrofuran, 7.0 mL, 7.00 mmol) followed by copper(I) iodide (0.010 g, 0.055 mmol). The resulting red-brown mixture was allowed to warm to room temperature and stir. After 16 h, the mixture was treated with 1N hydrochloric acid solution (25 mL) and allowed to stir. After 30 min, the mixture was adjusted pH 7 with saturated potassium carbonate solution (20 mL) and extracted with ethyl acetate (3×30 mL). The combined organic phases were dried over magnesium sulfate, filtered, and concentrated to provide 1.86 g of a brown oil. Chromatographic purification (CombiFlash, 40 g SiO$_2$ column, 25-50% ethyl acetate/heptane elute) afforded 1.44 g (77%) 1-(3-methoxy-4-((6-(trifluoromethyl)pyridin-3-yl)methoxy)phenyl)propan-1-one as an off-white solid.

Example 3-51-3: Preparation of 5-iodo-N-(1-(3-methoxy-4-((6-(trifluoromethyl)pyridin-3-yl)methoxy)phenyl)propyl)-3-nitropyridin-2-amine This compound was prepared from 1-(3-methoxy-4-((6-(trifluoromethyl)pyridin-3-yl)methoxy)phenyl)propan-1-one using the procedures described in Example 3-45-2 through Example 3-45-4.

Example 3-51-4: Preparation of 5-iodo-N$^2$-(1-(3-methoxy-4-((6-(trifluoromethyl)pyridin-3-yl)methoxy)phenyl)propyl)pyridine-2,3-diamine To a stirred suspension of 5-iodo-N-(1-(3-methoxy-4-((6-(trifluoromethyl)pyridin-3-yl)methoxy)phenyl)propyl)-3-nitropyridin-2-amine (1.25 g, 2.12 mmol) in acetic acid (20 mL) was added iron (0.714 g, 12.77 mmol). The yellow mixture was heated to 125° C. As the mixture was heated, the yellow color faded and a gray suspension formed. After 10 min, the mixture was allowed to cool to room temperature and was diluted with ethyl acetate (75 mL). The suspension was filtered through Celite with the aid of ethyl acetate (50 mL). The filtrate was washed with water (2×30 mL) and then with concentrated ammonium hydroxide (2×30 mL). The organic phase was dried over magnesium sulfate, filtered, and concentrated to provide 1.20 g (>100%) of 5-iodo-N$^2$-(1-(3-methoxy-4-((6-(trifluoromethyl)pyridin-3-yl)methoxy)phenyl)propyl)pyridine-2,3-diamine as a brown oil.

Example 3-51-5: Preparation of 3-(1-(3-methoxy-4-((6-(trifluoromethyl)pyridin-3-yl)methoxy)phenyl)propyl)-6-(1-methyl-1H-pyrazol-4-yl)-3H-imidazo[4,5-b]pyridin-2-amine This compound was prepared from 5-iodo-N$^2$-(1-(3-methoxy-4-((6-(trifluoromethyl)pyridin-3-yl)methoxy)phenyl)propyl)pyridine-2,3-diamine using the procedures described in Example 3-49-3 through Example 3-49-5: $^1$H NMR (400 MHz, CDCl$_3$) δ 8.79 (s, 1H), 8.25 (d, J=1.7 Hz, 1H), 7.98 (d, J=8.2 Hz, 1H), 7.81-7.59 (m, 4H), 7.01-6.84 (m, 3H), 5.80-5.70 (m, 1H), 5.21 (s, 2H), 4.68 (br s, 2H), 3.98 (s, 3H), 3.79 (s, 3H), 2.58-2.35 (m, 2H), 0.97-0.86 (m, 3H) ppm; (M+1)=538.

Example 3-52: Synthesis of 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridine

Example 3-52-1: Preparation of 6-iodo-3-(1-(3-methoxy-4-((6-(trifluoromethyl)pyridin-3-yl)methoxy)phenyl)ethyl)-3H-imidazo[4,5-b]pyridine To a stirred solution of 5-iodo-N$^2$-(1-(3-methoxy-4-((6-(trifluoromethyl)pyridin-3-yl)methoxy)phenyl)ethyl)pyridine-2,3-diamine [prepared from 5-(chloromethyl)-2-(trifluoromethyl)pyridine using the procedures described in Example 3-45-1 through Example 3-45-5] (0.710 g, 1.30 mmol) in ethanol (30 mL) was added triethyl orthoformate (1.0 mL, 5.89 mmol). The yellow solution was treated with p-toluenesulfonic acid monohydrate (0.025 g, 0.13 mmol) and heated to reflux. After 30 min, the mixture was allowed to cool to room temperature and was concentrated. The residue was partitioned between ethyl acetate (50 mL) and saturated potassium carbonate solution (50 mL). The phases were separated, and the organic phase was dried over magnesium sulfate, filtered, and concentrated to provide 0.739 g (>100%) of 6-iodo-3-(1-(3-methoxy-4-((6-(trifluoromethyl)pyridin-3-yl)methoxy)phenyl)ethyl)-3H-imidazo[4,5-b]pyridine as an orange solid.

Example 3-52-2: Preparation of 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridine This compound was prepared from 6-iodo-3-(1-(3-methoxy-4-((6-(trifluoromethyl)pyridin-3-yl)methoxy)phenyl)ethyl)-3H-imidazo[4,5-b]pyridine using the procedure described in Example 3-49-5: $^1$H NMR (400 MHz, CDCl$_3$) δ 8.78 (s, 1H), 8.55 (d, J=1.9 Hz, 1H), 8.15-7.93 (m, 3H), 7.79 (s, 1H), 7.74-7.62 (m, 2H), 6.97-6.83 (m, 3H), 5.99 (q, J=7.1 Hz, 1H), 5.20 (s, 2H), 3.98 (s, 3H), 3.83 (s, 3H), 2.00 (d, J=7.1 Hz, 3H) ppm; (M+1)=509.

Example 3-53: Synthesis of 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridin-2-amine Example 3-53-1: Preparation of Ethyl (6-iodo-3-(1-(3-methoxy-4-((6-(trifluoromethyl)pyridin-3-yl)methoxy)phenyl)ethyl)-3H-imidazo[4,5-b]pyridin-2-yl)carbamate To a stirred solution of 5-iodo-N$^2$-(1-(3-methoxy-4-((6-(trifluoromethyl)pyridin-3-yl)methoxy)phenyl)ethyl)pyridine-2,3-diamine [prepared from 5-(chloromethyl)-2-(trifluoromethyl)pyridine using the procedures described in Example 3-45-1 through Example 3-45-5] (1.66 g, 3.05 mmol) and triethylamine (0.64 mL, 4.57 mmol) in tetrahydrofuran (30 mL) was added ethoxycarbonyl isothiocyanate (0.44 mL, 3.66 mmol). After 30 min, the mixture was diluted with brine (100 mL) and extracted with ethyl acetate (3×50 mL). The combined organic phases were dried over magnesium sulfate, filtered, and concentrated to provide 2.18 g as a brown foamy solid. The crude material was dissolved in tetrahydrofuran (30 mL) and triethylamine (1.05 mL, 7.53 mmol). The light yellow solution was treated with benzenesulfonyl chloride (0.97 mL, 7.51 mmol) and allowed to stir at room temperature. After 17 h, the mixture was diluted with water (100 mL) and allowed to stir at room temperature. After 15 min, the reaction mixture was extracted with dichloromethane (3×50 mL). The combined organic phases were washed with saturated potassium carbonate solution (50 mL), dried over magnesium sulfate, filtered, and concentrated to provide 2.77 g of a brown oil. Chromatographic purification (CombiFlash, 40 g SiO$_2$ gold column, 20-40% ethyl acetate/heptane elute) afforded 1.53 g (79%) of ethyl (6-iodo-3-(1-(3-methoxy-4-((6-(trifluoromethyl)pyridin-3-yl)methoxy)phenyl)ethyl)-3H-imidazo[4,5-b]pyridin-2-yl)carbamate as a tan solid.

Example 3-53-2: Preparation of 6-iodo-3-(1-(3-methoxy-4-((6-(trifluoromethyl)pyridin-3-yl)methoxy)phenyl)ethyl)-3H-imidazo[4,5-b]pyridin-2-amine To a stirred solution of ethyl (6-iodo-3-(1-(3-methoxy-4-((6-(trifluoromethyl)pyridin-3-yl)methoxy)phenyl)ethyl)-3H-imidazo[4,5-b]pyridin-2-yl)carbamate (1.53 g, 2.39 mmol), in ethanol (10 mL)/water (4 mL) was added potassium phosphate tribasic (2.07 g, 9.54 mmol). The mixture was irradiated in a microwave reactor at 150° C. After 1 h, the mixture was subjected to an additional round of microwave heating (160° C., 30 min). After a total of 90 min, the mixture was diluted with water (100 mL) and extracted with dichloromethane (2×50 mL). The combined organic phases were dried over magnesium sulfate, filtered, and concentrated to provide 1.31 g (97%) of 6-iodo-3-(1-(3-methoxy-4-((6-(trifluoromethyl)pyridin-3-yl)methoxy)phenyl)ethyl)-3H-imidazo[4,5-b]pyridin-2-amine as an orange foamy solid.

Example 3-53-3: Preparation of 3-(1-(3-methoxy-4-((6-(trifluoromethyl)pyridin-3-yl)methoxy)phenyl)ethyl)-6-(1-methyl-1H-pyrazol-4-yl)-3H-imidazo[4,5-b]pyridin-2-amine This compound was prepared from 6-iodo-3-(1-(3-methoxy-4-((6-(trifluoromethyl)pyridin-3-yl)methoxy)phenyl)ethyl)-3H-imidazo[4,5-b]pyridin-2-amine using the procedure described in Example 3-49-5: $^1$H NMR (400 MHz, CDCl$_3$) δ 8.84-8.76 (m, 1H), 8.25 (d, J=1.9 Hz, 1H), 8.04-7.95 (m, 1H), 7.77 (d, J=0.8 Hz, 1H), 7.74-7.66 (m, 2H), 7.63 (d, J=0.8 Hz, 1H), 6.99-6.94 (m, 1H), 6.94-6.86 (m, 2H), 6.12 (q, J=7.1 Hz, 1H), 5.23 (s, 2H), 4.37 (s, 2H), 3.98 (s, 3H), 3.79 (s, 3H), 1.89 (d, J=7.1 Hz, 3H) ppm; (M+1)=524.

Example 3-54: Synthesis of 2-(4-(2-amino-3-(1-(3-methoxy-4-((6-(trifluoromethyl)pyridin-3-yl)methoxy)phenyl)ethyl)-3H-imidazo[4,5-b]pyridin-6-yl)-1H-pyrazol-1-yl)ethan-1-ol This compound was prepared from 6-iodo-3-(1-(3-methoxy-4-((6-(trifluoromethyl)pyridin-3-yl)methoxy)phenyl)ethyl)-3H-imidazo[4,5-b]pyridin-2-amine using the procedure described in Example 3-49-5 by employing the appropriate boronate ester coupling partner: $^1$H NMR (400 MHz, CDCl$_3$) δ 8.84-8.76 (m, 1H), 8.23 (d, J=1.9 Hz, 1H), 8.03-7.95 (m, 1H), 7.80 (d, J=0.8 Hz, 1H), 7.73-7.70 (m, 2H), 7.66 (d, J=1.9 Hz, 1H), 7.01-6.85 (m, 3H), 6.11 (q, J=7.1 Hz, 1H), 5.23 (s, 2H), 4.47 (s, 2H), 4.35-4.26 (m, 2H), 4.10-4.03 (m, 2H), 3.79 (s, 3H), 1.88 (d, J=7.1 Hz, 3H), 1.70 (br s, 1H) ppm; (M+1)=554.

Example 3-55: Synthesis of 4-(2-amino-3-(1-(3-methoxy-4-((6-(trifluoromethyl)pyridin-3-yl)methoxy)phenyl)ethyl)-3H-imidazo[4,5-b]pyridin-6-yl)but-3-yn-1-ol This compound was prepared from 6-iodo-3-(1-(3-methoxy-4-((6-(trifluoromethyl)pyridin-3-yl)methoxy)phenyl)ethyl)-3H-imidazo[4,5-b]pyridin-2-amine using the procedure described in Example 3-48-2: $^1$H NMR (400 MHz, CDCl$_3$) δ 8.80 (d, J=2.0 Hz, 1H), 8.18 (d, J=1.7 Hz, 1H), 8.04-7.95 (m, 1H), 7.72 (dd, J=8.1, 0.8 Hz, 1H), 7.64 (d, J=1.7 Hz, 1H), 6.98-6.88 (m, 2H), 6.84 (d, J=2.0 Hz, 1H), 6.10 (q, J=7.1 Hz, 1H), 5.22 (s, 2H), 4.44 (br s, 2H), 3.85 (t, J=6.2 Hz, 2H), 3.79 (s, 3H), 2.74 (t, J=6.2 Hz, 2H), 2.01 (br s, 1H), 1.86 (d, J=7.1 Hz, 3H) ppm; (M+1)=512.

Example 3-56: Synthesis of 4-(3-(4-((6-(difluoromethyl)pyridin-3-yl)methoxy)-3-methoxybenzyl)-3H-imidazo[4,5-b]pyridin-6-yl)but-3-yn-1-ol Example 3-56-1: Preparation of tert-butyl (4-((6-(difluoromethyl)pyridin-3-yl)methoxy)-3-methoxybenzyl)carbamate To a stirred solution of tert-butyl 4-hydroxy-3-methoxybenzylcarbamate (4.70 g, 18.56 mmol) and potassium carbonate (7.64 g, 55.28 mmol) in acetonitrile (50 mL) was added 5-(chloromethyl)-2-(difluoromethyl)pyridine hydrochloride (4.58 g, 21.40 mmol). The mixture was heated to reflux. After 3 h, the off-white suspension was allowed to cool to room temperature and was diluted with water (200 mL). The mixture was extracted with dichloromethane (3×75 mL). The combined organic phases were dried over magnesium sulfate, filtered, and concentrated to provide 7.74 g (>100%) of tert-butyl 4-((6-(difluoromethyl)pyridin-3-yl)methoxy)-3-methoxybenzylcarbamate as a waxy yellow solid.

Example 3-56-2: Preparation of (4-((6-(difluoromethyl)pyridin-3-yl)methoxy)-3-methoxyphenyl) methanamine To a stirred solution of tert-butyl 4-((6-(difluoromethyl)pyridin-3-yl)methoxy)-3-methoxybenzylcarbamate (7.32 g, 18.56 mmol) in dichloromethane (30 ml) was added trifluoroacetic acid (15 mL, 194.70 mmol). After 2 h, the reaction mixture was concentrated, and the residue was dissolved in water (75 mL). The acidic solution was extracted with diethyl ether (50 mL). The aqueous phase was retained and made basic with concentrated ammonium hydroxide solution (50 mL). The basic aqueous phase was extracted with dichloromethane (2×100 mL). The combined organic phases were dried over magnesium sulfate, filtered, and concentrated to provide 4.54 g (83%) of (4-((6-(difluoromethyl)pyridin-3-yl)methoxy)-3-methoxyphenyl)methanamine as a yellow solid.

Example 3-56-3: Preparation of 3-(4-((6-(difluoromethyl)pyridin-3-yl)methoxy)-3-methoxybenzyl)-6-iodo-3H-imidazo[4,5-b]pyridine To a stirred solution of $N^2$-(4-((6-(difluoromethyl)pyridin-3-yl)methoxy)-3-methoxybenzyl)-5-iodopyridine-2,3-diamine [prepared from (4-((6-(difluoromethyl)pyridin-3-yl)methoxy)-3-methoxyphenyl)methanamine using the procedures described in Example 3-45-4 and Example 3-45-5] (3.10 g, 6.05 mmol) in ethanol (50 mL) was added triethyl orthoformate (3.0 mL, 18.02 mmol). The mixture was treated with p-toluenesulfonic acid monohydrate (50 mg, 262.86 µmol) and was heated to reflux. After 45 min, the mixture was allowed to cool to room temperature, resulting in the formation of a precipitate. The mixture was concentrated, and the residue dissolved in chloroform (150 mL). The solution was washed with saturated potassium carbonate solution, dried over magnesium sulfate, filtered, and concentrated to provide 3.15 g (99%) of 3-(4-((6-(difluoromethyl)pyridin-3-yl)methoxy)-3-methoxybenzyl)-6-iodo-3H-imidazo[4,5-b]pyridine as a brown solid.

Example 3-56-4: Preparation of 4-(3-(4-((6-(difluoromethyl)pyridin-3-yl)methoxy)-3-methoxybenzyl)-3H-imidazo[4,5-b]pyridin-6-yl)but-3-yn-1-ol This compound was prepared from 3-(4-((6-(difluoromethyl)pyridin-3-yl)methoxy)-3-methoxybenzyl)-6-iodo-3H-imidazo[4,5-b]pyridine using the procedure described in Example 3-48-2: $^1$H NMR (400 MHz, CDCl$_3$) δ 8.71-8.69 (m, 1H), 8.48 (d, J=1.7 Hz, 1H), 8.10 (d, J=1.7 Hz, 1H), 8.02 (s, 1H), 7.92 (dd, J=8.1, 2.1 Hz, 1H), 7.65 (d, J=8.1 Hz, 1H), 6.92 (d, J=1.8 Hz, 1H), 6.87-6.80 (m, 2H), 6.64 (t, J=55.4 Hz, 1H), 5.38 (s, 2H), 5.17 (s, 2H), 3.87 (t, J=6.3 Hz, 2H), 3.82 (s, 3H), 2.75 (t, J=6.3 Hz, 2H), 2.11 (br s, 1H) ppm; (M+1)=465.

Example 3-57: Synthesis of 3-(3-methoxy-4-(1-(6-methoxypyridin-3-yl)ethoxy)benzyl)-6-(1-methyl-1H-pyrazol-4-yl)-3H-imidazo[4,5-b]pyridine Formate Example 3-57-1: Preparation of 4-(((5-iodo-3-nitropyridin-2-yl)amino)methyl)-2-methoxyphenol To a stirred suspension of 4-hydroxy-3-methoxybenzylamine hydrochloride (1.32 g, 6.82 mmol) and 2-chloro-5-iodo-3-nitropyridine (2.00 g, 6.82 mmol) in acetonitrile (20 mL) was added N, N-disopropylethylamine (5.96 ml, 34.10 mmol) The suspension was stirred and heated to 100° C. After 1 h, the mixture was allowed to cool to room temperature, and 2N aqueous potassium hydroxide solution (0.68 mL) was added. The mixture was concentrated to provide 4-(((5-iodo-3-nitropyridin-2-yl)amino)methyl)-2-methoxyphenol as an impure solid.

Example 3-57-2: Preparation of 4-((6-iodo-3H-imidazo[4,5-b]pyridin-3-yl)methyl)-2-methoxyphenol This compound was prepared in two steps from 4-(((5-iodo-3-nitropyridin-2-yl)amino)methyl)-2-methoxyphenol using the procedures described in Example 3-49-2 and Example 3-52-2.

Example 3-57-3: Preparation of 6-iodo-3-(3-methoxy-4-(1-(6-methoxypyridin-3-yl)ethoxy)benzyl)-3H-imidazo[4,5-b]pyridine To a stirred mixture of 4-((6-iodo-3H-imidazo[4,5-b]pyridin-3-yl)methyl)-2-methoxyphenol (1.32 g, 3.46 mmol) and potassium carbonate (1.30 g, 9.41 mmol) in acetonitrile (25 mL) was added 5-(1-chloroethyl)-2-methoxypyridine (0.72 g, 4.20 mmol). The mixture was heated at 100° C. After 6.5 h, an additional quantity 5-(1-chloroethyl)-2-methoxypyridine (0.300 g, 1.75 mmol) was added, and heating was continued. After 22 h, the mixture was allowed to cool to room temperature and was partitioned between water and 1:5 ethyl acetate/diethyl ether. The phases were separated, and the aqueous phase was extracted with diethyl ether. The combined organic phases were washed with water, dried over magnesium sulfate, filtered, and concentrated. Chromatographic purification (40 g SiO$_2$ column, 0-10% 0.01 M ammonia in methanol/dichlormethane elute) afforded 0.88 g (49%) of 6-iodo-3-(3-methoxy-4-(1-(6-methoxypyridin-3-yl)ethoxy)benzyl)-3H-imidazo[4,5-b]pyridine as an impure solid.

Example 3-57-4: Preparation of 3-(3-methoxy-4-(1-(6-methoxypyridin-3-yl)ethoxy)benzyl)-6-(1-methyl-1H-pyrazol-4-yl)-3H-imidazo[4,5-b]pyridine Formate To a stirred suspension of 6-iodo-3-(3-methoxy-4-(1-(6-methoxypyridin-3-yl)ethoxy)benzyl)-3H-imidazo[4,5-b]pyridine (0.200 g, 0.39 mmol), potassium phosphate tribasic (0.164 g, 0.77 mmol), 1-methyl-4-(4,4,5,5-tetramethyl-1,3,2-dioxaborolan-2-yl)-1H-pyrazole (0.100 g, 0.48 mmol) and tricyclohexylphosphine (0.008 g, 0.028 mmol) in 1,4-dioxane (3 mL)/water (1.5 mL) was added tris(dibenzylideneacetone)dipalladium(O) (0.012 g, 0.013 mmol). The mixture was degassed by bubbling nitrogen through the mixture for 2 min, and then the mixture was irradiated in a microwave reactor at 120° C. After 30 min, the mixture was allowed to cool to room temperature and was filtered through Celite. The filtrate was subjected to direct purification (50 g C$_{18}$ column, water/acetonitrile/0.1% formic acid elute) to provide an impure material. A second purification under the same conditions afforded 0.051 g (26%) of the product as a white solid: $^1$H NMR (400 MHz, CD$_3$D) δ 8.62 (d, J=1.9 Hz, 1H), 8.37 (s, 1H), 8.20-8.13 (m, 1H), 8.05 (dd, J=7.6, 1.6 Hz, 2H), 7.90 (d, J=0.8 Hz, 1H), 7.71 (dd, J=8.6, 2.5 Hz, 1H), 7.05 (d, J=1.9 Hz, 1H), 6.83-6.69 (m, 3H), 5.42

(s, 2H), 5.37 (q, J=6.4 Hz, 1H), 3.95 (s, 3H), 3.84 (s, 3H), 3.80 (s, 3H), 1.58 (d, J=6.4 Hz, 3H) ppm; (M+1)=471.

Example 3-58: Synthesis of Additional Compounds from 6-iodo-3-(3-methoxy-4-(1-(6-methoxypyridin-3-yl)ethoxy)benzyl)-3H-imidazo[4,5-b]pyridine The following compounds were prepared from 6-iodo-3-(3-methoxy-4-(1-(6-methoxypyridin-3-yl)ethoxy)benzyl)-3H-imidazo[4,5-b]pyridine using the procedure described in Example 3-57-4 by employing the appropriate boronic acid/boronate ester coupling partner.

Example 3-58-1: 3-(3-methoxy-4-(1-(6-methoxy-pyridin-3-yl)ethoxy)benzyl)-6-(1-methyl-1H-pyrazol-5-yl)-3H-imidazo[4,5-b]pyridine Formate (RA09683914A)

$^1$H NMR (400 MHz, CDCl$_3$) δ 8.49 (d, J=1.9 Hz, 1H), 8.17-8.03 (m, 3H), 7.64 (dd, J=8.6, 2.5 Hz, 1H), 7.57 (d, J=1.9 Hz, 1H), 6.90 (d, J=1.5 Hz, 1H), 6.78-6.65 (m, 3H), 6.39 (d, J=1.9 Hz, 1H), 5.39 (s, 2H), 5.29 (q, J=6.4 Hz, 1H), 3.92 (s, 3H), 3.90 (s, 3H), 3.83 (s, 3H), 3.49 (s, 1H), 1.66 (d, J=6.4 Hz, 3H) ppm; (M+1)=471.

Example 3-58-2: 3-(3-methoxy-4-(1-(6-methoxy-pyridin-3-yl)ethoxy)benzyl)-6-(6-methoxypyridin-3-yl)-3H-imidazo[4,5-b]pyridine Formate (RA09683951A)

$^1$H NMR (400 MHz, CDCl$_3$) δ 8.59 (d, J=2.0 Hz, 1H), 8.42 (dd, J=2.6, 0.8 Hz, 1H), 8.18 (d, J=2.0 Hz, 1H), 8.10 (d, J=2.4 Hz, 1H), 8.03 (s, 1H), 7.82 (dd, J=8.6, 2.6 Hz, 1H), 7.63 (dd, J=8.6, 2.5 Hz, 1H), 6.89 (d, J=0.9 Hz, 2H), 6.75-6.66 (m, 3H), 5.38 (s, 2H), 5.29 (q, J=6.4 Hz, 1H), 4.00 (s, 3H), 3.90 (s, 3H), 3.82 (s, 3H), 1.66 (d, J=6.5 Hz, 3H) ppm; (M+1)=498.

Example 3-58-3: 6-(2-fluoropyridin-4-yl)-3-(3-methoxy-4-(1-(6-methoxypyridin-3-yl)ethoxy)benzyl)-3H-imidazo[4,5-b]pyridine Formate (RA09683967A)

$^1$H NMR (400 MHz, CDCl$_3$) δ 8.70 (d, J=2.0 Hz, 1H), 8.35-8.29 (m, 2H), 8.10 (d, J=2.8 Hz, 2H), 7.64 (dd, J=8.6, 2.5 Hz, 1H), 7.46 (dt, J=5.3, 1.7 Hz, 1H), 7.19 (t, J=1.6 Hz, 1H), 6.89 (d, J=1.5 Hz, 1H), 6.75-6.72 (m, 2H), 6.71 (dd, J=8.6, 0.7 Hz, 1H), 5.39 (s, 2H), 5.29 (q, J=6.4 Hz, 1H), 3.90 (s, 3H), 3.83 (s, 3H), 1.66 (d, J=6.4 Hz, 3H) ppm; (M+1)=486.

The invention claimed is:

1. A method of inhibiting tropomyosin-related kinase A in a patient, comprising administering to the patient a pharmaceutical composition comprising a compound of Formula (I) in order to inhibit tropomyosin-related kinase A in the patient, wherein Formula I is represented by:

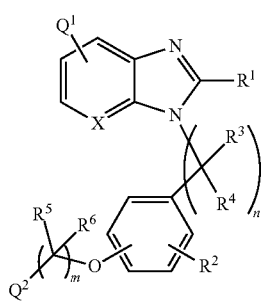

(I)

or a pharmaceutically acceptable salt thereof; wherein:

n is 1, 2, 3, 4 or 5;

m is 0, 1, 2, 3 or 4;

$Q^1$ is $(C_2-C_9)$heteroaryl optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8$N—, $R^7R^8$N(O)C—, $R^7(O)CR^8$N—, F$_3$C—, NC—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8$NO$_2$S—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, or $(C_2-C_9)$heteroaryl;

$Q^2$ is $(C_6-C_{14})$aryl, $(C_2-C_9)$heteroaryl, $(C_3-C_{10})$cycloalkyl, or $(C_2-C_9)$heterocycloalkyl, wherein the $(C_6-C_{14})$aryl, $(C_2-C_9)$heteroaryl, $(C_3-C_{10})$cycloalkyl, or $(C_2-C_9)$heterocycloalkyl is optionally substituted by one to four groups selected from $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkyl-C(O)O—, COOH—$(C_1-C_{10})$alkyl, COOH—$(C_3-C_{10})$cycloalkyl, $(C_1-C_{10})$alkyl-O—, —OH, —NH$_2$, $R^7R^8$N—, $R^7R^8$N(O)C—, $R^7(O)CR^8$N—, F$_3$C—, NC—, $(C_3-C_{10})$alkyl-S—, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_3-C_{10})$alkyl(O)S—, $(C_3-C_{10})$cycloalkyl(O)S—, $(C_6-C_{14})$aryl(O)S—, $(C_2-C_9)$heteroalkyl(O)S—, $(C_2-C_9)$heterocycloalkyl(O)S—, $(C_2-C_9)$heteroaryl(O)S—, $(C_3-C_{10})$alkyl-O$_2$S—, $(C_3-C_{10})$cycloalkyl-O$_2$S—, $(C_6-C_{14})$aryl-O$_2$S—, $(C_2-C_9)$heteroalkyl-O$_2$S—, $(C_2-C_9)$heterocycloalkyl-O$_2$S—, $(C_2-C_9)$heteroaryl-O$_2$S—, or $R^7R^8$NO$_2$S—, wherein $R^7$ and $R^8$ is each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, or $(C_2-C_9)$heteroaryl;

X is CH, N, or $CR^9$, wherein $R^9$ is $(C_1-C_{10})$alkyl;

$R^1$ is H, $(C_1-C_{10})$alkylamine, or NH$_2$;

$R^2$ is $(C_1-C_{10})$alkylamine or $(C_1-C_{10})$alkyl-O—;

$R^3$ and $R^4$ are each independently H or $(C_1-C_{10})$alkyl; and $R^5$ and $R^6$ are each independently H or $(C_1-C_{10})$alkyl.

2. The method of claim 1, wherein $Q^1$ is $(C_2-C_9)$heteroaryl substituted by $(C_1-C_{10})$alkyl.

3. The method of claim 1, wherein $Q^2$ is $(C_6-C_{14})$aryl substituted by $(C_1-C_{10})$alkyl-O—.

4. The method of claim 2, wherein $Q^2$ is $(C_6-C_{14})$aryl substituted by $(C_1-C_{10})$alkyl-O—.

5. The method of claim 1, wherein X is N.

6. The method of claim 4, wherein X is N.

7. The method of claim 1, wherein $R^1$ is NH$_2$.

8. The method of claim 6, wherein $R^1$ is NH$_2$.

9. The method of claim 1, wherein $R^2$ is $(C_1-C_{10})$alkyl-O—.

10. The method of claim 8, wherein $R^2$ is $(C_1\text{-}C_{10})$alkyl-O—.

11. The method of claim 1, wherein the compound is represented by Formula II:

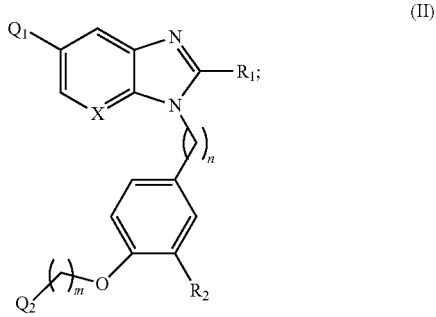

or a pharmaceutically acceptable salt thereof, wherein:
n is 1, 2, or 3;
m is 0, 1, 2, or 3;
$Q^1$ is $(C_2\text{-}C_9)$heteroaryl optionally substituted by one to four groups selected from $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_1\text{-}C_{10})$alkylamine, $(C_1\text{-}C_{10})$alkyl-C(O)O—, $(C_1\text{-}C_{10})$alkyl-O—, —OH, or —NH$_2$;
$Q^2$ is $(C_6\text{-}C_{14})$aryl, $(C_2\text{-}C_9)$heteroaryl, $(C_3\text{-}C_{10})$cycloalkyl, or $(C_2\text{-}C_9)$heterocycloalkyl,
 wherein the $(C_6\text{-}C_{14})$aryl, $(C_2\text{-}C_9)$heteroaryl, $(C_3\text{-}C_{10})$cycloalkyl, or $(C_2\text{-}C_9)$heterocycloalkyl is optionally substituted by one to four groups selected from $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_1\text{-}C_{10})$alkylamine, $(C_1\text{-}C_{10})$alkyl-C(O)O—, $(C_1\text{-}C_{10})$alkyl-O—, —OH, or —NH$_2$;
X is CH, N, or CR$^9$, wherein R$^9$ is $(C_1\text{-}C_{10})$alkyl;
$R^1$ is $(C_1\text{-}C_{10})$alkylamine or NH$_2$; and
$R^2$ is $(C_1\text{-}C_{10})$alkylamine or $(C_1\text{-}C_{10})$alkyl-O—.

12. The method of claim 11, wherein $Q^1$ is $(C_2\text{-}C_9)$heteroaryl substituted by $(C_1\text{-}C_{10})$alkyl.

13. The method of claim 11, wherein $Q^2$ is $(C_6\text{-}C_{14})$aryl substituted by $(C_1\text{-}C_{10})$alkyl-O—.

14. The method of claim 12, wherein $Q^2$ is $(C_6\text{-}C_{14})$aryl substituted by $(C_1\text{-}C_{10})$alkyl-O—.

15. The method of claim 11, wherein X is N.

16. The method of claim 14, wherein X is N.

17. The method of claim 11, wherein $R^1$ is NH$_2$.

18. The method of claim 16, wherein $R^1$ is NH$_2$.

19. The method of claim 11, wherein $R^2$ is $(C_1\text{-}C_{10})$alkyl-O—.

20. The method of claim 18, wherein $R^2$ is $(C_1\text{-}C_{10})$alkyl-O—.

21. The method of claim 1, wherein the compound is:

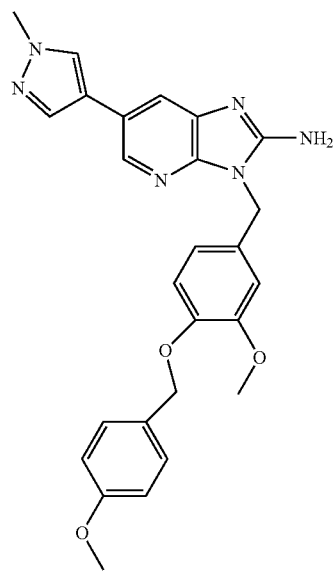 [SMILES: COc1ccc(COc2ccc(Cn3c(N)nc4cc(-c5cnn(C)c5)cnc43)cc2OC)cc1]

or a pharmaceutically acceptable salt thereof.

* * * * *